US009388208B2

(12) United States Patent
Clarke et al.

(10) Patent No.: US 9,388,208 B2
(45) Date of Patent: Jul. 12, 2016

(54) PYRROLO[1,2-F][1,2,4]TRIAZINES USEFUL FOR TREATING RESPIRATORY SYNCITIAL VIRUS INFECTIONS

(71) Applicant: Gilead Sciences, Inc., Foster City, CA (US)

(72) Inventors: Michael O'Neil Hanrahan Clarke, Redwood City, CA (US); Edward Doerffler, Foster City, CA (US); Richard L Mackman, Millbrae, CA (US); Dustin Siegel, San Carlos, CA (US)

(73) Assignee: GILEAD SCIENCES, INC., Foster City, CA (US)

( * ) Notice: Subject to any disclaimer, the term of this patent is extended or adjusted under 35 U.S.C. 154(b) by 0 days.

(21) Appl. No.: 14/534,715

(22) Filed: Nov. 6, 2014

(65) Prior Publication Data
US 2015/0133395 A1    May 14, 2015

Related U.S. Application Data

(60) Provisional application No. 61/902,544, filed on Nov. 11, 2013.

(51) Int. Cl.
C07H 7/06     (2006.01)
C07D 405/04   (2006.01)
C07D 405/14   (2006.01)
C07D 487/04   (2006.01)

(52) U.S. Cl.
CPC ............... C07H 7/06 (2013.01); C07D 405/04 (2013.01); C07D 405/14 (2013.01); C07D 487/04 (2013.01)

(58) Field of Classification Search
None
See application file for complete search history.

(56) References Cited

U.S. PATENT DOCUMENTS

| 8,008,264 B2 * | 8/2011 | Butler | C07H 19/23 514/23 |
|---|---|---|---|
| 8,318,682 B2 * | 11/2012 | Butler | C07H 19/23 514/23 |
| 8,853,171 B2 * | 10/2014 | Butler | C07H 19/23 514/23 |
| 2012/0009147 A1 | 1/2012 | Cho et al. | |
| 2012/0020921 A1 | 1/2012 | Cho et al. | |
| 2013/0243725 A1 * | 9/2013 | Clarke | A61K 31/706 424/85.4 |
| 2014/0099283 A1 | 4/2014 | Gosselin et al. | |

FOREIGN PATENT DOCUMENTS

| WO | WO-02/32920 A2 | 4/2002 |
|---|---|---|
| WO | WO-2008089105 A2 | 7/2008 |
| WO | WO-2008/141079 A1 | 11/2008 |
| WO | WO-2009132135 A2 | 1/2009 |
| WO | WO-2010/002877 A2 | 7/2010 |
| WO | WO-2011035231 A1 | 3/2011 |
| WO | WO-2011035250 A1 | 3/2011 |
| WO | WO-2011150288 A1 | 12/2011 |
| WO | WO-2012/012776 A1 | 1/2012 |
| WO | WO-2012012465 A1 | 1/2012 |
| WO | WO-2012037038 A1 | 3/2012 |
| WO | WO-2012087596 A1 | 6/2012 |
| WO | WO-2012142075 A1 | 10/2012 |
| WO | WO-2013138236 A1 | 9/2013 |

OTHER PUBLICATIONS

Chapman, J. et al. (2007) "RSV604, a Novel Inhibitor of Respiratory Syncytial Virus Replication" Antimicrobial Agents and Chemotherapy 51(9):3346-3353.
Cihlar, T. et al. (2008) "Design and Profiling of GS-9148, a Novel Nucleotide Analog Active against Nucleoside-Resistant Variants of Human Immunodeficiency Virus Type 1, and its Orally Bioavailable Phosphonoamidate Prodrug, GS-9131" Antimicrobial Agents and Chemotherapy 52(2):655-665.
Haraguchi, K. et al. (2005) "A New Approach to the Synthesis of 4'-Carbon-Substituted Nucleosides: Development of a Highly Active Anti-HIV Agent 2', 3',Didehydro-3'-Deoxy-4'-Ethynylthymidine" Nucleosides, Nucleotides, and Nucleic Acids 24(5-7):343-347.
International Search Report dated Dec. 23, 2014 for PCT/US2014/064412.
Mason, S. et al. (2004) "Polyadenylation-dependent screening assay for respiratory syncytial virus RNA transcriptase activity and identification of an inhibitor" Nucleic Acids Research 32(16):4758-4767.
Meppen, M. et al. (2009) "Cyclic Phosphoramidates as Prodrugs of 2'-C-Methylcytidine" European Journal of Medicinal Chemistry 44:3765-3770.
Patil, S. et al. (1994) "4-Aza-7,9-Dideazaadenosine, a New Cytotoxic Synthetic C-Nucleoside Analogue of Adenosine", Tetrahedron Letters, 35(30):5339-5342.

(Continued)

Primary Examiner — Traviss C McIntosh, III

(57) ABSTRACT

Provided herein are formulations, methods and substituted tetrahydrofuranyl-pyrrolo[1,2-f][1,2,4]triazine-4-amine compounds of Formula (I) for treating Pneumovirinae virus infections, including respiratory syncytial virus infections, as well as methods and intermediates for synthesis of tetrahydrofuranyl-pyrrolo[1,2-f][1,2,4]triazine-4-amine compounds.

30 Claims, No Drawings

(56) References Cited

OTHER PUBLICATIONS

Perrone, P. et al. (2007) "First Example of Phosphoramidate Approach Applied to a 4'-Substituted Purine Nucleoside (4'-Azidoadenosine): Converstion of an Inactive Nucleoside to a Submicromolar Compound versus Hepatitus C Virus" J. Med. Chem. 50:5463-5470.

Waga, T. et al. (1993) "Synthesis of 4'-C-Methylnucleosides" Bioscience, Biotechnology, and Biochemistry 57(9):1433-1438.

* cited by examiner

PYRROLO[1,2-F][1,2,4]TRIAZINES USEFUL FOR TREATING RESPIRATORY SYNCITIAL VIRUS INFECTIONS

CROSS REFERENCE TO RELATED APPLICATION

This application claims the benefit of and priority to U.S. Provisional Application Ser. No. 61/902,544, filed Nov. 11, 2013, the disclosure of which is hereby incorporated by reference in its entirety.

FIELD

Provided herein are substituted tetrahydrofuranyl-pyrrolo[1,2-f][1,2,4]triazine-4-amine compounds, methods and pharmaceutical formulations for treating Pneumovirinae virus infections, particularly including respiratory syncytial virus infections, as well as methods and intermediates useful for preparing the compounds.

BACKGROUND

Pneumovirinae viruses are negative-sense, single-stranded, RNA viruses that are responsible for many prevalent human and animal diseases. The Pneumovirinae subfamily of viruses is a part of the family Paramyxoviridae and includes human respiratory syncytial virus (HRSV). Almost all children will have had an HRSV infection by their second birthday. HRSV is the major cause of lower respiratory tract infections in infancy and childhood with 0.5% to 2% of those infected requiring hospitalization. The elderly and adults with chronic heart, lung disease or those that are immunosuppressed also have a high risk for developing severe HRSV disease (http://www.cdc.gov/rsv/index.html). No vaccine to prevent HRSV infection is currently available. The monoclonal antibody palivizumab is available for immunoprophylaxis, but its use is restricted to infants at high risk, e.g., premature infants or those with either congenital heart or lung disease, and the cost for general use is often prohibitive. In addition, nucleoside analog ribavirin has been approved as the only antiviral agent to treat HRSV infections but has limited efficacy. Therefore, there is a need for anti-Pneumovirinae therapeutics.

Examples of pyrrolo[2,3-d]pyrimidine compounds useful for treating viral infections are described in U.S. 2012/0009147 A1 (Cho et al.), U.S. 2012/0020921 A1 (Cho et al.), WO 2008/089105 A2 (Babu et al.), WO 2008/141079 A1 (Babu et al.), WO 2009/132135 A1 (Butler et al.), WO 2010/002877 A2 (Francom), WO 2011/035231 A1 (Cho et al.), WO 2011/035250 A1 (Butler et al.), WO 2011/150288 A1 (Cho et al.), WO 2012/012465 (Cho et al.), WO 2012/012776 A1 (Mackman et al.), WO 2012/037038 (Clarke et al.), WO 2012/087596 A1 (Delaney et al.), and WO 2012/142075 A1 (Girijavallabhan et al.).

There remains a need for new antiviral agents useful in treating Paramyxoviridae viral infections, including Pneumovirinae viral infections, such as HRSV infections, that are effective and have acceptable toxicity profiles.

SUMMARY

Provided are compounds, methods, and pharmaceutical formulations for the treatment of infections caused by the Pneumovirinae virus family, including treatment of infections caused by human respiratory syncytial virus.

Provided is a compound of the Formula (I), or a pharmaceutically acceptable salt thereof:

wherein:
$R^1$ is H or F;
$R^2$ is H or F;
$R^3$ is OH or F;
$R^4$ is CN, $C_1$-$C_4$ alkyl, $C_2$-$C_4$ alkenyl, $C_2$-$C_4$ alkynyl, $C_3$-$C_4$ cycloalkyl, azido, halogen, or $C_1$-$C_2$ haloalkyl;
$R^6$ is OH;
$R^5$ is selected from the group of H and:

wherein:
n' is selected from 1, 2, 3, and 4;
$R^8$ is selected from $C_1$-$C_8$ alkyl, —O—$C_1$-$C_8$ alkyl, benzyl, —O-benzyl, —$CH_2$—$C_3$-$C_6$ cycloalkyl, —O—$CH_2$—$C_3$-$C_6$ cycloalkyl, and $CF_3$;
$R^9$ is selected from phenyl, 1-naphthyl, 2-naphthyl, $R^{10}$ is selected from H and $CH_3$;
$R^{11}$ is selected from H or $C_1$-$C_6$ alkyl;
$R^{12}$ is selected from H, $C_1$-$C_8$ alkyl, benzyl, $C_3$-$C_6$ cycloalkyl, and —$CH_2$—$C_3$-$C_6$ cycloalkyl.

DETAILED DESCRIPTION

An embodiment herein comprises a compound of Formula (I), or a pharmaceutically acceptable salt thereof, wherein $R^1$ is H, and all other variables, including $R^2$, $R^3$, $R^4$, $R^5$, $R^6$, $R^7$, $R^8$, $R^9$, $R^{10}$, $R^{11}$, $R^{12}$, and n' are as defined above for Formula (I).

Another embodiment herein comprises a compound of Formula (I), or a pharmaceutically acceptable salt thereof, wherein $R^2$ is H, and all other variables, including $R^1$, $R^3$, $R^4$, $R^5$, $R^6$, $R^7$, $R^8$, $R^9$, $R^{10}$, $R^{11}$, $R^{12}$, and n' are as defined above for Formula (I).

A further embodiment herein comprises a compound of Formula (I), or a pharmaceutically acceptable salt thereof, wherein both $R^1$ and $R^2$ are H, and all other variables, including $R^3$, $R^4$, $R^5$, $R^6$, $R^7$, $R^8$, $R^9$, $R^{10}$, $R^{11}$, $R^{12}$, and n' are as defined above for Formula (I).

Still another embodiment herein comprises a compound of Formula (I), or a pharmaceutically acceptable salt thereof, wherein both $R^1$, $R^2$, and $R^5$ are H, and all other variables, including $R^3$, $R^4$, $R^6$, $R^7$, $R^8$, $R^9$, $R^{10}$, $R^{11}$, $R^{12}$ and n' are as defined above for Formula (I).

Another separate embodiment herein comprises a compound of Formula (I), or a pharmaceutically acceptable salt thereof, wherein both $R^1$ and $R^2$ are H, $R^3$ is OH, and all other variables, including $R^4$, $R^5$, $R^6$, $R^7$, $R^8$, $R^9$, $R^{10}$, $R^{11}$, $R^{12}$ and n' are as defined above for Formula (I).

Another separate embodiment herein comprises a compound of Formula (I), or a pharmaceutically acceptable salt thereof, wherein both $R^1$ and $R^2$ are H, $R^3$ is F, and all other variables, including $R^4$, $R^5$, $R^6$, $R^7$, $R^8$, $R^9$, $R^{10}$, $R^{11}$, $R^{12}$ and n' are as defined above for Formula (I).

Another embodiment provided herein comprises a compound of Formula (II), or a pharmaceutically acceptable salt thereof:

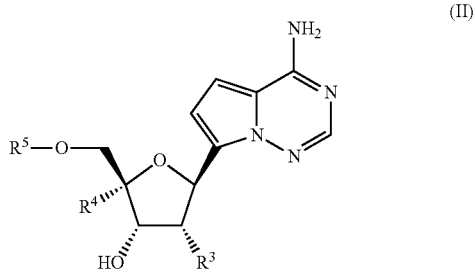

(II)

wherein:
$R^3$ is OH or F;
$R^4$ is CN, $C_1$-$C_4$ alkyl, $C_2$-$C_4$ alkenyl, $C_2$-$C_4$ alkynyl, $C_3$-$C_4$ cycloalkyl, azido, halogen, or $C_1$-$C_2$ haloalkyl;
$R^5$ is selected from the group of H and:

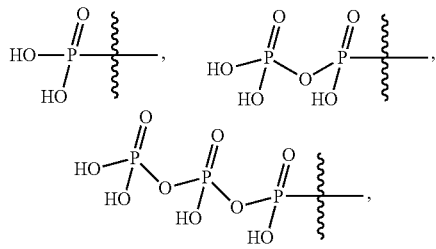

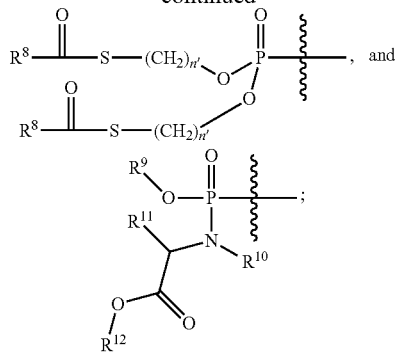

wherein:
n' is selected from 1, 2, 3, and 4;
$R^8$ is selected from $C_1$-$C_8$ alkyl, —O—$C_1$-$C_8$ alkyl, benzyl, —O-benzyl, —$CH_2$—$C_3$-$C_6$ cycloalkyl, —O—$CH_2$—$C_3$-$C_6$ cycloalkyl, and $CF_3$;
$R^9$ is phenyl;
$R^{10}$ is selected from H and $CH_3$;
$R^{11}$ is selected from H or $C_1$-$C_6$ alkyl;
$R^{12}$ is selected from H, $C_1$-$C_8$ alkyl, benzyl, $C_3$-$C_6$ cycloalkyl, and —$CH_2$—$C_3$-$C_6$ cycloalkyl.

A further embodiment comprises a compound of Formula (II), or a pharmaceutically acceptable salt thereof, wherein:
$R^3$ is OH or F;
$R^4$ is CN, methyl, ethyl, ethenyl, ethynyl, azido, F, Cl, —$CH_2Cl$, —$CH_2F$, —$CHF_2$, or —$CF_3$;
and $R^5$ and all other groups are as defined for Formula (II).

Also provided is an embodiment comprising a compound of Formula (II) or a pharmaceutically acceptable salt thereof, as described above, wherein $R^3$ is F.

Also provided is an embodiment comprising a compound of Formula (II) or a pharmaceutically acceptable salt thereof, as described above, wherein $R^3$ is OH.

Also provided is an embodiment comprising a compound of Formula (II) or a pharmaceutically acceptable salt thereof, as described above, wherein $R^3$ is F and $R^4$ is CN.

Also provided is an embodiment comprising a compound of Formula (II) or a pharmaceutically acceptable salt thereof, as described above, wherein $R^3$ is OH and $R^4$ is CN.

Also provided is an embodiment comprising a compound of Formula (II) or a pharmaceutically acceptable salt thereof, as described above, wherein both $R^1$ and $R^2$ are H, $R^3$ is F, and $R^4$ is methyl, ethyl, vinyl, or ethynyl.

Also provided is an embodiment comprising a compound of Formula (II) or a pharmaceutically acceptable salt thereof, as described above, wherein $R^3$ is OH, and $R^4$ is methyl, ethyl, vinyl, or ethynyl.

Also provided is an embodiment comprising a compound of Formula (II) or a pharmaceutically acceptable salt thereof, as described above, wherein $R^3$ is F and $R^4$ is halomethyl.

Also provided is an embodiment comprising a compound of Formula (II) or a pharmaceutically acceptable salt thereof, as described above, wherein $R^3$ is OH and $R^4$ is halomethyl.

Also provided is an embodiment comprising a compound of Formula (II) or a pharmaceutically acceptable salt thereof, as described above, wherein $R^5$ is H.

Also provided is an embodiment comprising a compound of Formula (II) or a pharmaceutically acceptable salt thereof, as described above, wherein each of $R^5$ is H, $R^3$ is OH, and $R^4$ is methyl, ethyl, vinyl, or ethynyl.

Also provided is an embodiment comprising a compound of Formula (II) or a pharmaceutically acceptable salt thereof, as described above, wherein $R^5$ is H, $R^3$ is F, and $R^4$ is halomethyl.

Also provided is an embodiment comprising a compound of Formula (II) or a pharmaceutically acceptable salt thereof, as described above, wherein $R^5$ are H, $R^3$ is OH, and $R^4$ is halomethyl.

Within each of the embodiments described above comprising a compound of Formula (II), or a pharmaceutically acceptable salt thereof, wherein $R^5$ may be other than H, there is a further embodiment wherein all other variables are as described for the embodiment and $R^5$ is selected from the group of:

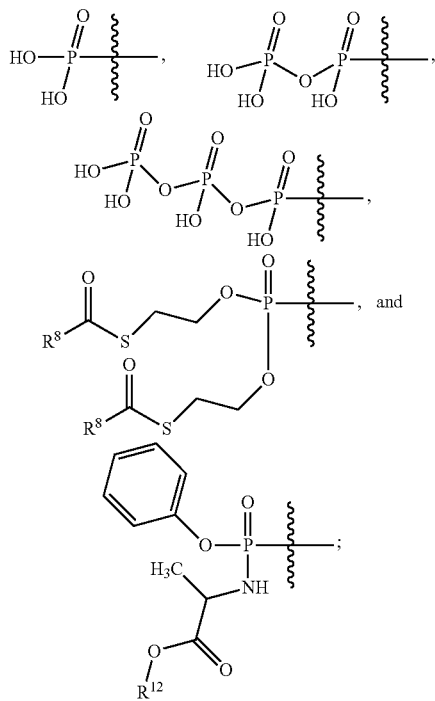

wherein:
$R^8$ is selected from $C_1$-$C_8$ alkyl, —O—$C_1$-$C_8$ alkyl, benzyl, and —$CH_2$—$C_3$-$C_6$ cycloalkyl; and
$R^{12}$ is selected from $C_1$-$C_8$ alkyl, benzyl, $C_3$-$C_6$ cycloalkyl, and —$CH_2$—$C_3$-$C_6$ cycloalkyl.

Within each of the embodiments described immediately above there is a further embodiment comprising a compound of Formula (II), or a pharmaceutically acceptable salt thereof, wherein all other variables are as described immediately above, except that $R^8$ and $R^9$ are each selected from $C_1$-$C_8$ alkyl. Within each of the embodiments described in the last sentence there is a further embodiment comprising a compound of Formula (II), or a pharmaceutically acceptable salt thereof, wherein all other variables are as described immediately above, except that $R^8$ and $R^9$ are each selected from $C_1$-$C_6$ alkyl. Within each of the embodiments described in the last sentence there is a further embodiment comprising a compound of Formula (II), or a pharmaceutically acceptable salt thereof, wherein all other variables are as described immediately above, except that $R^8$ and $R^9$ are each selected from $C_1$-$C_6$ alkyl. Within each of the embodiments described in the last sentence there is a further embodiment comprising a compound of Formula (II), or a pharmaceutically acceptable salt thereof, wherein all other variables are as described immediately above, except that $R^8$ and $R^9$ are each selected from $C_1$-$C_4$ alkyl.

Within each of the embodiments described herein comprising a compound of Formula (I) or of Formula (II) there is a further embodiment wherein all variables are as defined for the particular embodiment and further comprising the proviso that when $R^3$ is F, $R^4$ is not methyl.

DEFINITIONS

The terms halo and halogen refer to halogen atoms selected from F, Cl, Br, and I.

"Azido" refers to an azide group, i.e. the group —$N_3$. The term "n" as used herein refers to an integer, such as an integer selected from 1, 2, 3, 4, 5, 6, 7, 8, 9, 10, 11, 12, 13, 14, 15, 16, 17, 18, 19, and 20, i.e. 2 to 20 or 2-20. In some instances, "n" refers to groups of integers such as 1 to 3, 1 to 4, 1 to 6, 1 to 8, 2 to 4, 2 to 6, 2 to 8, etc.

The term "haloalkyl" as used herein refers to an alkyl as defined herein, wherein one or more hydrogen atoms are each replaced by a halo substituent. For example, a ($C_1$-$C_6$)haloalkyl is a ($C_1$-$C_6$)alkyl wherein one or more of the hydrogen atoms have been replaced by a halo substituent. Such a range includes one halo substituent on the alkyl group t to complete halogenation of the alkyl group.

The term "($C_{1-n}$)haloalkyl" as used herein, wherein n is an integer, either alone or in combination with another radical, is intended to mean an alkyl radical having 1 to n carbon atoms as defined above wherein one or more hydrogen atoms are each replaced by a halo substituent. Examples of ($C_{1-n}$)haloalkyl, wherein n is 2 include, but are not limited to, chloromethyl, chloroethyl, dichloroethyl, bromomethyl, bromoethyl, dibromoethyl, fluoromethyl, difluoromethyl, trifluoromethyl, fluoroethyl and difluoroethyl.

The term "($C_{1-n}$)alkyl" as used herein, wherein n is an integer, either alone or in combination with another radical, is intended to mean acyclic, straight or branched chain alkyl radicals containing from 1 to n carbon atoms. "($C_{1-4}$)alkyl" includes, but is not limited to, methyl, ethyl, propyl (n-propyl), butyl (n-butyl), 1-methylethyl (iso-propyl), 1-methylpropyl (sec-butyl), 2-methylpropyl (iso-butyl), and 1,1-dimethylethyl (tert-butyl or t-butyl). The abbreviation Me denotes a methyl group; Et denotes an ethyl group, Pr denotes a propyl group, iPr denotes a 1-methylethyl group, Bu denotes a butyl group and tBu denotes a 1,1-dimethylethyl group.

The term "alkyl" refers to a hydrocarbon containing normal, secondary, or tertiary atoms. For example, an alkyl group can have 1 to 4 carbon atoms (i.e., ($C_1$-$C_4$)alkyl), 1 to 3 carbon atoms (i.e., ($C_1$-$C_3$)alkyl), or 1 or 2 carbon atoms (i.e., ($C_1$-$C_2$)alkyl). Examples of suitable alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), and 2-methyl-2-propyl (t-Bu, t-butyl, —$C(CH_3)_3$). "Alkyl" also refers to a saturated, branched or straight chain hydrocarbon radical having two monovalent radical centers derived by the removal of two hydrogen atoms from the same or two different carbon atoms of a parent alkane. Typical alkyl radicals include, but are not limited to, methylene (—$CH_2$—), 1,1-ethyl (—$CH(CH_3)$—), 1,2-ethyl (—$CH_2CH_2$—), 1,1-propyl (—$CH(CH_2CH_3)$—), 1,2-propyl (—$CH_2CH(CH_3)$—), 1,3-propyl (—$CH_2CH_2CH_2$—), 1,4-butyl (—$CH_2CH_2CH_2CH_2$—), and the like.

"Alkenyl" is a straight or branched hydrocarbon containing normal, secondary or tertiary carbon atoms with at least one site of unsaturation, i.e. a carbon-carbon, sp$^2$ double bond. As examples, an alkenyl group can have 2 to 4 carbon atoms (i.e., $C_2$-$C_4$ alkenyl), or 2 to 3 carbon atoms (i.e., $C_2$-$C_3$ alkenyl). Examples of suitable alkenyl groups include, but are not limited to, ethylene or vinyl (—CH=CH$_2$) and allyl (—CH$_2$CH=CH$_2$).

The term "($C_{2-n}$)alkenyl", as used herein, wherein n is an integer, either alone or in combination with another radical, is intended to mean an unsaturated, acyclic straight or branched chain radical containing two to n carbon atoms, at least two of which are bonded to each other by a double bond. Examples of such radicals include, but are not limited to, ethenyl (vinyl), 1-propenyl, 2-propenyl, and 1-butenyl. Unless specified otherwise, the term "($C_{2-n}$)alkenyl" is understood to encompass individual stereoisomers where possible, including but not limited to (E) and (Z) isomers, and mixtures thereof. When a ($C_{2-n}$)alkenyl group is substituted, it is understood to be substituted on any carbon atom thereof which would otherwise bear a hydrogen atom, unless specified otherwise, such that the substitution would give rise to a chemically stable compound, such as are recognized by those skilled in the art.

"Alkynyl" is a straight or branched hydrocarbon containing normal, secondary or tertiary carbon atoms with at least one site of unsaturation, i.e. a carbon-carbon, sp triple bond. For example, an alkynyl group can have 2 to 4 carbon atoms (i.e., $C_2$-$C_4$ alkynyl) or 2 to 3 carbon atoms (i.e., $C_2$-$C_3$ alkyne,). Examples of suitable alkynyl groups include, but are not limited to, acetylenic (—C≡CH), propargyl (—CH$_2$C≡CH), and the like.

The term "($C_{2-n}$)alkynyl", as used herein, wherein n is an integer, either alone or in combination with another radical, is intended to mean an unsaturated, acyclic straight or branched chain radical containing two to n carbon atoms, at least two of which are bonded to each other by a triple bond. Examples of such radicals in which n is 4 include, but are not limited to, ethynyl, 1-propynyl, 2-propynyl, and 1-butynyl. When a ($C_{2-n}$)alkynyl group is substituted, it is understood to be substituted on any carbon atom thereof which would otherwise bear a hydrogen atom, unless specified otherwise, such that the substitution would give rise to a chemically stable compound, such as are recognized by those skilled in the art.

The term cycloalkyl refers to a cyclic aliphatic group. The cycloalkyl groups herein may be referenced by the number of carbon atoms in their ring, such as "$C_3$-$C_4$ cycloalkyl" referring to a cycloalkyl ring with 3 or 4 carbon ring atoms or "$C_3$-$C_6$ cycloalkyl" indicating a cycloalkyl ring with 3, 4, 5, or 6 carbon ring atoms, i.e. a cyclopropyl, cyclobutyl, cyclopentyl, or cyclohexyl ring.

The term "carbocycle" or "carbocyclyl" refers to a saturated (i.e., cycloalkyl) or partially unsaturated (e.g., cycloalkenyl, cycloalkadienyl, etc.) ring having the number of carbon atoms specified, such as 3 to 4 carbon atoms or 3 to 6 carbon atoms as a monocyclic ring system. In one embodiment the carbocycle is a monocycle comprising 3-6 ring carbons (i.e. ($C_3$-$C_6$)carbocycle). Non-limiting examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, and cyclohexa-1,3-dienyl rings.

Each carbocyclyl group may be substituted by 0, 1, 2, or 3 substituents independently selected from halogen, —OH, —CN, —NO$_2$, —NH$_2$, —NH($C_1$-$C_6$ alkyl), —N($C_1$-$C_6$ alkyl)$_2$, $C_1$-$C_6$ alkyl, $C_1$-$C_6$ alkoxy, and —CF$_3$.

Pharmaceutical Formulations

Also provided herein is a pharmaceutical formulation comprising a pharmaceutically effective amount of a compound of Formula (I) or a pharmaceutically acceptable salt, solvate, and/or ester thereof, and a pharmaceutically acceptable carrier or excipient. Also provided are separate pharmaceutical formulations, each comprising a pharmaceutically effective amount of a compound of Formula (II) or one of the specific compounds of the examples herein, or a pharmaceutically acceptable salt, solvate, and/or ester thereof, and a pharmaceutically acceptable carrier or excipient.

The compounds herein are formulated with conventional carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. All formulations will optionally contain excipients such as those set forth in the "Handbook of Pharmaceutical Excipients" (1986). Excipients include ascorbic acid and other antioxidants, chelating agents such as EDTA, carbohydrates such as dextran, hydroxyalkylcellulose, hydroxyalkylmethylcellulose, stearic acid and the like. The pH of the formulations ranges from about 3 to about 11, but is ordinarily about 7 to 10.

While it is possible for the active ingredients to be administered alone it may be preferable to present them as pharmaceutical formulations. The formulations, both for veterinary and for human use, comprise at least one active ingredient, as above defined, together with one or more acceptable carriers and optionally other therapeutic ingredients, particularly those additional therapeutic ingredients as discussed herein. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in Remington's Pharmaceutical Sciences (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

For infections of the eye or other external tissues e.g. mouth and skin, the formulations are preferably applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc.), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogs.

The oily phase of the emulsions may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation include Tween® 60, Span® 80, cetostearyl alcohol, benzyl alcohol, myristyl alcohol, glyceryl mono-stearate and sodium lauryl sulfate.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils are used.

Pharmaceutical formulations herein comprise a combination together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, solutions, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions contain the active materials in admixture with excipients suitable for the manufacture of aqueous suspensions. Such excipients include a suspending agent, such as sodium carboxymethylcellulose, methylcellulose, hydroxypropyl methylcelluose, sodium alginate, polyvinylpyrrolidone, gum tragacanth and gum acacia, and dispersing or wetting agents such as a naturally-occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally-occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents.

Syrups and elixirs may be formulated with sweetening agents, such as glycerol, sorbitol or sucrose. Such formulations may also contain a demulcent, a preservative, a flavoring or a coloring agent.

The pharmaceutical compositions may be in the form of a sterile injectable or intravenous preparations, such as a sterile injectable aqueous or oleaginous suspension. This suspension may be formulated according to the known art using those suitable dispersing or wetting agents and suspending agents which have been mentioned above. The sterile injectable or intravenous preparation may also be a sterile injectable solution or suspension in a non-toxic parenterally acceptable diluent or solvent, such as a solution in 1,3-butanedial or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 µg of the active ingredient per milliliter of solution in order that infusion of a suitable volume at a rate of about 30 mL/hr can occur.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10%, and particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns, such as 0.5, 1, 30, 35 etc., which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of Pneumovirinae infections as described below.

Another embodiments provides a novel, efficacious, safe, nonirritating and physiologically compatible inhalable composition comprising a compound of Formula (I) or Formula (II), or a pharmaceutically acceptable salt thereof, suitable for treating Pneumovirinae infections and potentially associated bronchiolitis. Preferred pharmaceutically acceptable salts are inorganic acid salts including hydrochloride, hydrobromide, sulfate or phosphate salts as they may cause less pulmonary irritation. Preferably, the inhalable formulation is delivered to the endobronchial space in an aerosol comprising particles with a mass median aerodynamic diameter (MMAD) between about 1 and about 5 µm. Preferably, the compound of Formula (I) or Formula (II) is formulated for aerosol delivery using a nebulizer, pressurized metered dose inhaler (pMDI), or dry powder inhaler (DPI).

Non-limiting examples of nebulizers include atomizing, jet, ultrasonic, pressurized, vibrating porous plate, or equivalent nebulizers including those nebulizers utilizing adaptive aerosol delivery technology (Denyer, *J. Aerosol medicine Pulmonary Drug Delivery* 2010, 23 Supp 1, S1-S10). A jet nebulizer utilizes air pressure to break a liquid solution into aerosol droplets. An ultrasonic nebulizer works by a piezoelectric crystal that shears a liquid into small aerosol droplets. A pressurized nebulization system forces solution under pressure through small pores to generate aerosol droplets. A vibrating porous plate device utilizes rapid vibration to shear a stream of liquid into appropriate droplet sizes.

In a preferred embodiment, the formulation for nebulization is delivered to the endobronchial space in an aerosol comprising particles with a MMAD predominantly between about 1 µm and about 5 µm using a nebulizer able to aerosolize the formulation of the compound of Formula (I) or Formula (II) into particles of the required MMAD. To be optimally therapeutically effective and to avoid upper respiratory and systemic side effects, the majority of aerosolized particles should not have a MMAD greater than about 5 µm. If an aerosol contains a large number of particles with a MMAD larger than 5 µm, the particles are deposited in the upper airways decreasing the amount of drug delivered to the site of inflammation and bronchoconstriction in the lower respiratory tract. If the MMAD of the aerosol is smaller than about 1 µm, then the particles have a tendency to remain suspended in the inhaled air and are subsequently exhaled during expiration.

When formulated and delivered according to the method herein, the aerosol formulation for nebulization delivers a therapeutically efficacious dose of the compound of Formula (I) or Formula (II) to the site of Pneumovirinae infection sufficient to treat the Pneumovirinae infection. The amount of drug administered must be adjusted to reflect the efficiency of the delivery of a therapeutically efficacious dose of the compound of Formula (I) or Formula (II). In a preferred embodiment, a combination of the aqueous aerosol formulation with the atomizing, jet, pressurized, vibrating porous plate, or ultrasonic nebulizer permits, depending on the nebulizer, about, at least, 20, to about 90%, typically about 70% delivery of the administered dose of the compound of Formula (I) or Formula (II) into the airways. In a preferred embodiment, at least about 30 to about 50% of the active compound is delivered. More preferably, about 70 to about 90% of the active compound is delivered.

In another embodiment, a compound of Formula (I) or Formula (II) or a pharmaceutically acceptable salt thereof, is delivered as a dry inhalable powder. The compounds are administered endobronchially as a dry powder formulation to efficacious deliver fine particles of compound into the endobronchial space using dry powder or metered dose inhalers. For delivery by DPI, the compound of Formula (I) or Formula (II) is processed into particles with, predominantly, MMAD between about 1 µm and about 5 µm by milling spray drying, critical fluid processing, or precipitation from solution.

Media milling, jet milling and spray-drying devices and procedures capable of producing the particle sizes with a MMAD between about 1 μm and about 5 μm are well known in the art. In one embodiment, excipients are added to the compound of Formula (I) or Formula (II) before processing into particles of the required sizes. In another embodiment, excipients are blended with the particles of the required size to aid in dispersion of the drug particles, for example by using lactose as an excipient.

Particle size determinations are made using devices well known in the art. For example a multi-stage Anderson cascade impactor or other suitable method such as those specifically cited within the US Pharmacopoeia Chapter 601 as characterizing devices for aerosols within metered-dose and dry powder inhalers.

In another preferred embodiment, a compound of Formula (I) or Formula (II) is delivered as a dry powder using a device such as a dry powder inhaler or other dry powder dispersion devices. Non-limiting examples of dry powder inhalers and devices include those disclosed in U.S. Pat. Nos. 5,458,135; 5,740,794; 5,775,320; 5,785,049; 3,906,950; 4,013,075; 4,069,819; 4,995,385; 5,522,385; 4,668,218; 4,667,668; 4,805,811 and 5,388,572. There are two major designs of dry powder inhalers. One design is a metering device in which a reservoir for the drug is place within the device and the patient adds a dose of the drug into the inhalation chamber. The second design is a factory-metered device in which each individual dose has been manufactured in a separate container. Both systems depend on the formulation of the drug into small particles of MMAD from 1 μm and about 5 μm and often involve co-formulation with larger excipient particles such as, but not limited to, lactose. Drug powder is placed in the inhalation chamber (either by device metering or by breakage of a factory-metered dosage) and the inspiratory flow of the patient accelerates the powder out of the device and into the oral cavity. Non-laminar flow characteristics of the powder path cause the excipient-drug aggregates to decompose, and the mass of the large excipient particles causes their impaction at the back of the throat, while the smaller drug particles are deposited deep in the lungs. In preferred embodiments, a compound of Formula (I) or Formula (II), or a pharmaceutically acceptable salt thereof, is delivered as a dry powder using either type of dry powder inhaler as described herein, wherein the MMAD of the dry powder, exclusive of any excipients, is predominantly in the range of 1 μm to about 5 μm.

In another embodiment, a compound of Formula (I) or Formula (II) is delivered as a dry powder using a metered dose inhaler. Non-limiting examples of metered dose inhalers and devices include those disclosed in U.S. Pat. Nos. 5,261,538; 5,544,647; 5,622,163; 4,955,371; 3,565,070; 3,361,306 and 6,116,234. In preferred embodiments, a compound of Formula (I) or Formula (II), or a pharmaceutically acceptable salt thereof, is delivered as a dry powder using a metered dose inhaler wherein the MMAD of the dry powder, exclusive of any excipients, is predominantly in the range of about 1-5 μm.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients particularly mentioned above the formulations may include other agents conventional in the art having regard to the type of formulation in question, for example those suitable for oral administration may include flavoring agents.

Further provided are veterinary compositions comprising at least one active ingredient as above defined together with a veterinary carrier therefor.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compounds herein are used to provide controlled release pharmaceutical formulations containing as active ingredient one or more of the compounds ("controlled release formulations") in which the release of the active ingredient are controlled and regulated to allow less frequency dosing or to improve the pharmacokinetic or toxicity profile of a given active ingredient.

Effective dose of active ingredient depends at least on the nature of the condition being treated, toxicity, whether the compound is being used prophylactically (lower doses) or against an active viral infection, the method of delivery, and the pharmaceutical formulation, and will be determined by the clinician using conventional dose escalation studies. It can be expected to be from about 0.0001 to about 100 mg/kg body weight per day; typically, from about 0.01 to about 10 mg/kg body weight per day; more typically, from about 0.01 to about 5 mg/kg body weight per day; most typically, from about 0.05 to about 0.5 mg/kg body weight per day. For example, the daily candidate dose for an adult human of approximately 70 kg body weight will range from 1 mg to 1000 mg, preferably between 5 mg and 500 mg, and may take the form of single or multiple doses.

Routes of Administration

One or more of the compounds (herein referred to as the active ingredients) are administered by any route appropriate to the condition to be treated. Suitable routes include oral, rectal, nasal, pulmonary, topical (including buccal and sublingual), vaginal and parenteral (including subcutaneous, intramuscular, intravenous, intradermal, intrathecal and epidural), and the like. It will be appreciated that the preferred route may vary with for example the condition of the recipient. An advantage of the compounds herein is that they are orally bioavailable and can be dosed orally.

Combination Therapy

Compositions are also used in combination with other active ingredients. For the treatment of Pneumovirinae virus infections, preferably, the other active therapeutic agent is active against Pneumovirinae virus infections, particularly respiratory syncytial virus infections. Non-limiting examples of these other active therapeutic agents are ribavirin, palivizumab, motavizumab, RSV-IGIV (RespiGam®), MEDI-557, A-60444 (also known as RSV604), MDT-637, BMS-433771, ALN-RSVO, ALX-0171 and mixtures thereof.

Many of the infections of the Pneumovirinae viruses are respiratory infections. Therefore, additional active therapeutics used to treat respiratory symptoms and sequelae of infection may be used in combination with the compounds of Formula (I) or Formula (II). The additional agents are preferably administered orally or by direct inhalation. For example, other preferred additional therapeutic agents in combination with the compounds of Formula (I) or Formula (II) for the treatment of viral respiratory infections include, but are not limited to, bronchodilators and corticosteroids.

Glucocorticoids, which were first introduced as an asthma therapy in 1950 (Carryer, Journal of Allergy, 21, 282-287, 1950), remain the most potent and consistently effective therapy for this disease, although their mechanism of action is not yet fully understood (Morris, J. Allergy Clin. Immunol., 75 (1 Pt) 1-13, 1985). Unfortunately, oral glucocorticoid therapies are associated with profound undesirable side effects such as truncal obesity, hypertension, glaucoma, glucose intolerance, acceleration of cataract formation, bone mineral loss, and psychological effects, all of which limit their use as long-term therapeutic agents (Goodman and Gilman, 10th edition, 2001). A solution to systemic side effects is to deliver steroid drugs directly to the site of inflammation. Inhaled corticosteroids (ICS) have been developed to mitigate the severe adverse effects of oral steroids. Non-limiting examples of corticosteroids that may be used in combinations with the compounds of Formula (I) or Formula (II) are dexamethasone, dexamethasone sodium phosphate, fluorometholone, fluorometholone acetate, loteprednol, loteprednol etabonate, hydrocortisone, prednisolone, fludrocortisones, triamcinolone, triamcinolone acetonide, betamethasone, beclomethasone diproprionate, methylprednisolone, fluocinolone, fluocinolone acetonide, flunisolide, fluocortin-21-butylate, flumethasone, flumethasone pivalate, budesonide, halobetasol propionate, mometasone furoate, fluticasone propionate, ciclesonide; or a pharmaceutically acceptable salts thereof.

Other anti-inflammatory agents working through anti-inflammatory cascade mechanisms are also useful as additional therapeutic agents in combination with the compounds of Formula (I) or Formula (II) for the treatment of viral respiratory infections. Applying "anti-inflammatory signal transduction modulators" (referred to in this text as AISTM), like phosphodiesterase inhibitors (e.g. PDE-4, PDE-5, or PDE-7 specific), transcription factor inhibitors (e.g. blocking NFκB through IKK inhibition), or kinase inhibitors (e.g. blocking P38 MAP, JNK, PI3K, EGFR or Syk) is a logical approach to switching off inflammation as these small molecules target a limited number of common intracellular pathways—those signal transduction pathways that are critical points for the anti-inflammatory therapeutic intervention (see review by P. J. Barnes, 2006). These non-limiting additional therapeutic agents include: 5-(2,4-Difluoro-phenoxy)-1-isobutyl-1H-indazole-6-carboxylic acid (2-dimethylamino-ethyl)-amide (P38 Map kinase inhibitor ARRY-797); 3-Cyclopropylmethoxy-N-(3,5-dichloro-pyridin-4-yl)-4-difluorormethoxy-benzamide (PDE-4 inhibitor Roflumilast); 4-[2-(3-cyclopentyloxy-4-methoxyphenyl)-2-phenyl-ethyl]-pyridine (PDE-4 inhibitor CDP-840); N-(3,5-dichloro-4-pyridinyl)-4-(difluoromethoxy)-8-[(methylsulfonyl)amino]-1-dibenzofurancarboxamide (PDE-4 inhibitor Oglemilast); N-(3,5-Dichloro-pyridin-4-yl)-2-[1-(4-fluorobenzyl)-5-hydroxy-1H-indol-3-yl]-2-oxo-acetamide (PDE-4 inhibitor AWD 12-281); 8-Methoxy-2-trifluoromethyl-quinoline-5-carboxylic acid (3,5-dichloro-1-oxy-pyridin-4-yl)-amide (PDE-4 inhibitor Sch 351591); 4-[5-(4-Fluorophenyl)-2-(4-methanesulfinyl-phenyl)-1H-imidazol-4-yl]-pyridine (P38 inhibitor SB-203850); 4-[4-(4-Fluoro-phenyl)-1-(3-phenyl-propyl)-5-pyridin-4-yl-1H-imidazol-2-yl]-but-3-yn-1-ol (P38 inhibitor RWJ-67657); 4-Cyano-4-(3-cyclopentyloxy-4-methoxy-phenyl)-cyclohexanecarboxylic acid 2-diethylamino-ethyl ester (2-diethyl-ethyl ester prodrug of Cilomilast, PDE-4 inhibitor); (3-Chloro-4-fluorophenyl)-[7-methoxy-6-(3-morpholin-4-yl-propoxy)-quinazolin-4-yl]-amine (Gefitinib, EGFR inhibitor); and 4-(4-Methyl-piperazin-1-ylmethyl)-N-[4-methyl-3-(4-pyridin-3-yl-pyrimidin-2-ylamino)-phenyl]-benzamide (Imatinib, EGFR inhibitor).

Combinations comprising inhaled β2-adrenoreceptor agonist bronchodilators such as formoterol, albuterol or salmeterol with the compounds of Formula (I) or Formula (II) are also suitable, but non-limiting, combinations useful for the treatment of respiratory viral infections.

Combinations of inhaled β2-adrenoreceptor agonist bronchodilators such as formoterol or salmeterol with ICS's are also used to treat both the bronchoconstriction and the inflammation (Symbicort® and Advair®, respectively). The combinations comprising these ICS and β2-adrenoreceptor agonist combinations along with the compounds of Formula (I) or Formula (II) are also suitable, but non-limiting, combinations useful for the treatment of respiratory viral infections.

For the treatment or prophylaxis of pulmonary bronchoconstriction, anticholinergics are of potential use and, therefore, useful as an additional therapeutic agents in combination with the compounds of Formula (I) or Formula (II) for the treatment of viral respiratory infections. These anticholinergics include, but are not limited to, antagonists of the muscarinic receptor (particularly of the M3 subtype) which have shown therapeutic efficacy in man for the control of cholinergic tone in COPD (Witek, 1999); 1-{4-Hydroxy-1-[3,3,3-tris-(4-fluoro-phenyl)-propionyl]-pyrrolidine-2-carbonyl}-pyrrolidine-2-carboxylic acid (1-methyl-piperidin-4-ylmethyl)-amide; 3-[3-(2-Diethylamino-acetoxy)-2-phenyl-propionyloxy]-8-isopropyl-8-methyl-8-azonia-bicyclo[3.2.1]octane (Ipratropium-N,N-diethylglycinate); 1-Cyclohexyl-3,4-dihydro-1H-isoquinoline-2-carboxylic acid 1-aza-bicyclo[2.2.2]oct-3-yl ester (Solifenacin); 2-Hydroxymethyl-4-methanesulfinyl-2-phenyl-butyric acid 1-aza-bicyclo[2.2.2]oct-3-yl ester (Revatropate); 2-{1-[2-(2,3-Dihydro-benzofuran-5-yl)-ethyl]-pyrrolidin-3-yl}-2,2-diphenyl-acetamide (Darifenacin); 4-Azepan-1-yl-2,2-diphenyl-butyramide (Buzepide); 7-[3-(2-Diethylamino-acetoxy)-2-phenyl-propionyloxy]-9-ethyl-9-methyl-3-oxa-9-azonia-tricyclo[3.3.1.02,4]nonane (Oxitropium-N,N-diethylglycinate); 7-[2-(2-Diethylamino-acetoxy)-2,2-di-thiophen-2-yl-acetoxy]-9,9-dimethyl-3-oxa-9-azonia-tricyclo[3.3.1.02,4]nonane (Tiotropium-N,N-diethylglycinate); Dimethylamino-acetic acid 2-(3-diisopropylamino-1-phenyl-propyl)-4-methyl-phenyl ester (Tolterodine-N,N-dimethylglycinate); 3-[4,4-Bis-(4-fluoro-phenyl)-2-oxo-imidazolidin-1-yl]-1-methyl-1-(2-oxo-2-pyridin-2-yl-ethyl)-pyrrolidinium; 1-[1-(3-Fluoro-benzyl)-piperidin-4-yl]-4,4-bis-(4-fluoro-phenyl)-imidazolidin-2-one; 1-Cyclooctyl-3-(3-methoxy-1-aza-bicyclo[2.2.2]oct-3-yl)-1-phenyl-prop-2-yn-1-ol; 3-[2-(2-Diethylamino-acetoxy)-2,2-di-thiophen-2-yl-acetoxy]-1-(3-phenoxy-propyl)-1-azonia-bicyclo[2.2.2]octane (Aclidinium-N,N-diethylglycinate); or (2-Diethylamino-acetoxy)-di-thiophen-2-yl-acetic acid 1-methyl-1-(2-phenoxy-ethyl)-piperidin-4-yl ester.

The compounds of Formula (I) or Formula (II) may also be combined with mucolytic agents to treat both the infection and symptoms of respiratory infections. A non-limiting example of a mucolytic agent is ambroxol. Similarly, the compounds of Formula (I) or Formula (II) may be combined with expectorants to treat both the infection and symptoms of respiratory infections. A non-limiting example of an expectorant is guaifenesin.

Nebulized hypertonic saline is used to improve immediate and long-term clearance of small airways in patients with lung diseases (Kuzik, *J. Pediatrics* 2007, 266). The compounds of Formula (I) or Formula (II) may also be combined with nebulized hypertonic saline particularly when the Pneumovirinae virus infection is complicated with bronchiolitis. The combination of the compounds of Formula (I) or Formula (II) with hypertonic saline may also comprise any of the additional agents discussed above. In one embodiment, nebulized about 3% hypertonic saline is used.

It is also possible to combine any compound with one or more additional active therapeutic agents in a unitary dosage form for simultaneous or sequential administration to a patient. The combination therapy may be administered as a simultaneous or sequential regimen. When administered sequentially, the combination may be administered in two or more administrations.

Co-administration of a compound herein with one or more other active therapeutic agents generally refers to simultaneous or sequential administration of a compound and one or more other active therapeutic agents, such that therapeutically effective amounts of the compound and one or more other active therapeutic agents are both present in the body of the patient.

Co-administration includes administration of unit dosages of the compounds before or after administration of unit dosages of one or more other active therapeutic agents, for example, administration of the compounds within seconds, minutes, or hours of the administration of one or more other active therapeutic agents. For example, a unit dose of a compound can be administered first, followed within seconds or minutes by administration of a unit dose of one or more other active therapeutic agents. Alternatively, a unit dose of one or more other therapeutic agents can be administered first, followed by administration of a unit dose of a compound within seconds or minutes. In some cases, it may be desirable to administer a unit dose of a compound first, followed, after a period of hours (e.g., 1-12 hours), by administration of a unit dose of one or more other active therapeutic agents. In other cases, it may be desirable to administer a unit dose of one or more other active therapeutic agents first, followed, after a period of hours (e.g., 1-12 hours), by administration of a unit dose of a compound herein.

The combination therapy may provide "synergy" and "synergistic", i.e. the effect achieved when the active ingredients used together is greater than the sum of the effects that results from using the compounds separately. A synergistic effect may be attained when the active ingredients are: (1) co-formulated and administered or delivered simultaneously in a combined formulation; (2) delivered by alternation or in parallel as separate formulations; or (3) by some other regimen. When delivered in alternation therapy, a synergistic effect may be attained when the compounds are administered or delivered sequentially, e.g. in separate tablets, pills or capsules, or by different injections in separate syringes. In general, during alternation therapy, an effective dosage of each active ingredient is administered sequentially, i.e. serially, whereas in combination therapy, effective dosages of two or more active ingredients are administered together. A synergistic anti-viral effect denotes an antiviral effect which is greater than the predicted purely additive effects of the individual compounds of the combination.

In still yet another embodiment, the present application provides a method of treating Pneumovirinae virus infection in a human, the method comprising administering to the human a therapeutically effective amount of a compound of Formula (I), or a pharmaceutically acceptable salt, solvate, and/or ester thereof. Also provided are separate methods of treating Pneumovirinae virus infection in a human, each comprising administering to the human a therapeutically effective a pharmaceutically effective amount of a compound of Formula (II) or one of the specific compounds of the examples herein, or a pharmaceutically acceptable salt, solvate, and/or ester thereof, and a pharmaceutically acceptable carrier or excipient.

In another embodiment, provided is a method of treating a Pneumovirinae infection in a human by administering to the human a therapeutically effective amount of a racemate, enantiomer, diastereomer, tautomer, polymorph, pseudopolymorph, amorphous form, hydrate or solvate of a compound of a compound of Formula (I), or a pharmaceutically acceptable salt or ester thereof.

Further provided are separate methods of treating a Pneumovirinae infection in a human in need thereof, each method comprising administering to the human a therapeutically effective amount of a racemate, enantiomer, diastereomer, tautomer, polymorph, pseudopolymorph, amorphous form, hydrate or solvate of a compound of Formula (II) or one of the specific compounds of the examples herein, or a pharmaceutically acceptable salt, solvate, and/or ester thereof.

In still yet another embodiment, the present application provides for a method of treating human respiratory syncytial virus infection in a human, the method comprising administering to the human a therapeutically effective amount of a compound of Formula (I), or a pharmaceutically acceptable salt, solvate, and/or ester thereof.

In still yet another embodiment, the present application provides for a method of treating human respiratory syncytial virus infection in a human, the method comprising administering to the human a therapeutically effective amount of a compound of Formula (I), or a pharmaceutically acceptable salt, solvate, and/or ester thereof, and at least one additional active therapeutic agent.

Further provided are separate methods of treating a human respiratory syncytial virus infection in a human in need thereof, each method comprising administering to the human a therapeutically effective amount of a compound of Formula (II) or one of the specific compounds of the examples herein, or a pharmaceutically acceptable salt, solvate, and/or ester thereof.

Also provided are separate methods of treating a human respiratory syncytial virus infection in a human in need thereof, each method comprising administering to the human a therapeutically effective amount of a compound of Formula (II) or one of the specific compounds of the examples herein, or a pharmaceutically acceptable salt, solvate, and/or ester thereof, and at least one additional active therapeutic agent.

Also provided are separate methods of treating a human respiratory syncytial virus infection in a human in need thereof, wherein the human is also experiencing bronchiolitis, each method comprising administering to the human a therapeutically effective amount of a compound of Formula (I), Formula (II), or one of the specific compounds of the examples herein, or a pharmaceutically acceptable salt, solvate, and/or ester thereof.

Also provided are separate methods of treating a human respiratory syncytial virus infection in a human in need thereof, wherein the human is also experiencing pneumonia, each method comprising administering to the human a therapeutically effective amount of a compound of Formula (I), Formula (II), or one of the specific compounds of the examples herein, or a pharmaceutically acceptable salt, solvate, and/or ester thereof.

Also provided are separate methods of improving respiratory symptoms in a human experiencing a human respiratory syncytial virus infection, each method comprising administering to the human a therapeutically effective amount of a compound of Formula (I), Formula (II), or one of the specific compounds of the examples herein, or a pharmaceutically acceptable salt, solvate, and/or ester thereof.

Respiratory symptoms in a human experiencing a respiratory syncytial virus infection may include congested or runny nose, coughing, wheezing, sneezing, rapid breathing or difficulty breathing, apnea, bronchiolitis, and pneumonia.

Also provided is an embodiment comprising the use of a compound of Formula (I), or a pharmaceutically acceptable salt, solvate, and/or ester thereof, for the manufacture of a medicament for the treatment of a Pneumovirinae virus infection or a respiratory syncytial virus infection.

Also provided is an embodiment comprising the use of a compound of Formula (H) or one of the specific compounds of the examples herein, or a pharmaceutically acceptable salt, solvate, and/or ester thereof, for the manufacture of a medicament for the treatment of a Pneumovirinae virus infection or a respiratory syncytial virus infection.

Also provided is a pharmaceutical formulation comprising a pharmaceutically effective amount of a compound of Formula (I), or a pharmaceutically acceptable salt, solvate, and/or ester thereof, and a pharmaceutically acceptable carrier or excipient. Further provided is a pharmaceutical formulation comprising a pharmaceutically effective amount of a compound of Formula (II) or one of the specific compounds of the examples herein, or a pharmaceutically acceptable salt, solvate, and/or ester thereof, and a pharmaceutically acceptable carrier or excipient.

Also provided is a pharmaceutical formulation comprising a pharmaceutically effective amount of a compound of Formula (I), or a pharmaceutically acceptable salt, solvate, and/or ester thereof, and a pharmaceutically acceptable carrier or excipient and a pharmaceutically effective amount of at least one additional active therapeutic agent. Further provided is a pharmaceutical formulation comprising a pharmaceutically effective amount of a compound of Formula (II) or one of the specific compounds of the examples herein, or a pharmaceutically acceptable salt, solvate, and/or ester thereof, and a pharmaceutically acceptable carrier or excipient and a pharmaceutically effective amount of at least one additional active therapeutic agent.

Also provided are separate embodiments comprising a compound of Formula (I), Formula (II), or one of the specific compounds of the examples herein, or a pharmaceutically acceptable salt, solvate, and/or ester thereof, for use in the treatment of a Pneumovirinae virus infection or a respiratory syncytial virus infection in a human.

Also provided are separate embodiments comprising a compound of Formula (I), Formula (II) or one of the specific compounds of the examples herein, or a pharmaceutically acceptable salt, solvate, and/or ester thereof, for use as a medicament.

Also provided are separate embodiments comprising a method for manufacturing a medicament intended for treatment of a Pneumovirinae virus infection or a respiratory syncytial virus infection in a human, characterized in that a compound of Formula (I), Formula (II), or one of the specific compounds of the examples herein, or a pharmaceutically acceptable salt, solvate, and/or ester thereof, is used.

Also provided is a compound of Formula (I), or a pharmaceutically acceptable salt, solvate, and/or ester thereof, for the treatment of a Pneumovirinae virus infection or a respiratory syncytial virus infection in a human.

Also provided are separate embodiments comprising that a compound of Formula (II) or one of the specific compounds of the examples herein, or a pharmaceutically acceptable salt, solvate, and/or ester thereof, for the treatment of a Pneumovirinae virus infection or a respiratory syncytial virus infection in a human.

Further provided is a compound as described in this specification. Also provided is a pharmaceutical composition as described in this specification. Also provided is a method of using a compound of Formula (I), as described in this specification. Further provided is a method of making a compound of Formula (I), as described in this specification.

Metabolites of the Compounds

Also falling within the scope herein are the in vivo metabolic products of the compounds described herein, to the extent such products are novel and unobvious over the prior art. Such products may result for example from the oxidation, reduction, hydrolysis, amidation, esterification and the like of the administered compound, primarily due to enzymatic processes. Accordingly, included are novel and unobvious compounds produced by a process comprising contacting a compound with a mammal for a period of time sufficient to yield a metabolic product thereof. Such products typically are identified by preparing a radiolabelled (e.g. $^{14}C$ or $^{3}H$) compound, administering it parenterally in a detectable dose (e.g. greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g. by MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of the compounds even if they possess no HSV antiviral activity of their own.

Recipes and methods for determining stability of compounds in surrogate gastrointestinal secretions are known. Compounds are defined herein as stable in the gastrointestinal tract where less than about 50 mole percent of the protected groups are deprotected in surrogate intestinal or gastric juice upon incubation for 1 hour at 37° C. Simply because the compounds are stable to the gastrointestinal tract does not mean that they cannot be hydrolyzed in vivo. The prodrugs typically will be stable in the digestive system but may be substantially hydrolyzed to the parental drug in the digestive lumen, liver, lung or other metabolic organ, or within cells in general. As used herein, a prodrug is understood to be a compound that is chemically designed to efficiently liberate the parent drug after overcoming biological barriers to oral delivery.

Abbreviations

Certain abbreviations and acronyms are used in describing the experimental details. Although most of these would be understood by one skilled in the art, Table 1 contains a list of many of these abbreviations and acronyms.

TABLE 1

List of abbreviations and acronyms.

| Abbreviation | Meaning |
|---|---|
| Ac | acetate |
| ACN | acetonitrile |
| AIBN | azobisisobutyronitrile |
| Bn | benzyl |
| Bu | butyl |
| Bz | benzoyl |
| BzCl | benzoyl chloride |
| CDI | 1,1'-carbonyldiimidazole |
| DAST | diethylaminosulfur trifluoride |
| DCE | 1,2-dichloroethane |
| DCM | dichloromethane |
| DMAP | 4-dimethylamiopyridine |
| DMDO | dimethyldioxirane |
| DMSO | dimethylsulfoxide |
| DMF | dimethylformamide |
| DMTrCl | 4,4'-dimethoxytritylchloride |
| DMTr | 4,4'-dimethoxytrityl |
| EDCl | N-(3-dimethylaminopropyl)-N'-ethylcarbodiimide hydrochloride |
| Et | ethyl |
| Imid | imidazole |
| KOtBu | potassium tert-butoxide |
| LC | liquid chromatography |
| MCPBA | meta-chloroperbenzoic acid |
| Me | methyl |
| m/z | mass to charge ratio |
| MS or ms | mass spectrum |
| NIS | N-iodosuccinimide |
| NMP | N-methyl-2-pyrrolidone |
| Ph | phenyl |
| Ph$_3$P | triphenylphosphine |
| PMB | para-methoxybenzyl |
| PMBCl | para-methoxybenzyl chloride |
| PhOC(S)Cl | phenylchlorothionoformate |
| (PhO)$_3$PMeI | methyltriphenoxyphosphonium iodide |
| Pyr | pyridine |
| RT | room temperature |
| TBAF | tetrabutylammonium fluoride |
| TBS | tert-butyldimethylsilyl |
| TBSCl | tert-Butyldimethylsilyl chloride |
| TMSN$_3$ | trimethylsilyl azide |
| TEA | triethylamine |
| TES | triethysilane |
| TFA | trifluoroacetic acid |
| THF | tetrahydrofuran |
| TMS | trimethylsilyl |
| TMSCl | trimethylsilyl chloride |
| Ts | 4-toluenesulfonyl |
| TsOH | tosylic acid |
| δ | parts per million referenced to residual non-deuterated solvent peak |

General Schemes

Scheme 1.

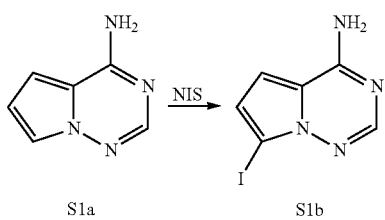

Scheme 1 shows a general synthesis of intermediates beginning with an iodination reaction (e.g. NIS) to generate nucleobase S1b.

Scheme 2.

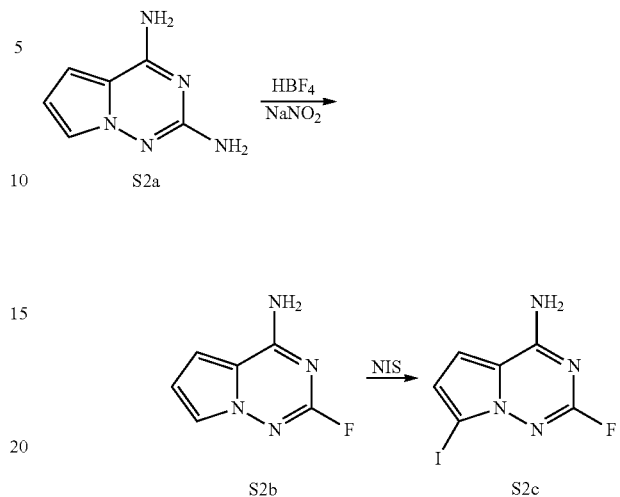

Scheme 2 shows a general synthesis of intermediates beginning with a fluorination reaction (e.g. HBF$_4$, NaNO$_2$) in a manner similar to that described in WO2012037038A1 to afford intermediate S2b. Intermediate S2b can then be iodinated (e.g. NIS) to generate nucleobase S2c.

Scheme 3.

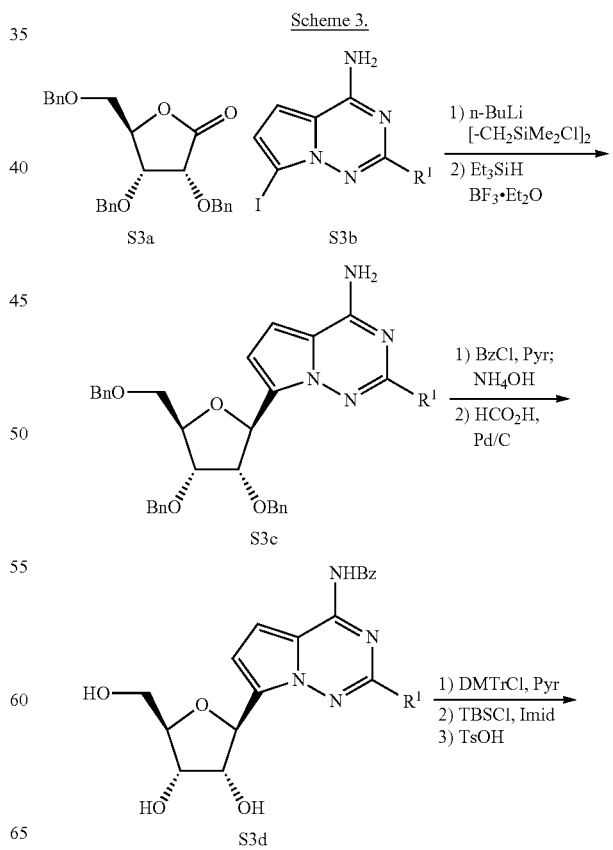

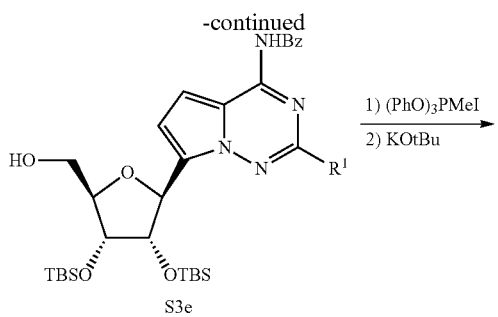

S3e

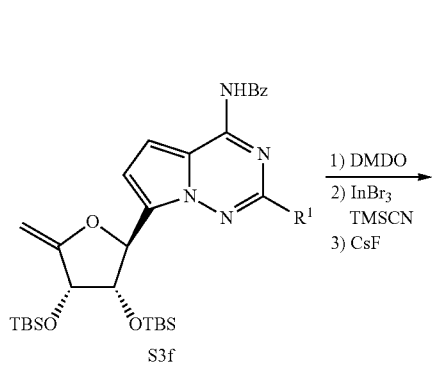

S3f

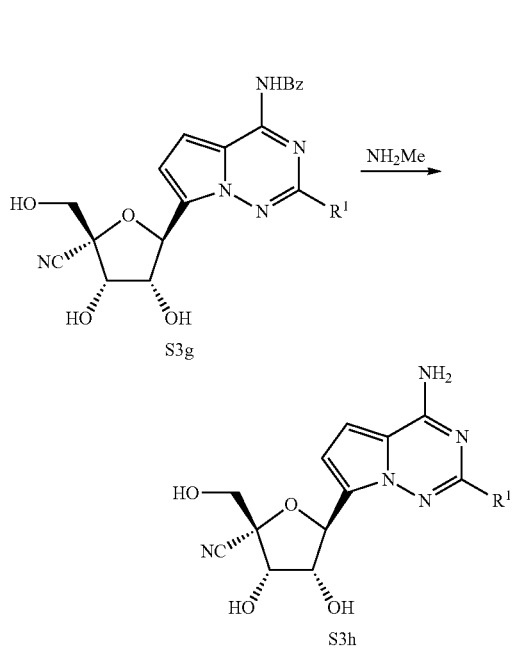

S3g

S3h tive removal of the 5' hydroxyl protecting group under acidic conditions (e.g. TsOH) furnishes intermediate S3e. The 5' hydroxyl group can then be converted to the corresponding iodide (e.g. (PhO)$_3$PMeI), which is then exposed to basic conditions (i.e. KOtBu) to effect an elimination reaction generating intermediate S3f. Oxidation of the olefin S3f (e.g. DMDO) followed by treatment with an appropriate nucleophile (e.g. TMSCN) under Lewis acidic conditions (e.g. InBr$_3$) and removal of the hydroxyl protecting groups (e.g. CsF) affords intermediate S3g. Removal of the nitrogen protecting group (e.g. NH$_2$Me) yields the final compounds of the type S3h.

Scheme 4.

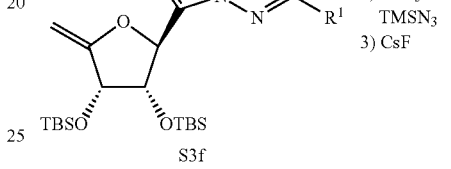

S3f

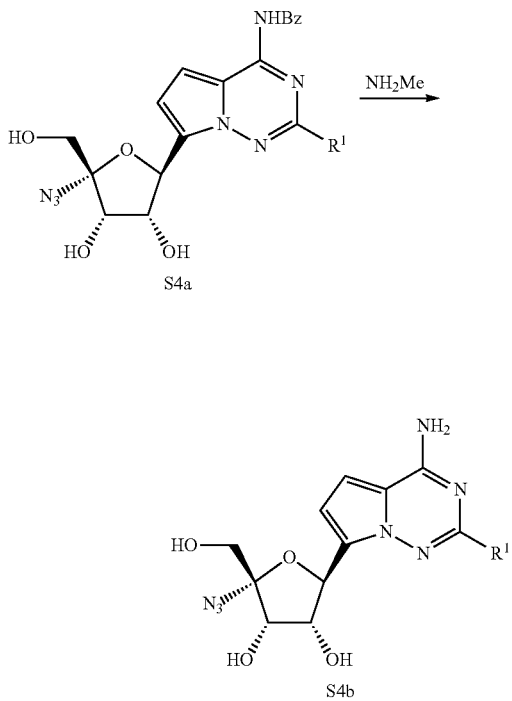

S4a

S4b

Scheme 3 shows a general synthesis of compounds beginning with a lithium-halogen exchange (e.g. n-BuLi, [—CH$_2$SiMe$_2$Cl]$_2$) reaction with an appropriate nucleobase Sib, followed by addition to the lactone S3a. Reduction of the pendant 1' hydroxyl group under Lewis acidic conditions (e.g. BF$_3$.Et$_2$O, Et$_3$SiH) generates intermediate S3c. Intermediate S3c can first be protected (e.g. BzCl, Pyr; NH$_4$OH) at the nitrogen functionality, and the benzyl groups can then be removed under reducing conditions (e.g. HCO$_2$H, Pd/C, BCl$_3$, BBr$_3$) to afford intermediate S3d. A sequence involving first selective 5' hydroxyl protection (e.g. DMTrCl), then 2' and 3' hydroxyl protection (e.g. TBSCl), followed by selec- Scheme 4 shows a general synthesis of compounds beginning with oxidation of the olefin S3f (e.g. DMDO) followed by treatment with an appropriate nucleophile (e.g. TMSN$_3$) under Lewis acidic conditions (e.g. InBr$_3$) in a manner similar to that described in *J. Med. Chem.* 2007, 50, 5463-5470. Removal of the hydroxyl protecting groups (e.g. CsF) then affords intermediate S4a. Removal of the nitrogen protecting group (e.g. NH$_2$Me) yields the final compounds of the type S4b.

Scheme 5.
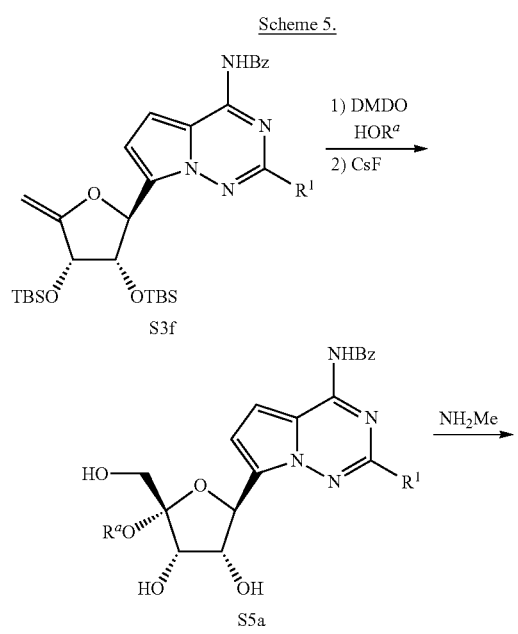
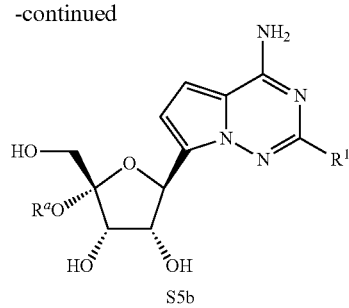
Scheme 5 shows a general synthesis of compounds beginning with oxidation of the olefin S3f (e.g. DMDO) in the presence of the appropriate alcohol HOR$^a$ followed by removal of the hydroxyl protecting groups (e.g. CsF) to afford intermediate S5a. Removal of the nitrogen protecting group (e.g. NH$_2$Me) yields the final compounds of the type S5b.
Scheme 6.
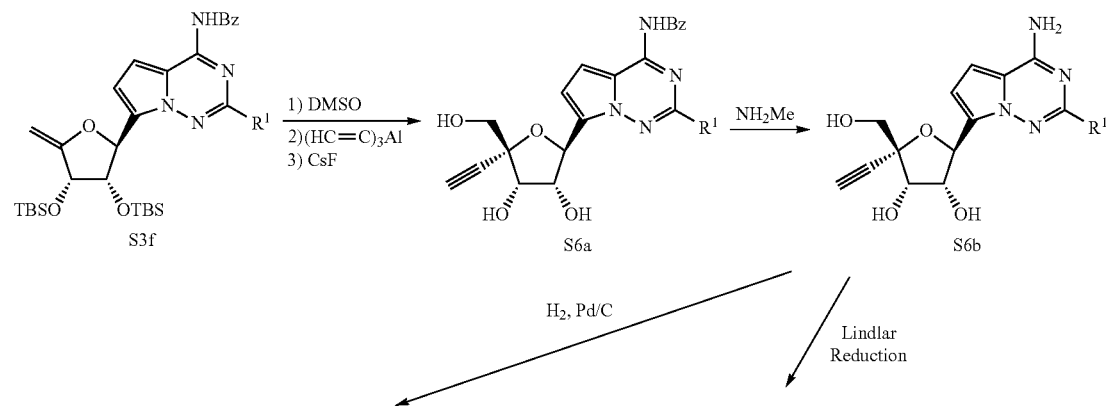
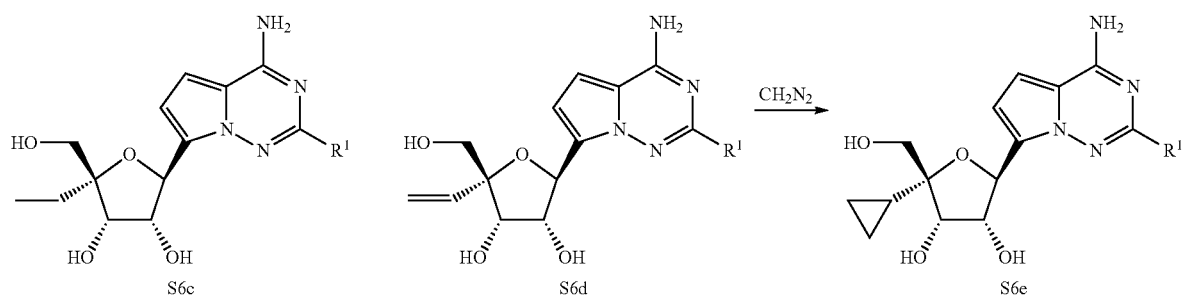

Scheme 6 shows a general synthesis of compounds beginning with oxidation of the olefin S3f (e.g. DMDO) followed by treatment with an appropriate nucleophile (e.g. (HC≡C)₃Al) in a manner similar to that described in *Nucleosides, Nucleotides, and Nucleic Acids* 2005, 24, 343-347. Removal of the hydroxyl protecting groups (e.g. CsF) then affords intermediate S6a. Removal of the nitrogen protecting group (e.g. NH₂Me) yields the final compounds of the type S6b. Elaboration of the final compound through hydrogenation conditions (e.g. H₂, Pd/C or Lindlar's conditions) can selectively afford the final compounds of the type S6c and S6d respectively. Elaboration of the final compound S6d through cyclopropanation conditions (e.g. CH₂N₂) can yield the final compounds of the type S6e.

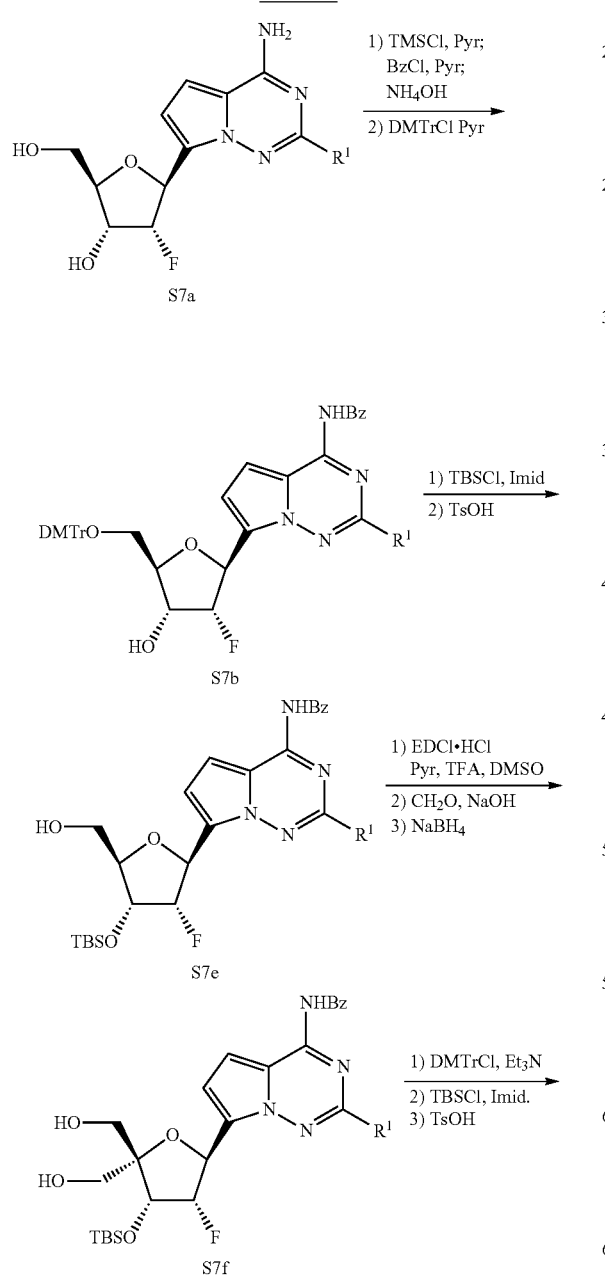

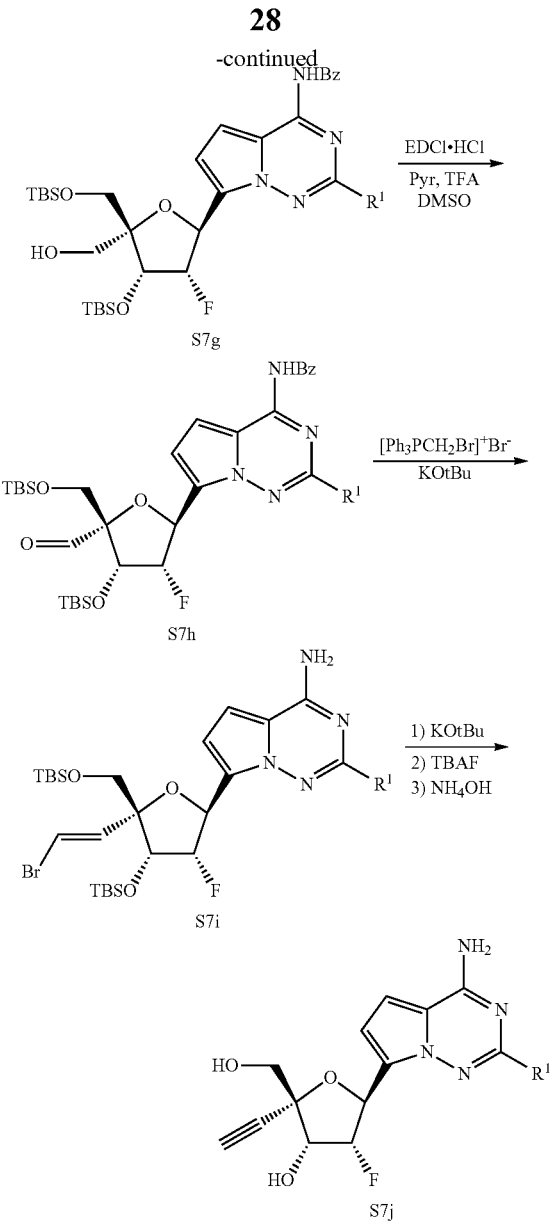

Scheme 7 shows a general synthesis of compounds beginning with a synthetic sequence to protect the nitrogen (e.g. TMSCl, Pyr; BzCl, Pyr; NH₄OH) of intermediate S7a, synthesized in a similar manner as described in WO2012037038A1. Selective protection of the 5' hydroxyl group (e.g. DMTrCl) then generates intermediate S7b. Protection of the 2' hydroxyl group (e.g. TBSCl) followed by removal of the 5' hydroxyl group under acidic conditions (e.g. TsOH) furnishes intermediate S7e. Conversion of the 5' hydroxyl group to the aldehyde under oxidative conditions (e.g. EDCl·HCl, Pyr, TFA, DMSO) followed by condensation of the corresponding enolate with formaldehyde and reduction (e.g. NaBH₄) yields intermediate S7f. Sequential selective protection of the hydroxyl moieties with orthogonal protecting groups (e.g. DMTrCl and TBSCl) followed by removal of the more labile protecting group under acidic conditions (e.g. TsOH) then affords intermediate S7g. Conversion of the hydroxyl group to the aldehyde under oxidative conditions (e.g. EDCl·HCl, Pyr, TFA, DMSO) generates intermediate S7h. Elaboration of the aldehyde S7h to the halo-olefin intermediate S7i can be effected under Wittig olefination conditions (e.g. [Ph₃PCH₂Br]⁺Br⁻, KOtBu). An elimination reaction under basic conditions (e.g. KOtBu) generates the alkyne, and removal of the hydroxyl protecting groups (e.g. TBAF) and nitrogen protecting group (e.g. NH₄OH) yields the final compounds of the type S7j.

Scheme 8.

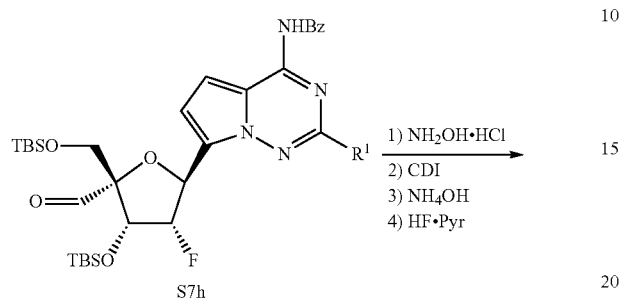

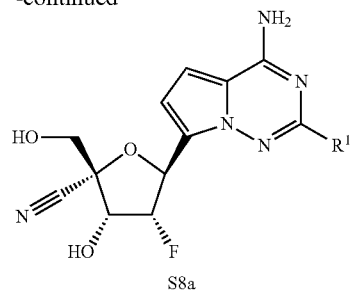

Scheme 8 shows a general synthesis of compounds beginning with oxime formation (e.g. NH₂OH.HCl), followed by conversion of the oxime to a nitrile group (e.g. CDI). Removal of the nitrogen protecting group (e.g. NH₄OH), and hydroxyl protecting groups (e.g. HF.Pyr) then yields the final compounds of the type S8a.

Scheme 9.

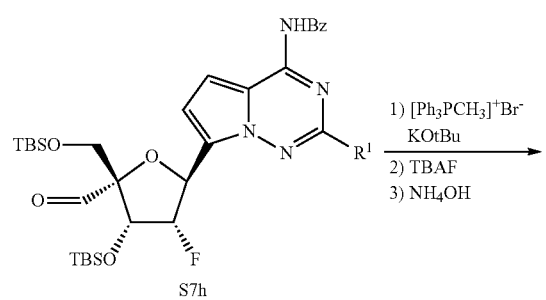

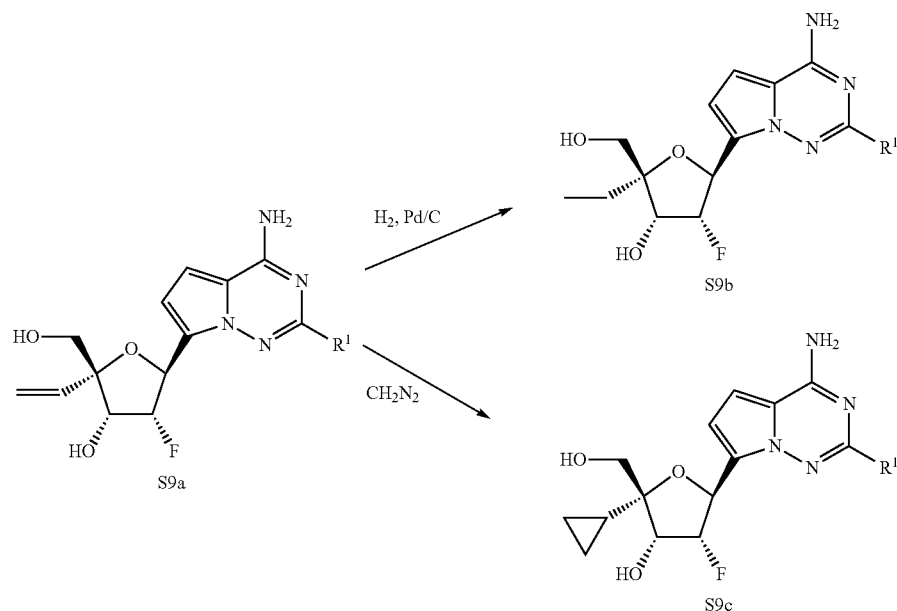

Scheme 9 shows a general synthesis of compounds beginning with elaboration of the aldehyde S7h to the olefin with Wittig olefination conditions (e.g. [Ph₃PCH₃]⁺Br⁻, KOtBu). Removal of the hydroxyl protecting groups (e.g. TBAF), and nitrogen protecting group (e.g. NH₄OH) yields the final compounds of the type S9a. Reducing conditions (e.g. H$_2$, Pd/C) then can generate the final compounds of the type S9b, and cyclopropanation conditions (e.g. CH$_2$N$_2$) can generate the final compounds of the type S9c.

Scheme 10.

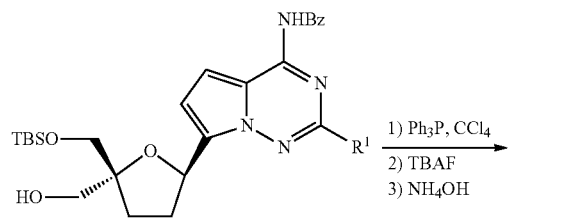

S7g

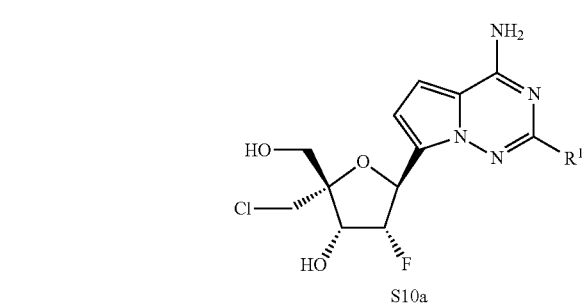

S10a

Scheme 10 shows a general synthesis of compounds beginning with an Appel reaction (e.g. Ph$_3$P, CCl$_4$) to convert the hydroxyl group into a chloride. Removal of the hydroxyl protecting groups (e.g. TBAF), and nitrogen protecting group (e.g. NH$_4$OH) yields the final compounds of the type S10a.

Scheme 11.

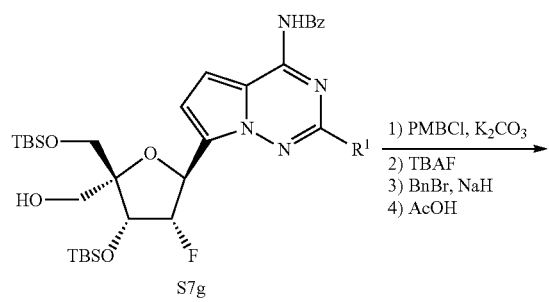

S7g

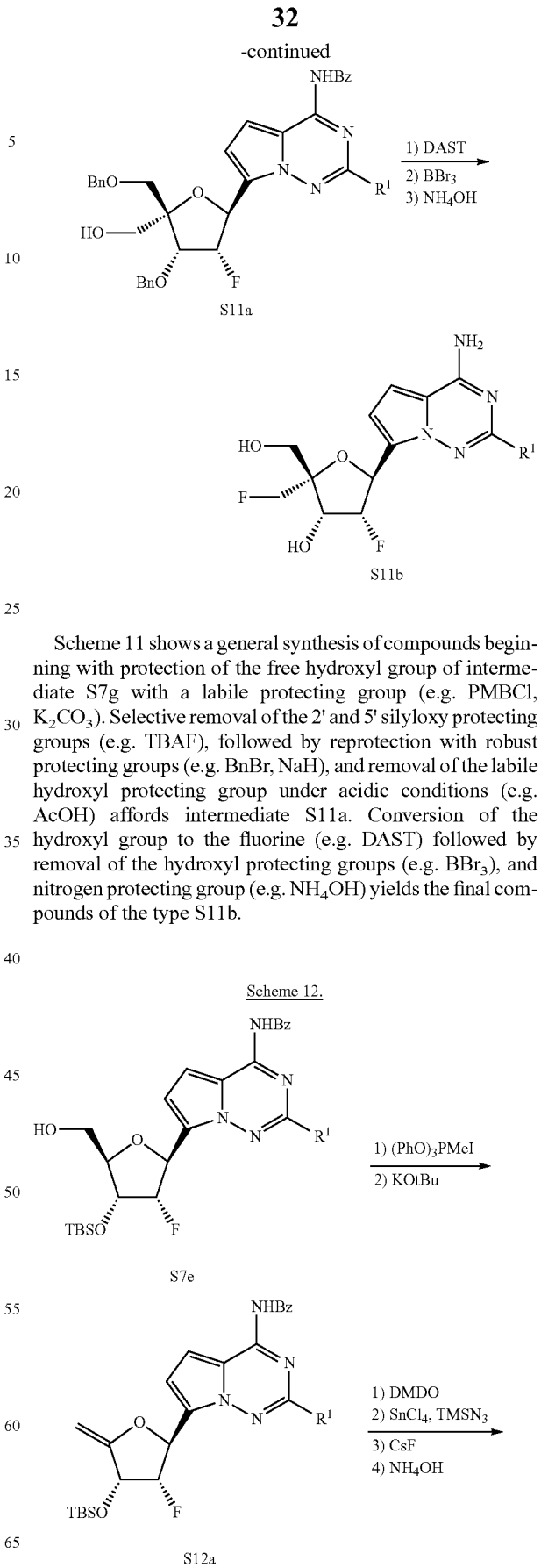

Scheme 11 shows a general synthesis of compounds beginning with protection of the free hydroxyl group of intermediate S7g with a labile protecting group (e.g. PMBCl, K$_2$CO$_3$). Selective removal of the 2' and 5' silyloxy protecting groups (e.g. TBAF), followed by reprotection with robust protecting groups (e.g. BnBr, NaH), and removal of the labile hydroxyl protecting group under acidic conditions (e.g. AcOH) affords intermediate S11a. Conversion of the hydroxyl group to the fluorine (e.g. DAST) followed by removal of the hydroxyl protecting groups (e.g. BBr$_3$), and nitrogen protecting group (e.g. NH$_4$OH) yields the final compounds of the type S11b.

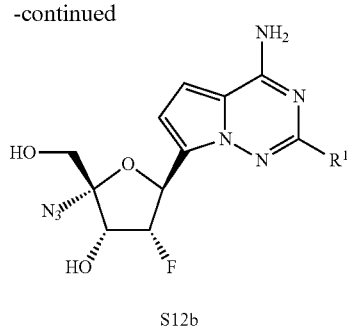

S12b

Scheme 12 shows a general synthesis of compounds beginning with conversion of the 5' hydroxyl group to the corresponding iodide (e.g. (PhO)$_3$PMeI), which is then treated with basic conditions (i.e. KOtBu) to effect an elimination reaction generating intermediate S12a. Oxidation of the olefin S12a (e.g. DMDO) followed by treatment with an appropriate nucleophile (e.g. TMSN$_3$) under Lewis acidic conditions (e.g. SnCl$_4$) in a manner similar to that described in *J. Med. Chem.* 2007, 50, 5463-5470, and removal of the hydroxyl protecting groups (e.g. CsF) and nitrogen protecting group (e.g. NH$_4$OH) yields the final compounds of the type S12b.

Scheme 13.

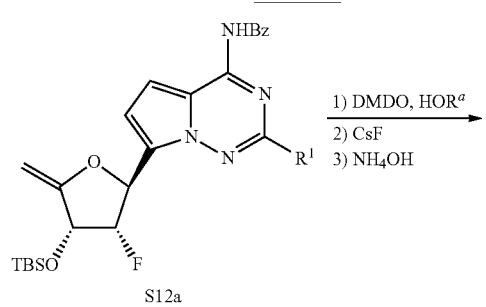

S12a

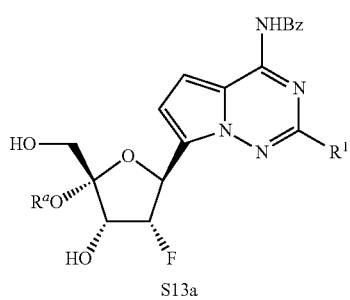

S13a

Scheme 13 shows a general synthesis of compounds beginning with oxidation of the olefin S12a (e.g. DMDO) in the presence of the appropriate alcohol HOW and removal of the hydroxyl protecting groups (e.g. CsF). Removal of the nitrogen protecting group (e.g. NH$_2$Me) yields the final compounds of the type S13a.

Scheme 14.

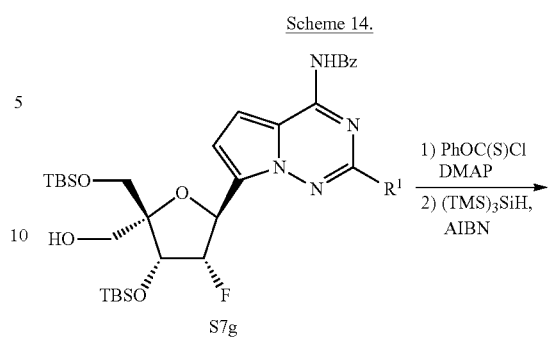

S7g

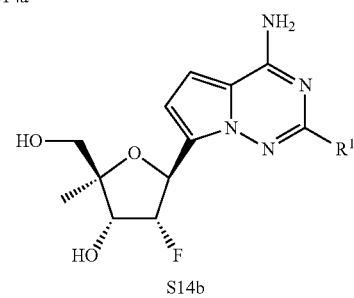

S14a

S14b

Scheme 14 shows a general synthesis of compounds beginning with xanthate formation (e.g. PhOC(S)Cl, DMAP) followed by a Barton-McCombie deoxygenation reaction (e.g. (TMS)$_3$SiH, AIBN) to generate intermediate S14a. Removal of the hydroxyl protecting groups (e.g. TBAF), and nitrogen protecting group (e.g. NH$_4$OH) yields the final compounds of the type S14b.

Scheme 15.

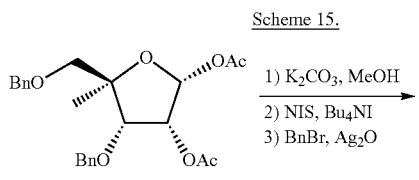

S15a

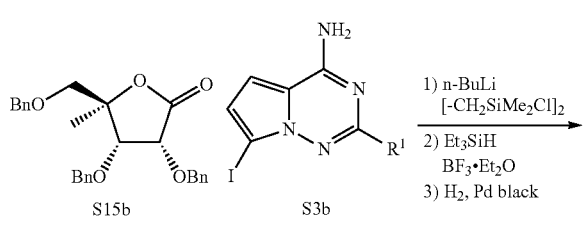

S15b            S3b

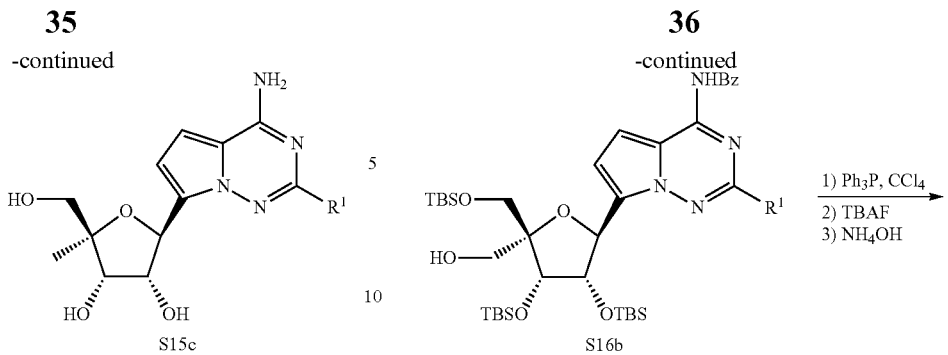

Scheme 15 shows a general synthesis of compounds beginning with intermediate S15a prepared in a manner similar to that described in *Biosci. Biotech. Biochem.* 1993, 57, 1433-1438. Removal of the acetate protecting groups using hydrolytic conditions (e.g. $K_2CO_3$, MeOH), followed by chemoselective oxidation conditions (e.g. NIS, $Bu_4NI$), and protection of the 2' hydroxyl group (e.g. BnBr, $Ag_2O$) generates intermediate S15b. Lithium-halogen exchange (e.g. n-BuLi, $[-CH_2SiMe_2Cl]_2$) with an appropriate nucleobase S3b and addition to the lactone S15b, followed by reduction of the 1' hydroxyl group under Lewis acidic conditions (e.g. $BF_3 \cdot Et_2O$, $Et_3SiH$), and deprotection (e.g. $H_2$, Pd black) yields the final compounds of the type S15c.

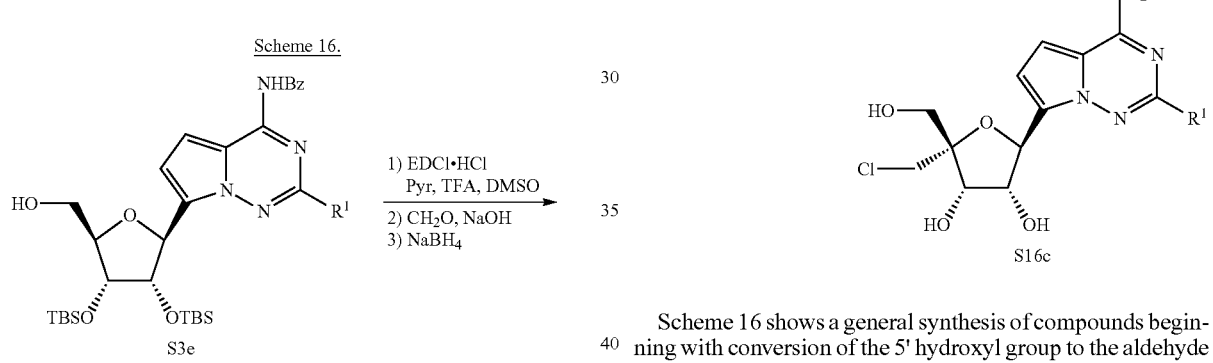

Scheme 16 shows a general synthesis of compounds beginning with conversion of the 5' hydroxyl group to the aldehyde under oxidative conditions (e.g. EDCl.HCl, Pyr, TFA, DMSO) followed by condensation of the corresponding enolate with formaldehyde and reduction (e.g. $NaBH_4$) to yields intermediate S16a. Sequential selective protection of the hydroxyl moieties with orthogonal protecting groups (e.g. DMTrCl and TBSCl) followed by removal of the more labile protecting group under acidic conditions (e.g. TsOH) then affords intermediate S16b. An Appel reaction (e.g. $Ph_3P$, $CCl_4$) then can convert the hydroxyl group into a chloride, and removal of the hydroxyl protecting groups (e.g. TBAF), and nitrogen protecting group (e.g. $NH_4OH$) yields the final compounds of the type S16c.

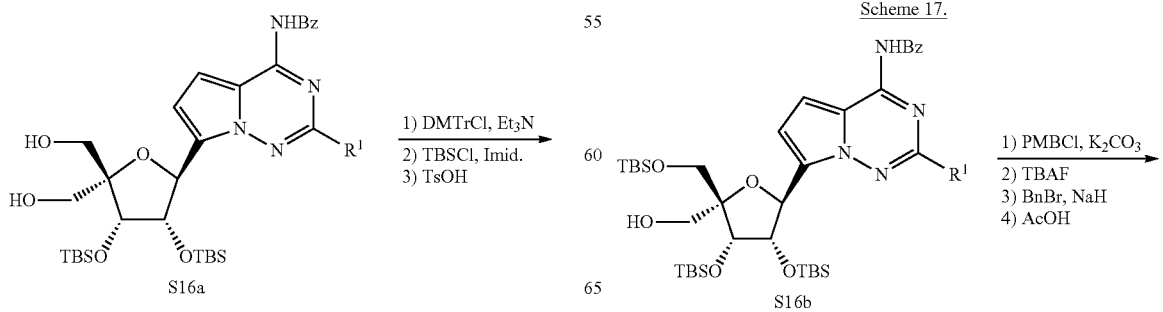

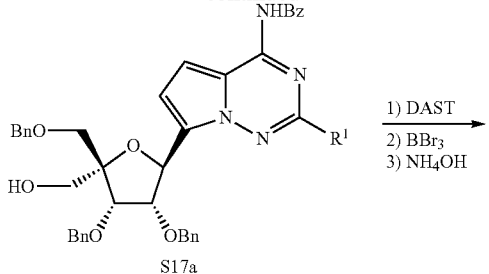

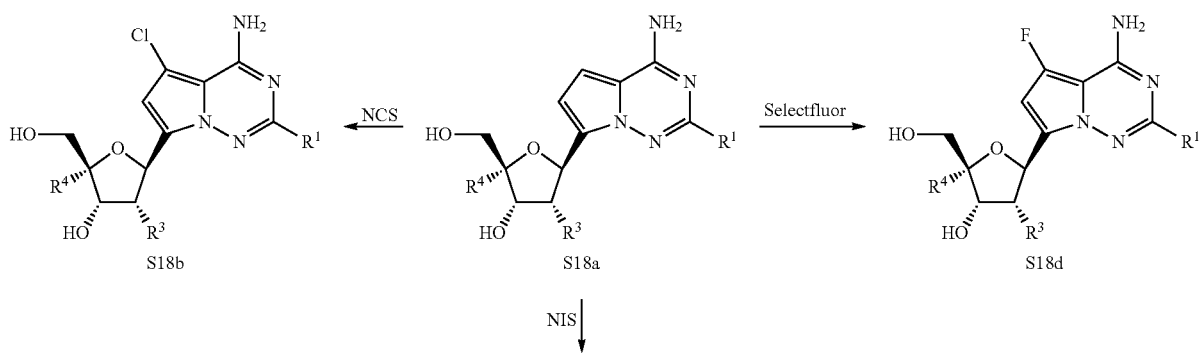

Scheme 17 shows a general synthesis of compounds beginning with protection of the free hydroxyl group of intermediate S16b with a labile protecting group (e.g. PMBCl, $K_2CO_3$). Selective removal of the 2', 3', and 5' silyloxy protecting groups (e.g. TBAF), followed by reprotection of with robust protecting groups (e.g. BnBr, NaH), and removal of the labile hydroxyl protecting group under acidic conditions (e.g. AcOH) affords intermediate S17a. Conversion of the hydroxyl group to the fluorine (e.g. DAST) followed by removal of the hydroxyl protecting groups (e.g. $BBr_3$), and nitrogen protecting group (e.g. $NH_4OH$) yields the final compounds of the type S17b.

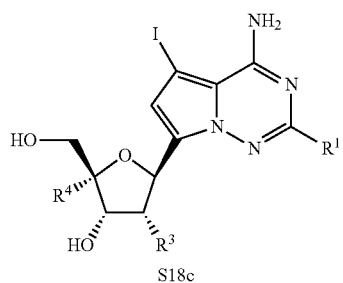

Scheme 18 shows a general synthesis of compounds through appropriate electrophilic halogenation reactions of intermediate S18a to afford the final compounds of the type S18b (e.g. NCS), S18c (e.g. NIS), and S18d (e.g. Selectfluor).

Scheme 19.

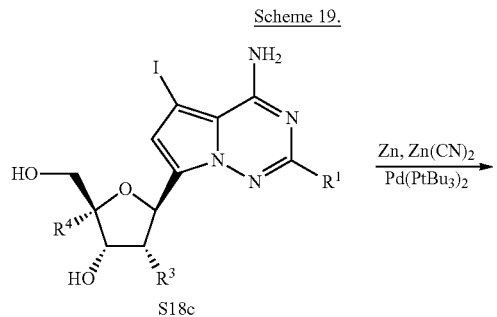

S18c

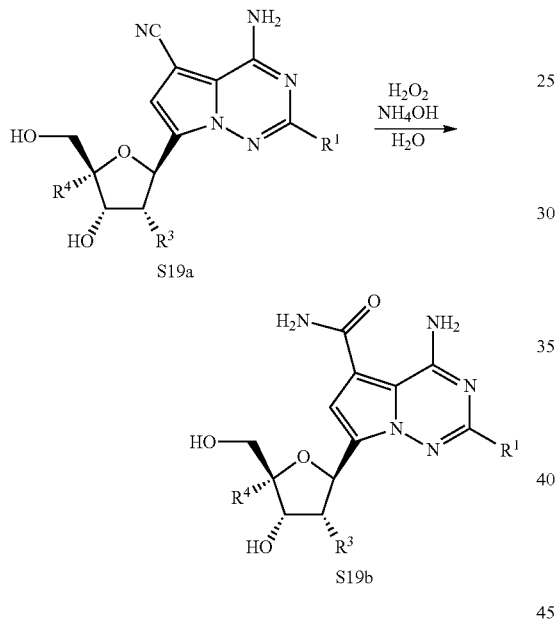

S19a

S19b

Scheme 19 shows a general synthesis of compounds beginning with a cross-coupling reaction (e.g. Zn(CN)$_2$, Pd(PtBu)$_3$) to yield the final compounds of the type S19a. Compound S19a can then be elaborated through a hydrolysis reaction of the nitrile (e.g. H$_2$O$_2$, NH$_4$OH, H$_2$O) to afford compounds of the type S19b.

Scheme 20.

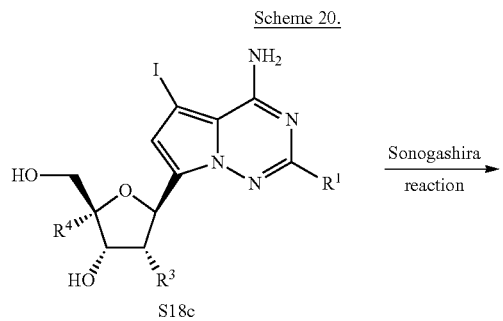

S18c

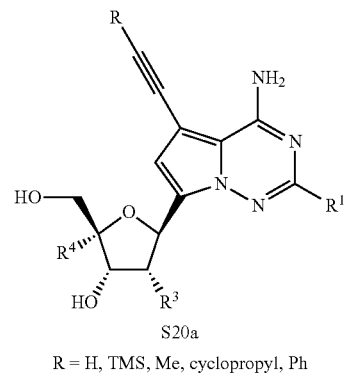

S20a

R = H, TMS, Me, cyclopropyl, Ph

Scheme 20 shows a general synthesis of compounds beginning with a Sonogashira reaction (e.g. CuI, PdCl$_2$(PPh$_3$)$_2$) to yield the final compounds of the type S20a.

Scheme 21.

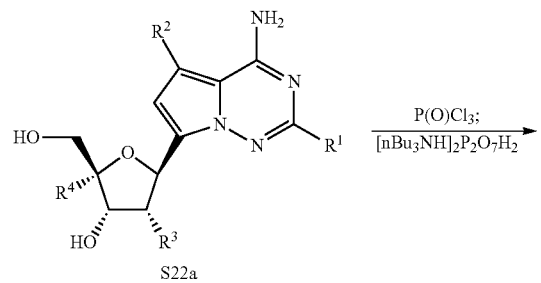

S18c

S21a

R = H, Me, Ph

Scheme 21 shows a general synthesis of compounds beginning with a cross-coupling reaction (e.g. Pd(dppf)Cl$_2$, Cs$_2$CO$_3$) to yield the final compounds of the type S21a.

Scheme 22.

S22a

-continued

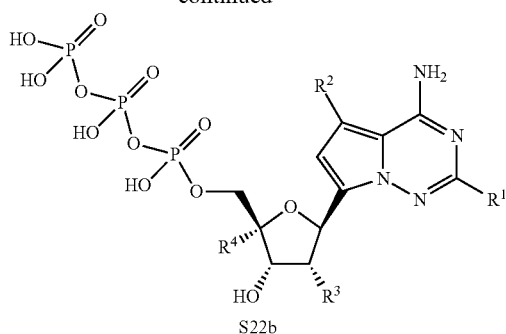

S22b

Scheme 22 shows a general synthesis of compounds involving synthesis of phosphorylated analogs of the type S22b.

Scheme 23.

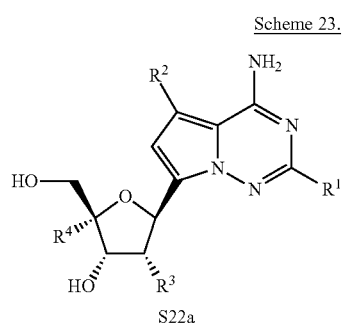

S22a

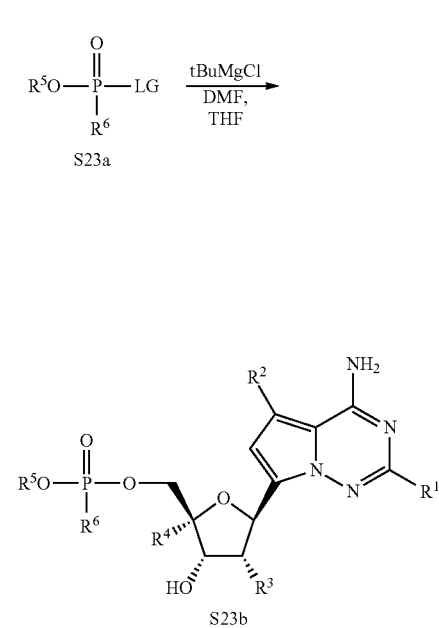

Scheme 23 shows a general synthesis of compounds involving synthesis of phosphorylated analogs of the type S23b.

Scheme 24.

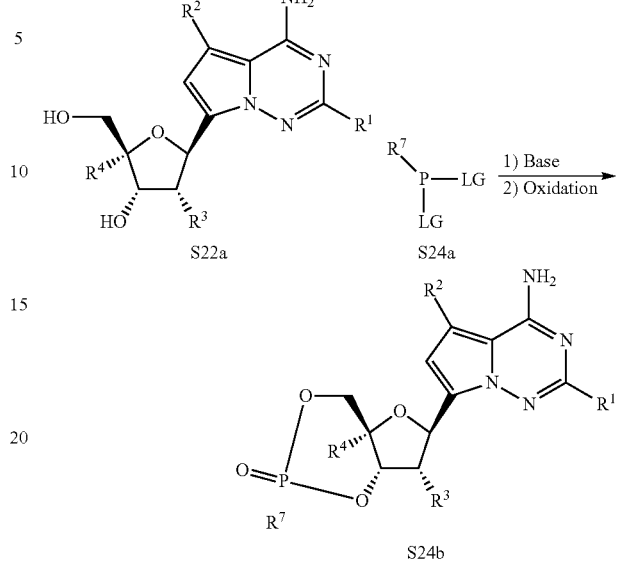

Scheme 24 shows a general synthesis of compounds involving synthesis of phosphorylated analogs of the type S24b.

EXPERIMENTALS

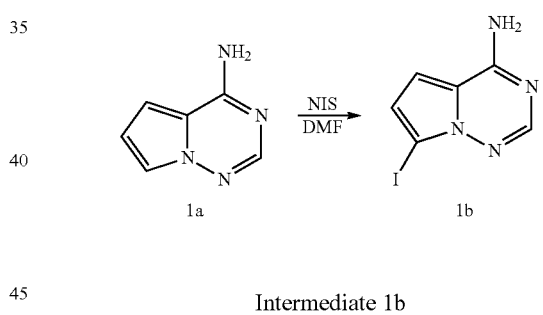

Intermediate 1b

To a solution of intermediate 1a (50 mg, 373 mmol) in DMF (1 mL) was charged N-iodosuccinimide (84 mg, 373 mmol) as a solid at RT. After 1.5 h, the reaction mixture was diluted 1M NaOH solution (10 mL), and the resulting slurry was stirred at RT. After 1 h, the solids were collected by vacuum filtration and dried under reduced pressure to afford intermediate 1b.

$^1$H NMR (400 MHz, DMSO-$d_6$) δ 7.89 (s, 1H), 7.78 (br-s, 1H), 6.98 (d, J=4.4 Hz, 1H), 6.82 (d, J=4.4 Hz, 1H), 3.30 (br-s, 1H).

LC/MS: $t_R$=1.21 min, MS m/z=261.02 [M+1]; LC system: Thermo Accela 1250 UHPLC

MS system: Thermo LCQ Fleet; Column: Kinetex 2.6µ XB-C18 100A, 50×4.6 mm

Solvents: Acetonitrile with 0.1% acetic acid, Water with 0.1% acetic acid; Gradient: 0 min-2.0 min 2-100% ACN, 2.0 min-3.05 min 100% ACN, 3.05 min-3.2 min 100%-2% ACN, 3.2 min-3.5 min 2% ACN at 2 µl/min.

HPLC: $t_r$=1.536 min; HPLC system: Agilent 1100 series.; Column: Gemini 5µ C18 110A, 50×4.6 mm; Solvents:

Acetonitrile with 0.1% TFA, Water with 0.1% TFA; Gradient: 0 min-5.0 min 2-98% ACN, 5.0 min-6.0 min 98% ACN at 2 mL/min.

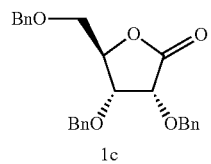

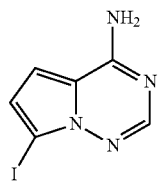
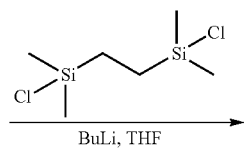

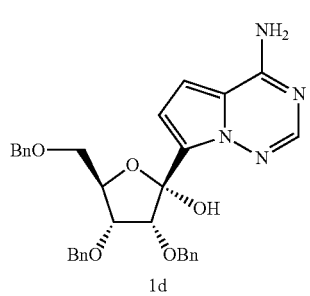

Intermediate 1d

-(2S,3R,4R,5R)-2-(4-aminopyrrolo[1,2-f][1,2,4]triazin-7-yl)-3,4-bis(benzyloxy)-5-(benzyloxymethyl)tetrahydrofuran-2-ol n-Butyllithium (2.5M in hexanes, 34.4 mL, 86.0 mmol) was added rapidly to a suspension of 7-iodopyrrolo[1,2-f][1,2,4]triazin-4-amine 1b (6.84 g, 26.3 mmol) and 1,2-bis(chlorodimethylsilyl)ethane (5.66 g, 26.3 mmol) in THF (200 mL) at −78° C. under an argon atmosphere. Over the course of the addition the internal temperature of the reaction mixture rose to −40.5° C., and the reaction mixture became a clear brown solution. After 15 min, a solution of (3R,4R,5R)-3,4-bis(benzyloxy)-5-(benzyloxymethyl)dihydrofuran-2(3H)-one (1c, Purchased from Carbosynth, 10 g, 23.9 mmol) in tetrahydrofuran (40 mL) precooled to −78° C., was added rapidly via cannula. After 1 h, the reaction mixture was quenched with acetic acid (15 mL), and the resulting mixture was allowed to warm to RT. The resulting mixture was diluted with ethyl acetate (800 mL) and was washed with saturated aqueous sodium bicarbonate solution (500 mL) and brine (500 mL). The organic layer was dried over anhydrous sodium sulfate, and was concentrated under reduced pressure. The crude residue was purified via $SiO_2$ column chromatography (220 g $SiO_2$ Combiflash HP Gold Column, 0-100% ethyl acetate/hexanes) to afford intermediate 1d.

LC/MS: $t_R$=1.50 min, MS m/z=553.34 [M+1]; LC system: Thermo Accela 1250 UHPLC

MS system: Thermo LCQ Fleet; Column: Kinetex 2.6μ XB-C18 100A, 50×4.6 mm

Solvents: Acetonitrile with 0.1% acetic acid, Water with 0.1% acetic acid; Gradient: 0 min-1.5 min 2-100% ACN, 1.5 min-2.2 min 100% ACN, 2.2 min-2.4 min 100%-2% ACN, 2.4 min-2.5 min 2% ACN.

HPLC: $t_r$=3.442 min; HPLC system: Agilent 1100 series.; Column: Gemini 5μ C18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min.

TLC: eluent: ethyl acetate, $R_f$=0.5 (UV)

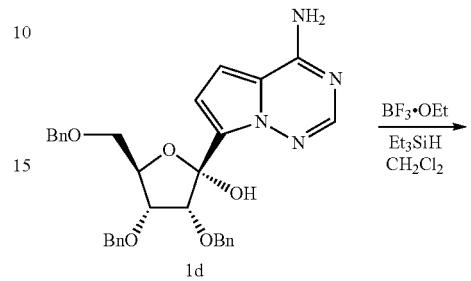

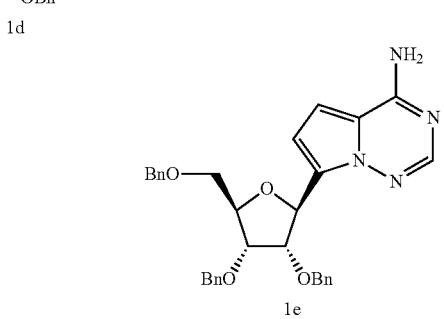

Intermediate 1e

-7-((2S,3S,4R,5R)-3,4-bis(benzyloxy)-5-(benzyloxymethyl)tetrahydrofuran-2-yl)pyrrolo[1,2-f][1,2,4]triazin-4-amine To a solution of intermediate 1d (4.74 g, 8.58 mmol) and triethylsilane (3.56 mL, 22.3 mmol), in DCM (43 mL) was added boron trifluoride diethyl etherate (1.59 ml, 12.9 mmol) slowly via syringe at 0° C. under an argon atmosphere. After 2 h, the reaction mixture was slowly diluted with saturated aqueous sodium bicarbonate solution (100 mL), and the resulting mixture was extracted with ethyl acetate (2×150 mL), was dried over anhydrous sodium sulfate, and was concentrated under reduced pressure. The crude residue was purified via $SiO_2$ column chromatography (24 g $SiO_2$ Combiflash HP Gold Column, 0-100% ethyl acetate/hexanes) to afford intermediate 1e.

$^1$H NMR (400 MHz, $CDCl_3$) δ 7.88 (s, 1H), 7.37-7.22 (m, 15H), 6.73 (d, J=4.6 Hz, 1H), 6.71 (d, J=4.6 Hz, 1H), 5.66 (d, J=4.2 Hz, 1H), 4.71 (s, 2H), 4.60 (d, J=12.0 Hz, 1H), 4.54 (s, 2H), 4.45 (d, J=11.9 Hz, 1H), 4.39 (dt, J=7.1, 3.6 Hz, 1H), 4.25 (t, J=4.6 Hz, 1H), 4.14-4.10 (m, 1H), 3.78 (dd, J=10.7, 3.4 Hz, 1H), 3.65 (dd, J=10.7, 4.0 Hz, 1H).

LC/MS: $t_R$=2.01 min, MS m/z=537.41 [M+1]; LC system: Thermo Accela 1250 UHPLC

MS system: Thermo LCQ Fleet; Column: Kinetex 2.6μ XB-C18 100A, 50×4.6 mm; Solvents: Acetonitrile with 0.1% acetic acid, Water with 0.1% acetic acid; Gradient: 0 min-1.5 min 2-100% ACN, 1.5 min-2.2 min 100% ACN, 2.2 min-2.4 min 100%-2% ACN, 2.4 min-2.5 min 2% ACN at 2 μl/min.

HPLC: $t_R$=3.596 min; HPLC system: Agilent 1100 series.; Column: Gemini 5μ C18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min.

TLC: eluent: ethyl acetate, $R_f$=0.3 (UV)

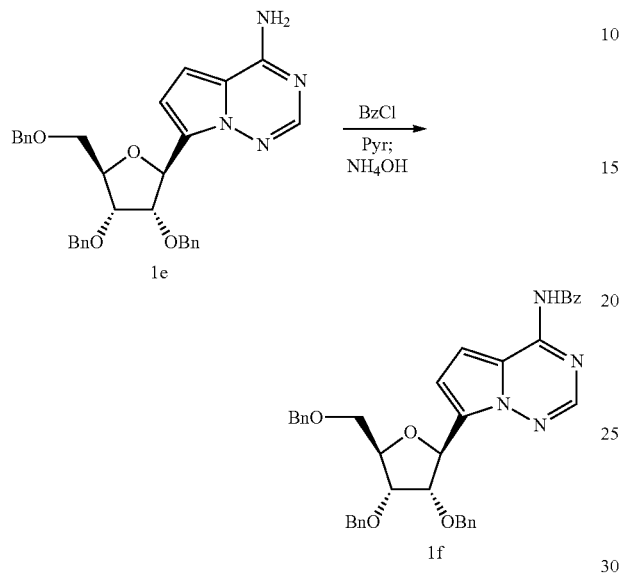

Intermediate 1f

-N-(7-((2S,3S,4R,5R)-3,4-bis(benzyloxy)-5-(benzyloxymethyl)tetrahydrofuran-2-yl)pyrrolo[1,2-f][1,2,4]triazin-4-yl)benzamide To a solution of intermediate 1e (3.94 g, 7.34 mmol) in pyridine (36.7 mL) was added benzoyl chloride (1.69 ml, 14.68 mmol) slowly at RT under an argon atmosphere. After 1 h, additional benzoyl chloride (1.69 ml, 14.68 mmol) was added slowly. After 19 h, water (20 mL) was added slowly and the reaction mixture became slightly cloudy. Ammonium Hydroxide (~10 mL) was then added slowly until the reaction mixture was basic at pH=10. After 1 h, water (150 mL) was added dropwise via addition funnel and white solids slowly began to precipitate from the reaction mixture over the course of the addition. The resulting mixture was stirred for 24 h and the white solids were collected by vacuum filtration and were dried azeotropically from toluene to afford intermediate 1f.

$^1$H NMR (400 MHz, CDCl$_3$) δ 8.23 (br s, 1H), 7.62 (t, J=7.8 Hz, 1H), 7.53 (t, J=7.6 Hz, 2H), 7.38-7.21 (m, 18H), 7.17 (d, J=7.6 Hz, 1H), 5.69 (d, J=4.1 Hz, 1H), 4.71 (s, 2H), 4.63-4.44 (m, 4H), 4.43-4.39 (m, 1H), 4.22 (t, J=4.5 Hz, 1H), 4.15-4.10 (m, 1H), 3.79 (dd, J=10.8, 3.2 Hz, 1H), 3.65 (dd, J=10.7, 3.7 Hz, 1H).

LC/MS: $t_R$=1.91 min, MS m/z=641.18 [M+1]; LC system: Thermo Accela 1250 UHPLC

MS system: Thermo LCQ Fleet; Column: Kinetex 2.6μ XB-C18 100A, 50×4.6 mm; Solvents:

Acetonitrile with 0.1% acetic acid, Water with 0.1% acetic acid; Gradient: 0 min-1.5 min 2-100% ACN, 1.5 min-2.2 min 100% ACN, 2.2 min-2.4 min 100%-2% ACN, 2.4 min-2.5 min 2% ACN at 2 μl/min.

TLC: eluent: 50% ethyl acetate in hexanes, $R_f$=0.6 (UV)

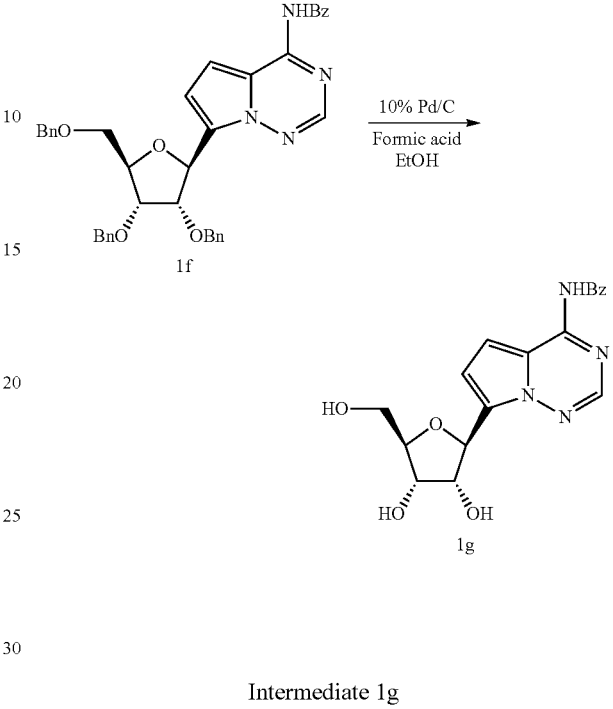

Intermediate 1g

-N-(7-((2S,3R,4S,5R)-3,4-dihydroxy-5-(hydroxymethyl)tetrahydrofuran-2-yl)pyrrolo[1,2-f][1,2,4]triazin-4-yl)benzamide Ethanol (68.5 mL) and formic acid (51.7 mL, 1.37 mol) were added sequentially to a mixture of intermediate 1f (4.39 g, 6.85 mmol) and palladium on carbon (10% by wt, 2.2 g) at RT under an argon atmosphere. After 3 d, the reaction mixture was filtered through a pad of celite, and the filtrate was concentrated under reduced pressure. The crude residue was azeotroped with toluene (3×20 mL) to afford intermediate 1g, which was used directly in the next step without further purification.

$^1$H NMR (400 MHz, CD$_3$OD) δ 8.15 (s, 1H), 7.67-7.40 (m, 5H), 7.23 (d, J=4.7 Hz, 1H), 7.00 (d, J=4.7 Hz, 1H), 5.40 (d, J=6.0 Hz, 1H), 4.44 (t, J=5.7 Hz, 1H), 4.17 (t, J=5.1 Hz, 1H), 4.03 (q, J=4.3 Hz, 1H), 3.81 (dd, J=12.1, 3.5 Hz, 1H), 3.71 (dd, J=12.0, 4.5 Hz, 1H).

LC/MS: $t_R$=1.04 min, MS m/z=371.15 [M+1]; LC system: Thermo Accela 1250 UHPLC

MS system: Thermo LCQ Fleet; Column: Kinetex 2.6μ XB-C18 100A, 50×4.6 mm

Solvents: Acetonitrile with 0.1% acetic acid, Water with 0.1% acetic acid; Gradient: 0 min-1.5 min 2-100% ACN, 1.5 min-2.2 min 100% ACN, 2.2 min-2.4 min 100%-2% ACN, 2.4 min-2.5 min 2% ACN at 2 μl/min.;

HPLC: $t_R$=2.055 min; HPLC system: Agilent 1100 series.; Column: Gemini 5μ C18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min.

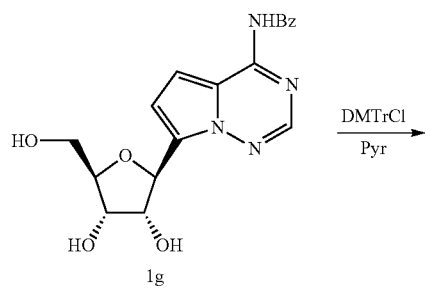

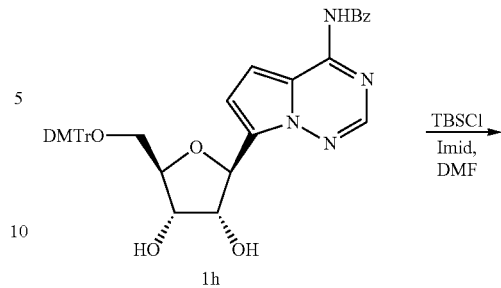

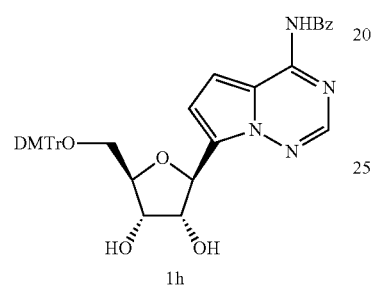

Intermediate 1h

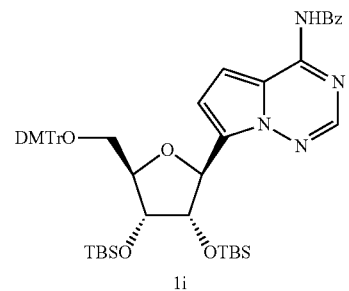

Intermediate 1i

-N-(7-((2S,3R,4S,5R)-5-((bis(4-methoxyphenyl) (phenyl)methoxy)methyl)-3,4-dihydroxytetrahydrofuran-2-yl)pyrrolo[1,2-f][1,2,4]triazin-4-yl)benzamide 4,4'-Dimethoxytrityl chloride (2.23 g, 6.59 mmol) was added as a solid in one portion to a solution of intermediate 1g (2.44 g, 6.59 mmol) in pyridine (32.5 mL) at RT. After 5.5 h, the reaction mixture was diluted with ethyl acetate (300 mL) and the resulting mixture was washed with brine (3×200 mL). The organic layer was concentrated under reduced pressure, and the crude residue was purified via SiO$_2$ column chromatography (80 g SiO$_2$ Combiflash HP Gold Column, 0-100% ethyl acetate/hexanes) to afford intermediate 1h.

LC/MS: $t_R$=1.68 min, MS m/z=673.22 [M+1]; LC system: Thermo Accela 1250 UHPLC

MS system: Thermo LCQ Fleet; Column: Kinetex 2.6μ XB-C18 100A, 50×4.6 m;

Solvents: Acetonitrile with 0.1% acetic acid, Water with 0.1% acetic acid; Gradient: 0 min-1.5 min 2-100% ACN, 1.5 min-2.2 min 100% ACN, 2.2 min-2.4 min 100%-2% ACN, 2.4 min-2.5 min 2% ACN at 2 μl/min.

HPLC: $t_R$=4.270 min; HPLC system: Agilent 1100 series.; Column: Gemini 5μ C18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min.

TLC: eluent: 50% ethyl acetate in hexanes, $R_f$=0.15 (UV)

-N-(7-((2S,3S,4R,5R)-5-((bis(4-methoxyphenyl) (phenyl)methoxy)methyl)-3,4-bis(tert-butyldimethyl-silyloxy)tetrahydrofuran-2-yl)pyrrolo[1,2-f][1,2,4]triazin-4-yl)benzamide tert-Butyldimethylsilyl chloride (2.47 g, 16.4 mmol) was added to a solution of intermediate 1h (1.84 g, 2.74 mmol) and imidazole (2.23 g, 32.8 mmol) in N,N-dimethylformamide (28.2 mL) at RT. After 17 h, saturated aqueous sodium bicarbonate solution (500 mL) was added slowly to the reaction mixture. The resulting mixture was extracted with ethyl acetate (500 mL), and the organic layer was washed with brine (2×400 mL), was dried over anhydrous sodium sulfate, and was concentrated under reduced pressure. The crude residue was purified via SiO$_2$ column chromatography (80 g SiO$_2$ Combiflash HP Gold Column, 0-100% ethyl acetate/hexanes) to afford intermediate 1i.

LC/MS: $t_R$=3.43 min, MS m/z=901.37 [M+1]; LC system: Thermo Accela 1250 UHPLC

MS system: Thermo LCQ Fleet; Column: Kinetex 2.6μ XB-C18 100A, 50×4.6 mm

Solvents: Acetonitrile with 0.1% acetic acid, Water with 0.1% acetic acid; Gradient: 0 min-2.0 min 2-100% ACN, 2.0 min-3.55 min 100% ACN, 3.55 min-4.2 min 100%-2% ACN at 2 μl/min HPLC: $t_R$=5.724 min; HPLC system: Agilent 1100 series.; Column: Gemini 5μ C18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min.

TLC: eluent: 50% ethyl acetate in hexanes, $R_f$=0.75 (UV)

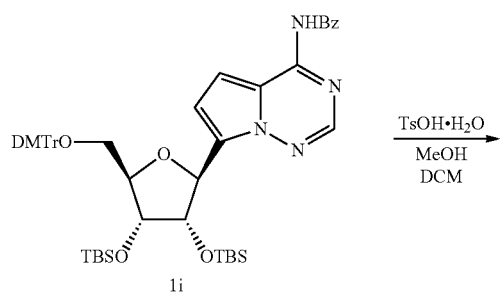

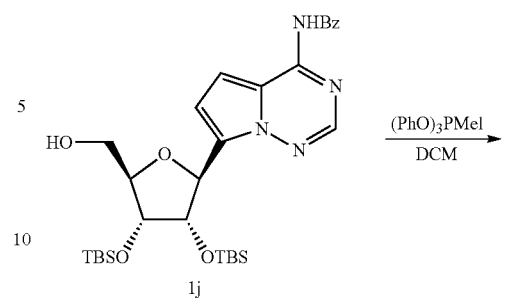

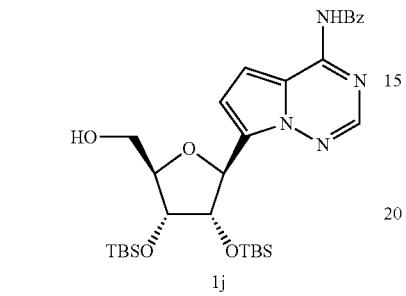

Intermediate 1j

-N-(7-((2S,3S,4R,5R)-3,4-bis(tert-butyldimethylsilyloxy)-5-(hydroxymethyl)tetrahydrofuran-2-yl)pyrrolo[1,24][1,2,4]triazin-4-yl)benzamide A solution of p-toluenesulfonic acid monohydrate (509 mg, 2.67 mmol) in methanol (3.7 mL) was slowly added to a solution of intermediate 1i (2.41 g, 2.67 mmol) in dichloromethane (22.3 mL) at 0° C. After 1.5 h, the reaction mixture was diluted with saturated aqueous bicarbonate solution (100 mL), and the resulting mixture was extracted with dichloromethane (2×100 mL). The combined organic extracts were dried over anhydrous sodium sulfate, and were concentrated under reduced pressure. The crude residue was purified via SiO$_2$ column chromatography (120 g SiO$_2$ Combiflash HP Gold Column, 0-100% ethyl acetate/hexanes) to afford intermediate 1j.

$^1$H NMR (400 MHz, CDCl$_3$) δ 8.72 (br-s, 1H), 8.16 (br-t, J=7.1 Hz, 2H), 8.07 (br-t, J=7.7 Hz, 3H), 7.49-7.43 (m, 1H), 5.75 (d, J=8.2 Hz, 1H), 5.28 (dd, J=8.1, 4.7 Hz, 1H), 4.81 (d, J=5.0 Hz, 1H), 4.70-4.63 (m, 1H), 4.44 (d, J=12.3 Hz, 1H), 4.24 (d, J=12.4 Hz, 1H), 1.48 (s, 9H), 1.30 (s, 9H), 0.65 (s, 3H), 0.64 (s, 3H), 0.41 (s, 3H), 0.00 (s, 3H).

LC/MS: t$_R$=2.66 min, MS m/z=599.19 [M+1]; LC system: Thermo Accela 1250 UHPLC

MS system: Thermo LCQ Fleet; Column: Kinetex 2.6µ XB-C18 100A, 50×4.6 mm

Solvents: Acetonitrile with 0.1% acetic acid, Water with 0.1% acetic acid; Gradient: 0 min-2.0 min 2-100% ACN, 2.0 min-3.05 min 100% ACN, 3.05 min-3.2 min 100%-2% ACN, 3.2 min-3.5 min 2% ACN at 2 µl/min.

HPLC: t$_R$=5.622 min; HPLC system: Agilent 1100 series.; Column: Gemini 5µ C18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min.

TLC: eluent: 50% ethyl acetate in hexanes, R$_f$=0.55 (UV)

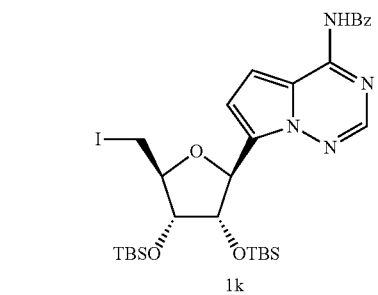

Intermediate 1k

-N-(7-((2S,3S,4R,5S)-3,4-bis(tert-butyldimethylsilyloxy)-5-(iodomethyl)tetrahydrofuran-2-yl)pyrrolo[1,2-f][1,2,4]triazin-4-yl)benzamide Intermediate 1j (1.19 g, 1.99 mmol) was added to a solution of methyltriphenoxyphosphonium iodide (0.99 g, 2.19 mmol) in DMF (9.9 mL) at RT. After 3 h, an additional portion of methyltriphenoxyphosphonium iodide (0.99 g, 2.19 mmol) was added. After 1 h, the reaction mixture was diluted with ethyl acetate (200 mL) and was washed with brine (3×100 mL). The organic layer was dried over anhydrous sodium sulfate, and was concentrated under reduced pressure. The crude residue was purified via SiO$_2$ column chromatography (80 g SiO$_2$ Combiflash HP Gold Column, 0-100% ethyl acetate/hexanes) to afford intermediate 1k.

$^1$H NMR (400 MHz, CDCl$_3$) δ 8.21 (br s, 1H), 7.61 (br t, J=7.2 Hz, 1H), 7.53 (br t, J=7.5 Hz, 3H), 7.05 (br s, 1H), 5.44 (d, J=4.5 Hz, 1H), 4.52 (t, J=4.3 Hz, 1H), 4.08-3.99 (m, 2H), 3.55 (dd, J=10.7, 5.2 Hz, 1H), 3.38 (dd, J=10.7, 5.0 Hz, 1H), 0.93 (s, 9H), 0.85 (s, 9H), 0.16 (s, 3H), 0.11 (s, 3H), −0.01 (s, 3H), −0.11 (s, 1H).

LC/MS: t$_R$=3.06 min, MS m/z=709.16 [M+1]; LC system: Thermo Accela 1250 UHPLC

MS system: Thermo LCQ Fleet; Column: Kinetex 2.6µ XB-C18 100A, 50×4.6 mm

Solvents: Acetonitrile with 0.1% acetic acid, Water with 0.1% acetic acid; Gradient: 0 min-2.0 min 2-100% ACN, 2.0 min-3.05 min 100% ACN, 3.05 min-3.2 min 100%-2% ACN, 3.2 min-3.5 min 2% ACN at 2 µl/min.

HPLC: t$_R$=5.837 min; HPLC system: Agilent 1100 series.; Column: Gemini 5µ C18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min.

TLC: eluent: 20% ethyl acetate in hexanes, R$_f$=0.45 (UV)

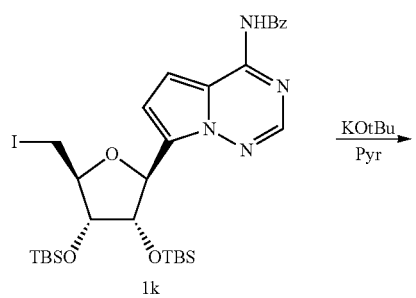

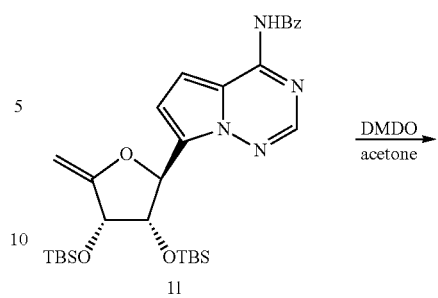

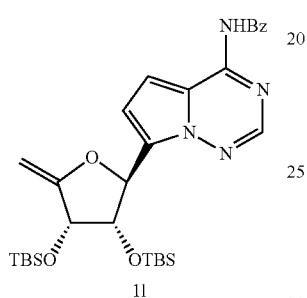

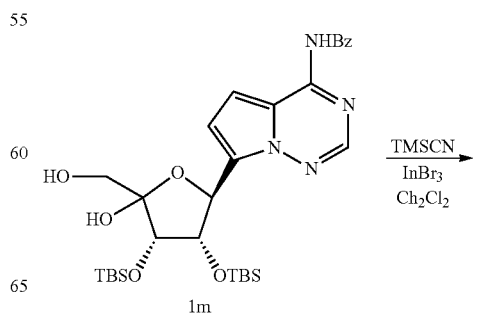

Intermediate 1l

-N-(7-((2S,3S,4S)-3,4-bis(tert-butyldimethylsily-loxy)-5-methylenetetrahydrofuran-2-yl)pyrrolo[1,2-f][1,2,4]triazin-4-yl)benzamide Potassium t-butoxide (700 mg, 6.24 mmol) was added to a solution of intermediate 1k (1.77 g, 2.5 mmol) in pyridine (25 mL) at RT. After 2 h, the reaction mixture was diluted with saturated aqueous sodium bicarbonate solution (25 mL) and brine (200 mL). The resulting mixture was extracted with ethyl acetate (300 mL). The organic layer was then washed with brine (200 mL), was dried over anhydrous sodium sulfate, and was concentrated under reduced pressure. The crude residue was purified via SiO₂ column chromatography (40 g SiO₂ Combiflash HP Gold Column, 0-100% ethyl acetate/hexanes) to afford intermediate 1l.

LC/MS: $t_R$=2.87 min, MS m/z=581.37 [M+1]; LC system: Thermo Accela 1250 UHPLC

MS system: Thermo LCQ Fleet; Column: Kinetex 2.6μ XB-C18 100A, 50×4.6 mm

Solvents: Acetonitrile with 0.1% acetic acid, Water with 0.1% acetic acid

Gradient: 0 min-2.0 min 2-100% ACN, 2.0 min-3.05 min 100% ACN, 3.05 min-3.2 min 100%-2% ACN, 3.2 min-3.5 min 2% ACN at 2 μl/min.

HPLC: $t_R$=5.750 min; HPLC system: Agilent 1100 series.; Column: Gemini 5μ C18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min.

TLC: eluent: 50% ethyl acetate in hexanes, $R_f$=0.20 (UV)

Intermediate 1m

-N-(7-((2S,3S,4S)-3,4-bis(tert-butyldimethylsily-loxy)-5-hydroxy-5-(hydroxymethyl)tetrahydrofuran-2-yl)pyrrolo[1,2-f][1,2,4]triazin-4-yl)benzamide DMDO (0.07M solution in acetone, 13.8 mL, 0.964 mmol) was added to a solution of intermediate 1l (560 mg, 0.964 mmol) in acetone (4.82 mL) at 0° C. After 10 min, the reaction mixture was concentrated under reduced pressure was dried azeotropically with toluene (2×1 mL) to afford 1m that was used immediately in the next step without further purification.

LC/MS: $t_R$=2.57 min, MS m/z=615.14 [M+1]; LC system: Thermo Accela 1250 UHPLC

MS system: Thermo LCQ Fleet; Column: Kinetex 2.6μ XB-C18 100A, 50×4.6 mm

Solvents: Acetonitrile with 0.1% acetic acid, Water with 0.1% acetic acid

Gradient: 0 min-2.0 min 2-100% ACN, 2.0 min-3.05 min 100% ACN, 3.05 min-3.2 min 100%-2% ACN, 3.2 min-3.5 min 2% ACN at 2 μl/min.

-continued

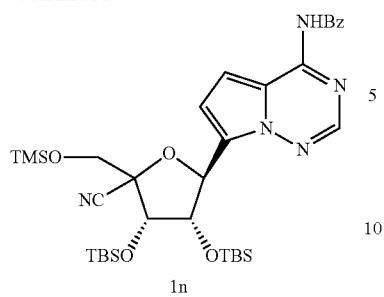

1n

Intermediate 1n

-N-(7-((2S,3S,4S)-3,4-bis(tert-butyldimethylsilyloxy)-5-cyano-5-((trimethylsilyloxy)methyl)tetrahydrofuran-2-yl)pyrrolo[1,2-f][1,2,4]triazin-4-yl)benzamide To a solution of crude intermediate 1m (—592 mg, ~0.964 mmol) and trimethylsilyl cyanide (640 μl, 4.80 mmol) in dichloromethane (19.2 mL) was added indium (III) bromide (681 mg, 1.92 mmol) at 0° C. under an argon atmosphere. After 4.5 h, the reaction mixture was quenched with saturated aqueous sodium bicarbonate solution (6 mL) and was allowed to warm to RT. The resulting mixture was partitioned between dichloromethane (20 mL) and saturated aqueous sodium bicarbonate solution (20 mL). The phases were split and the aqueous layer was extracted with dichloromethane (20 mL). The combined organic layers were dried over anhydrous sodium sulfate and were concentrated under reduced pressure to afford intermediate 1n (1:1 diastereomeric mixture) (710 mg) that was used directly in the next step without further purification.

LC/MS: first eluting isomer $t_r$=2.91 min, MS m/z=696.28 [M+1], second eluting isomer $t_R$=3.02 min, MS m/z=696.19 [M+1],; LC system: Thermo Accela 1250 UHPLC MS system: Thermo LCQ Fleet; Column: Kinetex 2.6μ XB-C18 100A, 50×4.6 mm Solvents: Acetonitrile with 0.1% acetic acid, Water with 0.1% acetic acid; Gradient: 0 min-2.0 min 2-100% ACN, 2.0 min-3.05 min 100% ACN, 3.05 min-3.2 min 100%-2% ACN, 3.2 min-3.5 min 2% ACN at 2 μl/min.

-continued

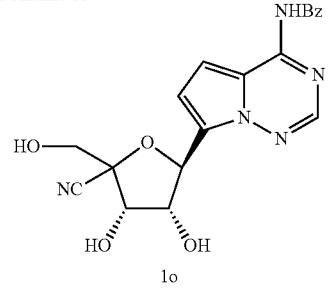

1o

Intermediate 1o

-N-(7-((2S,3R,4S)-5-cyano-3,4-dihydroxy-5-(hydroxymethyl)tetrahydrofuran-2-yl)pyrrolo[1,2-f][1,2,4]triazin-4-yl)benzamide To a solution of crude intermediate 1n (668.23 mg, 0.96 mmol) in DMF (9.6 mL) was added cesium fluoride (729 mg, 4.8 mmol) at RT. After 5 h, the reaction mixture was diluted with brine (100 mL), and the resulting mixture was extracted with dichloromethane (3×100 mL). The combined organic layers were dried over anhydrous sodium sulfate and were concentrated under reduced pressure to afford intermediate 1o (1:1 diastereomeric mixture) that was used directly in the next step without further purification.

LC/MS: first eluting isomer $t_R$=1.31 min, MS m/z=396.19 [M+1], second eluting isomer $t_R$=1.32 min, MS m/z=396.19 [M+1],; LC system: Thermo Accela 1250 UHPLC MS system: Thermo LCQ Fleet; Column: Kinetex 2.6μ XB-C18 100A, 50×4.6 mm Solvents: Acetonitrile with 0.1% acetic acid, Water with 0.1% acetic acid; Gradient: 0 min-2.0 min 2-100% ACN, 2.0 min-3.05 min 100% ACN, 3.05 min-3.2 min 100%-2% ACN, 3.2 min-3.5 min 2% ACN at 2 μl/min.

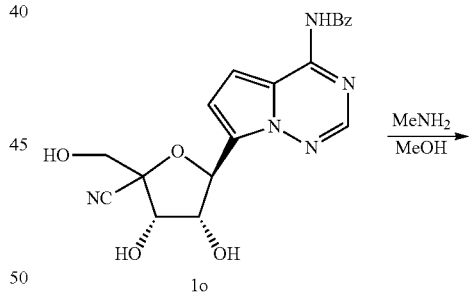

1o

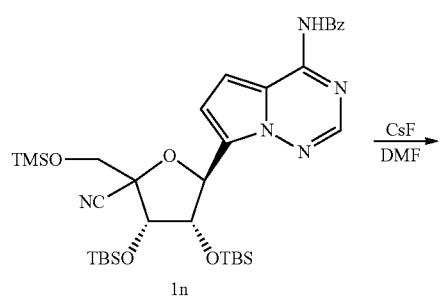

1n

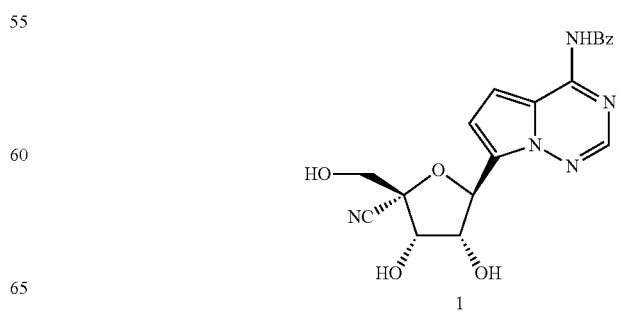

1

Example 1

-(2R,3S,4R,5S)-5-(4-aminopyrrolo[1,2-f][1,2,4]triazin-7-yl)-3,4-dihydroxy-2-(hydroxymethyl)tetrahydrofuran-2-carbonitrile Methylamine (40% in water, 0.3 mL) was added to a solution of crude intermediate 1o in methanol (1 mL) at RT. After 2.5 h, the reaction mixture was concentrated under reduced pressure, and was directly purified by preparatory HPLC (Phenominex Luna 5u C18 100 Å 100×30 mm column, 5-15% acetonitrile/water gradient, 25 min). The fractions containing the desired product and the 4' anomer were combined and were concentrated under reduced pressure. The 4' anomers were then separated by preparatory HPLC (Phenominex Luna 5u C18 100 Å 100×30 mm column, 5-15% acetonitrile/water gradient, 25 min). The fractions containing the desired product were combined and were lyophilized to afford Example 1.

$^1$H NMR (400 MHz, CD$_3$OD) δ 7.79 (s, 1H), 6.85 (d, J=4.5 Hz, 1H), 6.76 (d, J=4.5 Hz, 1H), 5.45 (d, J=5.9 Hz, 1H), 4.59 (t, J=5.7 Hz, 1H), 4.40 (d, J=5.6 Hz, 1H), 3.88 (d, J=12.0 Hz, 1H), 3.80 (d, J=12.0 Hz, 1H).

LC/MS: $t_R$=0.29 min, MS m/z=292.16 [M+1]; LC system: Thermo Accela 1250 UHPLC

MS system: Thermo LCQ Fleet; Column: Kinetex 2.6μ XB-C18 100A, 50×4.6 mm

Solvents: Acetonitrile with 0.1% acetic acid, Water with 0.1% acetic acid; Gradient: 0 min-1.5 min 2-100% ACN, 1.5 min-2.2 min 100% ACN, 2.2 min-2.4 min 100%-2% ACN, 2.4 min-2.5 min 2% ACN at 2 μl/min.

HPLC: $t_R$=0.377 min; HPLC system: Agilent 1100 series.; Column: Gemini 5μ C18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min.; HPLC: $t_R$=6.643 min; HPLC system: Agilent 1100 series.; Column: Luna 5μ C18(2) 110A, 250× 4.6 mm; Solvents: Acetonitrile, Water; Gradient: 5-15% ACN over 10 min at 2 mL/min

Intermediate 2b

-N-(7-((2S,3R,4R,5R)-3-fluoro-4-hydroxy-5-(hydroxymethyl)tetrahydrofuran-2-yl)pyrrolo[1,2-f][1,2,4]triazin-4-yl)benzamide To an N$_2$ purged flask was added intermediate 2a, (2R,3R,4R,5S)-5-(4-aminopyrrolo[1,2-f][1,2,4]triazin-7-yl)-4-fluoro-2-(hydroxymethyl)tetrahydrofuran-3-ol (prepared according to WO2012037038A1, 1.20 g, 4.01 mmol) (dried by coevaporation with pyridine 3 times), which was then dissolved in pyridine (18 mL). Chlorotrimethylsilane (1.54 mL, 13.13 mmol) was added in one portion at 0° C. and the resulting mixture was stirred under an N$_2$ atmosphere for 1 h. Benzoyl chloride (675 μL, 5.82 mmol) was added dropwise and the reaction mixture was stirred for 1h. An additional portion of benzoyl chloride (100 μL) was added to consume the remaining starting material. A mixture of mono- and bis-Bz protected products was observed. The reaction was quenched with H$_2$O (5 mL), and the resulting mixture was stirred for 5 min. Then concentrated NH$_4$OH$_{(aq)}$ (8 mL) was added in one portion and allowed to stir for 15 min at which point the bis-Bz product was converted to the desired product. The solvents were removed under reduced pressure, and then the residue was coevaporated with CH$_3$OH. Intermediate 2b was isolated after purification by silica gel chromatography, using an eluent ramp of 50%-100% EtOAc in hexanes.

$^1$H NMR (400 MHz, DMSO-d$_6$) δ 8.26-7.91 (m, 2H), 7.88-7.79 (m, 1H), 7.61 (t, J=7.5 Hz, 1H), 7.56-7.36 (m, 2H), 7.37-7.24 (m, 1H), 7.10 (d, J=4.6 Hz, 1H), 7.01 (s, 1H), 5.53 (d, J=23.4 Hz, 1H), 5.45 (d, J=6.5 Hz, 1H), 5.16-4.91 (m, 1H), 4.86 (t, J=5.6 Hz, 1H), 4.21-4.04 (m, 1H), 3.82 (dd, J=8.0, 3.9 Hz, 1H), 3.71 (ddd, J=12.3, 5.6, 2.6 Hz, 1H), 3.52 (ddd, J=12.2, 5.7, 4.5 Hz, 1H).

$^{19}$F NMR (376 MHz, DMSO-d$_6$) δ -196.33 (dt, J=55.1, 22.5 Hz).

LC/MS: $t_R$=0.77 min, MS m/z=373.14 [M+1]; LC system: Thermo Accela 1250 UHPLC

MS system: Thermo LCQ Fleet; Column: Kinetex 2.6μ C18 100A, 50×3.00 mm

Solvents: Acetonitrile with 0.1% formic acid, Water with 0.1% formic acid

Gradient: 0 min-1.4 min 2-100% ACN, 1.4 min-1.80 min 100% ACN, 1.8 min-1.85 min 100%-2% ACN, 1.85 min-2 min 2% ACN.

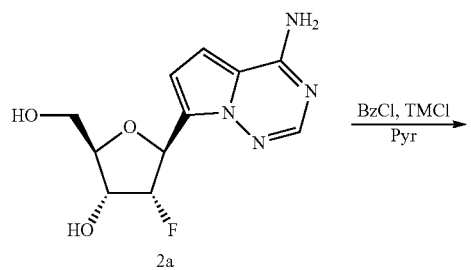

2a

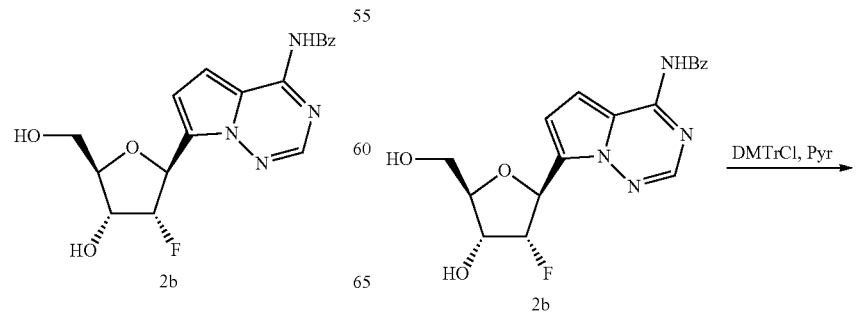

2b

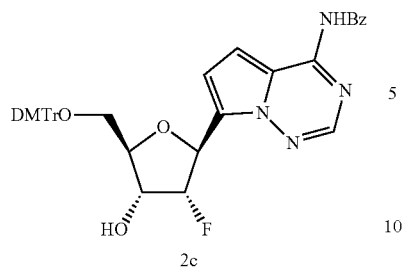

2c

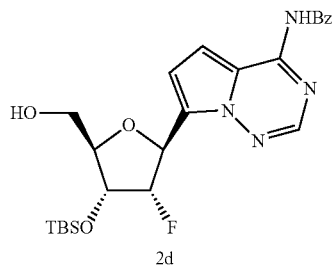

2d

Intermediate 2c

-N-(7-((2S,3R,4R,5R)-5-((bis(4-methoxyphenyl) (phenyl)methoxy)methyl)-3-fluoro-4-hydroxytetrahydrofuran-2-yl)pyrrolo[1,24][1,2,4]triazin-4-yl) benzamide Intermediate 2b (1.3 g, 3.49 mmol) was dried by coevaporation with pyridine. The dried material was then dissolved in pyridine (15 mL) under an $N_2$ atmosphere. 4,4'-Dimethoxytrityl chloride (1.71 g, 5.0 mmol) was added in one portion at room temperature and allowed to stir for 2 h. Ethanol (2 mL) was added and the resulting solution was stirred for 5 min. Solvents were removed under reduced pressure. The residue was purified by silica gel chromatography, using an eluent ramp of 0%-100% EtOAc in hexanes, to afford intermediate 2c.

$^1$H NMR (400 MHz, DMSO-$d_6$) δ 8.28-8.02 (m, 2H), 7.61 (t, J=7.5 Hz, 1H), 7.51 (t, J=7.6 Hz, 2H), 7.36 (ddt, J=6.0, 4.7, 2.0 Hz, 2H), 7.31-7.04 (m, 7H), 6.90-6.73 (m, 4H), 5.62 (d, J=24.4 Hz, 1H), 5.49 (d, J=7.0 Hz, 1H), 5.27-5.01 (m, 1H), 4.32-4.13 (m, 1H), 4.06-3.95 (m, 1H), 3.69 (s, 4H), 3.28 (s, 3H), 3.12 (dd, J=10.4, 5.2 Hz, 1H).

$^{19}$F NMR (376 MHz, DMSO-$d_6$) δ -195.58 (dt, J=52.1, 24.7 Hz).

LC/MS: $t_R$=1.37 min, MS m/z=675.29 [M+1]; LC system: Thermo Accela 1250 UHPLC

MS system: Thermo LCQ Fleet; Column: Kinetex 2.6μ C18 100A, 50×3.00 mm

Solvents: Acetonitrile with 0.1% formic acid, Water with 0.1% formic acid

Gradient: 0 min-1.4 min 2-100% ACN, 1.4 min-1.80 min 100% ACN, 1.8 min-1.85 min 100%-2% ACN, 1.85 min-2 min 2% ACN.

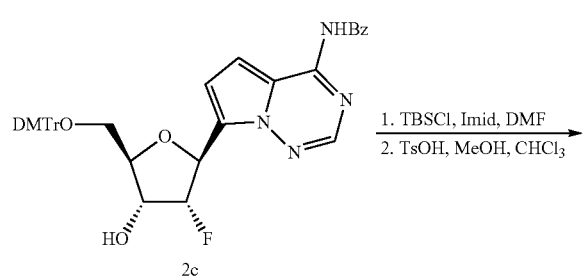

2c

Intermediate 2d

-N-(7-((2S,3S,4R,5R)-4-(tert-butyldimethylsilyloxy)-3-fluoro-5-(hydroxymethyl)tetrahydrofuran-2-yl)pyrrolo[1,2-f][1,2,4]triazin-4-yl)benzamide To a solution of intermediate 2c (1.47 g, 2.18 mmol) in DMF (8 mL), prepared under an $N_2$ atmosphere, was added imidazole (251 mg, 3.70 mmol), followed by tert-butylchlorodimethylsilane (492 mg, 3.27 mmol). The solution was allowed to stir at room temperature for 16 h. The solution was diluted with $H_2O$ (5 mL) and then the solvents were removed under reduced pressure. The residue was partitioned between EtOAc and $H_2O$. The layers were separated and the organic phase was then washed with brine. The organics were dried over $Na_2SO_4$, which was removed by filtration, and the filtrate was concentrated under reduced pressure. The crude material was used as is in the next step.

The crude material was dissolved in CHCl$_3$ (15 mL) and cooled to 0° C. p-Toluenesulfonic acid hydrate (414 mg, 2.18 mmol) dissolved in CH$_3$OH (6 mL) was added dropwise to the mixture and was allowed to stir for 15 min. The reaction was quenched with sat. NaHCO$_{3(aq)}$. The organics were washed with brine and dried over Na$_2$SO$_4$, filtered and the solvent was removed under reduced pressure. The residue was purified by silica gel chromatography, using an eluent ramp of 0%-50% EtOAc in hexanes, to afford intermediate 2d.

$^1$H NMR (400 MHz, DMSO-$d_6$) δ 8.21-7.98 (m, 2H), 7.51 (dt, J=39.9, 7.5 Hz, 3H), 7.12-6.86 (m, 2H), 5.48 (d, J=21.9 Hz, 1H), 5.07 (dt, J=54.6, 3.8 Hz, 1H), 4.86 (t, J=5.5 Hz, 1H), 4.28 (ddd, J=17.8, 7.1, 4.4 Hz, 1H), 3.83-3.72 (m, 1H), 3.63 (ddd, J=12.1, 5.2, 3.0 Hz, 1H), 3.43 (ddd, J=12.1, 6.0, 4.2 Hz, 1H), 0.80 (s, 9H), 0.01 (s, 3H), 0.00 (s, 3H).

$^{19}$F NMR (376 MHz, DMSO-$d_6$) δ -198.05 (dt, J=54.2, 19.8 Hz).

LC/MS: $t_R$=1.35 min, MS m/z=487.24 [M+1]; LC system: Thermo Accela 1250 UHPLC

MS system: Thermo LCQ Fleet; Column: Kinetex 2.6μ C18 100A, 50×3.00 mm

Solvents: Acetonitrile with 0.1% formic acid, Water with 0.1% formic acid

Gradient: 0 min-1.4 min 2-100% ACN, 1.4 min-1.80 min 100% ACN, 1.8 min-1.85 min 100%-2% ACN, 1.85 min-2 min 2% ACN.

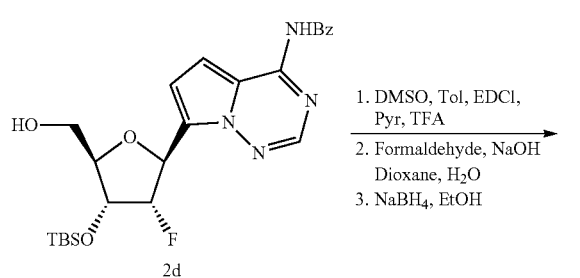

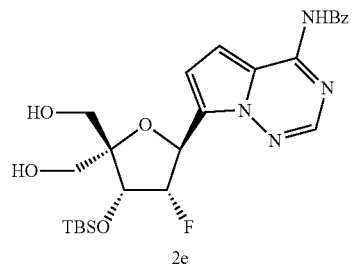

Intermediate 2e

-N-(7-((2S,3S,4R)-4-(tert-butyldimethylsilyloxy)-3-fluoro-5,5-bis(hydroxymethyl)tetrahydrofuran-2-yl)pyrrolo[1,2-f][1,2,4]triazin-4-yl)benzamide To solution of intermediate 2d (856 mg, 1.75 mmol) in toluene (4 mL), and DMSO (6 mL), prepared under an $N_2$ atmosphere, was added 1-ethyl-3-(3-dimethylaminopropyl)-carbodiimide hydrochloride (EDCl) (504 mg, 2.63 mmol). To this mixture was added pyridine (150 μL), and TFA (70 μL) and the mixture was stirred at RT for 15 min. Additional EDOI (100 mg) and pyridine (100 μL) was added and the mixture was stirred for an additional 45 min. The reaction was quenched with $H_2O$ (10 mL) and $CH_2Cl_2$ (10 mL). The organics were washed with brine and dried over $Na_2SO_4$, filtered, and the solvent was removed under reduced pressure to afford the crude aldehyde, which was used as is for the next step.

The crude aldehyde was dissolved in dioxane (5 mL) and 37% formaldehyde$_{(aq)}$ (925 μL) was added followed by 2N NaOH$_{(aq)}$ (925 μL). After stirring at room temperature for 3 h, the reaction was quenched with AcOH, diluted with EtOAc, and washed with $H_2O$. The organics were dried over $Na_2SO_4$, filtered, and the solvent was removed under reduced pressure to afford the crude aldol product, which was carried forward as is to the next step.

The crude aldol product was dissolved in EtOH (9 mL) under an $N_2$ atmosphere and cooled to 0° C. $NaBH_4$ (80 mg, 2.1 mmol) was added in one portion and the reaction was stirred for 10 min. The reaction was quenched with AcOH, diluted with $CH_2Cl_2$ and washed with a 1:1 solution of water and sat. $NaHCO_{3(aq)}$. The organic phase was dried over $Na_2SO_4$, filtered, and the solvent was removed under reduced pressure. The residue was purified by silica gel chromatography, using an eluent ramp from 0%-100% EtOAc in hexanes, to afford intermediate 2e.

$^1H$ NMR (400 MHz, DMSO-d$_6$) δ 8.20-7.99 (m, 2H), 7.51 (dt, J=39.5, 7.5 Hz, 3H), 7.15-6.93 (m, 2H), 5.50 (d, J=14.1 Hz, 1H), 5.24 (dt, J=54.2, 5.4 Hz, 1H), 4.78 (t, J=5.6 Hz, 1H), 4.48 (dd, J=10.7, 4.8 Hz, 1H), 4.34 (dd, J=6.7, 4.9 Hz, 1H), 3.62 (dd, J=11.9, 4.9 Hz, 1H), 3.55-3.35 (m, 3H), 0.82 (s, 9H), 0.07 (s, 3H), −0.09 (s, 3H).

$^{19}F$ NMR (376 MHz, DMSO-d$_6$) δ −200.37 (d, J=51.1 Hz).
LC/MS: $t_R$=1.25 min, MS m/z=517.21 [M+1]; LC system: Thermo Accela 1250 UHPLC
MS system: Thermo LCQ Fleet; Column: Kinetex 2.6μ C18 100A, 50×3.00 mm
Solvents: Acetonitrile with 0.1% formic acid, Water with 0.1% formic acid
Gradient: 0 min-1.4 min 2-100% ACN, 1.4 min-1.80 min 100% ACN, 1.8 min-1.85 min 100%-2% ACN, 1.85 min-2 min 2% ACN.

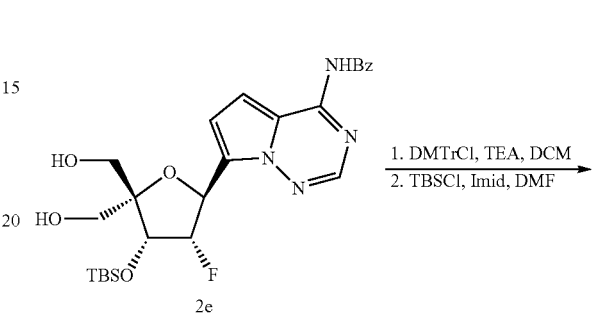

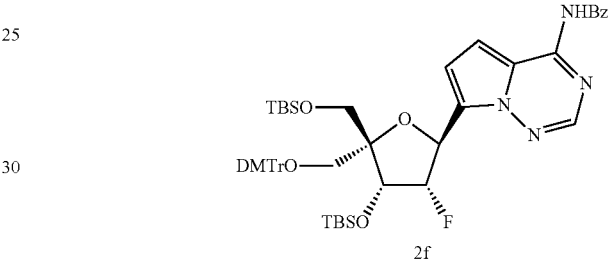

Intermediate 2f

-N-(7-((2S,3S,4R,5R)-5-((bis(4-methoxyphenyl)(phenyl)methoxy)methyl)-4-(tert-butyldimethylsilyloxy)-5-((tert-butyldimethylsilyloxy)methyl)-3-fluorotetrahydrofuran-2-yl)pyrrolo[1,24][1,2,4]triazin-4-yl)benzamide Intermediate 2e (370 mg, 0.717 mmol) was dissolved in $CH_2Cl_2$ (10 mL) and TEA (200 μL) under an $N_2$ atmosphere, and was then cooled to 0° C. 4,4'-Dimethoxytrityl chloride 4,4'-Dimethoxytrityl chloride (0.364g, 1.07 mmol) was added in one portion and the reaction mixture was allowed to stir for 30 min. $CH_3OH$ (2 mL) was added and the solution was diluted with $CH_2Cl_2$ and sat. $NaHCO_{3(aq)}$. The organic layer was washed with brine, dried over $Na_2SO_4$, filtered, and the solvents were removed under reduced pressure. The residue was purified by silica gel chromatography, using an eluent ramp of 5%-100% EtOAc in hexanes, to afford the crude product as a mixture of bis-DMTr and 4'β products. This mixture was carried forward without further purification.

To the crude product (574 mg, mixture) in DMF (3 mL), under an $N_2$ atmosphere, was added imidazole (143 mg, 2.10 mmol), followed by tert-butylchlorodimethylsilane (158 mg, 1.05 mmol). The solution was allowed to stir at room temperature for 2 h. The solution was diluted with $CH_3OH$ (1 mL) and EtOAc. The organics were washed with $H_2O$ and then with brine. The organic layer was dried over $Na_2SO_4$, filtered, and the solvent was removed under reduced pressure. The residue was purified by silica gel chromatography, using an eluent ramp of 0%-50% EtOAc in hexanes, to afford intermediate 2f that contained some bis-DMTr material.

LC/MS: $t_R$=2.25 min, MS m/z=933.52 [M+1]; LC system: Thermo Accela 1250 UHPLC

MS system: Thermo LCQ Fleet; Column: Kinetex 2.6μ C18 100A, 50×3.00 mm

Solvents: Acetonitrile with 0.1% formic acid, Water with 0.1% formic acid

Gradient: 0 min-1.5 min 2-100% ACN, 1.5 min-2.8 min 100% ACN, 2.8 min-2.85 min 100%-2% ACN, 2.85 min-3 min 2% ACN.

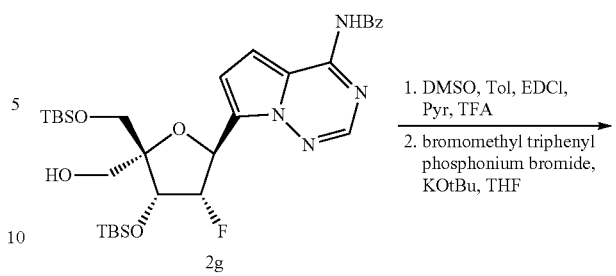

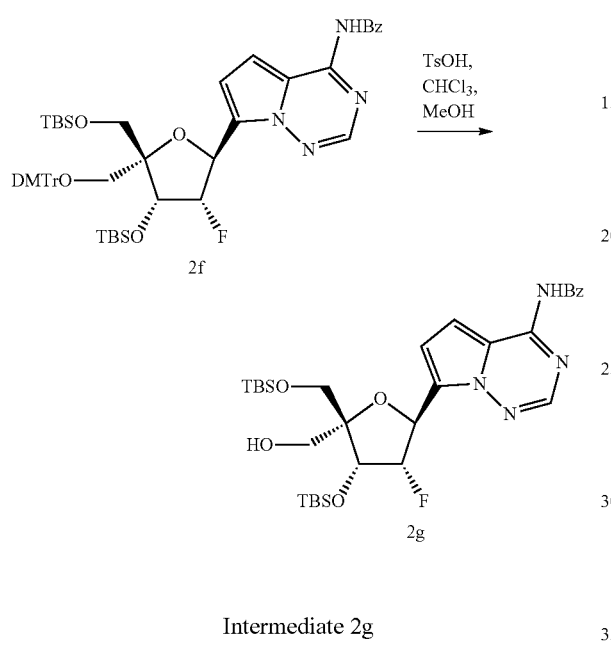

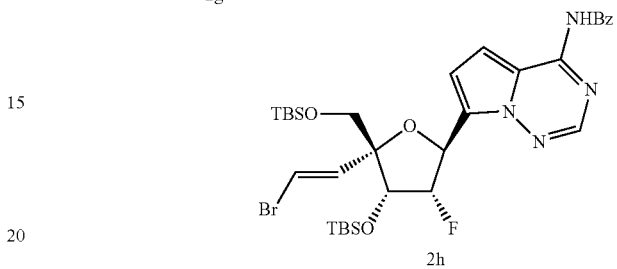

Intermediate 2g

-N-(7-((2S,3S,4R,5R)-4-(tert-butyldimethylsilyloxy)-5-((tert-butyldimethylsilyloxy)methyl)-3-fluoro-5-(hydroxymethyl)tetrahydrofuran-2-yl)pyrrolo[1,2-f][1,2,4]triazin-4-yl)benzamide Intermediate 2f was dissolved in CHCl₃ (5 mL) and was cooled to 0° C. p-Toluenesulfonic acid hydrate (90 mg, 0.474 mmol), dissolved in CH₃OH (4 mL) was added dropwise to the mixture and the reaction mixture was allowed to stir for 5 min. The reaction mixture was quenched with sat. NaHCO$_{3(aq)}$. The organics were washed with brine, dried over Na₂SO₄, filtered, and the solvent was removed under reduced pressure. The residue was purified by silica gel chromatography, using an eluent ramp of 0%-40% EtOAc in hexanes, to afford intermediate 2g.

$^1$H NMR (400 MHz, CDCl₃) δ 8.09-7.88 (m, 2H), 7.48 (dt, J=35.4, 7.4 Hz, 3H), 7.30 (d, J=4.6 Hz, 1H), 6.88 (s, 1H), 5.69 (dd, J=18.8, 4.2 Hz, 1H), 5.05 (dt, J=54.6, 4.7 Hz, 1H), 4.62 (dd, J=14.9, 5.1 Hz, 1H), 3.91-3.64 (m, 3H), 0.92-0.70 (m, 18H), 0.13-0.04 (m, 6H), 0.01 (m, 6H).

$^{19}$F NMR (376 MHz, CDCl₃) δ -196 (m)

LC/MS: $t_R$=2.61 min, MS m/z=631.43 [M+1]; C system: Thermo Accela 1250 UHPLC

MS system: Thermo LCQ Fleet; Column: Kinetex 2.6μ C18 100A, 50×3.00 mm

Solvents: Acetonitrile with 0.1% formic acid, Water with 0.1% formic acid

Gradient: 0 min-1.5 min 2-100% ACN, 1.5 min-2.8 min 100% ACN, 2.8 min-2.85 min 100%-2% ACN, 2.85 min-3 min 2% ACN.

Intermediate 2h

-N-(7-((2S,3S,4R,5R)-5-((E)-2-bromovinyl)-4-(tert-butyldimethylsilyloxy)-5-((tert-butyldimethylsilyloxy)methyl)-3-fluorotetrahydrofuran-2-yl)pyrrolo[1,2-f][1,2,4]triazin-4-yl)benzamide To solution of intermediate 2g (228 mg, 0.361 mmol) in toluene (0.75 mL), and DMSO (0.15 mL), was added 1-ethyl-3-(3-dimethylaminopropyl)carbodiimide hydrochloride (EDCl) (208 mg, 1.08 mmol) under an N₂ atmosphere. To this mixture was added pyridine (30 μL), and TFA (15 μL) and the mixture was stirred at RT for 30 min. The reaction was diluted with EtOAc and washed with H₂O followed by brine. The organics were dried over Na₂SO₄, filtered, and solvent was removed under reduced pressure to afford the crude aldehyde. This material was used as is for the next step.

To a suspension of bromomethyltriphenylphosphonium bromide (314 mg, 0.72 mmol) in THF (4 mL) at -40° C. was added KOtBu (1.0M in THF, 1.08 mL, 1.08 mmol) and the reaction mixture was stirred for 2 h under an N₂ atmosphere. The crude aldehyde was dissolved in THF (4 mL) and added dropwise. The reaction mixture was removed from the cold bath and allowed to warm to 10° C. over 1 h. The reaction mixture was re-cooled to -40° C. and the reaction mixture was quenched with sat NH$_4$Cl$_{(aq)}$. The layers were separated and the organics were dried over Na₂SO₄, filtered, and solvent was removed under reduced pressure. The residue was purified by silica gel chromatography, using an eluent of 0%-50% EtOAc in hexanes, to afford intermediate 2h.

$^1$H NMR (400 MHz, CDCl₃) δ 8.08-7.85 (m, 2H), 7.62-7.36 (m, 2H), 7.34-7.01 (m, 3H), 6.92 (s, 1H), 6.60-6.45 (m, 1H), 6.35 (d, J=8.2 Hz, 1H), 5.61 (d, J=25.1 Hz, 1H), 4.82 (dd, J=56.3, 4.9 Hz, 1H), 4.69-4.46 (m, 1H), 3.97 (d, J=11.4 Hz, 1H), 3.53 (d, J=11.4 Hz, 1H), 0.84 (d, J=3.9 Hz, 18H), 0.13--0.10 (m, 12H).

$^{19}$F NMR (376 MHz, CDCl₃) δ -190.60 (m).

LC/MS: $t_R$=2.10 min, MS m/z=705.54/707.29 [M+1]; LC system: Thermo Accela 1250 UHPLC; MS system: Thermo LCQ Fleet; Column: Kinetex 2.6μ C18 100A, 50×3.00 mm Solvents: Acetonitrile with 0.1% formic acid, Water with 0.1% formic acid Gradient: 0 min-1.5 min 2-100% ACN, 1.5 min-2.8 min 100% ACN, 2.8 min-2.85 min 100%-2% ACN, 2.85 min-3 min 2% ACN.

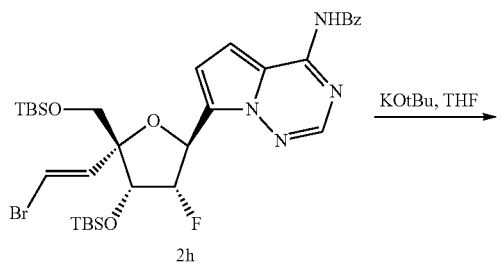

2h

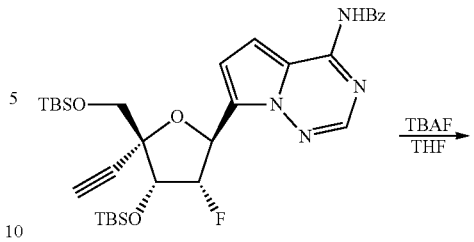

2i

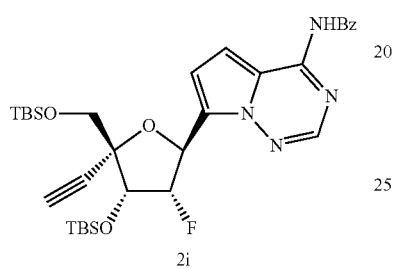

2i

Intermediate 2i

-N-(7-((2S,3S,4R,5R)-4-(tert-butyldimethylsilyloxy)-5-((tert-butyldimethylsilyloxy)methyl)-5-ethynyl-3-fluorotetrahydrofuran-2-yl)pyrrolo[1,2-f][1,2,4]triazin-4-yl)benzamide Intermediate 2h (204 mg, 0.289 mmol) was dissolved in THF (8 mL) under an N₂ atmosphere and cooled to −40° C. KOtBu (1.0M in THF, 1.08 mL, 1.08 mmol) was slowly added. The reaction was allowed to stir for 20 min as was quenched with sat. NH₄Cl$_{(aq)}$. The solution was diluted with EtOAc and washed with brine. The organics were dried over Na₂SO₄, filtered, and solvent was removed under reduced pressure. The residue was purified by silica gel chromatography, using an eluent ramp of 0%-50% EtOAc in hexanes, to afford intermediate 2i.

$^1$H NMR (400 MHz, CDCl₃) δ 8.12-7.88 (m, 2H), 7.51 (dt, J=36.5, 7.5 Hz, 2H), 7.32 (d, J=4.6 Hz, 1H), 6.88 (s, 1H), 5.79 (d, J=22.1 Hz, 1H), 5.02 (ddd, J=55.3, 5.1, 3.2 Hz, 1H), 4.56 (dd, J=18.1, 5.1 Hz, 1H), 3.91 (d, J=11.3 Hz, 1H), 3.83-3.62 (m, 1H), 2.55 (m, 1H), 0.90 (dd, J=25.3, 1.6 Hz, 18H), 0.20-−0.08 (m, 12H).

$^{19}$F NMR (376 MHz, CDCl₃) δ −193.10 (broad-s).

LC/MS: t$_R$=1.88 min, MS m/z=625.24 [M+1]; LC system: Thermo Accela 1250 UHPLC

MS system: Thermo LCQ Fleet; Column: Kinetex 2.6μ C18 100A, 50×3.00 mm

Solvents: Acetonitrile with 0.1% formic acid, Water with 0.1% formic acid

Gradient: 0 min-1.5 min 2-100% ACN, 1.5 min-2.8 min 100% ACN, 2.8 min-2.85 min 100%-2% ACN, 2.85 min-3 min 2% ACN.

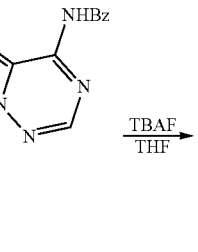

2j

Intermediate 2j

-N-(7-((2S,3R,4R,5R)-5-ethynyl-3-fluoro-4-hydroxy-5-(hydroxymethyl)tetrahydrofuran-2-yl)pyrrolo[1,2-f][1,2,4]triazin-4-yl)benzamide To a solution of intermediate 2i (152 mg, 0.243 mmol) in THF (3.5 mL) under an N₂ atmosphere was added TBAF (1.0M in THF, 700 μL, 0.700 mmol) at room temperature and the mixture was allowed to stir for 30 min. Solvents were removed under reduced pressure. The residue was purified by silica gel chromatography, using an eluent ramp of 40%-100% EtOAc in hexanes, to afford intermediate 2j.

LC/MS: t$_R$=0.88 min, MS m/z=397.16 [M+1]; LC system: Thermo Accela 1250 UHPLC

MS system: Thermo LCQ Fleet; Column: Kinetex 2.6μ C18 100A, 50×3.00 mm

Solvents: Acetonitrile with 0.1% formic acid, Water with 0.1% formic acid

Gradient: 0 min-1.5 min 2-100% ACN, 1.5 min-2.8 min 100% ACN, 2.8 min-2.85 min 100%-2% ACN, 2.85 min-3 min 2% ACN.

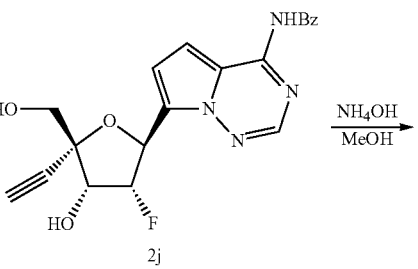

2j

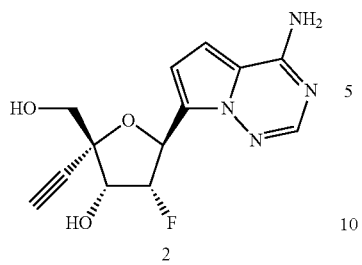

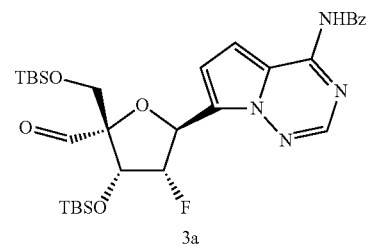

Example 2

-(2R,3R,4R,5S)-5-(4-aminopyrrolo[1,2-f][1,2,4]triazin-7-yl)-2-ethynyl-4-fluoro-2-(hydroxymethyl)tetrahydrofuran-3-ol To a solution of intermediate 2j (71 mg, 0.179 mmol) in CH₃OH (2 mL) was added con. NH₄OH$_{(aq)}$ (0.7 mL) and the resulting solution was stirred at room temperature for 16 h. Solvents were removed under reduced pressure. The residue was purified by silica gel chromatography, using an eluent ramp of 0%-20% CH₃OH in CH₂Cl₂, followed by reverse phase HPLC, using an eluent ramp of 0%-20% ACN in H₂O, to yield example 2.

$^1$H NMR (400 MHz, CD₃OD) δ 7.77 (s, 1H), 6.90-6.70 (m, 2H), 5.62 (dd, J=25.5, 2.6 Hz, 1H), 5.18 (ddd, J=56.0, 5.4, 2.7 Hz, 1H), 4.57 (dd, J=20.5, 5.4 Hz, 1H), 3.93-3.59 (m, 2H), 3.02 (d, J=0.7 Hz, 1H).

$^{19}$F NMR (376 MHz, CD₃OD) δ −193.76 (ddd, J=56.0, 25.5, 20.4 Hz).

LC/MS: $t_R$=0.45 min, MS m/z=293.13 [M+1]; LC system: Thermo Accela 1250 UHPLC

MS system: Thermo LCQ Fleet; Column: Kinetex 2.6μ C18 100A, 50×3.00 mm

Solvents: Acetonitrile with 0.1% formic acid, Water with 0.1% formic acid

Gradient: 0 min-1.4 min 2-100% ACN, 1.4 min-1.80 min 100% ACN, 1.8 min-1.85 min 100%-2% ACN, 1.85 min-2 min 2% ACN.

HPLC: $t_R$=3.112 min; HPLC system: Agilent 1100 series.

Column: Phenomenex Kinetex C18 2.6 μm 100A, 4.6×100 mm

Solvents: Acetonitrile with 0.1% TFA, Water with 0.1% TFA

Gradient: 0 min-8.0 min 2-98% ACN at 1.5 mL/min.

Intermediate 3a

-N-(7-((2S,3S,4R,5R)-4-(tert-butyldimethylsilyloxy)-5-((tert-butyldimethylsilyloxy)methyl)-3-fluoro-5-formyltetrahydrofuran-2-yl)pyrrolo[1,2-f][1,2,4]triazin-4-yl)benzamide To a solution of intermediate 2g (1.13 g, 1.79 mmol) in DMSO (1 mL) and toluene (10 mL), prepared under an N₂ atmosphere, was added EDCl.HCl (1.02 g, 5.36 mmol) and pyridine (149 μL, 1.92 mmol). TFA (74 μL, 0.97 mmol) was added drop-wise. After 1 hr the reaction was checked by LC/MS. A single peak was observed, with a retention time similar to the starting material's, but with an M+1 peak equal to that expected for the product. Another 50 μL of pyridine was added and the reaction was stirred for another 15 min. No change by LC/MS. The reaction was diluted with EtOAc and quenched with a 1:1 mixture of sat. NaHCO₃$_{(aq.)}$ and H₂O. The mixture was partitioned between EtOAc and more H₂O. The organic layer was separated and washed with H₂O, brine, and then dried over Na₂SO₄. The drying agent was removed by vacuum filtration and the filtrate was concentrated. The residue was taken up in CH₂Cl₂, concentrated, and the resulting material was placed under high vacuum for 1 h. The product, intermediate 3a was used as is in the next reaction.

LC/MS: $t_R$=1.90 min, MS m/z=629.46 [M+1]; LC system: Thermo Accela 1250 UHPLC

MS system: Thermo La) Fleet; Column: Kinetex 2.6μ C18 100A, 50×3.00 mm

Solvents: Acetonitrile with 0.1% formic acid, Water with 0.1% formic acid

Gradient: 0 min-1.5 min 2-100% ACN, 1.5 min-2.8 min 100% ACN, 2.8 min-2.85 min 100%-2% ACN, 2.85 min-3 min 2% ACN.

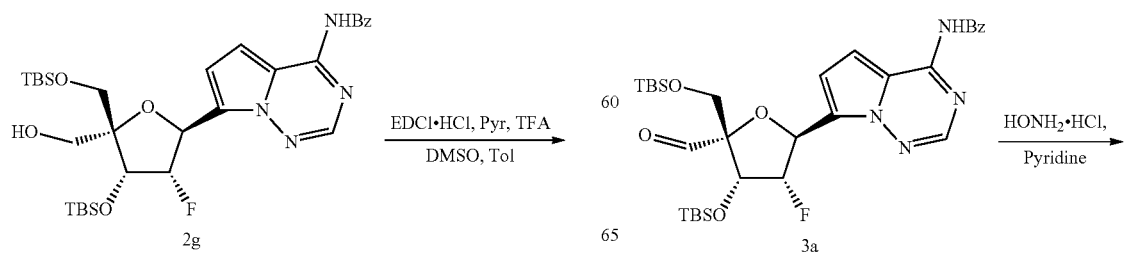

-continued

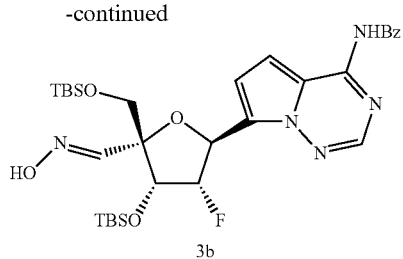

Intermediate 3b

-N-(7-((2S,3S,4R,5R)-4-(tert-butyldimethylsily-loxy)-5-((tert-butyldimethylsilyloxy)methyl)-3-fluoro-5-((E)-(hydroxyimino)methyl)tetrahydrofuran-2-yl)pyrrolo[1,2-f][1,2,4]triazin-4-yl)benzamide To a solution of intermediate 3a (crude material from previous step, assumed 1.79 mmol) in pyridine (11 mL), prepared under an N₂ atmosphere, was added HONH₂·HCl in one portion at room temperature. The reaction was checked by LC/MS 5 minutes later; starting material was consumed. The reaction was checked again 25 minutes later. There was no change from the first time point. The reaction was concentrated and the residue was partitioned between EtOAc and H₂O. The organic layer was separated, washed with brine, dried over Na₂SO₄ and filtered. The filtrate was concentrated, taken up in CH₂Cl₂, concentrated again, and the residue was placed under high vacuum. The product intermediate 3b was used as is in the next reaction.

LC/MS: $t_R$=1.83 min, MS m/z=644.55 [M+1]; LC system: Thermo Accela 1250 UHPLC

MS system: Thermo LCQ Fleet; Column: Kinetex 2.6μ C18 100A, 50×3.00 mm

Solvents: Acetonitrile with 0.1% formic acid, Water with 0.1% formic acid

Gradient: 0 min-1.5 min 2-100% ACN, 1.5 min-2.8 min 100% ACN, 2.8 min-2.85 min 100%-2% ACN, 2.85 min-3 min 2% ACN.

Intermediate 3c

-N-(7-((2S,3S,4R,5R)-4-(tert-butyldimethylsily-loxy)-5-((tert-butyldimethylsilyloxy)methyl)-5-cyano-3-fluorotetrahydrofuran-2-yl)pyrrolo[1,2-f][1,2,4]triazin-4-yl)benzamide To a solution of intermediate 3b (crude material from the previous step, assumed 1.79 mmol) in ACN (16 mL) was added CDI (436 mg, 2.69 mmol) in a single portion. The reaction was run under an N₂ atmosphere. The reaction was checked by LC/MS after 20 minutes. Peaks with the mass of starting material and product are barely time resolved. The reaction was checked 1.5 h later. The UV peak corresponding to the starting material was nearly gone and the intensity of the mass peak was diminished. The reaction was diluted with CH₂Cl₂ and quenched with a 1:1 mixture of sat. NaHCO₃(aq.) and H₂O. The layers were separated, the aqueous was back extracted with CH₂Cl₂ and the combined organics layers were extracted with a 1:1 mixture of brine and H₂O, dried over Na₂SO₄ and filtered. The filtrate was concentrated and intermediate 3c was isolated by silica gel column chromatography using the following solvent ramp: 0% EtOAc in hexanes ramping to 20% EtOAc in hexanes, pause at 20% EtOAc in hexanes and then ramping to 40% EtOAc in hexanes.

¹H NMR (400 MHz, DMSO-d₆) δ 8.31 (s, 1H), 8.07 (s, 1H), 7.65 (t, J=8 Hz, 1H), 7.54 (t, J=8 Hz, 1H), 7.15 (d, 4 Hz, 1H), 7.02 (s, 1H), 5.82 (d, J=24 Hz, 1H), 5.51 (ddd, J=52, 4.8, 2.8 Hz, 1H), 4.70 (dd, J=18.4, 4.4 Hz, 1H), 3.94 (dd, J=53.2, 11.2 Hz, 2H), 0.93 (s, 9H,), 0.84 (s, 9H), 0.17 (s, 3H), 0.16 (s, 3H), 0.05 (s, 3H), 0.01 (s, 3H).

¹⁹F NMR (376 MHz, DMSO-d₆) δ -194.658 (dt, J=53, 21.4 Hz).

LC/MS: $t_R$=1.84 min, MS m/z=626.60 [M+1]; LC system: Thermo Accela 1250 UHPLC

MS system: Thermo LCQ Fleet; Column: Kinetex 2.6μ C18 100A, 50×3.00 mm

Solvents: Acetonitrile with 0.1% formic acid, Water with 0.1% formic acid

Gradient: 0 min-1.5 min 2-100% ACN, 1.5 min-2.8 min 100% ACN, 2.8 min-2.85 min 100%-2% ACN, 2.85 min-3 min 2% ACN.

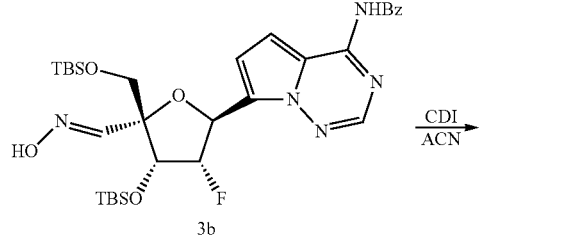

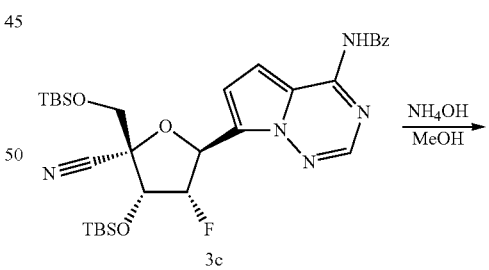

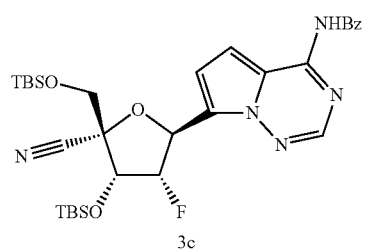

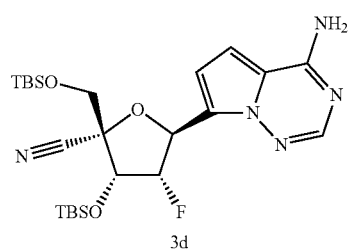

Intermediate 3d

-(2R,3R,4S,5S)-5-(4-aminopyrrolo[1,24][1,2,4]tri-azin-7-yl)-3-(tert-butyldimethylsilyloxy)-2-((tert-butyldimethylsilyloxy)methyl)-4-fluorotetrahydrofuran-2-carbonitrile To a solution of intermediate 3c (770 mg, 1.23 mmol) in MeOH (11.2 mL), cooled in an ice water bath, was added concentrated $NH_4OH_{(aq)}$ (3.74 mL). The cold bath was removed and the resulting heterogeneous solution was stirred overnight. The next day the reaction was incomplete as determined by LC/MS. Additional concentrated $NH_4OH_{(aq)}$ (4 mL) and 2-MeTHF (12 mL) was added. The reaction became homogenous but after 20 minutes there was no additional reaction progress. The reaction was concentrated and the residue was dissolved in THF (15 mL). To this mixture was added concentrated $NH_4OH_{(aq)}$ (5 mL) and enough MeOH (1.9 mL) to turn the solution homogenous and monophasic. The reaction was stirred at room temperature for 22 h. The reaction was nearly complete (about 5% of the starting material remains). The reaction was diluted with $CH_2Cl_2$ and $H_2O$. The layers were separated, and the aqueous layer was diluted with saturated $NaHCO_{3(aq)}$ and extracted with $CH_2Cl_2$. The aqueous layer was neutralized with 2N HCl and then extracted with $CH_2Cl_2$. The combined organic layers were dried over $Na_2SO_4$, which was removed by filtration. The filtrate was concentrated and intermediate 3d was isolated from the residue by silica gel column chromatography using the following solvent ramp: 0% EtOAc in hexanes ramping to 50% EtOAc in hexanes, pause at 50% EtOAc in hexanes and then ramping to 100% EtOAc in hexanes.

LC/MS: $t_R$=1.59 min, MS m/z=522.47 [M+1]; LC system: Thermo Accela 1250 UHPLC

MS system: Thermo LCQ Fleet; Column: Kinetex 2.6μ C18 100A, 50×3.00 mm

Solvents: Acetonitrile with 0.1% formic acid, Water with 0.1% formic acid

Gradient: 0 min-1.4 min 2-100% ACN, 1.4 min-1.8 min 100% ACN, 1.8 min-1.85 min 100%-2% ACN, 1.85 min-2 min 2% ACN.

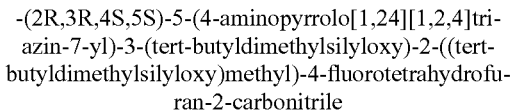

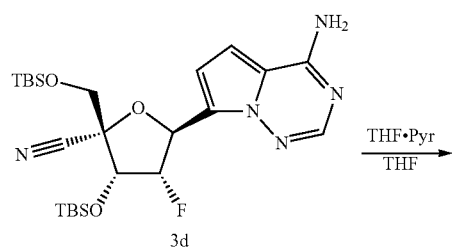

3d

Example 3

-(2R,3R,4R,5S)-5-(4-aminopyrrolo[1,24][1,2,4]tri-azin-7-yl)-4-fluoro-3-hydroxy-2-(hydroxymethyl) tetrahydrofuran-2-carbonitrile To a solution of intermediate 3d (100 mg, 0.191 mmol) in THF (2 mL), in a polypropylene tube, was added 70% HF.Pyridine in pyridine (60 μL, 0.478 mmol) at 0° C., under an $N_2$ atmosphere. The reaction was checked after 20 minutes; there was no reaction, so additional 70% HF.Pyridine in pyridine (150 μL) was added and the cold bath was removed. After 1 hour and 50 minutes additional 70% HF.Pyridine in pyridine (150 μL) was added. After another 2 hours additional 70% HF.Pyridine in pyridine (300 μL) was added. After another 2 hours and 15 minutes additional 70% HF.Pyridine in pyridine (1 mL) was added. The reaction turns clear and homogenous upon this final addition of 70% HF.Pyridine in pyridine. The reaction was stirred overnight. The reaction was complete the next day. The reaction was cooled in an ice bath and quenched with $H_2O$ and a small amount of saturated $NaHCO_{3(aq)}$. The mixture was concentrated and the residue was taken up in DMSO. Remaining insoluble material was removed by filtration and the filtrate was semipurified by HPLC. The isolated material was dissolved in DMF and purified by HPLC. Example 3 was isolated, with 0.5% as a TFA salt.

$^1$H NMR (400 MHz, DMF-$d_7$) δ 7.92 (s, 1H), 6.99 (d, J=4.4 Hz, 1H), 6.89 (d, J=4.9 Hz, 1H), 6.64 (d, J=6 Hz, 1H), 5.92 (t, J=6.4 Hz, 1H), 5.83 (dd, J=25.2, 2 Hz, 1H), 5.40 (ddd, J=54.8, 4.8, 2.4 Hz, 1H), 4.75 (dt, J=22, 5.2 Hz, 1H), 4.02 (dd, J=12, 6.4 Hz, 1H), 3.87 (dd, J=12, 6.4 Hz, 1H).

$^{19}$F NMR (376 MHz, DMF-$d_7$) δ −74.92 (s), −193.726 (dt, J=54.5, 23.3 Hz).

LC/MS: $t_R$=0.56 min, MS m/z=294.10 [M+1]; LC system: Thermo Accela 1250 UHPLC

MS system: Thermo LCQ Fleet; Column: Kinetex 2.6μ C18 100A, 50×3.00 mm

Solvents: Acetonitrile with 0.1% formic acid, Water with 0.1% formic acid

Gradient: 0 min-1.4 min 2-100% ACN, 1.4 min-1.8 min 100% ACN, 1.8 min-1.85 min 100%-2% ACN, 1.85 min-2 min 2% ACN.

HPLC: $t_R$=3.220 min; HPLC system: Agilent 1100 series.; Column: Phenomenex Kinetex C18 2.6 μm 100A, 4.6×100 mm; Solvents: Acetonitrile with 0.1% TFA, Water with 0.1% TFA Gradient: 0 min-8.0 min 2-98% ACN at 1.5 mL/min.

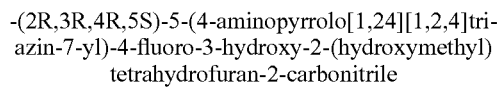

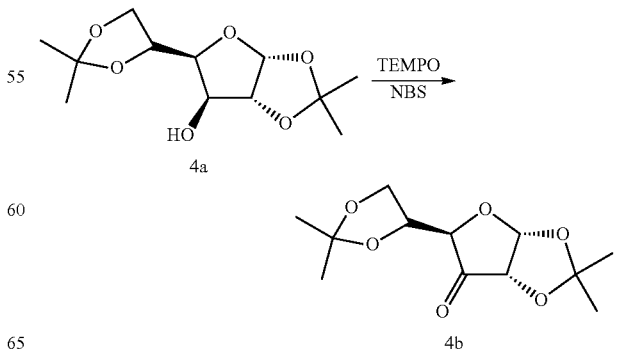

3

4a

4b

Intermediate 4b

-(3aR,5R,6aS)-5-((R)-2,2-dimethyl-1,3-dioxolan-4-yl)-2,2-dimethyldihydrofuro[3,2-d][1,3]dioxol-6(3aH)-one Into a 10-L 4-necked round-bottom flask, was placed a solution of intermediate 4a, (3aR,5S,6S,6aR)-5-((R)-2,2-dimethyl-1,3-dioxolan-4-yl-2,2-dimethyltetrahydrofuro[3,2-d][1,3]dioxol-6-ol (500 g, 1.90 mol) in dichloromethane/water (2.7 L/2.3 L) at room temperature. To this was added sodium carbonate (290 g, 3.42 mol). Addition of potassium carbonate (451 g, 3.24 mol) was next. This was followed by the addition of 2,2,6,6-tetramethylpiperidinooxy (TEMPO, 15.2 g, 96.31 mmol). To the mixture was added tetrabutylammonium bromide (31 g, 95.20 mmol). To the above was added N-bromosuccinimide (514 g, 2.86 mol), in portions at 35° C. The resulting solution was allowed to react, with stirring, for 2 h at room temperature. The resulting solution was extracted with 2×1 L of dichloromethane and the organic layers combined. The resulting mixture was washed with 1×1.5 L of water. The mixture was dried over anhydrous sodium sulfate and concentrated under vacuum. This resulted in (crude) intermediate 4b.

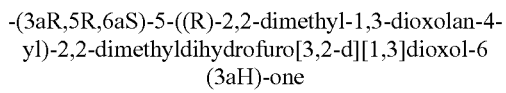

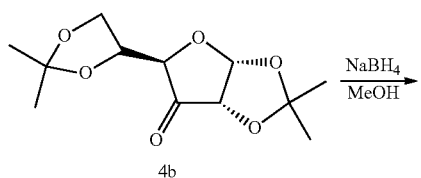

Intermediate 4c

-(3aR,5S,6R,6aR)-5-((R)-2,2-dimethyl-1,3-dioxolan-4-yl)-2,2-dimethyltetrahydrofuro[3,2-d][1,3]dioxol-6-ol Into a 2-L 4-necked round-bottom flask, was placed a solution of intermediate 4b (370 g, 1.29 mol) in methanol (1300 mL). To the above was added sodium borohydride (26.4 g, 706.38 mmol), in portions at room temperature. The resulting solution was allowed to react, with stirring, for 2 h at room temperature. The resulting mixture was concentrated under vacuum. The reaction was then quenched by the addition of 1000 mL of 5% aqueous ammonium chloride solution. The resulting solution was extracted with 3×500 mL of dichloromethane and the organic layers combined. The resulting solution was washed with 2×300 mL of water. The mixture was dried over anhydrous sodium sulfate and concentrated under vacuum. The crude product was purified by re-crystallization from petroleum ether. This resulted in intermediate 4c.

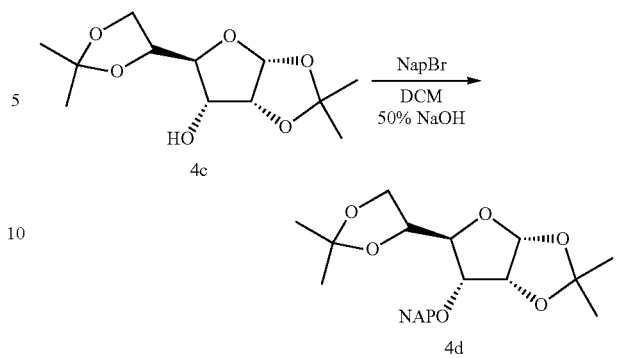

Intermediate 4d

Into a 5000-mL 4-necked round-bottom flask, was placed a solution of intermediate 4c (350 g, 1.34 mol) in dichloromethane (700 mL). To this was added tetrabutylammonium bromide (476.8 g, 1.48 mol). To the mixture was added 50% sodium hydroxide/water (700 g). To the above was added 2-(bromomethyl) naphthalene (340 g, 1.54 mol) in several batches. The resulting solution was allowed to react, with stirring, for 4 h at room temperature. The reaction was then quenched by the addition of 1800 mL of dichloromethane/water (1:1). The resulting solution was extracted with 2×1 L of dichloromethane and the organic layers combined. The resulting mixture was washed with 1×1000 mL of water. The residue was dissolved in 1000/1000 mL of petroleum ether/water. The crude product was purified by re-crystallization from petroleum ether. This resulted in intermediate 4d.

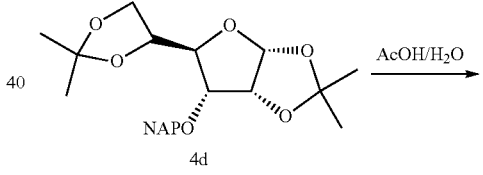

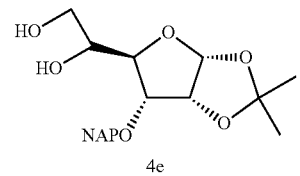

Intermediate 4e

-(R)-1-((3aR,5R,6R,6aR)-2,2-dimethyl-6-(naphthalen-2-ylmethoxy)tetrahydrofuro[3,2-d][1,3]dioxol-5-yl)ethane-1,2-diol Into a 5-L 4-necked round-bottom flask, was placed intermediate 4d (500 g, 1.25 mol). To this was added acetic acid (1.8 L). To the mixture was added water (600 mL). The resulting solution was allowed to react, with stirring, overnight at room temperature. The solids were filtered out. The resulting solution was extracted with 3×1 L of petroleum ether and the aqueous layers combined. The resulting solution was diluted with 2 L of ethyl acetate. The resulting mixture was washed with 2×2 L of sodium chloride$_{(aq)}$. The pH value of the solution was adjusted to 8 with sodium carbonate (50%). The resulting solution was extracted with 2×1 L of ethyl acetate and the organic layers combined and concentrated under vacuum. This resulted in intermediate 4e.

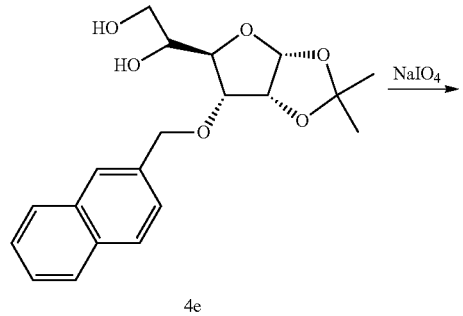

4e

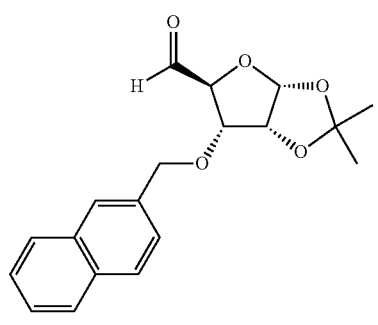

4f

Intermediate 4f

-(3aR,5S,6R,6aR)-2,2-dimethyl-6-(naphthalen-2-ylmethoxy)tetrahydrofuro[3,2-d][1,3]dioxole-5-carbaldehyde Into a 10 L 4-necked round-bottom flask, was placed a solution of intermediate 4e (300 g, 833.33 mmol) in 1,4-dioxane (2100 mL) at room temperature. This was followed by the addition of a solution of sodium periodate (250 g) in water (4000 mL) at room temperature in 0.5 h. The resulting solution was allowed to react, with stirring, for 0.5 hr at room temperature. The solids were filtered out. The resulting solution was extracted with 3×1000 mL of ethyl acetate and the organic layers combined. The resulting mixture was washed with 2×1000 mL of sodium chloride$_{(aq)}$. The resulting mixture was concentrated under vacuum. This resulted in intermediate 4f.

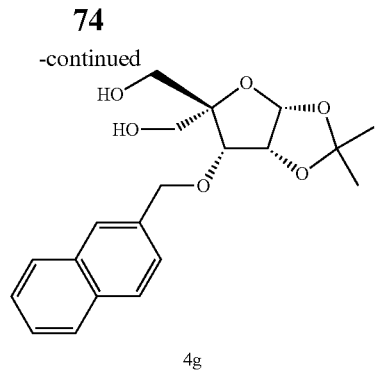

4g

Intermediate 4g

-((3aR,6S,6aR)-2,2-dimethyl-6-(naphthalen-2-ylmethoxy)tetrahydrofuro[3,2-d][1,3]dioxole-5,5-diyl)dimethanol Into a 10-L 4-necked round-bottom flask, was placed a solution of intermediate 4f (250 g, 761.36 mmol) in water/tetrahydrofuran (1250/1250 mL) at room temperature. To the above was added 2N sodium hydroxide$_{(aq)}$ (1500 mL) dropwise with stirring at 0-15° C. To the mixture was added formaldehyde (620 mL). The resulting solution was allowed to react, with stirring, overnight at room temperature. The resulting solution was extracted with 2×2000 mL of ethyl acetate. The resulting mixture was washed with 2×2000 mL of sodium chloride$_{(aq)}$. The organic layers combined and dried over anhydrous sodium sulfate. The residue was applied onto a silica gel column with petroleum ether: ethyl acetate (2/1). The crude product was re-crystallized from ethyl acetate:ethanol in the ratio of 1g/(1 mL:1 mL). This resulted in intermediate 4g.

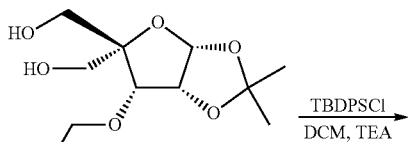

4g

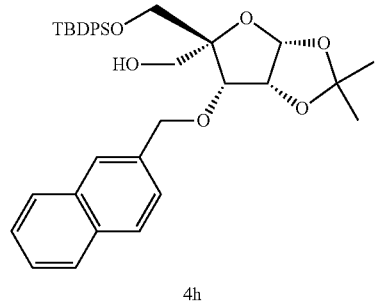

4h

Intermediate 4h

-((3aR,5R,6S,6aR)-5-((tert-butyldiphenylsilyloxy)methyl)-2,2-dimethyl-6-(naphthalen-2-ylmethoxy)tetrahydrofuro[3,2-d][1,3]dioxol-5-yl)methanol Into a 5-L 4-necked round-bottom flask purged and maintained with an inert atmosphere of nitrogen, was placed a solution of intermediate 4g (125 g, 346.84 mmol) in dichloromethane (2500 mL) at room temperature. To the mixture was added triethylamine (157.5 mL) at room temperature. To the above was added tert-butyldiphenylsilyl chloride (157.5 mL) dropwise with stirring at 0-10° C. The resulting solution was allowed to react, with stirring, overnight at room temperature. The reaction was then quenched by the addition of 37.5 mL of methanol. The resulting mixture was washed with 2×500 mL of 5% hydrogen chloride$_{(aq)}$ and 2×500 mL of sodium bicarbonate$_{(aq)}$. The resulting mixture was washed with 2×500 mL of 1N sodium hydroxide$_{(aq)}$. The mixture was dried over anhydrous sodium sulfate and concentrated under vacuum. The crude product was purified by re-crystallization from dichloromethane/hexane. This resulted in intermediate 4h.

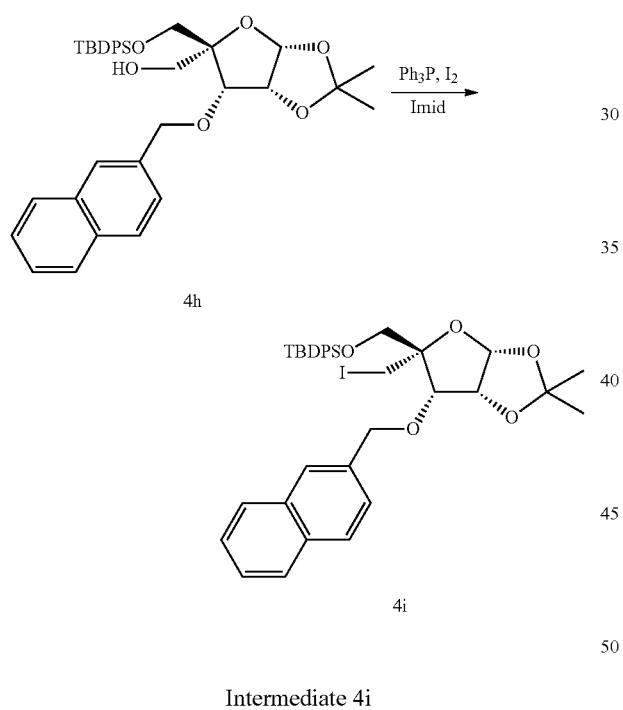

Intermediate 4i

-tert-butyl(a3aR,5R,6S,6aR)-5-(iodomethyl)-2,2-dimethyl-6-(naphthalen-2-ylmethoxy)tetrahydrofuro[3,2-d][1,3]dioxol-5-yl)methoxy)diphenylsilane Into a 1000-mL 3-necked round-bottom flask purged and maintained with an inert atmosphere of nitrogen, was placed a solution of intermediate 4h (20 g, 31.73 mmol) in toluene (320 mL), triphenylphosphine (35 g, 132.11 mmol), imidazole (8.96 g, 132.26 mmol). This was followed by the addition of iodine (16.95 g, 66.8 mmol) in several batches at 60° C. The resulting solution was stirred overnight at 80° C. in an oil bath. The reaction mixture was cooled to room temperature with a water/ice bath. The resulting solution was diluted with 1000 mL of ethyl acetate. The resulting mixture was washed with 2×300 mL of sodium thiosulfate$_{(aq)}$. The resulting mixture was washed with 1×300 mL of sodium chloride$_{(aq)}$. The mixture was dried over anhydrous sodium sulfate and concentrated under vacuum. The residue was applied onto a silica gel column with ethyl acetate/petroleum ether (1:10). This resulted in intermediate 4i.

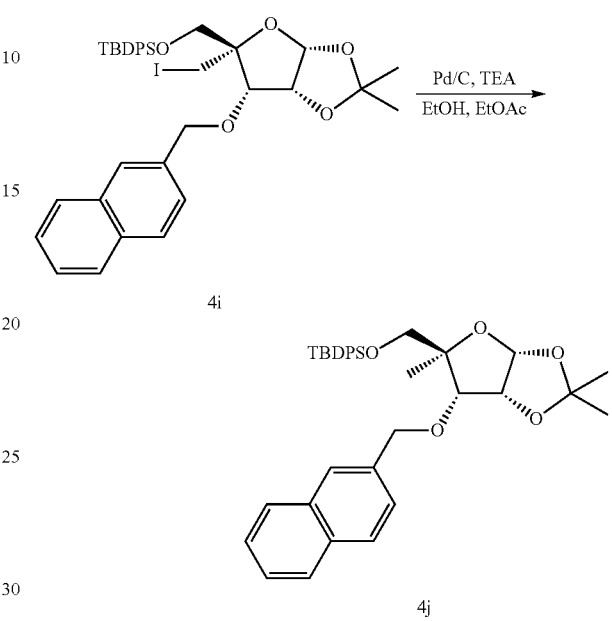

Intermediate 4j

-tert-butyldiphenyl(((3aR,5R,6S,6aR)-2,2,5-trimethyl-6-(naphthalen-2-ylmethoxy)tetrahydrofuro[3,2-d][1,3]dioxol-5-yl)methoxy)silane Into a 2000-mL round-bottom flask purged and maintained with an inert atmosphere of nitrogen, was placed a solution of intermediate 4i (66 g, 88.47 mmol) in ethanol/ethyl acetate (600/600 mL), triethylamine (20.7 g, 202.52 mmol), palladium on carbon (10% wt, 24.8 g, 23.30 mmol). The resulting solution was stirred for 3 h at 40° C. The solids were filtered out. The resulting mixture was concentrated under vacuum. The resulting solution was diluted with 1500 mL of ethyl acetate. The resulting mixture was washed with 1×500 mL of sodium chloride$_{(aq)}$. The mixture was dried over anhydrous sodium sulfate and concentrated under vacuum. This resulted in intermediate 4j.

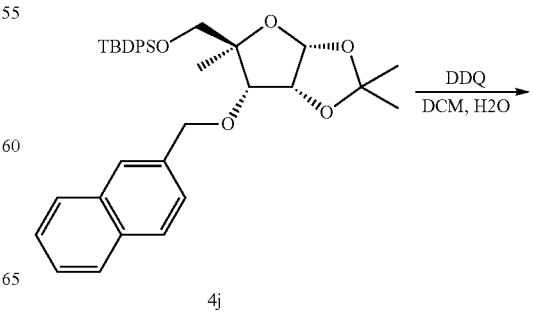

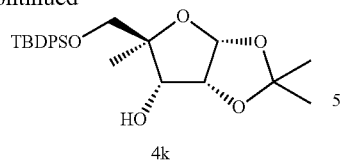

Intermediate 4k

-(3aR,5R,6S,6aR)-5-((tert-butyldiphenylsilyloxy)methyl)-2,2,5-trimethyltetrahydrofuro[3,2-d][1,3]dioxol-6-ol Into a 500-mL round-bottom flask, was placed a solution of intermediate 4j (1.0 g, 1.63 mmol) in dichloromethane (15 mL), water (1.25 mL), and 2,3-dichloro-5,6-dicyano-1,4-benzoquinone (DDQ, 780 mg, 3.40 mmol). The resulting solution was stirred for 1 h at room temperature. The resulting solution was diluted with 50 mL of dichloromethane. The resulting mixture was washed with 1×30 mL of water and 2×30 mL of sodium bicarbonate$_{(aq)}$. The resulting mixture was washed with 1×30 mL of sodium chloride$_{(aq)}$. The mixture was dried over anhydrous sodium sulfate and concentrated under vacuum. The residue was applied onto a silica gel column with ethyl acetate/petroleum ether (1:20-1:10). This resulted in intermediate 4k.

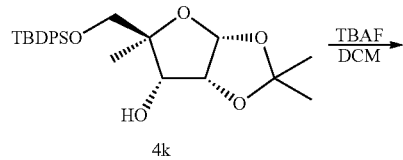

Intermediate 4l

-(3aR,5R,6S,6aR)-5-(hydroxymethyl)-2,2,5-trimethyltetrahydrofuro[3,2-d][1,3]dioxol-6-ol Into a 50-mL round-bottom flask, was placed a solution of intermediate 4k (520 mg, 1.12 mmol) in tetrahydrofuran (9 mL), Tetrabutylammonium fluoride (369 mg, 1.40 mmol). The resulting solution was stirred for 2 h at room temperature. The resulting mixture was concentrated under vacuum. The residue was applied onto a silica gel column with dichloromethane/methanol (100:1). This resulted in intermediate 4l.

$^1$H NMR (300 MHz, DMSO-d$_6$): δ 5.64 (d, J=3.9 Hz, 1H), 4.96 (d, J=6.6 Hz, 1H), 4.67 (m, 1H), 4.55 (m, 1H), 4.05 (m, 1H), 3.24-3.30 (m, 1H), 3.11-3.18 (m, 1H), 1.50 (s, 3H), 1.27 (s, 3H), 1.16 (s, 1H).

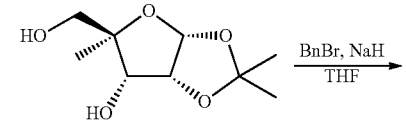

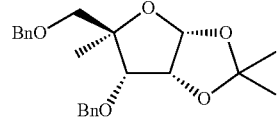

Intermediate 4m

-(3aR,5R,6S,6aR)-6-(benzyloxy)-5-(benzyloxymethyl)-2,2,5-trimethyltetrahydrofuro[3,2-d][1,3]dioxole Into a 50-mL 3-necked round-bottom flask purged and maintained with an inert atmosphere of nitrogen, was placed a solution of intermediate 4l (180 mg, 0.84 mmol) in tetrahydrofuran (4 mL). This was followed by the addition of sodium hydride (60% wt., 140 mg, 3.50 mmol), in portions at 0° C. The resulting solution was stirred for 30 min at 0° C. The resulting solution was allowed to react, with stirring, for an additional 30 min at room temperature. To this was added benzyl bromide (452 mg, 2.62 mmol) dropwise with stirring at 0° C. The resulting solution was allowed to react, with stirring, for an additional 3 h at room temperature. The reaction was then quenched by the addition of 30 mL of ammonium chloride$_{(aq)}$. The resulting solution was extracted with 50 mL of dichloromethane and the organic layers were combined and dried over anhydrous sodium sulfate and concentrated under vacuum. The residue was applied onto a silica gel column with ethyl acetate/petroleum ether (1:30-1:20). This resulted in intermediate 4m.

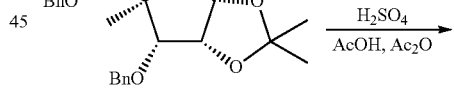

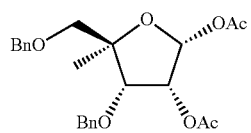

Intermediate 4n

-(2R,3R,4S,5R)-4-(benzyloxy)-5-(benzyloxymethyl)-5-methyltetrahydrofuran-2,3-diyl diacetate Into a 1000-mL round-bottom flask, was placed intermediate 4m (Also prepared according to Biosci. Biotech. Biochem. 1993, 57, 1433-1438, 45 g, 111.19 mmol), acetic acid (270 mL), acetic anhydride (90 mL), sulfuric acid (45 d). The resulting solution was stirred for 30 min at room temperature.

The reaction was then quenched by the addition of 1000 mL of water/ice. The resulting solution was diluted with 3000 mL of ethyl acetate. The resulting mixture was washed with 2×1000 mL of water and 4×1000 mL of sodium bicarbonate$_{(aq)}$. The resulting mixture was washed with 2×1000 mL of sodium chloride$_{(aq)}$. The mixture was dried over anhydrous sodium sulfate and concentrated under vacuum. The residue was applied onto a silica gel column with ethyl acetate/petroleum ether (1:30-1:20). This resulted in intermediate 4n.

$^1$H NMR (300 MHz, CDCl$_3$): δ 7.28-7.38 (m, 10H), 6.13 (s, 1H), 5.37 (d, J=4.8 Hz, 1H), 4.44-4.68 (m, 4H), 4.33 (d, J=5.1 Hz, 1H), 3.33-3.45 (m, 2H), 2.15 (s, 3H), 1.88 (s, 3H), 1.35 (s, 3H).
MS m/z=451 [M+Na]

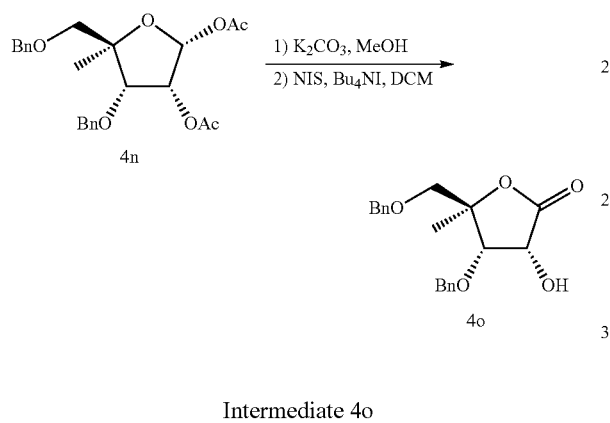

Intermediate 4o

-(3R,4S,5R)-4-(benzyloxy)-5-(benzyloxymethyl)-3-hydroxy-5-methyldihydrofuran-2(3H)-one Intermediate 4n (1.3 g, 3 mmol) was dissolved in anhydrous MeOH (15 mL). Potassium carbonate powder (456 mg, 3.3 mmol) was added, and the reaction mixture was stirred for 1 h. The reaction mixture was then concentrated under reduced pressure. Added acetonitrile and stirred for 5 minutes. Filtered off insoluble and washed with acetonitrile. Concentrated filtrate under reduced pressure. Dissolved resulting material in anhydrous DCM (20 mL). Added tetrabutylammonium iodine (1.66 g, 4.5 mmol) and N-iodo-succinimide (NIS, 1.69 g, 2.5 mmol). Stirred the reaction mixture in the dark for 16 h. Added more NIS (0.85 g, 1.25 mmol) and stirred for 4 hours. Added more NIS (0.85 g, 1.25 mmol) and stirred for 2 days in the dark. Diluted reaction with EtOAc and washed with aqueous sodium thiosulfate solution twice and then with saturated aqueous sodium chloride solution. Dried organic portion over anhydrous sodium sulfate and concentrated under reduced pressure. Purified with silica gel column (0-30% EtOAc in hexanes) to afford intermediate 4o.

$^1$H NMR (400 MHz, CDCl$_3$): δ 7.35-7.22 (m, 10H), 4.82 (bs, 1H), 4.75-4.66 (m, 2H), 4.55-4.44 (m, 2H), 4.13 (d, J=8 Hz, 1H), 3.70-3.45 (m, 2H), 1.38 (s, 3H).
LC/MS: t$_R$=2.58 min, MS m/z=342.9 [M+1], 360.0 [M+H$_2$O]; LC/MS system: Thermo LCQ Advantage; Phenomenex Gemini, C$_{18}$, 5u, 110A, 30×4.6 mm; Buffer A: 0.1% Acetic acid in Water; Buffer B: 0.1% Acetic acid in Acetonitrile 5-100% Buffer B in 2.5 mins then 100% for 0.9 min @ 2 mL/min.
HPLC: t$_R$=3.78 min; HPLC system: Agilent 1100; Phenomenex Gemini, C$_{18}$, 5u, 110A, 50×4.6 mm; Buffer A: 0.05% TFA in Water; Buffer B: 0.05% TFA in Acetonitrile; 2-98% Buffer B in 5 minutes @ 2 mL/min.

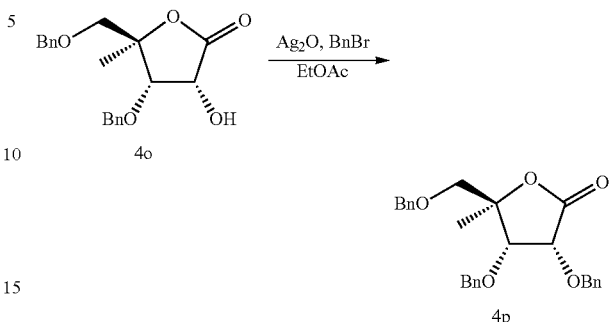

Intermediate 4p

-(3R,4S,5R)-3,4-bis(benzyloxy)-5-(benzyloxymethyl)-5-methyldihydrofuran-2(3H)-one Dissolved intermediate 4o (955 mg, 2.79 mmol) in EtOAc (10 mL). Added benzyl bromide (400 μL, 3.35 mmol) and silver(I) oxide (712 mg, 3.07 mmol). Stirred at 60° C. under N$_2$(g) in the dark for 3 h. Added more benzyl bromide (400 μL, 3.35 mmol) and stirred at 60° C. under N$_2$(g) in the dark for 16 h. Added more silver(I) oxide (350 mg, 1.5 mmol) and stirred at 60° C. under N$_2$(g) in the dark for 8 h. Cooled to room temperature. Filtered off solids and washed with EtOAc. Concentrated filtrate under reduced pressure to give an oil. Added hexanes and stirred for 2 h to give solid. Collected solid and washed with hexanes. Dried solid under high vacuum to afford intermediate 4p.

$^1$H NMR (400 MHz, CDCl$_3$): δ 7.35-7.16 (m, 15H), 5.03 (d, J=12 Hz, 1H), 4.79-4.71 (m, 2H), 4.52-4.40 (m, 4H), 4.06 (d, J=6 Hz, 1H), 3.49-3.39 (m, 2H), 1.38 (s, 3H).
LC/MS: t$_R$=2.91 min, MS m/z=433.1 [M+1], 450.1 [M+H$_2$O]; LC/MS system: Thermo LCQ Advantage; Phenomenex Gemini, C$_{18}$, 5u, 110A, 30×4.6 mm; Buffer A: 0.1% Acetic acid in Water; Buffer B: 0.1% Acetic acid in Acetonitrile; 5-100% Buffer B in 2.5 mins then 100% for 0.9 min @ 2 mL/min.
HPLC: t$_R$=4.54 min; HPLC system: Agilent 1100; Phenomenex Gemini, C$_{18}$, 5u, 110A, 50×4.6 mm; Buffer A: 0.05% TFA in Water; Buffer B: 0.05% TFA in Acetonitrile 2-98% Buffer B in 5 minutes @ 2 mL/min.

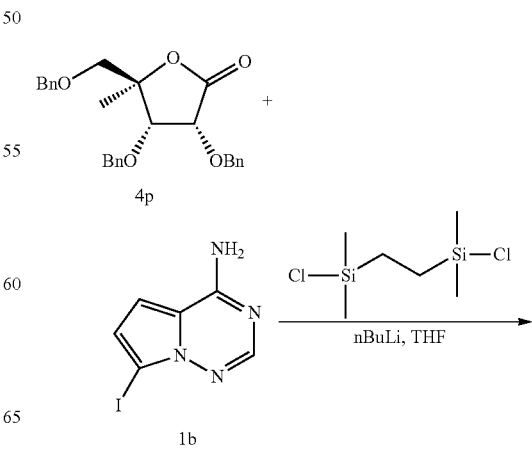

-continued

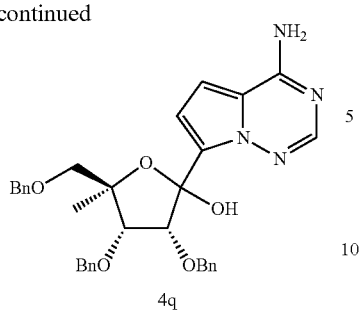

4q

Intermediate 4q

-(3R,4S,5R)-2-(4-aminopyrrolo[1,2-f][1,2,4]triazin-7-yl)-3,4-bis(benzyloxy)-5-(benzyloxymethyl)-5-methyltetrahydrofuran-2-ol Intermediate 1b (148 mg, 0.570 mmol) and 1,2-bis(chlorodimethylsilyl)ethane (123 mg, 0.570 mmol) were dissolved in anhydrous THF (20 mL) and stirred under Ar(g) at −70° C. Added n-butyllithium (2.5M solution in hexanes, 684 μL, 1.71 mmol) dropwise to the reaction mixture while maintaining internal temperature below −65° C. Allowed the reaction to warm to −40° C. and kept for 15 min. A solution of intermediate 4p (224 mg, 0.518 mmol) in THF (10 mL) precooled to −70° C. was then added to the reaction mixture under Ar(g). The resulting solution was stirred for 2 h at −40° C. The reaction mixture was then poured into a stirring mixture of EtOAc and citric acid$_{(aq)}$. Stirred for 5 min. Collected organic layer and washed with saturated NaCl$_{(aq)}$. Dried organic layer over anhydrous Na$_2$SO$_4$ and concentrated under reduced pressure. Purified with prep HPLC to afford intermediate 4q.

LC/MS: t$_R$=2.60 min, MS m/z=567.3 [M+1], 565.1 [M−1]; LC/MS system: Thermo LCQ Advantage; Phenomenex Gemini, C$_{18}$, 5u, 110A, 30×4.6 mm; Buffer A: 0.1% Acetic acid in Water; Buffer B: 0.1% Acetic acid in Acetonitrile; 5-100% Buffer B in 2.5 mins then 100% for 0.9 min @ 2 mL/min.

HPLC: t$_R$=3.22 min; HPLC system: Agilent 1100; Phenomenex Gemini, C$_{18}$, 5u, 110A, 50×4.6 mm; Buffer A: 0.05% TFA in Water; Buffer B: 0.05% TFA in Acetonitrile; 2-98% Buffer B in 5 minutes @ 2 mL/min.

-continued

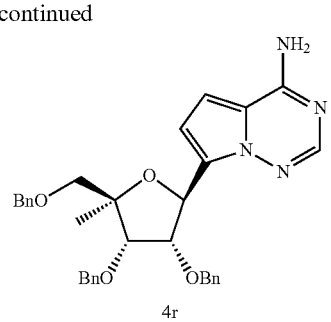

4r

Intermediate 4r

-7-((2S,3S,4S,5R)-3,4-bis(benzyloxy)-5-(benzyloxymethyl)-5-methyltetrahydrofuran-2-yl)pyrrolo[1,24][1,2,4]triazin-4-amine Intermediate 4q (81 mg, 0.143 mmol) was dissolved in anhydrous DCM (15 mL) and stirred under N$_2$(g) in an ice bath. Added triethylsilane (114 μL, 0.715 mmol) in one portion. Added boron trifluoride diethyl etherate (27 μL, 0.215 mmol) dropwise. Stirred for 15 min and then removed ice bath. Stirred for 60 min. Added triethylamine (100 μL, 0.715 mmol) and concentrated under reduced pressure. Dissolved in EtOAc and washed with saturated NaHCO$_{3(aq)}$ (2×) and then saturated with NaCl$_{(aq)}$. Dried organic over anhydrous Na$_2$SO$_4$ and concentrated under reduced pressure. Purified with silica gel column (0-80% EtOAc in hexanes to afford intermediate 4r.

$^1$H NMR (400 MHz, CDCl$_3$): δ 7.71 (s, 1H), 7.35-7.10 (m, 16H), 6.82-6.78 (m, 1H), 5.57 (d, J=4.4 Hz, 1H), 4.70-4.45 (m, 6H), 4.25-4.15 (m, 2H), 3.55-3.40 (m, 2H), 1.42 (s, 3H).

LC/MS: t$_R$=2.75 min, MS m/z=551.4 [M+1]; LC/MS system: Thermo LCQ Advantage

Phenomenex Gemini, C$_{18}$, 5u, 110A, 30×4.6 mm; Buffer A: 0.1% Acetic acid in Water; Buffer B: 0.1% Acetic acid in Acetonitrile; 5-100% Buffer B in 2.5 mins then 100% for 0.9 min @ 2 mL/min.

HPLC: t$_R$=3.57 min; HPLC system: Agilent 1100; Phenomenex Gemini, C$_{18}$, 5u, 110A, 50×4.6 mm; Buffer A: 0.05% TFA in Water; Buffer B: 0.05% TFA in Acetonitrile; 2-98% Buffer B in 5 minutes @ 2 mL/min.

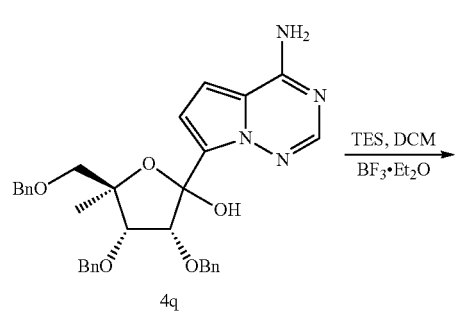

4q

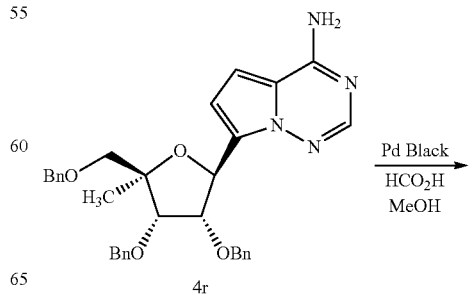

4r

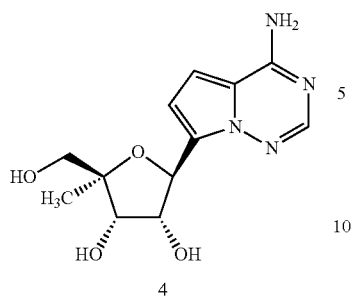

4

Example 4

-(2R,3S,4R,5S)-5-(4-aminopyrrolo[1,2-f][1,2,4]tri-azin-7-yl)-2-(hydroxymethyl)-2-methyltetrahydrofuran-3,4-diol Intermediate 4r (23 mg, 0.042 mmol) was dissolved into a formic acid/MeOH solution (1:9, 10 mL). Added palladium black and stirred at 60° C. for 90 min. Cooled to room temperature and filtered through Celite. Concentrated filtrate under reduced pressure. Purified with prep HPLC. Concentrated under reduced pressure. Dissolved in NaHCO$_{3(aq)}$ and purified with HPLC under neutral condition to afford example 4.

Prep HPLC system: Gilson 215 Liquid Handler; Phenomenex Gemini, C$_{18}$ 4 u, 100×30.0 mm Buffer A: 0.1% TFA in Water; Buffer B: 0.1% TFA in Acetonitrile; 5-100% Buffer B in 13 minutes @ 20 mL/min.

$^1$H NMR (400 MHz, CDCl$_3$): δ 8.01 (s, 1H), 7.41 (d, J=4.8 Hz, 1H), 7.02 (d, J=4.8 Hz, 1H), 5.33 (d, J=8 Hz, 1H), 4.53-4.49 (m, 1H), 4.15 (d, J=5.6 Hz, 1H), 3.50 (m, 2H), 1.27 (s, 3H).

LC/MS: t$_R$=0.30 min, MS m/z=281.3 [M+1], 279.0 [M-1]; LC/MS system: Thermo LCQ Advantage; Phenomenex Gemini, C$_{18}$, 5u, 110A, 30×4.6 mm; Buffer A: 0.1% Acetic acid in Water; Buffer B: 0.1% Acetic acid in Acetonitrile; 5-100% Buffer B in 2.5 mins then 100% for 0.9 min @ 2 mL/min.

HPLC: t$_R$=0.42 min; HPLC system: Agilent 1100; Phenomenex Gemini, C$_{18}$, 5u, 110A, 50×4.6 mm; Buffer A: 0.05% TFA in Water; Buffer B: 0.05% TFA in Acetonitrile; 2-98% Buffer B in 5 minutes @ 2 mL/min.

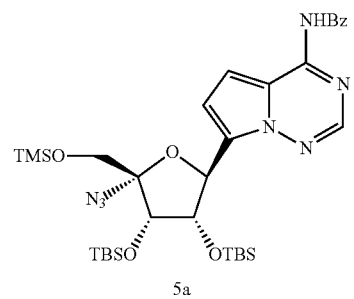

5a

Intermediate 5a

-N-(7-((2S,3S,4S,5R)-5-azido-3,4-bis(tert-butyldimethylsilyloxy)-5-((trimethylsilyloxy)methyl)tetrahydrofuran-2-yl)pyrrolo[1,2-f][1,2,4]triazin-4-yl)benzamide To a solution of crude intermediate 1m, N-(7-((2S,3S,4S)-3,4-bis(tert-butyldimethylsilyloxy)-5-hydroxy-5-(hydroxymethyl)tetrahydrofuran-2-yl)pyrrolo[1,2-f][1,2,4]triazin-4-yl)benzamide, (~110 mg, ~0.18 mmol) and azidotrimethysilane (242 μl, 1.84 mmol) in dichloromethane (1.5 mL) was added indium (III) bromide (130 mg, 0.369 mmol) at RT under an argon atmosphere. After 1 h, the reaction mixture was quenched with saturated aqueous sodium bicarbonate solution (1 mL). The resulting mixture was partitioned between dichloromethane (20 mL) and saturated aqueous sodium bicarbonate solution (20 mL). The phases were split and the aqueous layer was extracted with dichloromethane (20 mL). The combined organic layers were dried over anhydrous sodium sulfate and were concentrated under reduced pressure to afford intermediate 5a that was used directly in the next step without further purification.

LC/MS: t$_R$=3.52 min, MS m/z=712.16 [M+1]; LC system: Thermo Accela 1250 UHPLC

MS system: Thermo LCQ Fleet; Column: Kinetex 2.6μ XB-C18 100A, 50×4.6 mm

Solvents: Acetonitrile with 0.1% acetic acid, Water with 0.1% acetic acid; Gradient: 0 min-2.0 min 2-100% ACN, 2.0 min-3.55 min 100% ACN, 3.55 min-4.2 min 100%-2% ACN at 2 μl/min.

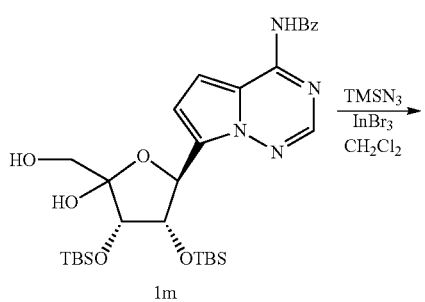

1m

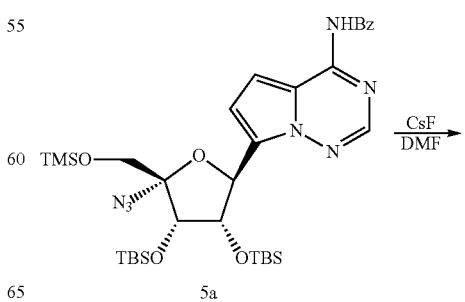

5a

-continued

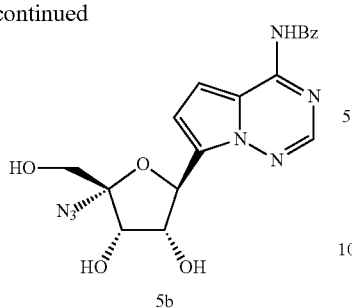

Intermediate 5b

-N-(7-((2S,3R,4S,5R)-5-azido-3,4-dihydroxy-5-(hydroxymethyl)tetrahydrofuran-2-yl)pyrrolo[1,2-f][1,2,4]triazin-4-yl)benzamide To a solution of crude intermediate 5a (~120 mg, ~0.168 mmol) in DMF (5 mL) was added cesium fluoride (256 mg, 1.68 mmol) at RT. After 25 h, the reaction mixture was diluted with brine (100 mL), and the resulting mixture was extracted with ethyl acetate (3×100 mL). The combined organic layers were dried over anhydrous sodium sulfate and were concentrated under reduced pressure to afford intermediate 5b that was used directly in the next step without further purification.
LC/MS: $t_R$=1.40 min, MS m/z=412.17 [M+1]; LC system: Thermo Accela 1250 UHPLC
MS system: Thermo LCQ Fleet; Column: Kinetex 2.6μ XB-C18 100A, 50×4.6 mm; Solvents:
Acetonitrile with 0.1% acetic acid, Water with 0.1% acetic acid; Gradient: 0 min-2.0 min 2-100% ACN, 2.0 min-3.05 min 100% ACN, 3.05 min-3.2 min 100%-2% ACN, 3.2 min-3.5 min 2% ACN at 2 μl/min.
HPLC: $t_R$=2.46 min' HPLC system: Agilent 1100 series.; Column: Gemini 5μ C18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min.

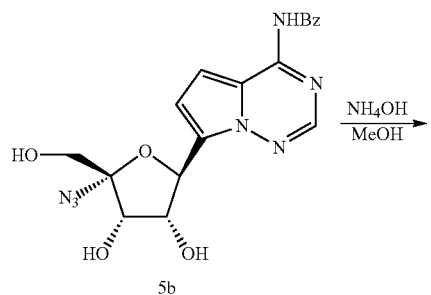

Example 5

-(2R,3S,4R,5S)-5-(4-aminopyrrolo[1,2-f][1,2,4]triazin-7-yl)-2-azido-2-(hydroxymethyl)tetrahydrofuran-3,4-diol Concentrated ammonium hydroxide (1 mL) was added to a solution of crude intermediate 5b in methanol (1 mL) at RT. After 2 d, the reaction mixture was concentrated under reduced pressure, and was directly purified by preparatory HPLC (Phenominex Synergi 4u Hydro-RR80 Å 150×30 mm column, 5-100% acetonitrile/water gradient). The fractions containing the desired were combined and were concentrated under reduced pressure. The residue repurified via SiO2 column chromatography (4 g SiO2 Combiflash HP Gold Column, 0-20% methanol/dichloromethane) to afford example 5.
$^1$H NMR (400 MHz, CD$_3$OD) δ 7.79 (s, 1H), 6.86 (d, J=4.5 Hz, 1H), 6.77 (d, J=4.5 Hz, 1H), 5.51 (d, J=6.0 Hz, 1H), 4.63 (t, J=5.8 Hz, 1H), 4.37 (d, J=5.7 Hz, 1H), 3.69 (d, J=12.0 Hz, 1H), 3.59 (d, J=12.0 Hz, 1H).
LC/MS: $t_R$=0.76 min, MS m/z=308.08 [M+1]; LC system: Thermo Accela 1250 UHPLC
MS system: Thermo LCQ Fleet; Column: Kinetex 2.6μ XB-C18 100A, 50×4.6 mm; Solvents: Acetonitrile with 0.1% acetic acid, Water with 0.1% acetic acid; Gradient: 0 min-1.5 min 2-100% ACN, 1.5 min-2.2 min 100% ACN, 2.2 min-2.4 min 100%-2% ACN, 2.4 min-2.5 min 2% ACN at 2 μl/min.
HPLC: $t_R$=1.287 min; HPLC system: Agilent 1100 series.; Column: Gemini 5μ C18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min.;
TLC: eluent: 20% methanol in dichloromethane, $R_f$=0.4 (UV)

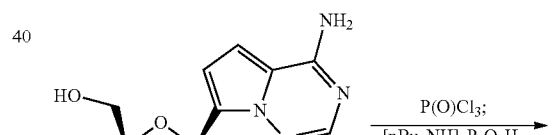

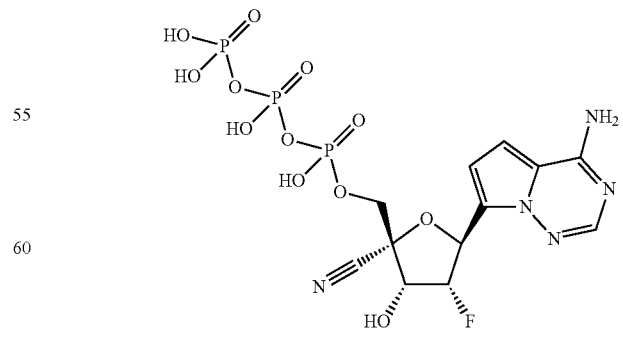

Example 6

Example 6 (also referred to as TP-1)

-((2R,3R,4R,5S)-5-(4-aminopyrrolo[1,2-f][1,2,4]triazin-7-yl)-2-cyano-4-fluoro-3-hydroxytetrahydrofuran-2-yl)methyl tetrahydrogen triphosphate Example 3 (15.0 mg, 0.05 mmol) was dried in a flask under vacuum overnight. Trimethylphosphate (0.5 mL) and 1,8-bis(dimethylamino)naphthalene (25 mg, 0.12 mmol) were added to the flask and the solution was allowed to stir under $N_2$ cooled by an ice/water bath. Distilled phosphorus oxychloride (10 μL, 0.11 mmol) was added and the reaction was allowed to stir for 4 h with cooling. Tributylamine (0.1 ml, 0.42 mmol) and tributylammonium pyrophosphate (0.8 mL of a 0.5 M solution in DMF, 0.4 mmol) were added and the reaction was allowed to stir for an additional 45 min with cooling. The reaction was quenched with triethylammonium bicarbonate (0.5 M, 5 mL). The solvents were removed by rotary evaporation and the remaining crude mixture was dissolved in 2 mL of water. The product was purified using a Sephadex DEAE A-25 column with a linear gradient of 0-1 M triethylammonium bicarbonate. The product containing fractions were pooled and concentrated to give example 6 (TP1), which was then dissolved in 1 mL of water to give a 10 mM solution.

MS m/z=532.0 [M−1]

Ion Exchange HPLC Retention time: 12.015 min; Column: DNAPac PA-100 4×250 mm SN

Solvent A: milliQ water; Solvent B: 0.5 M tetraethylammonium bromide; Solvent gradient program: equilibrate using 100% A for 10 min, then ramp 0-80% B over 14 min.; Flow: 1 mL/min.

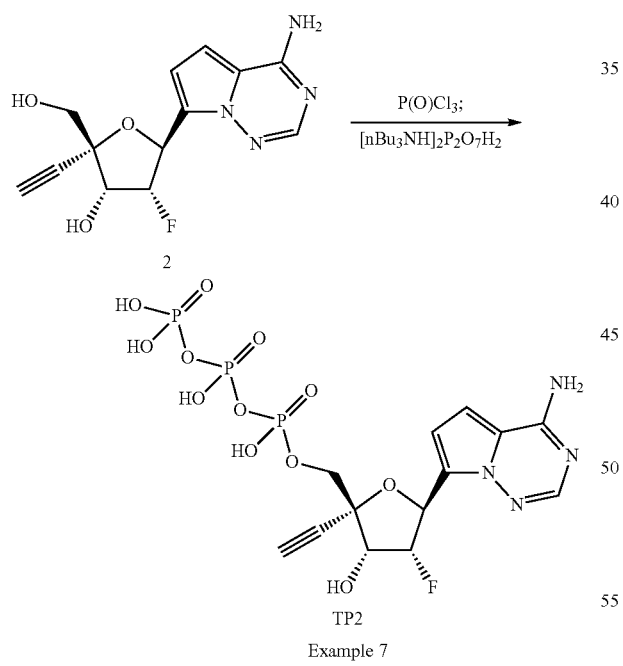

TP2

Example 7

Example 7 (also TP2)

-((2R,3R,4R,5S)-5-(4-aminopyrrolo[1,24][1,2,4]triazin-7-yl)-2-ethynyl-4-fluoro-3-hydroxytetrahydrofuran-2-yl)methyl tetrahydrogen triphosphate Example 2 (16.0 mg, 0.055 mmol) was dried in a flask under vacuum overnight. Trimethylphosphate (0.5 mL) and 1,8-bis(dimethylamino)naphthalene (28 mg, 0.13 mmol) were added to the flask and the solution was allowed to stir under $N_2$ cooled by an ice/water bath. Distilled phosphorus oxychloride (11 μL, 0.12 mmol) was added and the reaction was allowed to stir for 4 h with cooling. Tributylamine (0.11 mL, 0.42 mmol) and tributylammonium pyrophosphate (0.9 mL of a 0.5 M solution in DMF, 0.45 mmol) were added and the reaction was allowed to stir for an additional 45 min with cooling. The reaction was quenched with triethylammonium bicarbonate (0.5 M, 5 mL). The solvents were removed by rotary evaporation and the remaining crude mixture was dissolved in 2 mL of water. The product was purified using a Sephadex DEAE A-25 column with a linear gradient of 0-1 M triethylammonium bicarbonate. The product containing fractions were pooled and concentrated to give example 7 (TP2), which was then dissolved in 1.4 mL of water to give a 10 mM solution.

MS m/z=531.0 [M−1]

Ion Exchange HPLC Retention time: 19.829 min; Column: DNAPac PA-100 4×250 mm SN

Solvent A: milliQ water; Solvent B: 0.5 M tetraethylammonium bromide; Solvent gradient program: equilibrate using 100% A for 10 min, then ramp 0-80% B over 14 min.; Flow: 1 mL/min

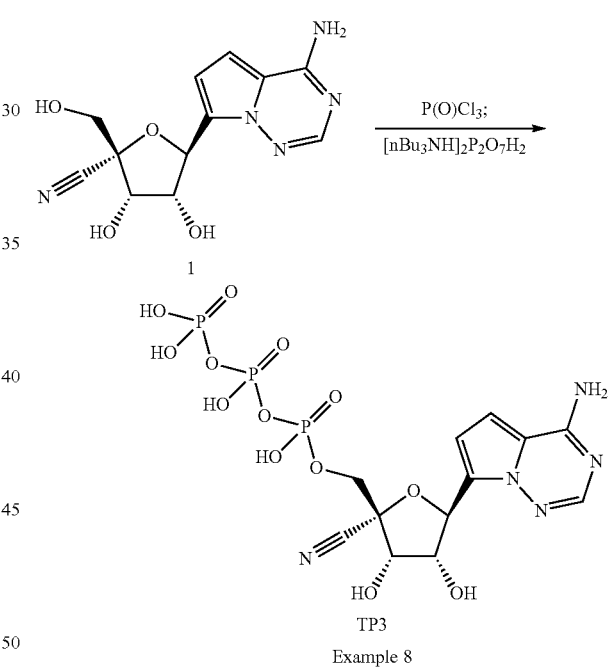

TP3

Example 8

Example 8 (TP3)

-((2R,3S,4R,5S)-5-(4-aminopyrrolo[1,2-f][1,2,4]triazin-7-yl)-2-cyano-3,4-dihydroxytetrahydrofuran-2-yl)methyl tetrahydrogen triphosphate To a solution of example 1 (5.0 mg, 0.017 mmol) in $PO(OMe)_3$ (0.6 mL) at 0° C. was added $POCl_3$ (45 mg, 0.29 mmol). The reaction mixture was stirred at 0° C. for 10 h, at which point Ion-exchange HPLC showed approximately 50% conversion. A solution of pyrophosphate tributylamine salts (250 mg) in ACN (0.6 mL) was added, followed by tributylamine (110 mg, 0.59 mmol). The reaction mixture was stirred at 0° C. for 0.5 h, and ion-exchange HPLC showed the reaction was completed. The reaction was quenched with triethylammonium bicarbonate buffer (1 M, 5 mL). The reaction mixture was stirred at RT for 0.5 h, then concentrated and co-evaporated with water twice. The residue was dissolved in $H_2O$ (5 mL) and loaded to a ion-exchange column, eluted with $H_2O$, then 5-35% triethylammonium bicarbonate buffer (1 M)-$H_2O$. The product fractions were combined, concentrated and co-evaporated with $H_2O$. The residue was purified by ion-exchange column again to give crude material. $^{31}P$ NMR showed this material contained impurities, so the material was repurified with C-18 column, eluted with 0-15% ACN—$H_2O$ containing 0.05% TEA, and the fractions containing product were combined and concentrated to give 3.6 mg material, which contained only 1.5 equiv of TEA as indicated by $^1H$ NMR analysis. The material was dissolved in $H_2O$ (1 mL) and triethylammonium bicarbonate buffer (1 M, 0.1 mL) was added. The resulting mixture was concentrated under reduced pressure and co-evaporated with $H_2O$ twice under reduced pressure to give example 8 (TP3), as a tetra-TEA salt.

$^1H$ NMR (400 MHz, $D_2O$): δ 7.78 (s, 1H), 6.85 (d, J=2.4 Hz, 1H), 6.82 (d, J=2.4 Hz, 1H), 5.51 (d, J=3.0 Hz, 1H), 4.65-4.55 (m, 2H), 4.20-4.08 (m, 2H), 3.15-3.00 (m, 24H), 1.18-1.08 (m, 36H).

$^{31}P$ NMR (162 MHz, $D_2O$): δ −6.25 (d, J=52 Hz), −12.21 (d, J=52 Hz), −22.32 (t, J=52 Hz).

MS m/z=530.2 [M−1], 532.1 [M+1]

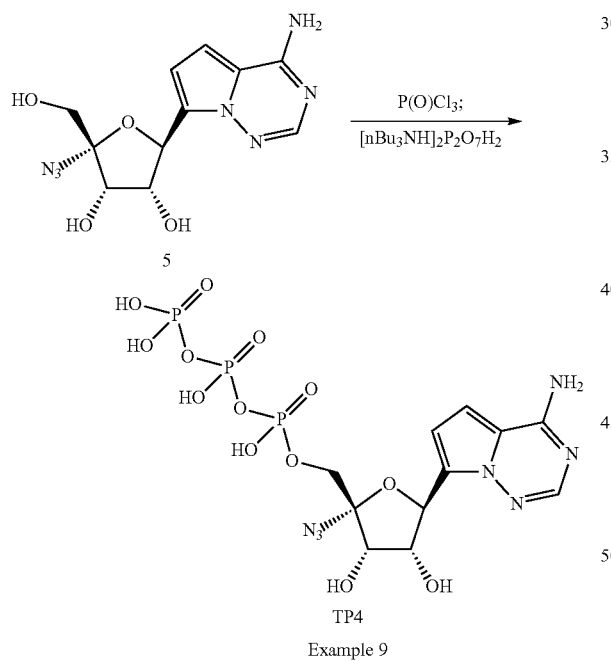

Example 9

Example 9 (TP4)

((2R,3S,4R,5S)-5-(4-aminopyrrolo[2,1-f][1,2,4]triazin-7-yl)-2-azido-3,4-dihydroxytetrahydrofuran-2-yl)methyl tetrahydrogen triphosphate To a solution of example 5 (6.0 mg, 0.019 mmol) in PO(OMe)$_3$ (0.6 mL) at 0° C. was added POCl$_3$ (45 mg, 0.29 mmol). The reaction mixture was stirred at 0° C. for 10 h, at which point Ion-exchange HPLC showed approximately 50% conversion. A solution of pyrophosphate tributylamine salts (250 mg) in ACN (0.6 mL) was added, followed by tributylamine (110 mg, 0.59 mmol). The reaction mixture was stirred at 0° C. for 6 h. The reaction was quenched with triethylammonium bicarbonate buffer (1 M, 5 mL). The reaction mixture was stirred at RT for 0.5 h, then concentrated and co-evaporated with water twice. The residue was dissolved in $H_2O$ (5 mL) and loaded to a ion-exchange column, eluted with $H_2O$, then 5-35% triethylammonium bicarbonate buffer (1 M)-$H_2O$. The product fractions were combined, concentrated and co-evaporated with $H_2O$. The residue was purified by ion-exchange column again to give crude material. $^{31}P$ NMR showed this material contained impurities, so the material was repurified with ion-exchange column again to give crude material. The material was treated with NaHCO$_3$ (10 mg) and the mixture was concentrated under reduced pressure. The solid residue was dissolved in 0.5 mL of $H_2O$ and 40 µL of NaOH (1N) was added. The resulting mixture was purified with C-18 column, eluted with $H_2O$, and the fractions containing product were combined and concentrated under reduced pressure to afford Example 9 (TP4) as the tetrasodium salt.

$^1H$ NMR (400 MHz, $D_2O$): δ 7.76 (s, 1H), 6.88 (d, J=4.3 Hz, 1H), 6.81 (d, J=4.6 Hz, 1H), 5.59 (d, J=5.5 Hz, 1H), 4.60 (t, J=5.6 Hz, 1H), 4.55 (d, J=5.8 Hz, 1H), 3.99 (qd, J=11.2, 5.5 Hz, 3H).

$^{31}P$ NMR (162 MHz, $D_2O$): δ −8.13 (d, J=19.8 Hz), −14.04 (d, J=18.9 Hz), −24.00 (t, J=19.3 Hz).

MS m/z=546.1 [M−1], 547.9 [M+1]

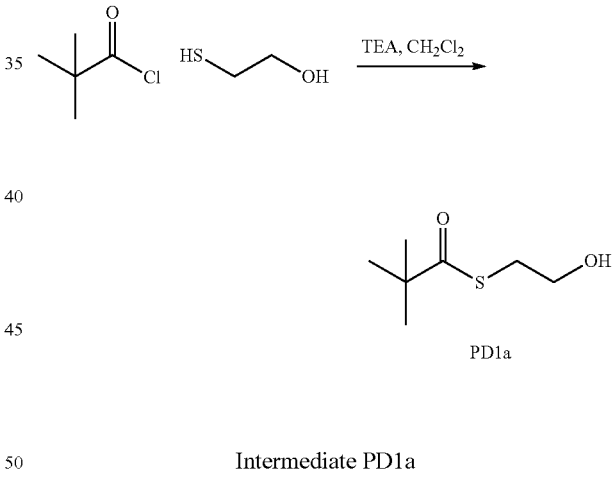

Intermediate PD1a

-S-2-hydroxyethyl 2,2-dimethylpropanethioate

To a solution of 2-thioethanol (3.50 mL, 50.0 mmol) and triethylamine (7.02 mL, 50.0 mmol) in CH$_2$Cl$_2$, that has been cooled to −78° C. was added pivaloyl chloride (6.15 mL, 50.0 mmol) dropwise over 30 min. The reaction was allowed to warm slowly to room temperature and progression was monitored by TLC. After 30 min, the reaction was determined to be complete and was quenched with water. The layers were separated and the aqueous was washed with CH$_2$Cl$_2$. The organics were combined and dried over sodium sulfate. The solids were filtered and the solvent was removed under reduced pressure. The crude was purified by silica gel chromatography 0-50% EtOAc/hexanes to afford intermediate PD1a.

¹H NMR (400 MHz, DMSO-d₆) δ 4.89 (t, J=5.5 Hz, 1H), 3.49-3.36 (m, 2H), 2.86 (t, J=6.7 Hz, 2H), 1.14 (s, 9H).

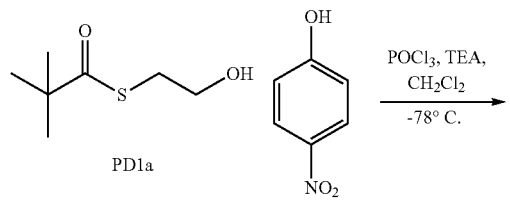

showed only one spot, but LC/MS had two peaks (product and bis-p-nitrophenolate). The solution was diluted with ether and the solids were removed by filtration and discarded. The mother liquor was concentrated and purified by silica gel chromatography to give a mixture of product and bis-p-nitrophenolate. The mixture was then repurified by HPLC to afford intermediate PD1b, S,S'-2,2'-(((4-nitrophenoxy)phosphoryl)bis(oxy)bis(ethane-2,1-diyl)bis(2,2-dimethylpropanethioate).

¹H NMR (400 MHz, CDCl₃) δ 8.29-8.21 (m, 2H), 7.46-7.36 (m, 2H), 4.23 (br q, J=7.7 Hz, 4H), 3.16 (br t, J=6.7 Hz, 4H), 1.23 (s, 18H).

³¹P NMR (162 MHz, CDCl₃) δ −7.72 (s).

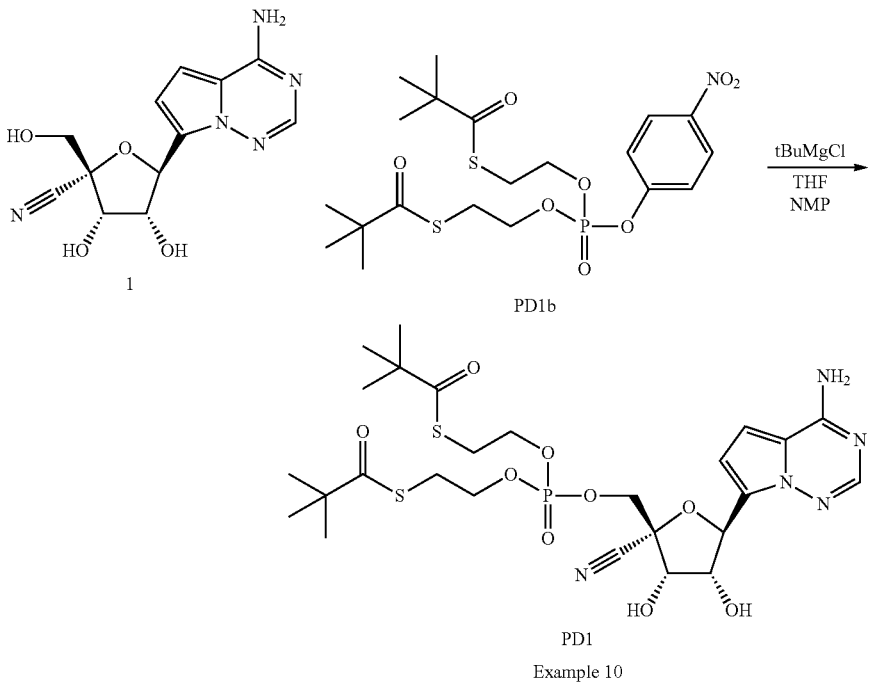

Example 10

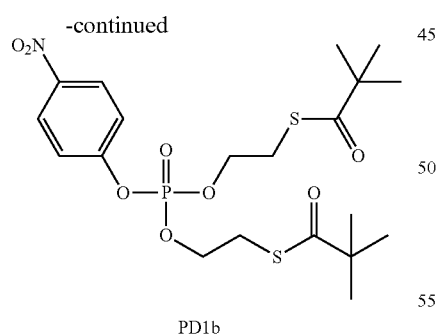

Take up phosphorous oxychloride (281 μL, 3.08 mmol) in CH₂Cl₂ (5 mL) and cool the solution to −78° C. Take up the thioester PD1a (1.00 g, 6.17 mmol) in CH₂Cl₂ (5 mL) and add slowly to the POCl₃ solution. Next add TEA (891 μL, 6.16 mmol) dropwise and allow to stir cold for 30 min. Then warm to room temperature and allow to stir for 2 h. Add the p-nitrophenol (428 mg, 3.08 mmol) in one portion followed by a slow addition of TEA (449 μL, 3.08 mmol). Stir at room temperature for 30 min. TLC (70:30 Hexanes/EtOAC)

Example 10 (also referred to as PD1)

-S,S'-2,2'-((((2R,3S,4R,5S)-5-(4-aminopyrrolo[1,2-f][1,2,4]triazin-7-yl)-2-cyano-3,4-dihydroxytetrahydrofuran-2-yl)methoxy)phosphoryl)bis(oxy)bis(ethane-2,1-diyl)bis(2,2-dimethylpropanethioate).

Example 1 (6.0 mg, 0.02 mmol) was dissolved in NMP (0.1 mL), and THF (0.2 mL) was added. tert-Butyl magnesium chloride (1.0 M solution in THF, 0.031 mL, 0.031 mmol) was then added at RT under an argon atmosphere. After 10 min, a solution of intermediate PD1b (15.7 mg, 0.031 mmol) in THF (0.1 mL) was added and the resulting mixture was warmed to 50° C. After 5 h, the resulting residue was purified by preparatory HPLC (Phenominex Synergi 4u Hydro-RR 80 Å 150× 30 mm column, 40-100% acetonitrile/water gradient). The fractions containing the desired product were combined and were lyophilized to afford example 10 (PD1).

¹H NMR (400 MHz, CDCl₃) δ 7.82 (s, 1H), 6.69 (d, J=4.5 Hz, 1H), 6.64 (d, J=4.5 Hz, 1H), 5.56 (d, J=3.4 Hz, 1H), 4.61 (br s, 2H), 4.45-4.32 (m, 2H), 4.22-4.06 (m, 4H), 3.13 (dt, J=11.7, 6.7 Hz, 4H), 1.23 (s, 9H), 1.21 (s, 9H).

³¹P NMR (162 MHz, CDCl₃) δ −2.34 (s).

LC/MS: $t_R$=1.70 min, MS m/z=660.02 [M+1],; LC system: Thermo Accela 1250 UHPLC
MS system: Thermo LCQ Fleet; Column: Kinetex 2.6μ XB-C18 100A, 50×4.6 mm
Solvents: Acetonitrile with 0.1% acetic acid, Water with 0.1% acetic acid; Gradient: 0 min-2.0 min 2-100% ACN, 2.0 min-3.05 min 100% ACN, 3.05 min-3.2 min 100%-2% ACN, 3.2 min-3.5 min 2% ACN at 2 μl/min.
HPLC: $t_R$=3.204 min; HPLC system: Agilent 1100 series.; Column: Gemini 5μ C18 110A, 50×4.6 mm; Solvents: Acetonitrile with 0.1% TFA, Water with 0.1% TFA
Gradient: 0 min-5.0 min 2-98% ACN, 5.0 min-6.0 min 98% ACN at 2 mL/min.

$^{31}$P NMR (162 MHz, CDCl$_3$) δ −2.10 (s).
$^{19}$F NMR (376 MHz, CDCl$_3$) δ −191.64 (ddd, J=55.0, 27.8, 21.3 Hz).
LC/MS: $t_R$=1.85 min, MS m/z=662.03 [M+1],; LC system: Thermo Accela 1250 UHPLC
MS system: Thermo LCQ Fleet; Column: Kinetex 2.6μ XB-C18 100A, 50×4.6 mm; Solvents: Acetonitrile with 0.1% acetic acid, Water with 0.1% acetic acid; Gradient: 0 min-2.0 min 2-100% ACN, 2.0 min-3.05 min 100% ACN, 3.05 min-3.2 min 100%-2% ACN, 3.2 min-3.5 min 2% ACN at 2 μl/min.
HPLC: $t_R$=3.385 min; HPLC system: Agilent 1100 series.; Column: Gemini 5μ C18 110A, 50×4.6 mm; Solvents:

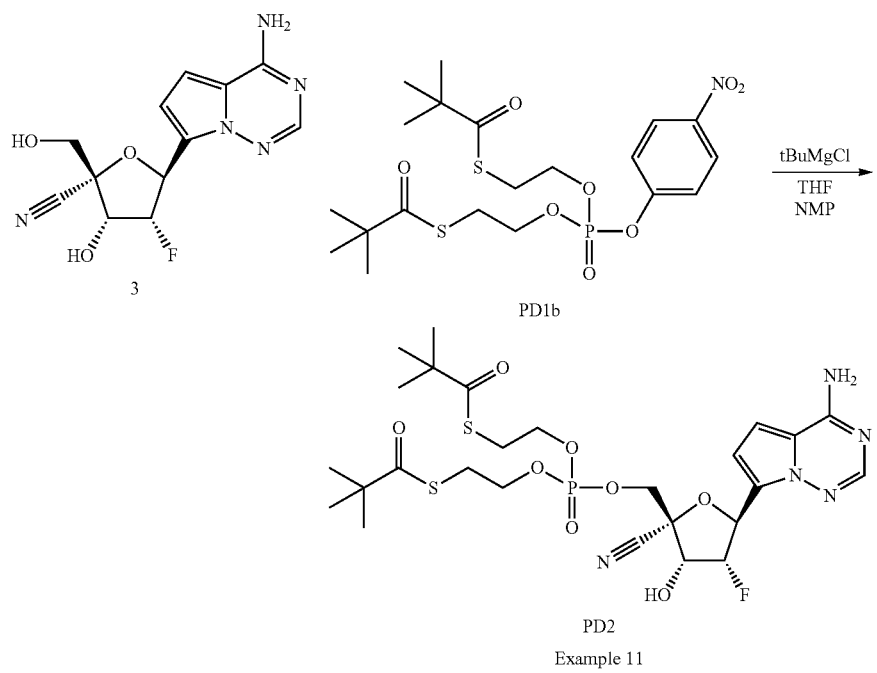

Example 11

Example 11 (PD2)

-S,S'-2,2'-((((2R,3R,4R,5S)-5-(4-aminopyrrolo[1,2-f][1,2,4]triazin-7-yl)-2-cyano-4-fluoro-3-hydroxytetrahydrofuran-2-yl)methoxy)phosphoryl)bis(oxy)bis(ethane-2,1-diyl)bis(2,2-dimethylpropanethioate)

Example 3 (10.5 mg, 0.036 mmol) was dissolved in NMP (0.1 mL), and THF (0.1 mL) was added. tert-Butyl magnesium chloride (1.0 M solution in THF, 0.054 mL, 0.054 mmol) was then added at RT under an argon atmosphere. After 10 min, a solution of intermediate PD1b (27.3 mg, 0.054 mmol) in THF (0.1 mL) was added and the resulting mixture was warmed to 50° C. After 24 h, the resulting residue was purified by preparatory HPLC (Phenominex Synergi 4u Hydro-RR 80 Å 150×30 mm column, 40-100% acetonitrile/water gradient). The fractions containing the desired product were combined and were lyophilized to afford example 11 (PD2).

$^1$H NMR (400 MHz, CDCl$_3$) δ 7.94 (s, 1H), 6.75 (d, J=4.5 Hz, 1H), 6.67 (d, J=4.5 Hz, 1H), 5.77 (dd, J=27.8, 1.4 Hz, 1H), 5.43 (ddd, J=55.2, 4.9, 1.3 Hz, 1H), 4.93 (dd, J=21.2, 4.9 Hz, 1H), 4.49 (dd, J=11.3, 7.8 Hz, 1H), 4.40 (dd, J=11.3, 7.8 Hz, 1H), 4.10 (ddt, J=15.9, 8.0, 6.7 Hz, 4H), 3.16-3.04 (m, 4H), 1.23 (s, 9H), 1.21 (s, 9H).

Acetonitrile with 0.1% TFA, Water with 0.1% TFA; Gradient: 0 min-5.0 min 2-98% ACN, 5.0 min-6.0 min 98% ACN at 2 mL/min.

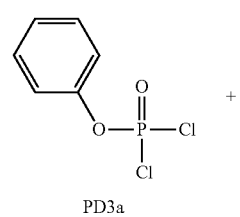

PD3a

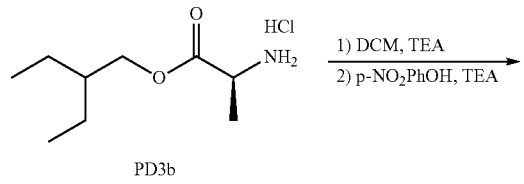

PD3b

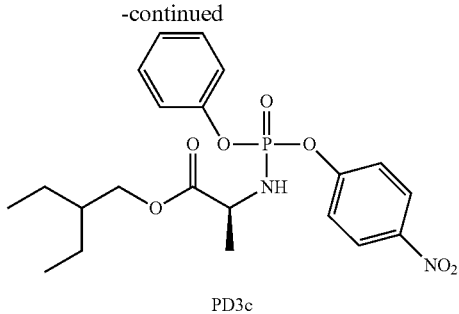

Intermediate PD3c

-(2S)-2-ethylbutyl 2-((4-nitrophenoxy)(phenoxy)phosphorylamino)propanoate

Dissolved phenyl dichlorophosphate PD3a (1.5 mL, 10 mmol) in 30 mL anhydrous DCM and stirred under $N_2(g)$ in an ice bath. Added amino ester HCl salt PD3b, (S)-2-ethylbutyl 2-aminopropanoate hydrochloride, (prepared according to Eur. *J. Med. Chem.* 2009, 44, 3765-3770, 2.1 g, 10 mmol) in one portion. Added TEA (3 mL, 22 mmol) dropwise. Stirred for 1 h at 0° C. Added p-nitrophenol (1.4 g, 10 mmol) in one portion and TEA (1.5 mL, 11 mmol). The reaction mixture was then stirred at room temperature for 16 h. Diluted with DCM and washed with saturated $NaHCO_{3(aq)}$. Dried organic over anhydrous $Na_2SO_4$ and concentrated under reduced pressure. Purified with silica gel column (0-15% EtOAc in hexanes) to afford intermediate PD3c.

$^1$H NMR (400 MHz, $CDCl_3$) δ 8.23 (d, J=8.8 Hz, 2H), 7.41-7.30 (m, 4H), 7.25-7.19 (m, 3H), 4.10-4.00 (m, 3H), 3.90-3.83 (m, 1H), 1.55-1.45 (m, 1H), 1.42-1.31 (m, 7H), 0.87 (t, J=7.2 Hz, 6H).

$^{31}$P NMR (162 MHz, $CDCl_3$) δ −3.04 (s), −3.10 (s).

LC/MS: $t_R$=2.87 min, MS m/z=451.1 [M+1], 449.0 [M−1]; LC/MS system: Thermo LCQ Advantage; Phenomenex Gemini, $C_{18}$, 5u, 110A, 30×4.6 mm; Buffer A: 0.1% Acetic acid in Water; Buffer B: 0.1% Acetic acid in Acetonitrile; 5-100% Buffer B in 2.5 mins then 100% for 0.9 min @ 2 mL/min.

HPLC: $t_R$=4.40 min; HPLC system: Agilent 1100; Phenomenex Gemini, $C_{18}$, 5u, 110A, 50×4.6 mm; Buffer A: 0.05% TFA in Water; Buffer B: 0.05% TFA in Acetonitrile; 2-98% Buffer B in 5 minutes @ 2 mL/min.

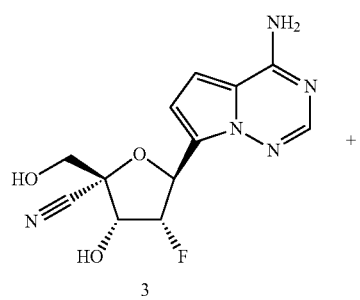

3

+

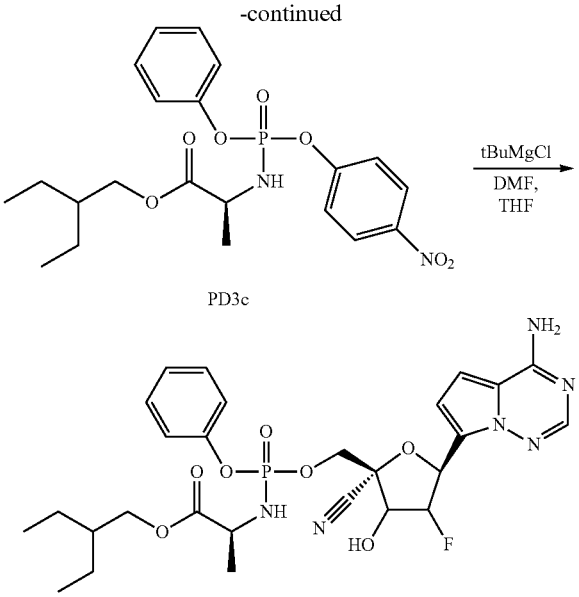

PD3

Example 12

Example 12 (PD3)

-(2S)-2-ethylbutyl 2-((((2R,3R,4R,5S)-5-(4-aminopyrrolo[1,2-f][1,2,4]triazin-7-yl)-2-cyano-4-fluoro-3-hydroxytetrahydrofuran-2-yl)methoxy)(phenoxy)phosphorylamino)propanoate.

Dissolved example 3 (15 mg, 0.051 mmol) in anhydrous DMF (1 mL) and stirred under $N_2(g)$. Dissolved p-nitrophenylphosphoamidate PD3c (35 mg, 0.077 mmol) in anhydrous DMF (0.5 mL) and added to the reaction mixture in one portion. Added tBuMgCl in THF (1M in THF, 77 µL, 0.077 mmol) dropwise. Stirred for 2 h. Added more p-nitrophenylphosphoamidate (35 mg in 0.5 mL anhydrous DMF) and more tBuMgCl (1 M in THF, 50 µL, 0.050 mmol). Stirred for 2 h. Added more p-nitrophenylphosphoamidate (35 mg in 0.5 mL anhydrous DMF) and more tBuMgCl solution (1M in THF, 50 µL, 0.050 mmol). Stirred for 16 hours. Diluted with EtOAc and washed with saturated $NaHCO_{3(aq)}$ (3×). Washed with saturated $NaCl_{(aq)}$ and dried organic over anhydrous $Na_2SO_4$. Concentrated under reduced pressure. Purified with silica gel column (0-5% MeOH in DCM). Combined fractions and concentrated under reduced pressure. Purified with preparatory HPLC with TFA as modifier to afford example 12 (PD3).

Prep HPLC system: Gilson 215 Liquid Handler; Phenomenex Gemini, $C_{18}$ 4 u, 100×30.0 mm
Buffer A: 0.1% TFA in Water; Buffer B: 0.1% TFA in Acetonitrile; 5-100% Buffer B in 13 minutes @ 20 mL/min.

$^1$H NMR (400 MHz, $CDCl_3$) δ 7.89 (s, 1H), 7.31-7.13 (m, 6H), 6.80-6.75 (m, 1H), 5.80-5.70 (m, 1H), 5.35-5.20 (m, 1H), 4.80-4.62 (m, 1H), 4.60-4.45 (m, 2H), 4.35-4.10 (m, 1H), 4.06-3.96 (m, 3H), 1.49-1.28 (m, 8H), 0.90-0.82 (m, 6H).

$^{31}$P NMR (162 MHz, $CDCl_3$) δ 2.36 (s), 2.22 (s).

HPLC: $t_R$=3.00 min; HPLC system: Agilent 1100; Phenomenex Gemini, $C_{18}$, 5u, 110A, 50×4.6 mm; Buffer A: 0.05% TFA in Water; Buffer B: 0.05% TFA in Acetonitrile; 2-98% Buffer B in 5 minutes @ 2 mL/min.

LC/MS: $t_R$=2.39 min, MS m/z=605.1 [M+1], 603.0 [M−1]; LC/MS system: Thermo LCQ Advantage; Phenomenex Gemini, $C_{18}$, 5u, 110A, 30×4.6 mm; Buffer A: 0.1% Acetic acid in Water; Buffer B: 0.1% Acetic acid in Acetonitrile; 5-100% Buffer B in 2.5 mins then 100% for 0.9 min @ 2 mL/min.

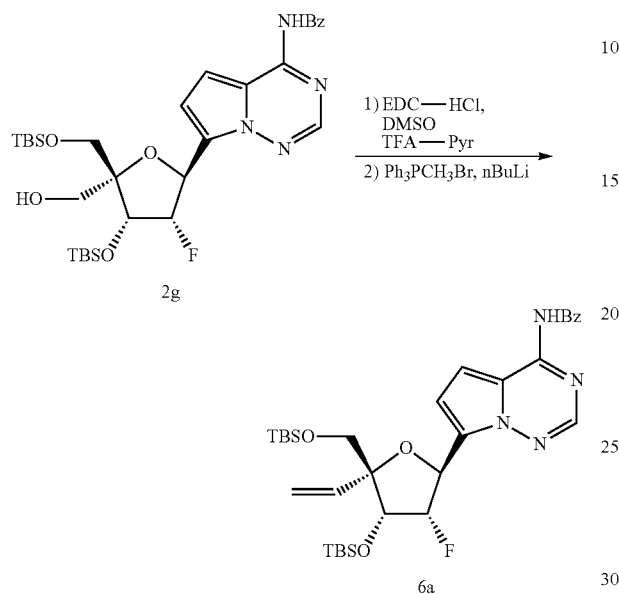

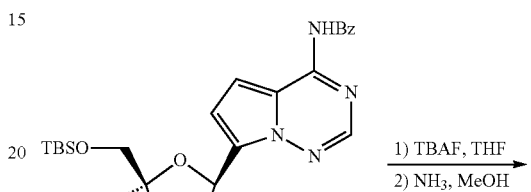

organic over anhydrous $Na_2SO_4$ and concentrated under reduced pressure. Purified with silica gel column (0-20% EtOAc in hexanes) to afford intermediate 6a.

$^1$H NMR (400 MHz, DMSO-d6) δ 8.22 (br s, 1H), 8.03 (br s, 2H), 7.58 (dt, J=40.4, 7.4 Hz, 3H), 7.12 (d, J=4.7 Hz, 1H), 6.97 (s, 1H), 6.01 (dd, J=17.5, 10.9 Hz, 1H), 5.58 (d, J=22.8 Hz, 1H), 5.46 (dd, J=17.5, 2.1 Hz, 1H), 5.25 (dd, J=11.0, 2.0 Hz, 1H), 5.14 (ddd, J=55.4, 4.9, 2.7 Hz, 1H), 4.61 (dd, J=20.8, 4.8 Hz, 1H), 3.63-3.40 (m, 2H), 0.89 (s, 9H), 0.84 (s, 9H), 0.09 (d, J=8.4 Hz, 6H), 0.00 (d, J=14.1 Hz, 6H).

$^{19}$F NMR (376 MHz, DMSO-d6) δ −191.86 (d, J=56.8 Hz). MS m/z=627.3 [M+1].

Intermediate 6a

-N-(7-((2S,3S,4R,5R)-4-(tert-butyldimethylsilyloxy)-5-((tert-butyldimethylsilyloxy)methyl)-3-fluoro-5-vinyltetrahydrofuran-2-yl)pyrrolo[1,2-f][1,2,4]triazin-4-yl)benzamide Intermediate 2g, N-(7-((2S,3S,4R,5R)-4-(tert-butyldimethylsilyloxy)-5-((tert-butyldimethylsilyloxy)methyl)-3-fluoro-5-(hydroxymethyl)tetrahydrofuran-2-yl)pyrrolo[1,2-f][1,2,4]triazin-4-yl)benzamide, (220 mg, 0.35 mmol) was dissolved in 5 mL of anhydrous DMSO and stirred under $N_2$(g). Added EDCl (100 mg, 0.52 mmol) and then TFA-Pyridine (34 mg, 0.18 mmol). Stirred for 1 h. Added more EDCl (100 mg, 0.52 mmol) and stirred for 1 h. Monitoring by LC/MS showed starting material alcohol remained. Added more EDCl (100 mg, 0.52 mmol) and stirred for 1 h. Monitoring by LC/MS showed that the reaction reached full conversion. Diluted with ethyl acetate and washed with saturated $NaHCO_{3(aq)}$ (2×) and then saturated $NaCl_{(aq)}$. Dried organic layer over anhydrous $Na_2SO_4$ and concentrated under reduced pressure. Purified with silica gel column (0-20% EtOAc in hexanes). Combined fractions and concentrated under reduced pressure to give aldehyde as solid. Suspended Methyl triphenylphosphonium bromide (500 mg, 1.40 mmol) in 10 mL anhydrous THF and stirred at −78° C. under $Ar_{(g)}$. Added 2.5 M n-butyllithium solution in hexane (560 μL, 1.40 mmol) dropwise. Stirred reaction mixture in an ice bath for 1 h to give a yellow mixture. Dissolved above prepared aldehyde in 5 mL of anhydrous THF and added to reaction dropwise. Removed ice bath and let reaction warmed to RT. Stirred for 3 h at RT. Added saturated aqueous $NH_4Cl$ solution and extracted with ethyl acetate. Washed organic extract with saturated $NaHCO_{3(aq)}$ and then saturated $NaCl_{(aq)}$. Dried

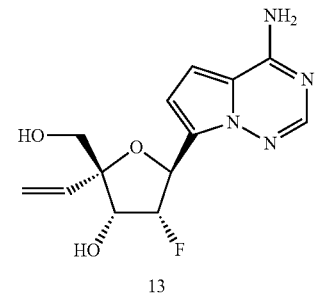

Example 13

(2R,3R,4R,5S)-5-(4-aminopyrrolo[1,2-f][1,2,4]triazin-7-yl)-4-fluoro-2-(hydroxymethyl)-2-vinyltetrahydrofuran-3-ol Intermediate 6a (146 mg, 0.23 mmol) was dissolved into THF (10 mL) and the resulting solution was stirred in an ice bath. Added 1M TBAF solution in THF (700 μL, 0.70 mmol) and stirred for 2 h. Diluted with EtOAc and washed with saturated $NaCl_{(aq)}$ (5×). Dried organic layer over anhydrous $Na_2SO_4$ and concentrated under reduced pressure. Dissolved in 7 M ammonia in MeOH (7 mL) and stirred for 18 h. Concentrated reaction under reduced pressure. Purified with $C_{18}$ preparatory HPLC with TFA as modifier. Combined fractions and concentrated under reduced pressure. Dissolved in $NaHCO_{3(aq)}$ and repurified with preparatory HPLC under neutral condition. Combined fractions and freeze-dried to afford example 13.

¹H NMR (400 MHz, D₂O) δ 7.54 (s, 1H), 6.62-6.49 (m, 2H), 5.98-5.79 (m, 1H), 5.55-5.36 (m, 2H), 5.31 (d, J=11.1 Hz, 1H), 5.11 (ddd, J=54.8, 5.2, 2.9 Hz, 1H), 4.42 (dd, J=20.6, 4.8 Hz, 1H), 3.62-3.43 (m, 2H).
¹⁹F NMR (376 MHz, D₂O) δ-193.23 (dd, J=54.7, 44.2 Hz). MS m/z=295.2 [M+1]

Example 14

(2R,3R,4R,5S)-5-(4-aminopyrrolo[1,24][1,2,4]triazin-7-yl)-2-ethyl-4-fluoro-2-(hydroxymethyl)tetrahydrofuran-3-ol

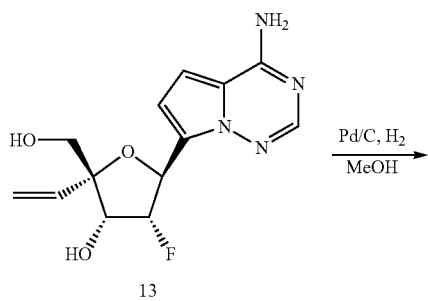

Example 13 (5 mg, 0.017 mmol) was dissolved into methanol (2 mL). 10% Pd/C Degussa Catalyst (2 mg) was then added and the resulting mixture was stirred under atmosphere of hydrogen gas. After 40 min, the resulting mixture was filtered to remove Pd/C and the filtrate was concentrated under reduced pressure. The residue was dissolved in water and freeze-dried to afford example 14.

¹H NMR (400 MHz, D₂O) δ 7.67 (s, 1H), 6.79-6:55 (m, 2H), 5.54-5.12 (m, 2H), 4.46 (dd, J=15.1, 5.5 Hz, 1H), 3.65-3.44 (m, 2H), 1.89-1.44 (m, 2H), 0.84 (t, J=7.6 Hz, 3H).

¹⁹F NMR (376 MHz, D₂O) δ −197.62 (ddd, J=54.5, 20.6, 15.0 Hz).

MS m/z=297.3 [M+1].

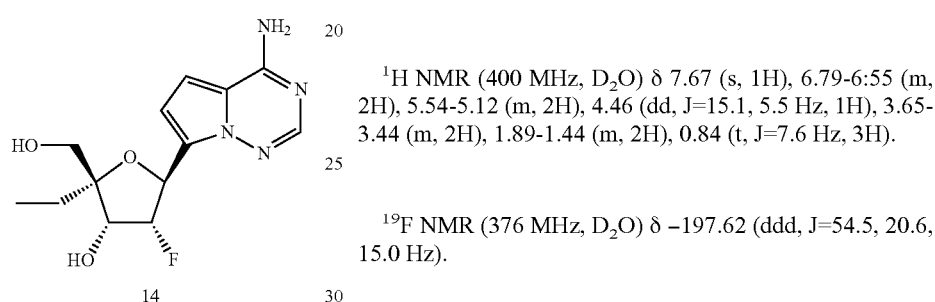

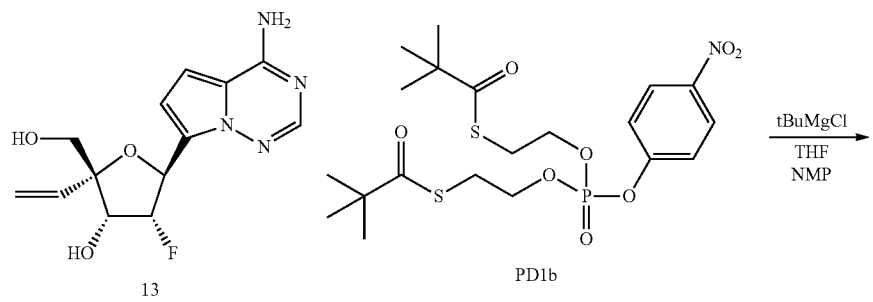

PD1b

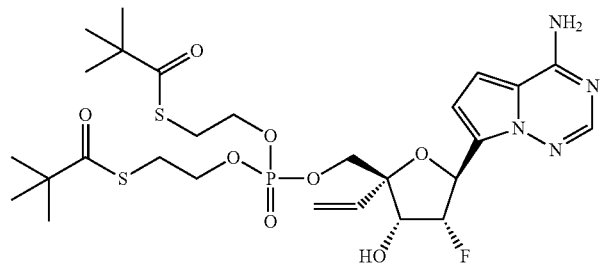

PD4

Example 15

Example 15 (PD4)

S,S'-2,2'-(((((2R,3R,4R,5S)-5-(4-aminopyrrolo[1,2-f][1,2,4]triazin-7-yl)-4-fluoro-3-hydroxy-2-vinyltetrahydrofuran-2-yl)methoxy)phosphoryl)bis(oxy)bis(ethane-2,1-diyl)bis(2,2-dimethylpropanethioate)

Example 13 (5 mg, 0.017 mmol) was dissolved into anhydrous DMF (0.5 mL). Added p-nitro-phenonate (13 mg, 0.026 mmol) in one portion. Added 1M t-butylmagnesium chloride in THF (25 µL, 0.026 mmol) dropwise. Stirred for 1 h. Warmed to 50° C. and stirred for 2 h. Added more p-nitrophenonate (13 mg, 0.026 mmol) and stirred for 2 h. Added more 1M t-butylmagnesium chloride in THF (25 µL, 0.026 mmol) and stirred for 16 h at 50° C. Cooled to RT. The resulting mixture was purified directly by preparatory HPLC column and eluted with linear gradient 0-100% ACN in water to afford example 15 (PD4).

$^1$H NMR (400 MHz, CD$_3$OD) δ 7.84 (s, 1H), 6.92 (d, J=4.5 Hz, 1H), 6.80 (d, J=4.5 Hz, 1H), 6.10 (dd, J=17.4, 10.9 Hz, 1H), 5.67 (dd, J=5.8, 1.9 Hz, 1H), 5.61 (s, 1H), 5.45-5.35 (m, 1H), 5.15 (ddd, J=55.6, 5.0, 2.2 Hz, 1H), 4.65 (dd, J=22.5, 5.1 Hz, 1H), 4.13 (dd, J=11.1, 5.2 Hz, 1H), 4.08-3.95 (m, 5H), 3.06 (dd, J=7.0, 6.1 Hz, 4H), 1.21 (s, 9H), 1.18 (s, 9H).

$^{19}$F NMR (376 MHz, CD$_3$OD) δ 192.99 (td, J=55.7, 23.6 Hz).

MS m/z=663.0 [M+1].

Example 16 (PD5)

(2S)-2-ethylbutyl 2-(((((2R,3S,4R,5S)-5-(4-aminopyrrolo[2,1-f][1,2,4]triazin-7-yl)-2-azido-3,4-dihydroxytetrahydrofuran-2-yl)methoxy)(phenoxy)phosphoryl)amino)propanoate Example 5 (5 mg, 0.016 mmol) was dissolved in anhydrous N-methyl-2-pyrrolidone (0.2 mL) and THF (0.1 mL) was added under an argon atmosphere. tert-Butyl magnesium chloride (1 M in THF, 24 µL, 0.024 mmol) was then added at RT, and white solids precipitated. After 5 min, a solution of p-nitrophenylphosphoamidate PD3c (15 mg, 0.032 mmol) in THF (0.1 mL) was added to the reaction mixture in one portion, and the resulting mixture was heated to 50° C. After 3.5 h, the reaction mixture was allowed to cool to RT and was stirred for 18 h. p-Nitrophenylphosphoamidate PD3c (50 mg, 0.111 mmol) and tert-butyl magnesium chloride (1M in THF, 24 µL, 0.024 mmol) were then added and the reaction mixture was stirred for an additional 5 d. The resulting residue was then purified directly by preparatory HPLC (Phenominex Synergi 4u Hydro-RR 80A 150×30 mm column, 40-100% acetonitrile/water gradient). The fractions containing the desired product were combined and were lyophilized to afford example 16 (PD5) (2:1 diastereomeric mixture).

$^1$H NMR (400 MHz, CDCl$_3$) δ 7.88 (br s, 1H), 7.33-7.22 (br m, 2H), 7.22-7.10 (br m, 3H), 6.69 (br d, J=4.4 Hz, 1H), 6.61 (br d, J=4.5 Hz, 1H), 5.64-5.56 (m, 1H), 4.54 (d, J=6.3 Hz, 1H), 4.50-4.20 (m, 3H), 4.11-3.94 (m, 3H), 3.90-3.76 (m, 1H), 1.49 (s, J=6.2 Hz, 1H), 1.40-1.24 (m, 7H), 0.86 (t, J=7.4 Hz, 6H).

$^{31}$P NMR (162 MHz, CDCl$_3$) δ 2.68 (s), 2.56 (s).

LC/MS: t$_R$=1.70 min, MS m/z=619.09 [M+1]; LC system: Thermo Accela 1250 UHPLC.

MS system: Thermo LCQ Fleet; Column: Kinetex 2.6µ XB-C18 100A, 50×4.6 mm; Solvents: Acetonitrile with 0.1% acetic acid, Water with 0.1% acetic acid; Gradient: 0 min-2.0 min 2-100% ACN, 2.0 min-3.05 min 100% ACN, 3.05 min-3.2 min 100%-2% ACN, 3.2 min-3.5 min 2% ACN at 2 µl/min.

HPLC: t$_R$=3.010 min; HPLC system: Agilent 1100 series.; Column: Gemini 5µ C18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min.

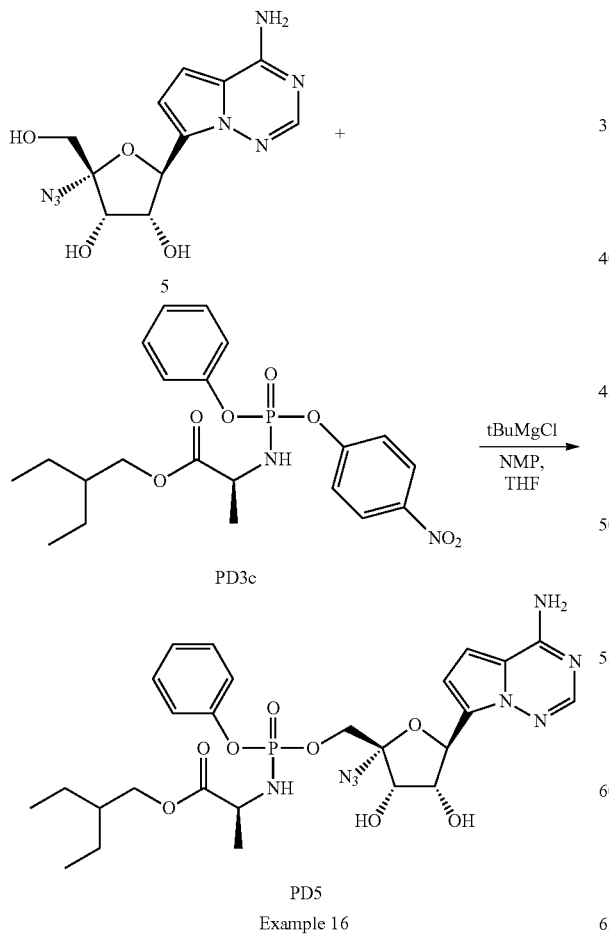

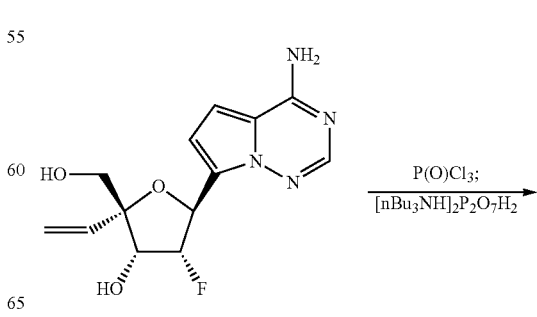

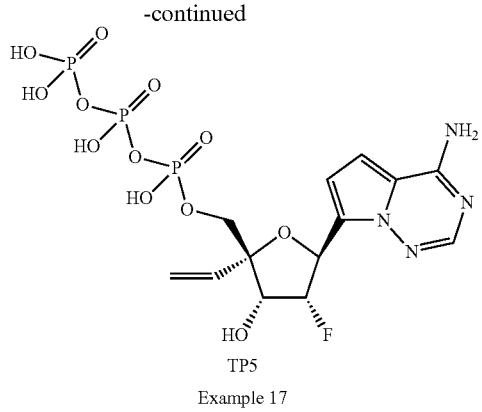

TP5
Example 17

Example 17 (TP5)

((2R,3R,4R,5S)-5-(4-aminopyrrolo[2,1-f][1,2,4]tri-azin-7-yl)-4-fluoro-3-hydroxy-2-vinyltetrahydrofuran-2-yl)methyl tetrahydrogen triphosphate To a solution of example 13 (6.0 mg, 0.020 mmol) in PO(OMe)$_3$ (0.6 mL) at 0° C. was added POCl$_3$ (50 mg, 0.32 mmol). The reaction mixture was stirred at 0° C. for 6 h, at which point Ion-exchange HPLC showed approximately 90% conversion. A solution of pyrophosphate tributylamine salts (250 mg) in ACN (0.6 mL) was added, followed by tributylamine (110 mg, 0.59 mmol). The reaction mixture was stirred at 0° C. for 1 h. The reaction was quenched with triethylammonium bicarbonate buffer (1 M, 5 mL). The reaction mixture was stirred at RT for 0.5 h, then concentrated and co-evaporated with water twice. The residue was dissolved in H$_2$O (5 mL) and loaded to a ion-exchange column, eluted with H$_2$O, then 5-35% triethylammonium bicarbonate buffer (1 M)-H$_2$O. The product fractions were combined, concentrated and co-evaporated with H$_2$O. The solid residue was dissolved in 3 mL of H$_2$O and 100 μL of NaOH (1 N) was added. The resulting mixture was purified with C-18 column, eluted with H$_2$O, and the fractions containing product were combined and concentrated under reduced pressure to afford Example 17 (TP5) as the tetra-sodium salt.

$^1$H NMR (400 MHz, D$_2$O): δ 7.74 (s, 1H), 6.89 (d, J=4.4 Hz, 1H), 6.81 (d, J=4.6 Hz, 1H), 6.00 (dd, J=17.4, 11.1 Hz, 1H), 5.72 (d, J=23.3 Hz, 1H), 5.49 (d, J=16.9 Hz, 1H), 5.32 (d, J=11.1 Hz, 1H), 5.14 (dd, J=54.0, 4.6 Hz, 1H), 4.72 (dd, J=23.7, 4.5 Hz, 1H), 4.09 (dd, J=11.3, 5.8 Hz, 1H), 3.79 (dd, J=11.6, 3.8 Hz, 1H).

$^{31}$P NMR (162 MHz, D$_2$O): δ −8.38 (d, J=20.5 Hz), −13.67 (d, J=19.3 Hz), −24.20 (t, J=19.9 Hz).

$^{19}$F NMR (376 MHz, CDCl$_3$) δ −194.58 (dt, J=55.0, 23.8 Hz).

MS m/z=533.0[M−1], 535.0 [M−1].

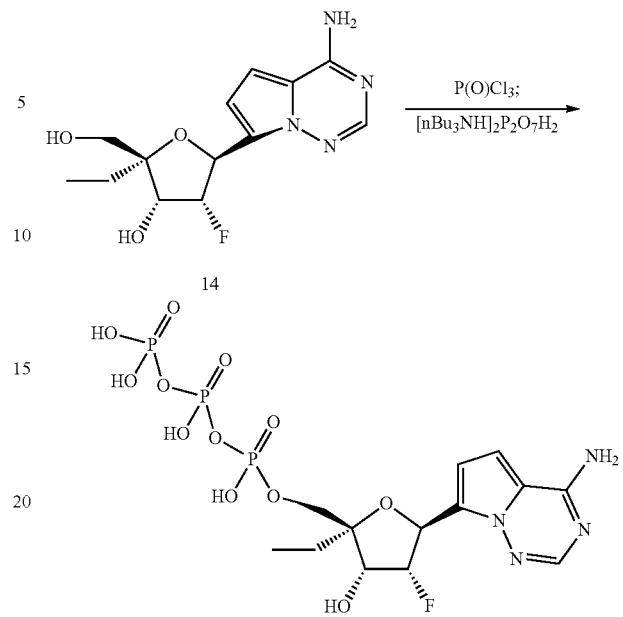

Example 18
TP6

Example 18 (TP6)

((2R,3R,4R,5S)-5-(4-aminopyrrolo[2,1-f][1,2,4]tri-azin-7-yl)-2-ethyl-4-fluoro-3-hydroxytetrahydrofuran-2-yl)methyl tetrahydrogen triphosphate To a solution of example 14 (5.0 mg, 0.017 mmol) in PO(OMe)$_3$ (0.6 mL) at 0° C. was added POCl$_3$ (45 mg, 0.30 mmol). The reaction mixture was stirred at 0° C. for 6 h, at which point Ion-exchange HPLC showed approximately 90% conversion. A solution of pyrophosphate tributylamine salts (250 mg) in ACN (0.6 mL) was added, followed by tributylamine (110 mg, 0.59 mmol). The reaction mixture was stirred at 0° C. for 1 h. The reaction was quenched with triethylammonium bicarbonate buffer (1 M, 5 mL). The reaction mixture was stirred at RT for 0.5 h, then concentrated and co-evaporated with water twice. The residue was dissolved in H$_2$O (5 mL) and loaded to a ion-exchange column, eluted with H$_2$O, then 5-35% triethylammonium bicarbonate buffer (1 M)-H$_2$O. The product fractions were combined, concentrated and co-evaporated with H$_2$O. The solid residue was dissolved in 3 mL of H$_2$O and 100 μL of NaOH (1 N) was added. The resulting mixture was purified with C-18 column, eluted with H$_2$O, and the fractions containing product were combined and concentrated under reduced pressure to afford 18 (TP6) as the tetra-sodium salt.

$^1$H NMR (400 MHz, D$_2$O): δ 7.73 (s, 1H), 6.86 (d, J=4.6 Hz, 1H), 6.80 (d, J=4.6 Hz, 1H), 5.60 (dd, J=21.9, 3.5 Hz, 1H), 5.23 (dt, J=55.2, 4.2 Hz, 1H), 4.65 (dd, J=20.6, 5.3 Hz, 1H), 4.08-3.84 (m, 3H), 1.83 (dq, J=14.4, 7.4, 6.9 Hz, 1H), 1.62 (dq, J=15.0, 7.5 Hz, 1H), 0.87 (t, J=7.5 Hz, 3H).

$^{31}$P NMR (162 MHz, D$_2$O): −5.72 (d, J=20.2 Hz), −10.81 (d, J=19.3 Hz), −21.60 (t, J=19.8 Hz).

$^{19}$F NMR (376 MHz, CDCl$_3$) δ −194.77 (dt, J=55.2, 21.2 Hz).

MS m/z=535.1[M−1], 536.9.0 [M+1].

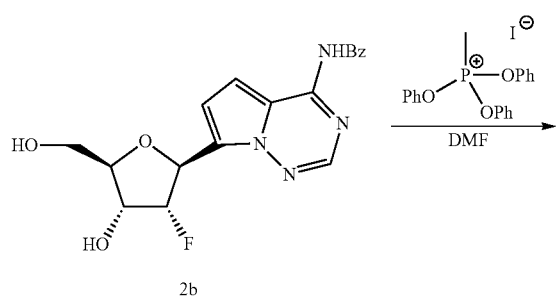
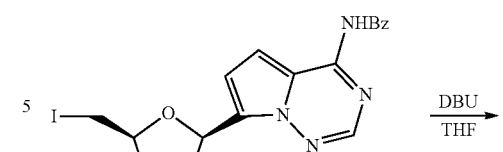

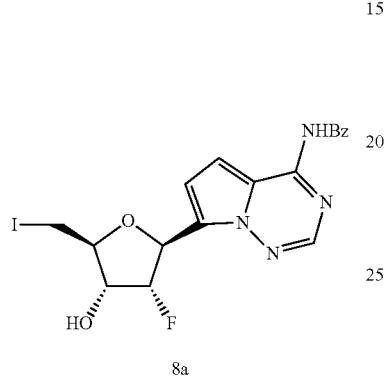

Intermediate 8a—N-(7-((2S,3R,4R,5S)-3-fluoro-4-hydroxy-5-(iodomethyl)tetrahydrofuran-2-yl)pyrrolo[2,1-f][1,2,4]triazin-4-yl)benzamide To an argon purged flask was added 2b (68 mg, 0.183 mmol) in DMF (2 mL) followed by methyltriphenoxyphosphonium iodide (124 mg, 0.274 mmol). The reaction was allowed to stir at room temperature for 5 min where complete conversion to product was observed by LCMS. The reaction was quenched with methanol and solvents were removed under reduced pressure. The crude material was partitioned between EtOAc and H₂O. The organics were separated and washed with brine. The resulting material was dried over Na₂SO₄, filtered and solvent removed under reduced pressure. The crude material was purified by silica gel chromatography (20-100% EtOAc/Hexanes) to afford intermediate 8a.

$^1$H NMR (400 MHz, DMSO-$d_6$) δ 8.17 (m, 3H), 7.63 (t, J=7.4 Hz, 1H), 7.53 (t, J=7.6 Hz, 2H), 7.17-6.96 (m, 2H), 5.74 (s, 1H), 5.60 (d, J=24.9 Hz, 1H), 5.19 (ddd, J=54.6, 4.5, 2.1 Hz, 1H), 4.09-3.92 (m, 1H), 3.72 (t, J=6.4 Hz, 1H), 3.63 (dd, J=11.0, 3.4 Hz, 1H), 3.44 (dd, J=11.0, 5.9 Hz, 1H).

$^{19}$F NMR (376 MHz, DMSO-$d_6$) δ −194.23 (m).

LC/MS: $t_R$=1.13 min, MS m/z=483.23 [M+1]

LC system: Thermo Accela 1250 UHPLC

MS system: Thermo LCQ Fleet; Column: Kinetex 2.6µ C18 100A, 50×3.00 mm

Solvents: Acetonitrile with 0.1% formic acid, Water with 0.1% formic acid

Gradient: 0 min-1.4 min 2-100% ACN, 1.4 min-1.80 min 100% ACN, 1.8 min-1.85 min 100%-2% ACN, 1.85 min-2 min 2% ACN.

Intermediate 8b—(3R,4R,5S)-5-(4-aminopyrrolo[2,1-f][1,2,4]triazin-7-yl)-4-fluoro-2-methylenetetrahydrofuran-3-ol Intermediate 8a (80 mg, 0.166 mmol) was dissolved into THF. DBU (0.074 mL, 0.498 mmol) was added in one portion. The reaction was then heated to 60° C. in an oil bath for 16 h. The reaction was cooled to room temperature and the solvent was removed under reduced pressure. The crude material was purified by silica gel chromatography (0-70% EtOAc/Hex) to afford intermediate 8b.

$^1$H NMR (400 MHz, DMSO-$d_6$) δ 8.34-8.05 (m, 3H), 7.63 (t, J=7.4 Hz, 1H), 7.53 (t, J=7.6 Hz, 2H), 7.13 (d, J=4.7 Hz, 1H), 6.85 (d, J=4.4 Hz, 1H), 5.97-5.82 (m, 2H), 5.39-5.13 (m, 1H), 4.89-4.69 (m, 1H), 4.38 (d, J=2.1 Hz, 1H), 4.16 (t, J=1.8 Hz, 1H).

$^{19}$F NMR (376 MHz, DMSO-$d_6$) δ −198.14 (ddd, J=53.9, 24.7, 20.9 Hz).

LC/MS: $t_R$=1.05 min, MS m/z=355.15 [M+1]

LC system: Thermo Accela 1250 UHPLC

MS system: Thermo LCQ Fleet; Column: Kinetex 2.6µ C18 100A, 50×3.00 mm

Solvents: Acetonitrile with 0.1% formic acid, Water with 0.1% formic acid

Gradient: 0 min-1.4 min 2-100% ACN, 1.4 min-1.80 min 100% ACN, 1.8 min-1.85 min 100%-2% ACN, 1.85 min-2 min 2% ACN.

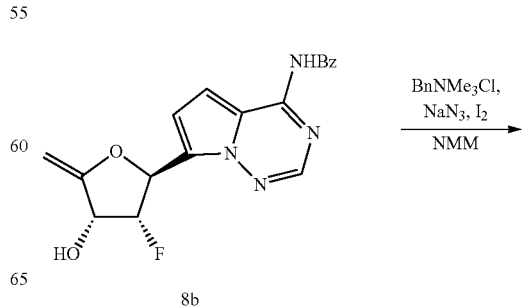

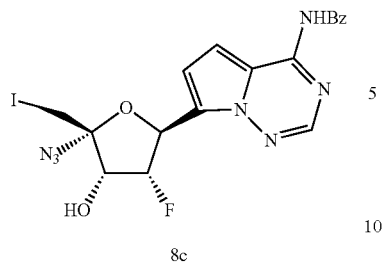

8c

Intermediate 8c—(2S,3R,4R,5S)-5-(4-aminopyrrolo[2,1-f][1,2,4]triazin-7-yl)-2-azido-4-fluoro-2-(iodomethyl)tetrahydrofuran-3-ol Benzyltrimethylammonium chloride (55 mg, 0.296 mmol) and sodium azide (19.3 mg, 0.296 mmol) were dissolved into ACN (1 mL). The resulting mixture was stirred at RT overnight and was then filtered and added via syringe to a solution of intermediate 8b (50 mg, 0.141 mmol) in THF (1 mL). N-methylmorpholine (0.078 mL, 0.706 mmol) was then added followed by the dropwise addition of a solution of iodine (65 mg, 0.25 mmol) in THF (1 mL). After 15 min, N-acetyl cysteine was added until the evolution of gas was no longer observable. Then saturated aqueous sodium thiosulfate was added until the solution was light yellow. The crude mixture was partitioned between EtOAc and H$_2$O. The phases were split and the organic layer was dried over sodium sulfate, filtered, and concentrated under reduced pressure. The crude material was purified by silica gel chromatography (0-60% EtOAc/Hex) to afford intermediate 8c.

$^1$H NMR (400 MHz, DMSO-d$_6$) δ 8.31-8.05 (m, 3H), 7.63 (t, J=7.5 Hz, 1H), 7.53 (t, J=7.6 Hz, 2H), 7.14 (d, J=4.6 Hz, 1H), 7.04 (s, 1H), 6.34 (d, J=6.9 Hz, 1H), 5.80 (d, J=23.7 Hz, 1H), 5.55-5.31 (m, 1H), 4.62 (dt, J=21.9, 5.9 Hz, 1H), 3.78-3.56 (m, 2H).

$^{19}$F NMR (376 MHz, DMSO-d$_6$) δ −194.44 (dt, J=54.7, 22.8 Hz).

LC/MS: t$_R$=1.19 min, MS m/z=524.09 [M+1]; LC system: Thermo Accela 1250 UHPLC

MS system: Thermo LCQ Fleet; Column: Kinetex 2.6μ C18 100A, 50×3.00 mm

Solvents: Acetonitrile with 0.1% formic acid, Water with 0.1% formic acid

Gradient: 0 min-1.4 min 2-100% ACN, 1.4 min-1.80 min 100% ACN, 1.8 min-1.85 min 100%-2% ACN, 1.85 min-2 min 2% ACN.

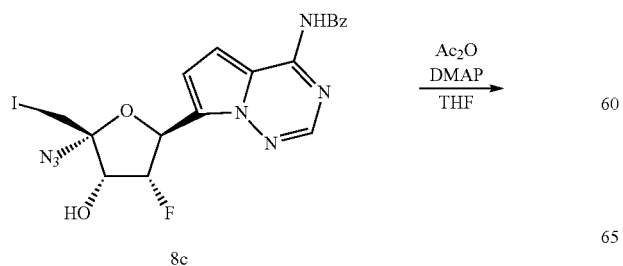

8c

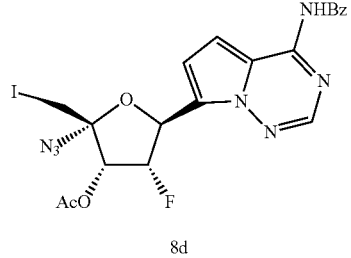

8d

Intermediate 8d—(2S,3R,4S,5S)-5-(4-aminopyrrolo[2,1f-][1,2,4]triazin-7-yl)-2-azido-4-fluoro-2-(iodomethyl)tetrahydrofuran-3-yl acetate To a solution of intermediate 8c (40 mg, 0.076 mmol) in THF (1 mL) was added acetic anhydride (0.009 mL, 0.092 mmol) followed by DMAP (10 mg, 0.082 mmol) at RT. After 15 min, the reaction mixture was quenched with methanol, and the resulting mixture concentrated under reduced pressure. The crude was purified by silica gel chromatography (0-50% EtOAc/Hex) to afford intermediate 8d.

$^1$H NMR (400 MHz, CDCl$_3$) δ 8.15-8.02 (m, 3H), 7.62 (t, J=7.3 Hz, 1H), 7.53 (t, J=7.6 Hz, 2H), 7.44 (d, J=4.6 Hz, 1H), 7.00 (d, J=4.6 Hz, 1H), 5.95-5.80 (m, 1H), 5.70-5.43 (m, 2H), 3.71 (d, J=11.3 Hz, 1H), 3.60 (d, J=11.3 Hz, 1H), 2.25 (s, 3H).

$^{19}$F NMR (376 MHz, CDCl$_3$) δ −192.78 (ddd, J=55.7, 24.6, 18.5 Hz).

LC/MS: t$_R$=1.35 min, MS m/z=566.14 [M+1]; LC system: Thermo Accela 1250 UHPLC

MS system: Thermo LCQ Fleet; Column: Kinetex 2.6μ C18 100A, 50×3.00 mm

Solvents: Acetonitrile with 0.1% formic acid, Water with 0.1% formic acid

Gradient: 0 min-1.4 min 2-100% ACN, 1.4 min-1.80 min 100% ACN, 1.8 min-1.85 min 100%-2% ACN, 1.85 min-2 min 2% ACN.

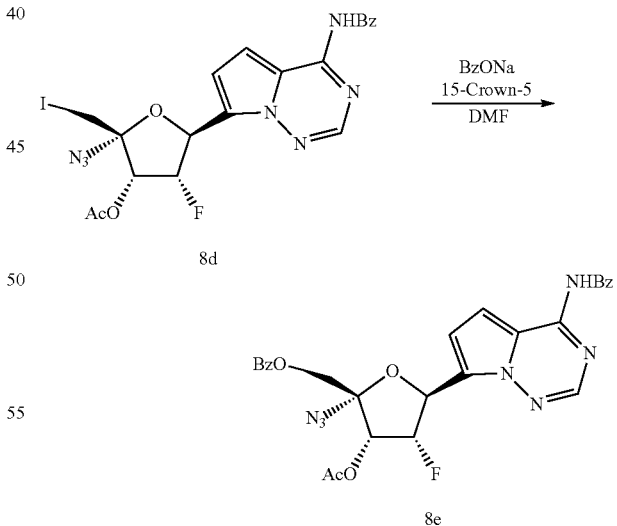

Intermediate 8e—((2R,3R,4S,5S)-3-acetoxy-2-azido-5-(4-benzamidopyrrolo[2,1-f][1,2,4]triazin-7-yl)-4-fluorotetrahydrofuran-2-yl)methyl benzoate To a solution of intermediate 8d (30 mgs, 0.053 mmol) in DMF (2 mL) was added 15-Crown-5 (0.105 mL, 0.531 mmol) and sodium benzoate (77 mg, 0.531 mmol) at RT. The reaction was then heated to 105° C. After 30 h, the reaction mixture was allowed to RT and was partitioned between 5% LiCl$_{(aq)}$ and EtOAc. The phases were split and the aqueous phase was washed with EtOAc (2×). The combined organic extracts were dried over anhydrous sodium sulfate, and were concentrated under reduced pressure. The crude residue was purified by silica gel chromatography (0-60% EtOAc/Hex) to afford intermediate 8e.

$^1$H NMR (400 MHz, CDCl$_3$) δ 8.25-7.97 (m, 4H), 7.69-7.40 (m, 6H), 7.36 (d, J=4.7 Hz, 1H), 6.95-6.80 (m, 1H), 5.90 (d, J=25.0 Hz, 1H), 5.65 (d, J=1.9 Hz, 1H), 5.62-5.48 (m, 1H), 4.69 (dd, J=79.3, 12.0 Hz, 2H), 2.20 (s, 3H).

$^{19}$F NMR (376 MHz, CDCl$_3$) δ −192.57 (ddd, J=53.9, 25.1, 22.0 Hz).

LC/MS: t$_R$=1.45 min, MS m/z=560.14 [M+1]; LC system: Thermo Accela 1250 UHPLC

MS system: Thermo LCQ Fleet; Column: Kinetex 2.6μ C18 100A, 50×3.00 mm

Solvents: Acetonitrile with 0.1% formic acid, Water with 0.1% formic acid

Gradient: 0 min-1.4 min 2-100% ACN, 1.4 min-1.80 min 100% ACN, 1.8 min-1.85 min 100%-2% ACN, 1.85 min-2 min 2% ACN.

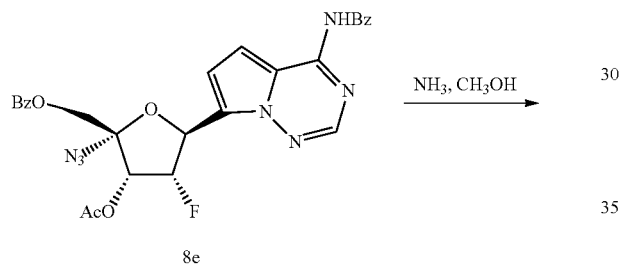

8e

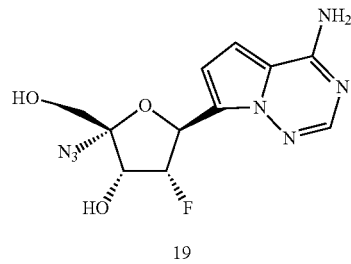

19

Example 19

(2R,3R,4R,5S)-5-(4-aminopyrrolo[2,1-f][1,2,4]triazin-7-yl)-2-azido-4-fluoro-2-(hydroxymethyl)tetrahydrofuran-3-ol To intermediate 8e (24 mg, 0.043 mmol) was added 7N NH$_3$ in CH$_3$OH (2 mL) at RT. After 16 h, the resulting mixture was concentrated under reduced pressure. The crude residue was purified by reverse phase HPLC without acid modifier to afford example 19.

$^1$H NMR (400 MHz, Methanol-d$_4$) δ 7.81 (s, 1H), 6.85 (d, J=4.5 Hz, 1H), 6.80 (d, J=4.5 Hz, 1H), 5.80 (dd, J=24.7, 1.9 Hz, 1H), 5.22 (ddd, J=55.6, 5.1, 1.9 Hz, 1H), 4.63 (dd, J=22.9, 5.1 Hz, 1H), 3.81 (d, J=12.1 Hz, 1H), 3.70 (d, J=12.2 Hz, 1H).

$^{19}$F NMR (376 MHz, Methanol-d$_4$) δ −195.30 (ddd, J=55.5, 24.6, 22.9 Hz).

LC/MS: t$_R$=0.61 min, MS m/z=310.02 [M+1]; LC system: Thermo Accela 1250 UHPLC

MS system: Thermo LCQ Fleet; Column: Kinetex 2.6μ C18 100A, 50×3.00 mm

Solvents: Acetonitrile with 0.1% formic acid, Water with 0.1% formic acid

Gradient: 0 min-1.4 min 2-100% ACN, 1.4 min-1.80 min 100% ACN, 1.8 min-1.85 min 100%-2% ACN, 1.85 min-2 min 2% ACN.

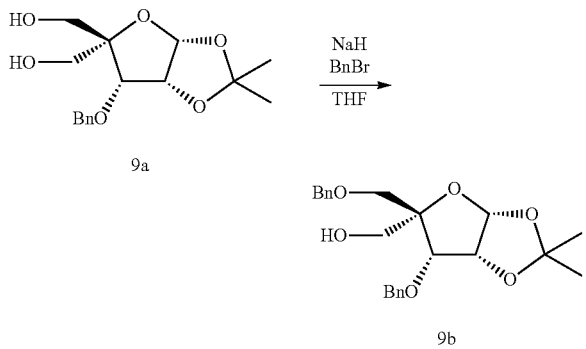

Intermediate 9b—((3aR,5R,6S,6aR)-6-(benzyloxy)-5-((benzyloxy)methyl)-2,2-dimethyltetrahydrofuro[2,3-d][1,3]dioxol-5-yl)methanol ((3aR,6S,6aR)-6-(benzyloxy)-2,2-dimethyltetrahydrofuro[2,3-d][1,3]dioxole-5,5-diyl)dimethanol (9a, Purchased from Carbosynth, 10.0 g, 32.2 mmol) was added to a solution of sodium hydride (60% by wt, 1.55 g, 38.7 mmol) in THF (100 mL) at 0° C. under an argon atmosphere. After 10 min, benzyl bromide (4.54 mL, 38.6 mmol) was added and the reaction mixture was allowed to warm to RT. After 2 h, the reaction was quenched with saturated aqueous ammonium chloride solution (500 mL). The resulting mixture was extracted with ethyl acetate (500 mL). The organic phase was then washed with brine (400 mL), was dried over anhydrous sodium sulfate, and was concentrated under reduced pressure to afford a colorless oil. The crude residue was purified via SiO$_2$ column chromatography (220 g SiO$_2$ Combiflash HP Gold Column, 0-100% ethyl acetate/hexanes) to afford intermediate 9a (9.49 g, 73%) as a colorless oil.

$^1$H NMR (400 MHz, DMSO-d$_6$) δ 7.38-7.19 (m, 10H), 5.68 (app t, J=3.6 Hz, 1H), 4.73 (q, J=4.4 Hz, 1H), 4.63 (d, J=12.1 Hz, 1H), 4.49-4.36 (m, 3H), 4.24 (br s, 1H), 4.20-4.13 (m, 1H), 3.81 (d, J=11.9 Hz, 1H), 3.56 (d, J=11.9 Hz, 1H), 3.46 (q, J=10.3 Hz, 2H), 1.47 (s, 3H), 1.25 (s, 3H).

LC/MS: t$_R$=1.88 min, MS m/z=423.31 [M+Na]; LC system: Thermo Accela 1250 UHPLC; MS system: Thermo LCQ Fleet; Column: Kinetex 2.6μ XB-C18 100A, 50×4.6 mm; Solvents: Acetonitrile with 0.1% acetic acid, Water with 0.1% acetic acid; Gradient: 0 min-2.0 min 2-100% ACN, 2.0 min-3.05 min 100% ACN, 3.05 min-3.2 min 100%-2% ACN, 3.2 min-3.5 min 2% ACN at 2 μl/min.

HPLC: t$_R$=3.79 min; HPLC system: Agilent 1100 series.; Column: Gemini 5μ C18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min.

TLC: eluent: 40% ethyl acetate in hexanes, $R_f$=0.4 (UV)

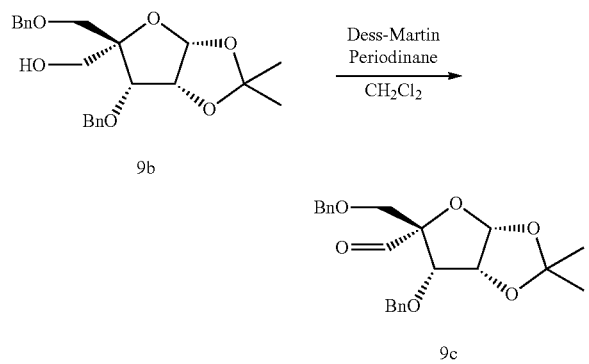

9b

9c

Intermediate 9c—(3aR,5R,6S,6aR)-6-(benzyloxy)-5-((benzyloxy)methyl)-2,2-dimethyltetrahydrofuro[2,3-d][1,3]dioxole-5-carbaldehyde Dess-Martin Periodinane (3.1 g, 7.3 mmol) was added to a solution of intermediate 9b (1.95 g, 4.87 mmol) in dichloromethane (24.5 mL) at RT. After 1.5 h, the reaction mixture was purified via $SiO_2$ column chromatography (80 g $SiO_2$ Combiflash HP Gold Column, 0-100% ethyl acetate/hexanes) to afford intermediate 9c (1.94 g, 100%) as a colorless oil.

$^1$H NMR (400 MHz, CDCl$_3$) δ 9.91 (s, 1H), 7.36-7.11 (m, 10H), 5.84 (d, J=3.4 Hz, 1H), 4.71 (d, J=12.1 Hz, 1H), 4.59 (d, J=12.2 Hz, 1H), 4.59-4.58 (m, 1H), 4.52 (d, J=12.0 Hz, 1H), 4.46 (d, J=12.0 Hz, 1H), 4.37 (d, J=4.4 Hz, 1H), 3.68 (d, J=11.0 Hz, 1H), 3.61 (d, J=11.0 Hz, 1H), 1.60 (s, 3H), 1.35 (s, 3H).

LC/MS: $t_R$=1.99 min, MS m/z=421.25 [M+Na]; LC system: Thermo Accela 1250 UHPLC; MS system: Thermo LCQ Fleet; Column: Kinetex 2.6μ XB-C18 100A, 50×4.6 mm; Solvents: Acetonitrile with 0.1% acetic acid, Water with 0.1% acetic acid; Gradient: 0 min-2.0 min 2-100% ACN, 2.0 min-3.05 min 100% ACN, 3.05 min-3.2 min 100%-2% ACN, 3.2 min-3.5 min 2% ACN at 2 μl/min.

HPLC: $t_R$=4.09 min; HPLC system: Agilent 1100 series.; Column: Gemini 5μ C18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min.

TLC: eluent: 40% ethyl acetate in hexanes, $R_f$=0.6 (UV)

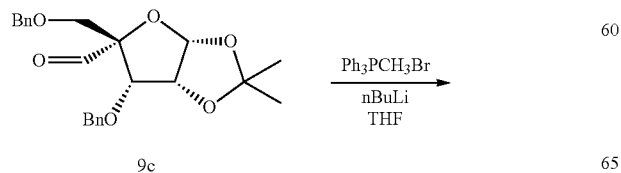

9c

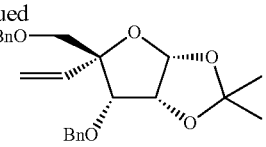

9d

Intermediate 9d—(3aR,5R,6S,6aR)-6-(benzyloxy)-5-((benzyloxy)methyl)-2,2-dimethyl-5-vinyltetrahydrofuro[2,3-d][1,3]dioxole 2.5M n-butyllithium (6.02 mL) was added to a solution of methyltriphenylphosphonium bromide (5.38 g, 15.1 mmol) in tetrahydrofuran (20 mL) at −78° C. The reaction was allowed to warm to 0° C., and a solution of intermediate 9c (2.00 g, 5.02 mmol) in tetrahydrofuran (5 mL) was added slowly via syringe. The reaction mixture was allowed to warm to RT, and was stirred for 4 h. The reaction mixture was then quenched with saturated aqueous ammonium chloride solution (10 mL) and was partitioned between water (200 mL) and ethyl acetate (200 mL). The layers were split and the organic layer was washed with brine (200 mL), dried over anhydrous sodium sulfate, and was concentrated under reduced pressure. The crude residue was purified via $SiO_2$ column chromatography (120 g $SiO_2$ Combiflash HP Gold Column, 0-50% ethyl acetate/hexanes) to afford intermediate 9d (1.01 g, 51%) as a colorless oil.

$^1$H NMR (400 MHz, CDCl$_3$) δ 7.42-7.17 (m, 10H), 6.19 (dd, J=17.6, 11.0 Hz, 1H), 5.76 (d, J=3.9 Hz, 1H), 5.52 (dd, J=17.5, 1.9 Hz, 1H), 5.25 (dd, J=11.1, 1.8 Hz, 1H), 4.76 (d, J=12.3 Hz, 1H), 4.62-4.55 (m, 2H), 4.52 (d, J=12.1 Hz, 1H), 4.41 (d, J=12.1 Hz, 1H), 4.25 (d, J=4.9 Hz, 1H), 3.32 (d, J=1.5 Hz, 2H), 1.52 (s, 3H), 1.29 (s, 3H)

LC/MS: $t_R$=2.13 min, MS m/z=419.24 [M+Na]; LC system: Thermo Accela 1250 UHPLC; MS system: Thermo LCQ Fleet; Column: Kinetex 2.6μ XB-C18 100A, 50×4.6 mm; Solvents: Acetonitrile with 0.1% acetic acid, Water with 0.1% acetic acid; Gradient: 0 min-2.0 min 2-100% ACN, 2.0 min-3.05 min 100% ACN, 3.05 min-3.2 min 100%-2% ACN, 3.2 min-3.5 min 2% ACN at 2 μl/min.

HPLC: $t_R$=4.37 min; HPLC system: Agilent 1100 series.; Column: Gemini 5μ C18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min.

TLC: eluent: 50% ethyl acetate in hexanes, $R_f$=0.55 (UV)

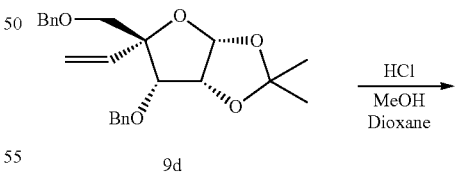

9d

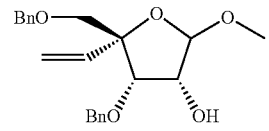

9e

Intermediate 9e—(3R,4S,5R)-4-(benzyloxy)-5-((benzyloxy)methyl)-2-methoxy-5-vinyltetrahydrofuran-3-ol 4M HCl in dioxane (320 µL) was added to a solution of intermediate 9d (1.01 g, 2.55 mmol) in methanol (12.5 mL) at RT. After 1.25 h, the reaction mixture was partitioned between ethyl acetate (100 mL) and saturated aqueous sodium bicarbonate solution (100 mL). The phases were split and the organic phase was washed with brine (100 mL), was dried over anhydrous sodium sulfate, and was concentrated under reduced pressure to afford crude intermediate 9e (1.05 g, ~2.5:1 mixture of 1' anomers) as a colorless oil.

LC/MS: major anomer $t_R$=2.00 min, MS m/z=393.22 [M+Na], minor anomer $t_R$=1.98 min, MS m/z=393.22 [M+Na]; LC system: Thermo Accela 1250 UHPLC; MS system: Thermo LCQ Fleet; Column: Kinetex 2.6µ XB-C18 100A, 50×4.6 mm; Solvents: Acetonitrile with 0.1% acetic acid, Water with 0.1% acetic acid; Gradient: 0 min-2.0 min 2-100% ACN, 2.0 min-3.05 min 100% ACN, 3.05 min-3.2 min 100%-2% ACN, 3.2 min-3.5 min 2% ACN at 2 µl/min.

HPLC: major anomer $t_R$=4.01 min, minor anomer $t_R$=3.955 min; HPLC system: Agilent 1100 series.; Column: Gemini 5µ C18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min.

TLC: eluent: 25% ethyl acetate in hexanes, Major anomer $R_f$=0.30 (UV), Minor anomer $R_f$=0.25 (UV)

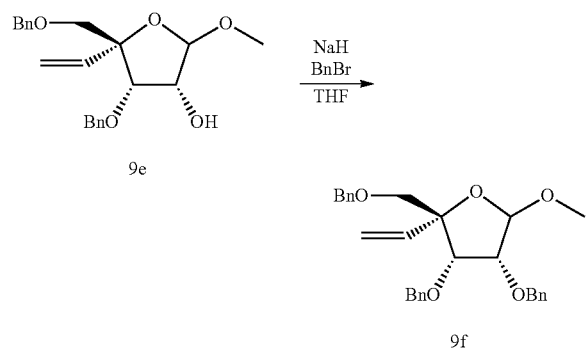

9e

Intermediate 9f—(2R,3S,4R)-3,4-bis(benzyloxy)-2-((benzyloxy)methyl)-5-methoxy-2-vinyltetrahydrofuran NaH (60% wt, 130 mg, 3.2 mmol) was added as a solid to a solution of intermediate 9e (1.0 g, 2.7 mmol) in THF (13.5 mL) at RT under an argon atmosphere. After 15 min, benzyl bromide (0.38 mL, 3.2 mmol) was added and the reaction mixture was stirred for 4 h. The reaction mixture was quenched with saturated aqueous ammonium chloride solution (5 mL) and was partitioned between ethyl acetate (100 mL) and brine (100 mL). The phases were split and the organic layer was dried over anhydrous sodium sulfate, and was concentrated under reduced pressure to afford crude intermediate 9f (1.57 g, ~2:1 mixture of 1' anomers) as a colorless oil.

LC/MS: major anomer $t_R$=1.88 min, MS m/z=483.36 [M+Na], minor anomer $t_R$=1.83 min, MS m/z=483.36 [M+Na]; LC system: Thermo Accela 1250 UHPLC; MS system: Thermo LCQ Fleet; Column: Kinetex 2.6µ XB-C18 100A, 50×4.6 mm; Solvents: Acetonitrile with 0.1% acetic acid, Water with 0.1% acetic acid; Gradient: 0 min-1.5 min 2-100% ACN, 1.5 min-2.2 min 100% ACN, 2.2 min-2.4 min 100%-2% ACN, 2.4 min-2.5 min 2% ACN at 2 µl/min.

HPLC: major anomer $t_R$=4.83 min, minor anomer $t_R$=4.62 min; HPLC system: Agilent 1100 series.; Column: Gemini 5µ C18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min.

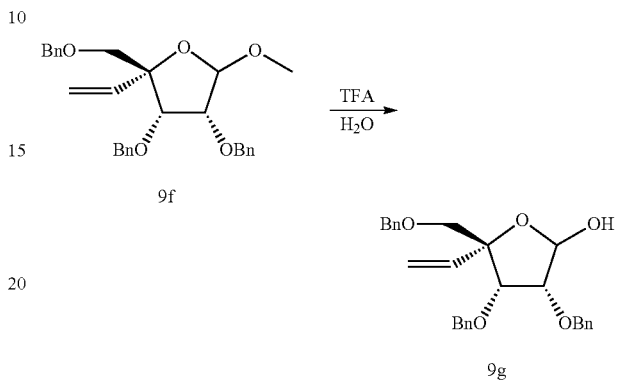

Intermediate 9g—(3R,4S,5R)-3,4-bis(benzyloxy)-5-((benzyloxy)methyl)-5-vinyltetrahydrofuran-2-ol A solution of TFA (16 mL) and water (1.6 mL) was added to intermediate 9f (1.5 g, 3.2 mmol) at 0° C., and the reaction mixture was allowed to warm to RT. After 9 h, water (1 mL) was added and the reaction mixture was allowed to stir an additional 10 h. The reaction mixture was then concentrated under reduced pressure. The crude residue was dissolved into ethyl acetate (200 mL) and was washed with saturated aqueous sodium bicarbonate solution (2×150 mL) and brine (150 mL). The organic layer was dried over anhydrous sodium sulfate and was concentrated under reduced pressure. The residue was purified via 'SiO$_2$ column chromatography (24 g SiO$_2$ Combiflash HP Gold Column, 0-100% ethyl acetate/hexanes). The fractions containing the desired product were combined to afford intermediate 9g (580 mg) as a colorless oil that was a mixture with other impurities. The mixture was used directly in the following step.

LC/MS: $t_R$=3.13 min, MS m/z=463.88 [M+OH]; LC system: Thermo Accela 1250 UHPLC; MS system: Thermo LCQ Fleet; Column: Kinetex 2.6µ XB-C18 100A, 50×4.6 mm; Solvents: Acetonitrile with 0.1% acetic acid, Water with 0.1% acetic acid; Gradient: 0 min-2.0 min 2-100% ACN, 2.0 min-3.05 min 100% ACN, 3.05 min-3.2 min 100%-2% ACN, 3.2 min-3.5 min 2% ACN at 2 µl/min.

HPLC: $t_R$=4.34 min; HPLC system: Agilent 1100 series.; Column: Gemini 5µ C18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min.

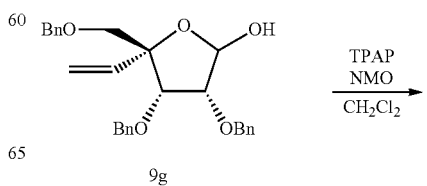

9g

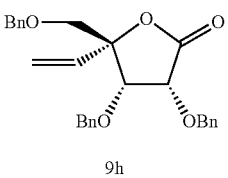

9h

Intermediate 9h—(3R,4S,5R)-3,4-bis(benzyloxy)-5-((benzyloxy)methyl)-5-vinyldihydrofuran-2(3H)-one Tetrapropylammonium perruthenate (45.7 mg, 130 μmol) and 4-methylmorpholine N-oxide (457 mg, 3.89 mmol) were added to a solution of intermediate 9g (580 mg, 1.30 mmol) and 4A MS (100 mg) in DCM (6.45 mL) at RT. After 1 h, silica gel (~500 mg) was added to the reaction mixture and the resulting slurry was filtered through a plug of silica gel (~1 g). The filtrate was concentrated under reduced pressure. The crude residue was purified via SiO$_2$ column chromatography (12 g SiO$_2$ Combiflash HP Gold Column, 0-100% ethyl acetate/hexanes) to afford intermediate 9h (254 mg, 18% over two steps) as a colorless oil.

$^1$H NMR (400 MHz, CDCl$_3$) δ 7.38-7.23 (m, 13H), 7.20-7.13 (m, 2H), 5.91 (dd, J=17.5, 11.2 Hz, 1H), 5.49 (dd, J=17.5, 0.9 Hz, 1H), 5.33 (dd, J=11.2, 0.9 Hz, 1H), 4.96 (d, J=12.0 Hz, 1H). 4.74-4.68 (m, 2H), 4.55-4.47 (m, 3H), 4.39 (d, J=11.9 Hz, 1H), 4.20 (d, J=6.0 Hz, 1H), 3.55 (d, J=10.8 Hz, 1H), 3.46 (d, J=10.8 Hz, 1H)

LC/MS: t$_R$=2.19 min, MS m/z=444.78 [M+H]; LC system: Thermo Accela 1250 UHPLC; MS system: Thermo LCQ Fleet; Column: Kinetex 2.6μ XB-C18 100A, 50×4.6 mm; Solvents: Acetonitrile with 0.1% acetic acid, Water with 0.1% acetic acid; Gradient: 0 min-2.0 min 2-100% ACN, 2.0 min-3.05 min 100% ACN, 3.05 min-3.2 min 100%-2% ACN, 3.2 min-3.5 min 2% ACN at 2 μl/min.

HPLC: t$_R$=4.53 min; HPLC system: Agilent 1100 series.; Column: Gemini 5μ C18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min.

TLC: eluent: 25% ethyl acetate in hexanes, R$_f$=0.45 (UV)

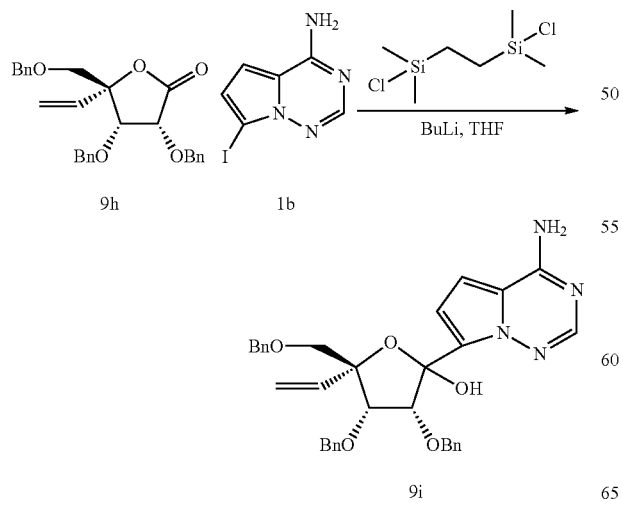

Intermediate 9i—(3R,4S,5R)-2-(4-aminopyrrolo[2,1-f][1,2,4]triazin-7-yl)-3,4-bis(benzyloxy)-5-((benzyloxy)methyl)-5-vinyltetrahydrofuran-2-ol n-Butyllithium (2.5M in hexanes, 1.0 mL, 2.5 mmol) was added rapidly to a suspension of intermediate 1b (0.21 g, 0.81 mmol) and 1,2-bis(chlorodimethylsilyl)ethane (0.17 g, 0.81 mmol) in THF (4 mL) at −78° C. under an argon atmosphere. The resulting mixture was then transferred via cannula to a solution of 9h (0.18 g, 0.41 mmol) in THF (1 mL) at −78° C. under an argon atmosphere. After 20 min, the reaction mixture was allowed to warm to 0° C. and was stirred for 15 min. The reaction mixture was quenched with saturated aqueous ammonium chloride solution (1 mL). The resulting mixture was diluted with ethyl acetate (100 mL) and was washed with saturated aqueous sodium bicarbonate solution (100 mL) and brine (100 mL). The organic layer was dried over anhydrous sodium sulfate, and was concentrated under reduced pressure. The crude residue was purified via SiO$_2$ column chromatography (12 g SiO$_2$ Combiflash HP Gold Column, 0-100% ethyl acetate/hexanes) to afford intermediate 9i (11.1 mg, 5%, mixture of isomers) as a colorless oil.

LC/MS: t$_R$=1.97 min, MS m/z=579.27 [M+H]; LC system: Thermo Accela 1250 UHPLC; MS system: Thermo LCQ Fleet; Column: Kinetex 2.6μ XB-C18 100A, 50×4.6 mm; Solvents: Acetonitrile with 0.1% acetic acid, Water with 0.1% acetic acid; Gradient: 0 min-2.0 min 2-100% ACN, 2.0 min-3.05 min 100% ACN, 3.05 min-3.2 min 100%-2% ACN, 3.2 min-3.5 min 2% ACN at 2 μl/min.

HPLC: t$_R$=3.37 min; HPLC system: Agilent 1100 series.; Column: Gemini 5μ C18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min.

TLC: eluent: ethyl acetate, R$_f$=0.3 (UV)

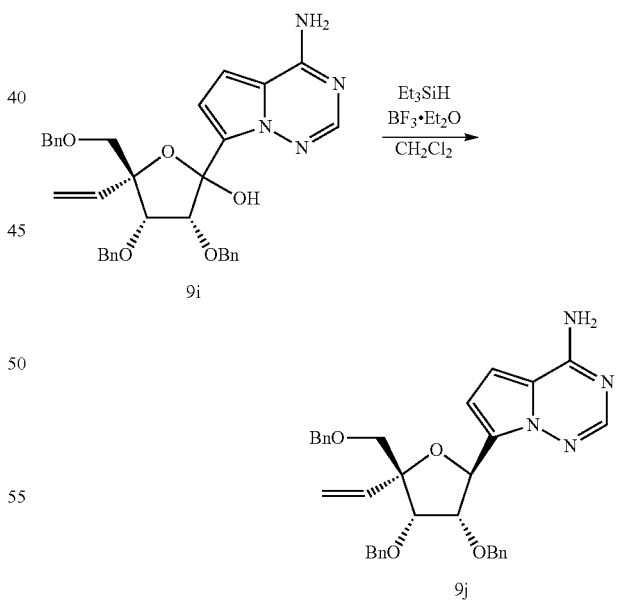

Intermediate 9j—7-((2S,3S,4S,5R)-3,4-bis(benzyloxy)-5-((benzyloxy)methyl)-5-vinyltetrahydrofuran-2-yl)pyrrolo[2,1-f][1,2,4]triazin-4-amine To a solution of intermediate 9i (11.0 mg, 19.0 μmol) and triethylsilane (0.5 mL) in DCM (1 mL) was added boron trifluoride diethyl etherate (0.1 mL) slowly at 0° C. under an argon atmosphere. After 1 h, the reaction mixture was slowly diluted with saturated aqueous sodium bicarbonate solution (10 mL), and the resulting mixture was extracted with ethyl acetate (2×10 mL), was dried over anhydrous sodium sulfate, and was concentrated under reduced pressure. The crude residue was purified via SiO$_2$ column chromatography (4 g SiO$_2$ Combiflash HP Gold Column, 0-100% ethyl acetate/hexanes) to afford intermediate 9j (7.7 mg, 72%) as a colorless film.

$^1$H NMR (400 MHz, CDCl$_3$) δ 7.87 (s, 1H), 7.37-7.17 (m, 15H), 6.73 (d, J=4.5 Hz, 1H), 6.51 (d, J=4.5 Hz, 1H), 6.23 (dd, J=17.5, 10.9 Hz, 1H), 5.70 (d, J=3.9 Hz, 1H), 5.59 (dd, J=17.5, 1.8 Hz, 1H), 5.32 (dd, J=10.9, 1.7 Hz, 1H), 4.72-4.56 (m, 4H), 4.49 (d, J=11.9 Hz, 2H), 4.43 (d, J=5.6 Hz, 1H), 4.25 (dd, J=5.6, 4.0 Hz, 1H), 3.56 (s, 2H).

LC/MS: t$_R$=2.32 min, MS m/z=563.33 [M+H]; LC system: Thermo Accela 1250 UHPLC; MS system: Thermo LCQ Fleet; Column: Kinetex 2.6µ XB-C18 100A, 50×4.6 mm; Solvents: Acetonitrile with 0.1% acetic acid, Water with 0.1% acetic acid; Gradient: 0 min-2.0 min 2-100% ACN, 2.0 min-3.05 min 100% ACN, 3.05 min-3.2 min 100%-2% ACN, 3.2 min-3.5 min 2% ACN at 2 µl/min.

HPLC: t$_R$=3.51 min; HPLC system: Agilent 1100 series.; Column: Gemini 5µ C18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min.

TLC: eluent: ethyl acetate, R$_f$=0.40 (UV)

cooled to −78° C. and was quenched with a 2:1 methanol/pyridine solution (1.5 mL). The resulting mixture was allowed to warm to RT, and was concentrated under reduced pressure. The crude residue was purified by preparatory HPLC (Phenominex Synergi 4u Hydro-RR 80A 150×30 mm column, 0-100% acetonitrile/water gradient) to afford example 20 (0.5 mg, 13%) as a white solid.

$^1$H NMR (400 MHz, CD$_3$OD) δ 7.78 (s, 1H), 6.88 (d, J=4.5 Hz, 1H), 6.76 (d, J=4.5 Hz, 1H), 6.02 (dd, J=17.4, 11.0 Hz, 1H), 5.47 (dd, J=17.4, 2.0 Hz, 1H), 5.23 (dd, J=10.9, 2.1 Hz, 1H), 5.15 (d, J=8.3 Hz, 1H), 4.72 (dd, J=8.2, 5.7 Hz, 1H), 4.34 (d, J=5.7 Hz, 1H), 3.60 (d, J=11.8 Hz, 1H), 3.49 (d, J=11.8 Hz, 1H)

LC/MS: t$_R$=0.84 min, MS m/z=293.19 [M+H]; LC system: Thermo Accela 1250 UHPLC; MS system: Thermo LCQ Fleet; Column: Kinetex 2.6µ XB-C18 100A, 50×4.6 mm; Solvents: Acetonitrile with 0.1% acetic acid, Water with 0.1% acetic acid; Gradient: 0 min-1.5 min 2-100% ACN, 1.5 min-2.2 min 100% ACN, 2.2 min-2.4 min 100%-2% ACN, 2.4 min-2.5 min 2% ACN at 2 µl/min HPLC: t$_R$=2.181 min; HPLC system: Agilent 1100 series.; Column: Gemini 5µ C18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min.

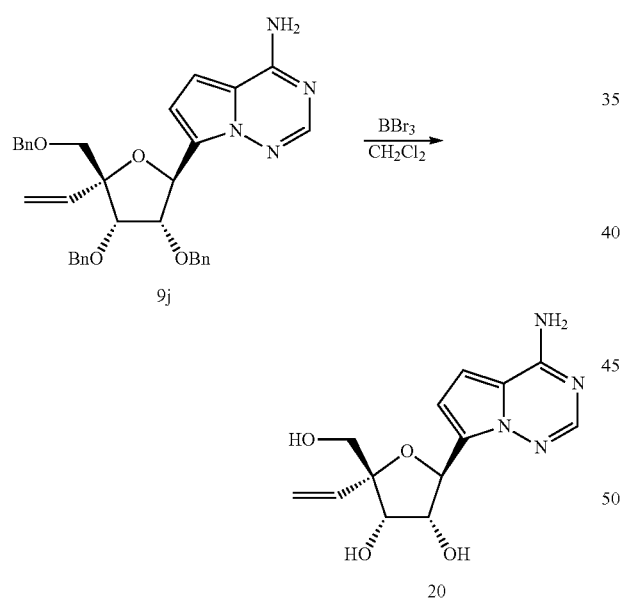

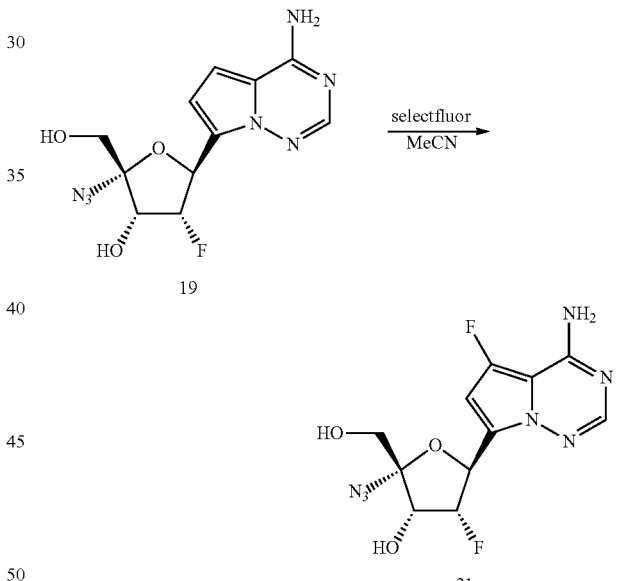

Example 20

(2R,3S,4R,5S)-5-(4-aminopyrrolo[2,1-f][1,2,4]triazin-7-yl)-2-(hydroxymethyl)-2-vinyltetrahydrofuran-3,4-diol Boron tribromide (1 M, 0.06 mL, 60 µmol) was added dropwise to a solution of intermediate 9j (7.7 mg, 13.7 µmol) in dichloromethane (1 mL) at −78° C. under an argon atmosphere. After 1 h, the reaction mixture was allowed to warm to 0° C., and was stirred an additional 1.5 h. The reaction was Example 21

(2R,3R,4R,5S)-5-(4-amino-5-fluoropyrrolo[2,1-f][1,2,4]triazin-7-yl)-2-azido-4-fluoro-2-(hydroxymethyl)tetrahydrofuran-3-ol Example 19 (237 mg, 0.766 mmol) and selectfluor (407 mg, 1.15 mmol) were suspended in acetonitrile (5 mL), and AcOH (0.2 mL) was added. The resulting mixture was stirred at room temperature for 30 min, and was then neutralized with sodium bicarbonate solution and filtered to remove solids. Upon concentration in vacuo, the residue was purified by preparative HPLC (acetonitrile 0 to 30% in water) to give example 21 (27 mg, 11%) as an off-white solid.

¹H NMR (400 MHz, CD₃OD) δ 7.73 (s, 1H), 6.63 (s, 1H), 5.80 (dd, J=23.9, 1.7 Hz, 1H), 5.16 (ddd, J=55.3, 5.0, 1.7 Hz, 1H), 4.56 (dd, J=23.5, 5.0 Hz, 1H), 3.94-3.60 (m, 2H) ¹⁹F NMR (376 MHz, CD₃OD) δ −161.76 (s), −195.42 (d, J=55.4 Hz)

MS m/z=328 [M+H]. MS system: Thermo LCQ Fleet

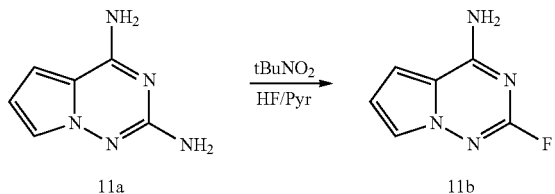 [SMILES: "tBuNO2" ; Nc1nc(N)c2cccn2n1 ; Nc1nc(F)nn2cccc12]

Intermediate 11b—2-fluoropyrrolo[2,1-f][1,2,4]triazin-4-amine—

Intermediate 11a (2.0 g, 13.4 mmol) was charged to a polyTube vessel. The reaction vessel was then placed in an ice bath and both 70% HF/Pyr (18 mL) and pyridine (9 mL) were added sequentially. Immediately after the addition of pyridine, tBuNO₂ (2.07 mL, 17.43 mmol) was then added slowly over 20 min. The solution goes from tan to black with an exotherm and outgassing. The reaction was then stirred for an additional 20 min, and the reaction mixture was then diluted with water, and was concentrated under reduced pressure. The crude residue was partitioned between ethyl acetate and water. The organics were separated and the aqueous was washed with ethyl acetate three times. The organics were combined and washed with brine. The crude was dried over Na₂SO₄, filtered, and the solvent was removed under reduced pressure. The crude residue was purified by silica gel chromatography (50-100% EtOAc/Hex) to afford intermediate 11b (1.68 g, 82%) as a tan solid.

¹H NMR (400 MHz, DMSO-d₆) δ 8.49-8.09 (m, 2H), 7.58 (t, J=2.0 Hz, 1H), 6.95 (d, J=4.5, 1 H), 6.59 (d, J=4.5, 1 H).
¹⁹F NMR (376 MHz, DMSO-d₆) δ −73.42 (s).
LC/MS: $t_R$=1.03 min, MS m/z=153.08 [M+H]; LC system: Thermo Accela 1250 UHPLC; MS system: Thermo LCQ Fleet; Column: Kinetex 2.6μ XB-C18 100A, 50×3.00 mm; Solvents: Acetonitrile with 0.1% formic acid, Water with 0.1% formic acid; Gradient: 0 min-1.4 min 2-100% ACN, 1.4 min-1.80 min 100% ACN, 1.8 min-1.85 min 100%-2% ACN, 1.85 min-2 min 2% ACN at 1.8 mL/min.

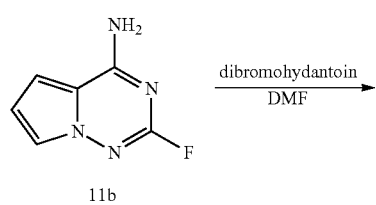

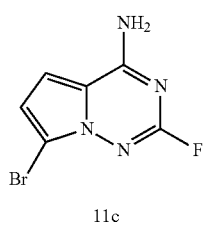

Intermediate 11c—7-bromo-2-fluoropyrrolo[2,1-f][1,2,4]triazin-4-amine

A solution of 11b (3.36 g, 22.1 mmol) in DMF (50 mL) was cooled to 0° C. in an ice bath. A solution of 1,3-dibromo-5,5-dimethylhydantoin (3.16 g, 11.0 mmol) in DMF (50 mL) was added dropwise by addition funnel over 40 min. After 1 h, the reaction was quenched with sat. Na₂S₂O₃₍aq₎ and the crude was partitioned between EtOAc and 5% LiCl₍aq₎. The organics were extracted with 5% LiCl₍aq₎ (4×) followed by brine. The organics were dried over Na₂SO₄, the solids were removed by filtration, and the filtrate was concentrated under reduced pressure. The crude residue was sonicated with CH₂Cl₂, and the solids were collected by filtration, and were dried under high vacuum to afford intermediate 11c (3.93 g, 77%) as a yellow solid.

¹H NMR (400 MHz, DMSO-d₆) δ 8.49-8.44 (m, 2H), 7.08 (d, J=4.6 Hz, 1H), 6.76 (d, J=4.6 Hz, 1H).
¹⁹F NMR (376 MHz, DMSO-d₆) δ −71.45 (s).
LC/MS: $t_R$=1.22 min, MS m/z=232.98 [M+H]; LC system: Thermo Accela 1250 UHPLC; MS system: Thermo LCQ Fleet; Column: Kinetex 2.6μ XB-C18 100A, 50×3.00 mm; Solvents: Acetonitrile with 0.1% formic acid, Water with 0.1% formic acid; Gradient: 0 min-1.4 min 2-100% ACN, 1.4 min-1.80 min 100% ACN, 1.8 min-1.85 min 100%-2% ACN, 1.85 min-2 min 2% ACN at 1.8 mL/min.

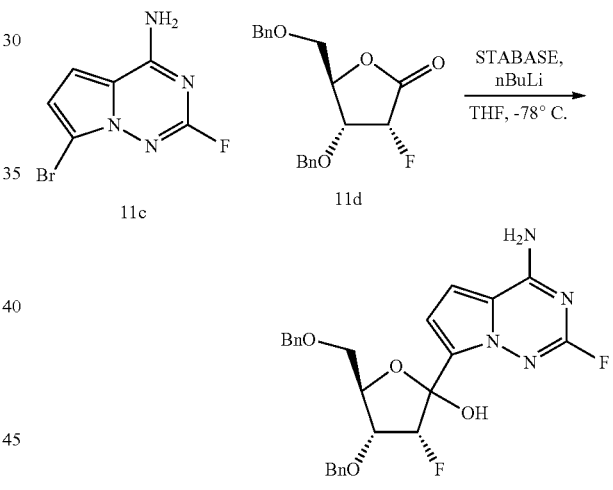

Intermediate 11e—(3R,4R,5R)-2-(4-amino-2-fluoropyrrolo[2,1-f][1,2,4]triazin-7-yl)-4-(benzyloxy)-5-((benzyloxy)methyl)-3-fluorotetrahydrofuran-2-ol To a solution of 11c (2.09 g, 9.08 mmol) in THF (30 mL) was added 1,2-bis(chlorodimethylsilyl)ethane (STABASE, 1.96 g, 9.08 mmol) in one portion, and the resulting mixture was allowed to stir at ambient temperature for 1 h. The reaction was then cooled to −78° C. using a dry ice bath with methanol. nBuLi (2.5M in hexanes, 10.9 mL, 27.2 mmol) was added in a manner to maintain an internal temperature of −65° C. A solution of intermediate 11d (Prepared according to WO2012012776, 2.5 g, 7.5 mmol) in THF (25 mL) was then added to the reaction mixture over 1 min. After 5 min, the reaction mixture was quenched with acetic acid and was allowed to come to ambient temperature. The solvents were removed under reduced pressure and the residue was taken up into ethyl acetate. The organics were washed with water followed by brine. The layers were separated and the organics were dried over Na$_2$SO$_4$, filtered, and concentrated under reduced pressure to afford crude 11e as a mixture of isomers, which was used as is for the next step.

LC/MS: t$_R$=1.32 and 1.40 min, MS m/z=483.15 [M+H]; LC system: Thermo Accela 1250 UHPLC; MS system: Thermo LCQ Fleet; Column: Kinetex 2.6μ XB-C18 100A, 50×3.00 mm; Solvents: Acetonitrile with 0.1% formic acid, Water with 0.1% formic acid; Gradient: 0 min-1.4 min 2-100% ACN, 1.4 min-1.80 min 100% ACN, 1.8 min-1.85 min 100%-2% ACN, 1.85 min-2 min 2% ACN at 1.8 mL/min.

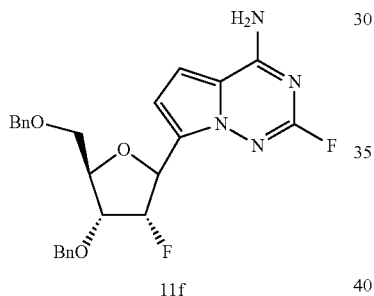

11e

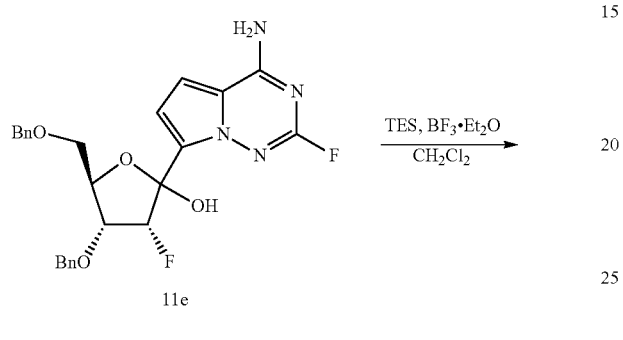

11f

Intermediate 11f—7-((2S,3S,4R,5R)-4-(benzyloxy)-5-((benzyloxy)methyl)-3-fluorotetrahydrofuran-2-yl)-2-fluoropyrrolo[2,1-f][1,2,4]triazin-4-amine Intermediate 11e (1.99 g, 3.72 mmol) was dissolved into CH$_2$Cl$_2$ (80 mL) and TES (4.75 mL, 29.7 mmol) was added to the mixture. The reaction mixture was cooled to 0° C. and BF$_3$·Et$_2$O (1.07 mL, 4.09 mmol) was slowly added. After 15 min, the reaction mixture was quenched with sat. NaHCO$_{3(aq)}$ and the layers were separated. The aqueous layer was washed with CH$_2$Cl$_2$. The organic layers were combined and were washed with sat. NaHCO$_{3(aq)}$. The organics were dried over Na$_2$SO$_4$, filtered, and were concentrated under reduced pressure. The crude was purified by silica gel chromatography (0-60% EtOAc/Hex) to afford intermediate 11f (1.12 g, 64%, 2:1 mixture of 1' anomers).

LC/MS: t$_R$=1.55 min, MS m/z=467.47 [M+H]; LC system: Thermo Accela 1250 UHPLC; MS system: Thermo LCQ Fleet; Column: Kinetex 2.6μ XB-C18 100A, 50×3.00 mm; Solvents: Acetonitrile with 0.1% formic acid, Water with 0.1% formic acid; Gradient: 0 min-1.4 min 2-100% ACN, 1.4 min-1.80 min 100% ACN, 1.8 min-1.85 min 100%-2% ACN, 1.85 min-2 min 2% ACN at 1.8 mL/min.

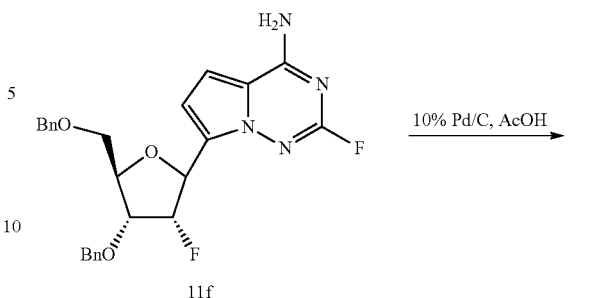

11f

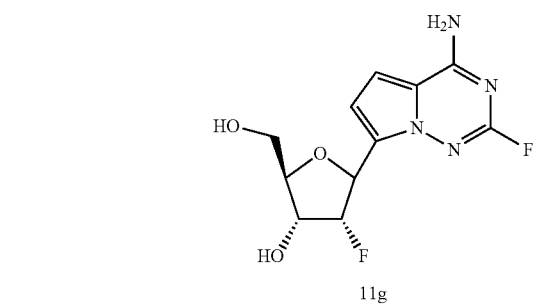

11g

Intermediate 11g—(2R,3R,4R,5S)-5-(4-amino-2-fluoropyrrolo[2,1-f][1,2,4]triazin-7-yl)-4-fluoro-2-(hydroxymethyl)tetrahydrofuran-3-ol Intermediate 11f (0.82 g, 1.76 mmol) was dissolved in acetic acid (25 mL). The reaction vessel was purged with Argon and 10% Pd/C (468 mg, 0.439 mmol) was added. The vessel was evacuated and backfilled with H$_{2(g)}$ (3×). After 1 h, the reaction vessel was purged with nitrogen. The resulting mixture was filtered through a pad of celite and the filter cake was washed with CH$_3$OH. The filtrate was concentrated under reduced pressure and then coevaporated with ethyl acetate followed by hexanes to afford intermediate 11g (503 mg, 98%, 2:1 mixture of 1' anomers).

LC/MS: t$_R$=0.81 min, MS m/z=286.97 [M+H]; LC system: Thermo Accela 1250 UHPLC; MS system: Thermo LCQ Fleet; Column: Kinetex 2.6μ XB-C18 100A, 50×3.00 mm; Solvents: Acetonitrile with 0.1% formic acid, Water with 0.1% formic acid; Gradient: 0 min-1.4 min 2-100% ACN, 1.4 min-1.80 min 100% ACN, 1.8 min-1.85 min 100%-2% ACN, 1.85 min-2 min 2% ACN at 1.8 mL/min.

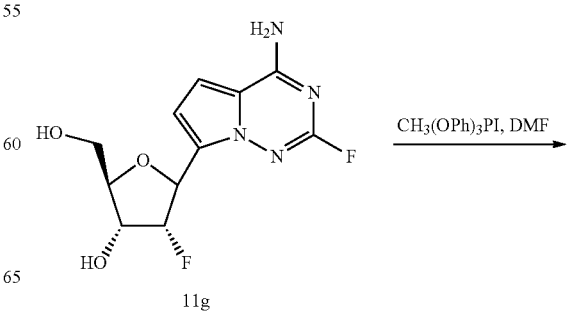

11g

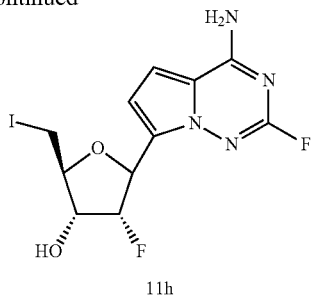

11h

Intermediate 11h—(2S,3R,4R,5S)-5-(4-amino-2-fluoropyrrolo[2,1-f][1,2,4]triazin-7-yl)-4-fluoro-2-(iodomethyl)tetrahydrofuran-3-ol To an argon purged flask was added a solution of 11g (283 mg, 0.989 mmol) in DMF (10 mL) followed by a solution of methyl triphenoxyphosphonium iodide (0.536 g, 1.19 mmol) in 4 mL DMF. The reaction mixture was allowed to stir at 0° C. for 10 min and was then warmed to ambient temperature. After 30 min, the reaction was quenched with sat. Na$_2$S$_2$O$_{3(aq)}$. The crude material was partitioned between EtOAc and 5% LiCl$_{(aq)}$. The organics were separated and washed with brine. The organics were dried over Na$_2$SO$_4$, filtered, and concentrated under reduced pressure. The crude residue was taken up in ACN and purified by HPLC without acid modifier to afford intermediate 11h (201 mg, 52%, 2:1 mixture of 1' anomers) as a white solid.

LC/MS: $t_R$=1.08 min, MS m/z=397.12 [M+H]; LC system: Thermo Accela 1250 UHPLC; MS system: Thermo LCQ Fleet; Column: Kinetex 2.6μ XB-C18 100A, 50×3.00 mm; Solvents: Acetonitrile with 0.1% formic acid, Water with 0.1% formic acid; Gradient: 0 min-1.4 min 2-100% ACN, 1.4 min-1.80 min 100% ACN, 1.8 min-1.85 min 100%-2% ACN, 1.85 min-2 min 2% ACN at 1.8 mL/min.

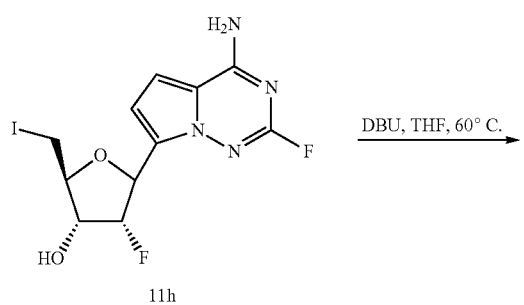

11h → 11i (DBU, THF, 60° C.)

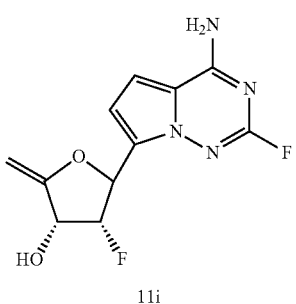

11i

Intermediate 11i—(3R,4R,5S)-5-(4-amino-2-fluoropyrrolo[2,1-f][1,2,4]triazin-7-yl)-4-fluoro-2-methylenetetrahydrofuran-3-ol To a solution of 11h (356 mg, 0.899 mmol) in THF (8 mL) was added DBU (0.403 mL, 2.70 mmol) and the resulting mixture was heated to 60° C. After 3 h, the reaction mixture was concentrated under reduced pressure. The crude residue was purified by silica gel chromatography (40-100% EtOAc/Hex) to afford intermediate 11i (201 mg, 83%, 2:1 mixture of 1' anomers) as a white solid.

LC/MS: $t_R$=1.04 min, MS m/z=269.14 [M+1]; LC system: Thermo Accela 1250 UHPLC; MS system: Thermo LCQ Fleet; Column: Kinetex 2.6μ XB-C18 100A, 50×3.00 mm; Solvents: Acetonitrile with 0.1% formic acid, Water with 0.1% formic acid; Gradient: 0 min-1.4 min 2-100% ACN, 1.4 min-1.80 min 100% ACN, 1.8 min-1.85 min 100%-2% ACN, 1.85 min-2 min 2% ACN at 1.8 mL/min.

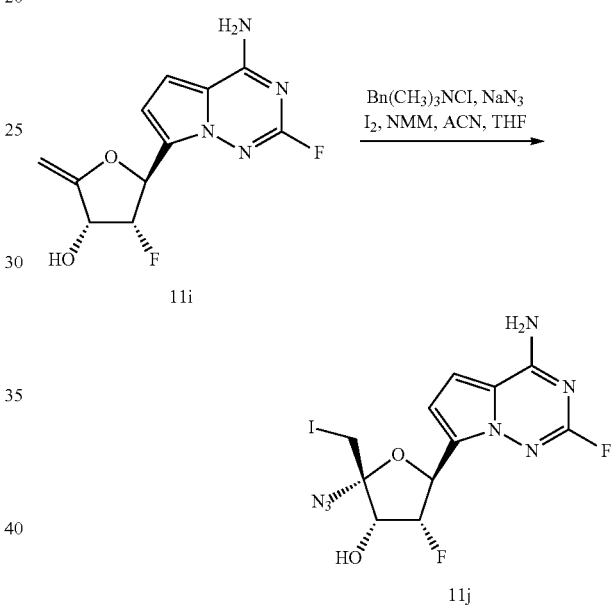

11i → 11j (Bn(CH$_3$)$_3$NCl, NaN$_3$, I$_2$, NMM, ACN, THF)

Intermediate 11j—(2S,3R,4R,5S)-5-(4-amino-2-fluoropyrrolo[2,1-f][1,2,4]triazin-7-yl)-2-azido-4-fluoro-2-(iodomethyl)tetrahydrofuran-3-ol Benzyltrimethylammonium chloride (292 mg, 1.57 mmol) and sodium azide (102 mg, 1.57 mmol) were dissolved in ACN (4 mL), and the resulting mixture was stirred at ambient temperature for 4 h. The mixture was filtered and the filtrate was added to a solution of 11i (0.201 g, 0.749 mmol) in THF (4 mL). NMM (0.412 mL, 3.75 mmol) was added followed by the dropwise addition of a solution of iodine (0.342 g, 1.35 mmol) in THF (4 mL). After 15 min, N-acetyl cysteine was added portion wise until no outgassing was observed. Sat. Na$_2$S$_2$O$_{3(aq)}$ was added until the solution was a light yellow. The resulting mixture was partitioned between water and ethyl acetate. The layers were separated and the organic layer was dried over Na$_2$SO$_4$, filtered, and concentrated under reduced pressure. The crude residue was purified by silica gel chromatography (20-100% EtOAc/Hex) to afford intermediate 11j (183 mg, 56%) as a single isomer.

$^1$H NMR (400 MHz, DMSO-d$_6$) δ 8.44 (d, J=28.6 Hz, 2H), 6.98 (d, J=4.6 Hz, 1H), 6.79 (d, J=4.6 Hz, 1H), 6.32 (d, J=6.9

Hz, 1H), 5.60 (dd, J=23.8, 2.5 Hz, 1H), 5.36 (ddd, J=54.9, 5.0, 2.6 Hz, 1H), 4.60 (ddd, J=21.5, 6.9, 5.0 Hz, 1H), 3.63 (ABq, Δδ=0.09 ppm, J=8 Hz, 2H).

$^{19}$F NMR (376 MHz, DMSO-d$_6$) δ −71.74 (s), −194.57 (ddd, J=54.9, 24.0, 21.7 Hz)

LC/MS: t$_R$=1.71 min, MS m/z=437.93 [M+1]; LC system: Thermo Accela 1250 UHPLC; MS system: Thermo LCQ Fleet; Column: Kinetex 2.6μ XB-C18 100A, 50×3.00 mm; Solvents: Acetonitrile with 0.1% formic acid, Water with 0.1% formic acid; Gradient: 0 min-2.4 min 2-100% ACN, 2.4 min-2.80 min 100% ACN, 2.8 min-2.85 min 100%-2% ACN, 2.85 min-3.0 min 2% ACN at 1.8 mL/min.

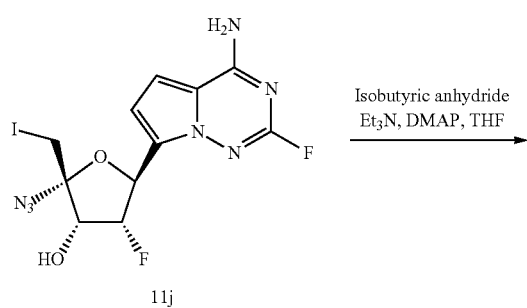

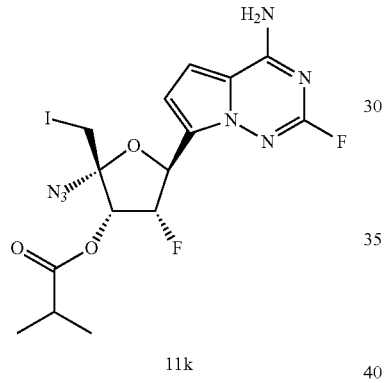

11k

Intermediate 11k—(2S,3R,4S5S)-5-(4-amino-2-fluoropyrrolo[2,1-f][1,2,4]triazin-7-yl)-2-azido-4-fluoro-2-(iodomethyl)tetrahydrofuran-3-yl isobutyrate To a solution of 11j (0.183 g, 0.419 mmol) in THF (10 mL) was added isobutyric anhydride (0.083 mL, 0.502 mmol), TEA (0.118 mL, 0.837 mmol), and DMAP (10 mg, 0.084 mmol). The reaction was allowed to stir at ambient temperature for 15 min, and the reaction was quenched with CH$_3$OH. The reaction mixture was concentrated under reduced pressure and the crude residue was purified by silica gel chromatography (0-50% EtOAc/Hex) to afford intermediate 11k (0.198 g, 93%) as a white solid.

$^1$H NMR (400 MHz, DMSO-d$_6$) δ 8.48 (d, J=30.7 Hz, 2H), 6.99 (d, J=4.6 Hz, 1H), 6.84 (d, J=4.6 Hz, 1H), 5.77-5.47 (m, 3H), 3.69 (ABq, 46=0.05 ppm, J=12 Hz, 2H), 2.70 (p, J=7.0 Hz, 1H), 1.24-1.05 (d, J=7.0 Hz, 6H).

$^{19}$F NMR (376 MHz, DMSO-d$_6$) δ −71.58 (s), −194.89 (ddd, J=55.0, 24.3, 16.8 Hz).

LC/MS: t$_R$=1,56 min, MS m/z=508.13 [M+1]; LC system: Thermo Accela 1250 UHPLC; MS system: Thermo LCQ Fleet; Column: Kinetex 2.6μ XB-C18 100A, 50×3.00 mm; Solvents: Acetonitrile with 0.1% formic acid, Water with 0.1% formic acid; Gradient: 0 min-2.4 min 2-100% ACN, 2.4 min-2.80 min 100% ACN, 2.8 min-2.85 min 100%-2% ACN, 2.85 min-3.0 min 2% ACN at 1.8 mL/min.

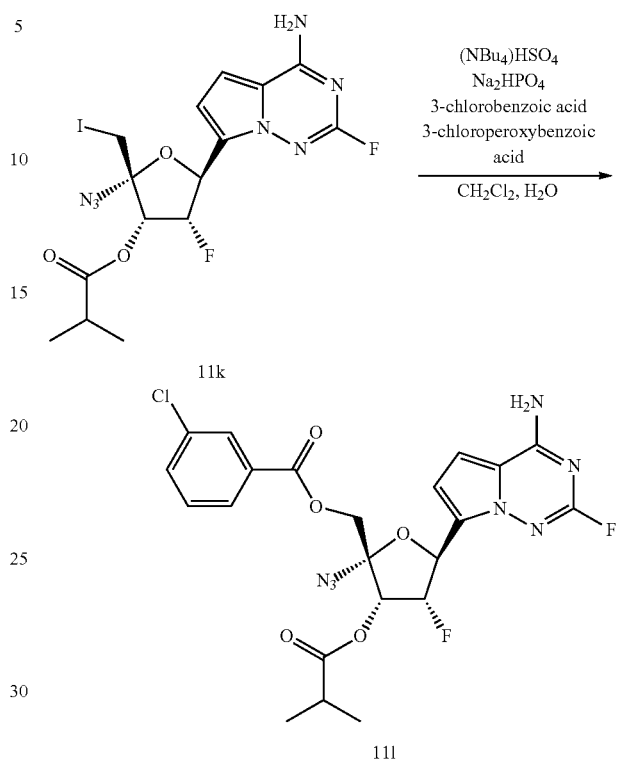

Intermediate 11l—((2R,3R,4S,5S)-5-(4-amino-2-fluoropyrrolo[2,1-f][1,2,4]triazin-7-yl)-2-azido-4-fluoro-3-(isobutyryloxy)tetrahydrofuran-2-yl)methyl 3-chlorobenzoate Intermediate 11k (0.153 g, 0.302 mmol) was dissolved in CH$_2$Cl$_2$ (10 mL) and H$_2$O (6 mL). Potassium phosphate dibasic (0.138 g, 0.603 mmol), tetrabutylammonium bisulfate (0.210 g, 0.618 mmol), and 3-chlorobenzoic acid (0.097 g, 0.618 mmol) were added sequentially. The resulting mixture was cooled to 0° C. and MCPBA (0.203 g, 0.905 mmol) was added. The reaction mixture was allowed to warm to ambient temperature and was stirred for 16 h. The reaction mixture was then quenched with sat Na$_2$S$_2$O$_{3(aq)}$, and was concentrated under reduced pressure. The crude aqueous residue was diluted with ACN and purified by preparative HPLC without acid modifier to afford intermediate 11l (20 mg, 13%) as a white solid.

$^1$H NMR (400 MHz, DMSO-d$_6$) δ 8.46 (d, J=26.4 Hz, 2H), 7.96-7.81 (m, 2H), 7.81-7.66 (m, 1H), 7.62-7.46 (m, 1H), 6.94 (d, J=4.5 Hz, 1H), 6.80 (d, J=4.5 Hz, 1H), 5.73 (s, 3H), 4.60 (ABq, Δδ=0.08 ppm, J=12 Hz, 2H), 2.66 (p, J=7.0 Hz, 1H), 1.20-1.01 (m, 6H).

$^{19}$F NMR (376 MHz, DMSO-d$_6$) δ=−71.45 (s), −193.41 (ddd, J=54.4, 25.4, 21.2 Hz,).

LC/MS: t$_R$=2.22 min, MS m/z=536.17 [M+1]; LC system: Thermo Accela 1250 UHPLC; MS system: Thermo LCQ Fleet; Column: Kinetex 2.6μ XB-C18 100A, 50×3.00 mm; Solvents: Acetonitrile with 0.1% formic acid, Water with 0.1% formic acid; Gradient: 0 min-2.4 min 2-100% ACN, 2.4 min-2.80 min 100% ACN, 2.8 min-2.85 min 100%-2% ACN, 2.85 min-3.0 min 2% ACN at 1.8 mL/min.

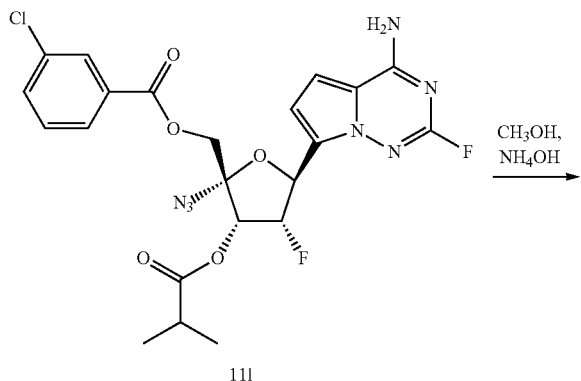

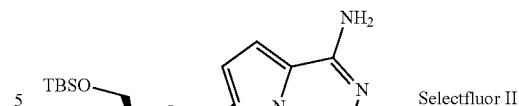

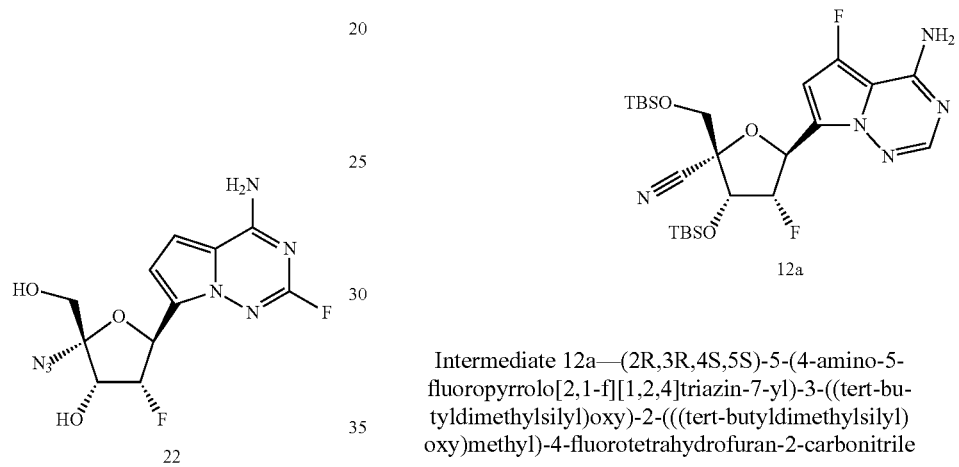

Example 22

(2R,3R,4R,5S)-5-(4-amino-2-fluoropyrrolo[2,1-f][1,2,4]triazin-7-yl)-2-azido-4-fluoro-2-(hydroxymethyl)tetrahydrofuran-3-ol To a solution of intermediate 111 (22 mg, 0.041 mmol) in $CH_3OH$ (1 mL) was added conc. $NH_4OH$ (1 mL) at RT. After 30 min, the reaction mixture was concentrated under reduced pressure. The crude residue was diluted with minimal $H_2O$ and was purified by preparative HPLC without modifier to afford example 22 (10 mg, 77%) as a white solid.

$^1$H NMR (400 MHz, DMSO-$d_6$) δ 8.40 (d, J=30.9 Hz, 2H), 6.95 (d, J=4.5 Hz, 1H), 6.78 (d, J=4.5 Hz, 1H), 5.89 (d, J=7.5 Hz, 1H), 5.61 (dd, J=23.8, 2.1 Hz, 1H), 5.44 (t, J=6.1 Hz, 1H), 5.18 (ddd, J=55.3, 5.1, 2.2 Hz, 1H), 4.44 (ddd, J=23.7, 7.5, 5.0 Hz, 1H), 3.59 (ddd, J=48.5, 12.0, 6.1 Hz, 2H).

$^{19}$F NMR (376 MHz, DMSO-$d_6$) δ −71.18 (s), −193.48 (dt, J=55.3, 23.8 Hz).

LC/MS: $t_R$=1.13 min, MS m/z=327.86 [M+1]; LC system: Thermo Accela 1250 UHPLC; MS system: Thermo LCQ Fleet; Column: Kinetex 2.6μ XB-C18 100A, 50×3.00 mm; Solvents: Acetonitrile with 0.1% formic acid, Water with 0.1% formic acid; Gradient: 0 min-2.4 min 2-100% ACN, 2.4 min-2.80 min 100% ACN, 2.8 min-2.85 min 100%-2% ACN, 2.85 min-3.0 min 2% ACN at 1.8mL/min.

Intermediate 12a—(2R,3R,4S,5S)-5-(4-amino-5-fluoropyrrolo[2,1-f][1,2,4]triazin-7-yl)-3-((tert-butyldimethylsilyl)oxy)-2-(((tert-butyldimethylsilyl)oxy)methyl)-4-fluorotetrahydrofuran-2-carbonitrile To a solution of intermediate 3d (57 mg, 0.109 mmol) in ACN (3 mL), was added Selectfluor II in one portion (52 mg, 0.164 mmol). After 1.5 h, the reaction was quenched by the addition of saturated $NaHCO_{3(aq)}$. Ethyl acetate (4 mL) was added and the biphasic mixture was stirred vigorously for 5 min. The reaction was further diluted with EtOAc and saturated $NaHCO_{3(aq)}$. The layers were separated and the organic phase was extracted with water and then brine. The organic layer was dried over $Na_2SO_4$. The drying agent was removed by vacuum filtration and the filtrate was concentrated under reduced pressure. Intermediate 12a (11 mg, 18.7%) was isolated from the concentrated crude material by silica gel column chromatography using the following solvent ramp: 0% EtOAc in hexanes ramping to 70% EtOAc in hexanes, quickly ramping to 100% EtOAc once the starting material elutes off the column.

$^1$H NMR (400 MHz, $CD_3OD$) δ 7.72 (s, 1H), 7.55 (s, 1H), 5.65 (dd, J=24.8, 2.4 Hz, 1H), 5.38 (dq, J=54.4, 2 Hz, 1H), 4.88 (dd, J=19.2, 4.4 Hz, 1H), 3.96 (ABq, Δδ$_{AB}$=0.141 ppm, J=11 Hz, 2H), 0.99 (s, 9H), 0.86 (s, 9H), 0.21 (s, 6H), 0.07 (s, 3H), −0.02 (s, 3H).

$^{19}$F NMR (376 MHz, $CD_3OD$) δ −161.795 (s), −194.806 (ddd, J=54.5, 19.2, 18.8 Hz).

LC/MS: $R_T$=2.06 min, MS m/z=540.64 [M+1]; LC system: Thermo Accela 1250 UHPLC; MS: Thermo LCQ Fleet; Column: Kinetex 2.6μ C18 100A, 50×3.00 mm; Solvents: Acetonitrile with 0.1% formic acid, Water with 0.1% formic acid; Gradient: 0 min-2.4 min 2-100% ACN, 2.4 min-2.8 min 100% ACN, 2.8 min-2.85 min 100%-2% ACN, 2.85 min-3 min 2% ACN.

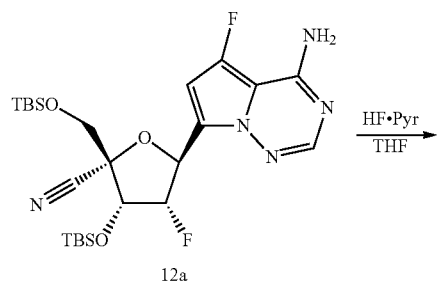
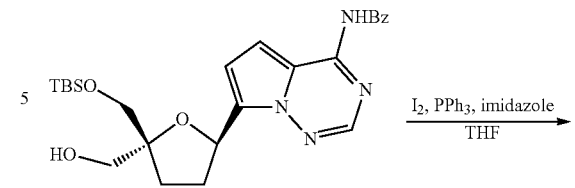

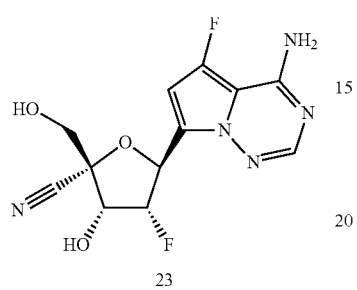

Example 23

(2R,3R,4R,5S)-5-(4-amino-5-fluoropyrrolo[2,1-f][1,2,4]triazin-7-yl)-4-fluoro-3-hydroxy-2-(hydroxymethyl)tetrahydrofuran-2-carbonitrile To a solution of intermediate 12a (29 mg, 0.054 mmol) in THF (2 mL) in a polypropylene tube was added 70% HF·Pyridine in pyridine (51 µL, 1.97 mmol) at 0° C., under an $N_2$ atmosphere. After 1.5 h, the reaction was removed from the ice bath. Additional 70% HF.Pyridine in pyridine was added after 3 h (150 µL), 5 h 45 min (200 µL), and 21 h 15 min (0.7 mL). The reaction mixture was then stirred for another 24 h at which point the reaction mixture was cooled in an ice bath and then quenched with water and saturated $NaHCO_{3(aq)}$. The mixture was concentrated under reduced pressure and the residue was taken up in DMF. The resulting solution/suspension was filtered through a syringe filter (Whatman 0.45 µm PTFE w/GMF). The filtrate was injected on an HPLC and the semi-purified product was further purified by silica gel column chromatography using the following solvent ramp: 0% MeOH in DCM ramping to 20% MeOH in DCM. Product containing fractions were concentrated and the residue was lyophilized to afford example 23 (5 mg, 30%) as a white powder.

$^1$H NMR (400 MHz, DMF-$d_7$) δ 7.74 (s, 1H), 6.61 (s, 1H), 5.75 (dd, J=25.2, 1.6 Hz, 1H), 5.23 (ddd, J=54.8, 4.8, 1.6 Hz, 1H), 4.64 (dd, J=22, 4.4 Hz, 1H), 3.90 (ABq, Δδ$_{AB}$=0.151 ppm, J=12 Hz, 2H).

$^{19}$F NMR (376 MHz, DMF-$d_7$) δ −161.727 (s), −193.726 (ddd, J=54.5, 22.9, 21.8 Hz).

LC/MS: R$_T$=0.81 min, MS m/z=312.13 [M+1]; LC: Thermo Accela 1250 UHPLC; MS: Thermo LCQ Fleet; Column: Kinetex 2.6µ C18 100A, 50×3.00 mm; Solvents: Acetonitrile with 0.1% formic acid, Water with 0.1% formic acid; Gradient: 0 min-2.4 min 2-100% ACN, 2.4 min-2.8 min 100% ACN, 2.8 min-2.85 min 100%-2% ACN, 2.85 min-3 min 2% ACN.

Intermediate 13a—N-(7-((2S,3S,4R,5R)-4-((tert-butyldimethylsilyl)oxy)-5-(((tert-butyldimethylsilyl)oxy)methyl)-3-fluoro-5-(iodomethyl)tetrahydrofuran-2-yl)pyrrolo[2,1-f][1,2,4]triazin-4-yl)benzamide To a solution of triphenylphosphine (973 mg, 3.71 mmol) and imidazole (252 mg, 3.71 mmol) in THF (5 mL) was added iodine (253 mg, 1.86 mmol) at room temperature. Upon complete dissolution of iodine, a solution of compound 2g (650 mg, 0.93 mmol) in THF (5 mL) was added dropwise slowly. The resulting mixture was stirred at 80° C. for 3 days and was then concentrated in vacuo. The residue was purified by silica gel column chromatography (0 to 50% EtOAc in hexanes) to give intermediate 13a (230 mg, 33%) as an oil.

MS m/z=742 [M+H]. MS system: Thermo LCQ Fleet.

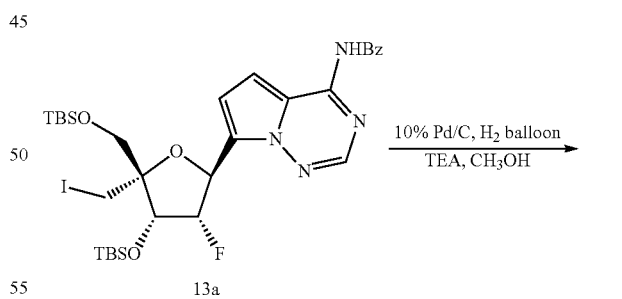
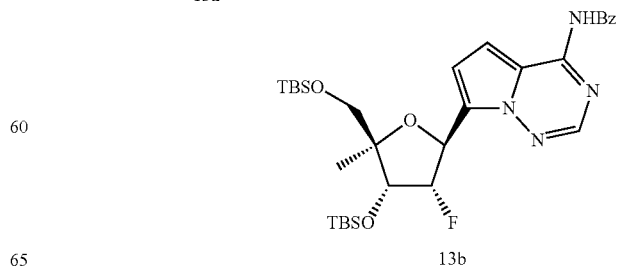

Intermediate 13b—N-(7-((2S,3S,4R,5R)-4-((tert-butyldimethylsilyl)oxy)-5-(((tert-butyldimethylsilyl)oxy)methyl)-3-fluoro-5-methyltetrahydrofuran-2-yl)pyrrolo[2,1-f][1,2,4]triazin-4-yl)benzamide Intermediate 13a (200 mg, 0.243 mmol) was dissolved in methanol (10 mL) and under nitrogen atmosphere, 10% Pd/C (100 mg, 0.094 mmol) and TEA (0.035 mL, 0.243 mmol) were added. The resulting mixture was then stirred under $H_2$ atmosphere (balloon) at room temperature for 40 min. The resulting mixture was filtered, and concentrated in vacuo and the residue was purified by silica gel column chromatography (0 to 40% EtOAc in hexanes) to give intermediate 13b (145 mg, 72%) as a white solid with 75% purity.

MS m/z=616 [M+H]. MS system: Thermo LCQ Fleet

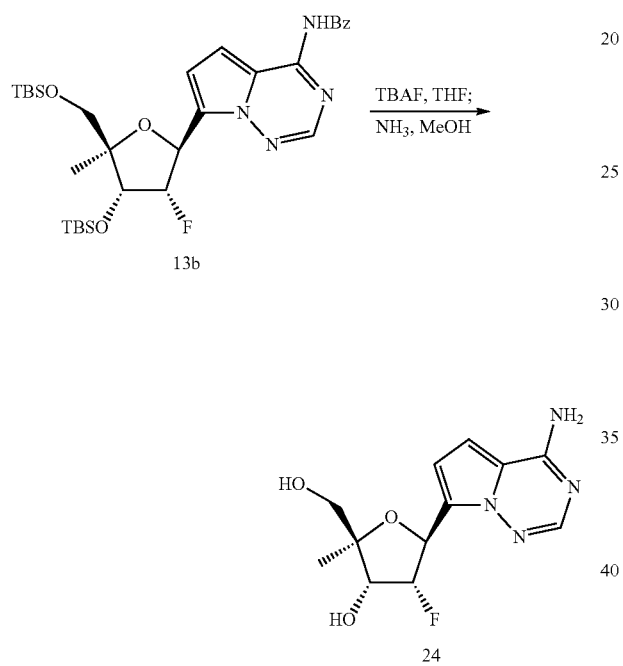

Example 24

(2R,3R,4R,5S)-5-(4-aminopyrrolo[2,1-f][1,2,4]triazin-7-yl)-4-fluoro-2-(hydroxymethyl)-2-methyltetrahydrofuran-3-ol Intermediate 13b (145 mg, 75% purity, 0.177 mmol) was dissolved in THF (10 mL) and TBAF (1M in THF, 0.53 mL, 0.531 mmol) was added. The resulting mixture was stirred at room temperature for 2 h and then methanolic ammonia (7N, 10 mL) was added. The resulting mixture was stirred for 24 h and was concentrated under reduced pressure. The crude residue was purified by preparative HPLC (0 to 35% acetonitrile in water in 20 min) to afford example 24 (30 mg, 60%) as a white solid.

$^1$H NMR (400 MHz, CD$_3$OD) δ 7.78 (s, 1H), 6.84 (d, J=4.5 Hz, 1H), 6.76 (d, J=4.5 Hz, 1H), 5.53 (dd, J=21.5, 4.0 Hz, 1H), 5.25 (ddd, J=55.5, 5.3, 4.1 Hz, 1H), 4.44 (dd, J=17.2, 5.2 Hz, 1H), 3.65-3.43 (m, 2H), 1.27 (s, 3H)

$^{19}$F NMR (376 MHz, CD$_3$OD) δ −197.08 (ddd, J=55.4, 21.5, 17.1 Hz)

MS m/z=282 [M+H]. MS system: Thermo LCQ Fleet.

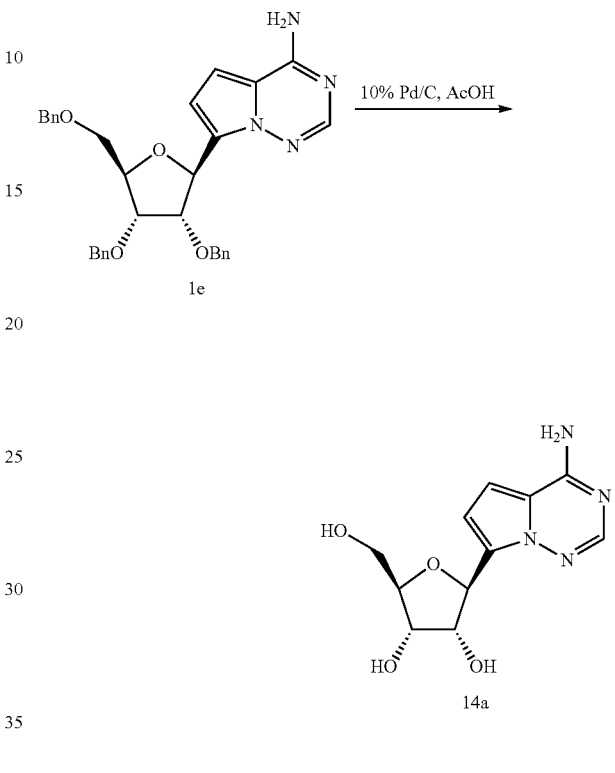

Intermediate 14a—(2S,3R,4S,5R)-2-(4-aminopyrrolo[2,1-f][1,2,4]triazin-7-yl)-5-(hydroxymethyl)tetrahydrofuran-3,4-diol Intermediate 1e (2.64 g, 4.91 mmol) was dissolved in acetic acid (50 mL). The flask was purged with Argon and 10% Pd/C (1.05 g, 0.982 mmol) was added. The flask was evacuated and backfilled with H$_{2(g)}$ three times. The reaction mixture was stirred under an atmosphere of H$_{2(g)}$. After 1 h, the flask was purged with nitrogen and the reaction mixture was filtered through a celite pad with CH$_3$OH washings. The filtrate was concentrated under reduced pressure and then coevaporated with EtOAc followed by hexanes. The residue was placed under high vacuum to afford intermediate 14a (1.31 g, 99%) as a white solid.

$^1$H NMR (400 MHz, DMSO-d$_6$) δ 7.80 (s, 1H), 7.66 (s, 2H), 6.82 (d, J=4.4 Hz, 1H), 6.66 (d, J=4.4 Hz, 1H), 5.09 (d, J=6.5 Hz, 1H), 5.06-4.56 (m, 3H), 4.21 (t, J=5.9 Hz, 1H), 3.93 (t, J=4.9 Hz, 1H), 3.77 (q, J=4.5 Hz, 1H), 3.48 (ddd, J=38.9, 11.8, 4.4 Hz, 2H).

LC/MS: t$_R$=0.47 min, MS m/z=267.13 [M+H]; LC system: Thermo Accela 1250 UHPLC

MS system: Thermo LCQ Fleet; Column: Kinetex 2.6μ XB-C18 100A, 50×3.00 mm; Solvents: Acetonitrile with 0.1% formic acid, Water with 0.1% formic acid; Gradient: 0 min-2.4 min 2-100% ACN, 2.4 min-2.80 min 100% ACN, 2.8 min-2.85 min 100%-2% ACN, 2.85 min-3.0 min 2% ACN at 1.8 mL/min.

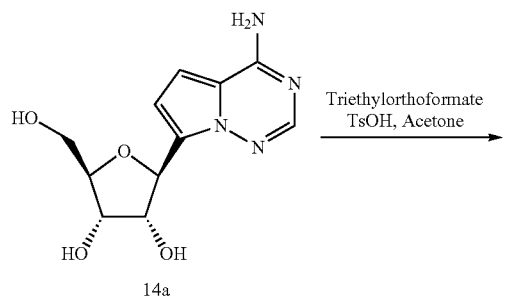

14a

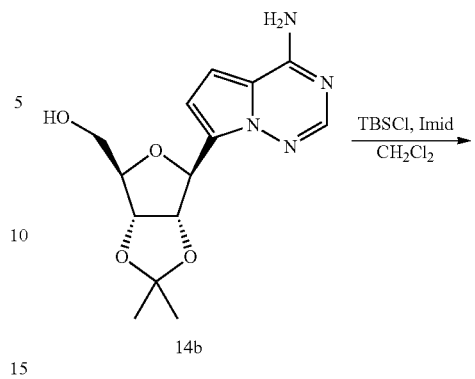

14b

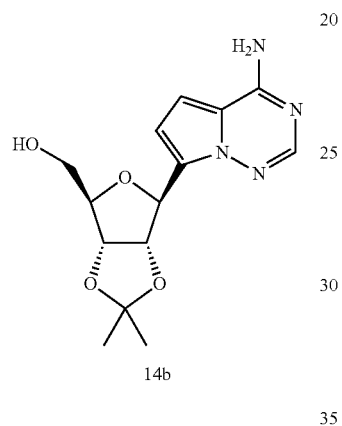

14b

Intermediate 14b—((3aR,4R,6S,6aS)-6-(4-aminopyrrolo[2,1-f][1,2,4]triazin-7-yl)-2,2-dimethyltetrahydrofuro[3,4-d][1,3]dioxol-4-yl)methanol Intermediate 14a (3.13 g, 11.7 mmol) was dissolved in acetone (80 mL) and TsOH (6.00 g, 31.5 mmol) was added. Triethylorthoformate (6.0 mL, 36.1 mmol) was slowly added over 10 min. The resulting mixture was allowed to stir at ambient temperature overnight. Saturated aqueous sodium carbonate solution was added until the reaction mixture was pH=8. The solids were removed by filtration and the filtrate was concentrated under reduced pressure. The crude residue was partitioned between EtOAc and brine. The phases were split and the organics were dried over $Na_2SO_4$, were filtered, and were concentrated under reduced pressure. The crude was purified by silica gel chromatography (60-100% EtOAc/Hex-20% MeOH/EtOAc) to afford intermediate 14b (2.55 g, 71%) as a white solid.

$^1$H NMR (400 MHz, DMSO-$d_6$) δ 7.83 (s, 1H), 7.71 (s, 2H), 6.83 (d, J=4.4 Hz, 1H), 6.73 (d, J=4.5 Hz, 1H), 5.21 (d, J=4.9 Hz, 1H), 5.01 (dd, J=6.6, 4.9 Hz, 1H), 4.84 (t, J=5.7 Hz, 1H), 4.71 (dd, J=6.7, 3.7 Hz, 1H), 3.99-3.85 (m, 1H), 3.46 (t, J=5.5 Hz, 2H), 1.48 (s, 3H), 1.29 (s, 3H).

LC/MS: $t_R$=0.87 min, MS m/z=307.21 [M+H]; LC system: Thermo Accela 1250 UHPLC; MS system: Thermo LCQ Fleet; Column: Kinetex 2.6μ XB-C18 100A, 50×3.00 mm; Solvents: Acetonitrile with 0.1% formic acid, Water with 0.1% formic acid; Gradient: 0 min-1.4 min 2-100% ACN, 1.4 min-1.80 min 100% ACN, 1.8 min-1.85 min 100%-2% ACN, 1.85 min-2 min 2% ACN at 1.8 mL/min.

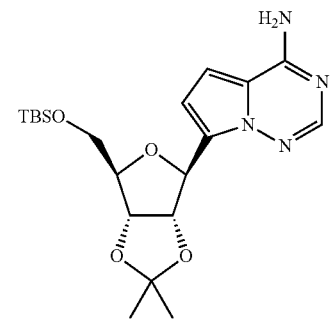

14c

Intermediate 14c—7-((3aS,4S,6R,6aR)-6-(((tert-butyldimethylsilyl)oxy)methyl)-2,2-dimethyltetrahydrofuro[3,4-d][1,3]dioxol-4-yl)pyrrolo[2,1-f][1,2,4]triazin-4-amine Intermediate 14b (2.55 g, 8.32 mmol) was dissolved in DCM (50 mL) and the mixture was cooled to 0° C. Imidazole (1.70 g, 24.9 mmol) was added followed by TBSCl (1.88 g, 12.5 mmol). After 16 h, the reaction was quenched with methanol. The resulting mixture was concentrated under reduced pressure and the crude residue was partitioned between water and EtOAc. The organics were dried over $Na_2SO_4$, were filtered, and were concentrated under reduced pressure. The crude residue was purified by silica gel chromatography (50-100% EtOAc/Hex) to afford intermediate 14c (2.60 g, 74%) as a white solid.

$^1$H NMR (400 MHz, DMSO-$d_6$) δ 7.83 (s, 1H), 7.74 (s, 2H), 6.82 (d, J=4.4 Hz, 1H), 6.68 (d, J=4.4 Hz, 1H), 5.26 (d, J=4.4 Hz, 1H), 5.00 (dd, J=6.5, 4.5 Hz, 1H), 4.71 (dd, J=6.5, 3.7 Hz, 1H), 3.97 (td, J=5.1, 3.6 Hz, 1H), 3.64 (d, J=5.2 Hz, 2H), 1.48 (s, 3H), 1.28 (s, 3H), 0.83 (s, 9H), −0.02 (s, 6H).

LC/MS: $t_R$=1.91 min, MS m/z=421.60 [M+1]; LC system: Thermo Accela 1250 UHPLC MS system: Thermo LCQ Fleet; Column: Kinetex 2.6μ XB-C18 100A, 50×3.00 mm; Solvents: Acetonitrile with 0.1% formic acid, Water with 0.1% formic acid; Gradient: 0 min-2.4 min 2-100% ACN, 2.4 min-2.80 min 100% ACN, 2.8 min-2.85 min 100%-2% ACN, 2.85 min-3.0 min 2% ACN at 1.8 mL/min.

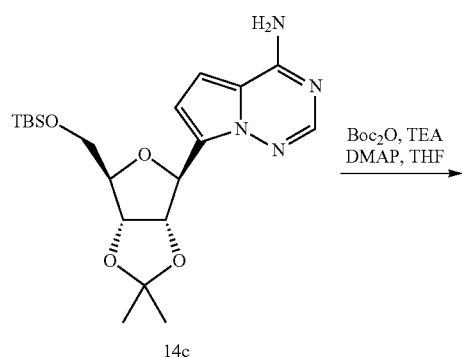

14c

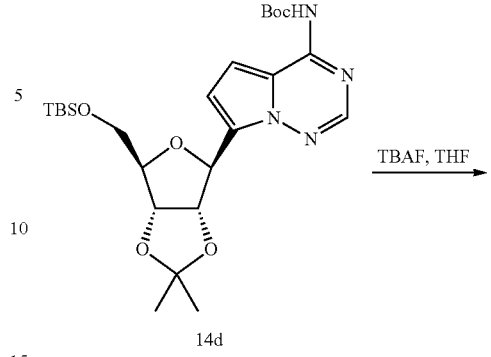

14d

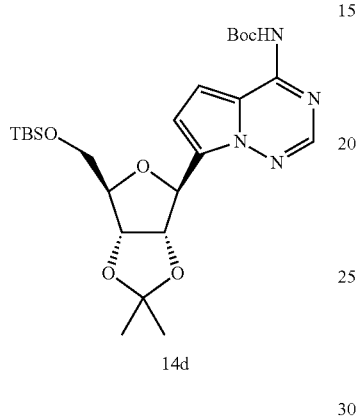

14d

Intermediate 14d—tert-butyl (7-((3aS,4S,6R,6aR)-6-(((tert-butyldimethylsilyl)oxy)methyl)-2,2-dimethyltetrahydrofuro[3,4-d][1,3]dioxol-4-yl)pyrrolo[2,1-f][1,2,4]triazin-4-yl)carbamate Intermediate 14c (2.59 g, 6.16 mmol) was dissolved in THF (60 mL) and the resulting solution was cooled to 0° C. Boc$_2$O (2.69 g, 12.3 mmol) and DMAP (0.3 g, 2.46 mmol) were then added. TEA (2.56 mL, 18.3 mmol) was slowly added and the reaction mixture was allowed to warm to RT. After 3 h, the reaction mixture was cooled to 0° C. and MeOH (10 mL) was added followed conc. NH$_4$OH$_{(aq)}$(50 mL). The resulting mixture was allowed to warm to RT and was stirred overnight. The reaction mixture was concentrated under reduced pressure and the crude residue was partitioned between EtOAc and water. The layers were separated and the organic layer was dried over Na$_2$SO$_4$, was filtered, and was concentrated under reduced pressure. The crude residue was purified by silica gel chromatography (0-100% EtOAc/Hex) to afford intermediate 14d (2.82 g, 88%) as a white solid.

$^1$H NMR (400 MHz, DMSO-d$_6$) δ 10.46 (s, 1H), 8.20 (s, 1H), 7.19 (d, J=4.6 Hz, 1H), 6.90 (d, J=4.6 Hz, 1H), 5.33 (d, J=4.2 Hz, 1H), 5.02 (dd, J=6.5, 4.3 Hz, 1H), 4.72 (dd, J=6.5, 3.6 Hz, 1H), 4.01 (q, J=5.0 Hz, 1H), 3.64 (d, J=5.1 Hz, 2H), 1.49 (s, 9H), 1.32 (d, J=22.7 Hz, 6H), 0.82 (s, 9H), −0.03 (s, 6H).

LC/MS: t$_R$=1.89 min, MS m/z=521.27 [M+H]; LC system: Thermo Accela 1250 UHPLC; MS system: Thermo LCQ Fleet; Column: Kinetex 2.6μ XB-C18 100A, 50×3.00 mm; Solvents: Acetonitrile with 0.1% formic acid, Water with 0.1% formic acid; Gradient: 0 min-2.4 min 2-100% ACN, 2.4 min-2.80 min 100% ACN, 2.8 min-2.85 min 100%-2% ACN, 2.85 min-3.0 min 2% ACN at 1.8 mL/min.

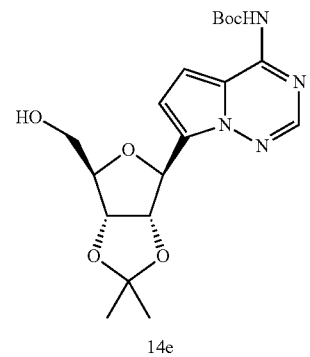

14e

Intermediate 14e—tert-butyl (7-((3aS,4S,6R,6aR)-6-(hydroxymethyl)-2,2-dimethyltetrahydrofuro[3,4-d][1,3]dioxol-4-yl)pyrrolo[2,1-f][1,2,4]triazin-4-yl)carbamate Intermediate 14d (2.8 g, 5.4 mmol) was dissolved in THF (50 mL), and TBAF (1.0M in THF, 5.92 mL, 5.92 mmol) was added. After 30 min, additional TBAF (1.0M in THF, 5.92 mL, 5.92 mmol) was added. After another 30 min, the reaction mixture was quenched with water and the resulting mixture was extracted with EtOAc (2×). The combine the organic layers were washed with brine, were dried over Na$_2$SO$_4$, were filtered, and were concentrated under reduced pressure. The crude residue was purified by silica gel chromatography (10-100% EtOAc/Hex) to afford intermediate 14e (2.19 g, 86%) as a white solid.

$^1$H NMR (400 MHz, DMSO-d$_6$) δ 10.46 (s, 1H), 8.22 (s, 1H), 7.20 (s, 1H), 6.95 (s, 1H), 5.29 (d, J=4.6 Hz, 1H), 5.03 (dd, J=6.6, 4.7 Hz, 1H), 4.85 (t, J=5.7 Hz, 1H), 4.72 (dd, J=6.6, 3.6 Hz, 1H), 4.05-3.90 (m, 1H), 3.46 (t, J=5.6 Hz, 2H), 1.50 (s, 12H), 1.29 (s, 3H).

LC/MS: t$_R$=1.52 min, MS m/z=407.05 [M+H]; LC system: Thermo Accela 1250 UHPLC; MS system: Thermo LCQ Fleet; Column: Kinetex 2.6μ XB-C18 100A, 50×3.00 mm; Solvents: Acetonitrile with 0.1% formic acid, Water with 0.1% formic acid; Gradient: 0 min-2.4 min 2-100% ACN, 2.4 min-2.80 min 100% ACN, 2.8 min-2.85 min 100%-2% ACN, 2.85 min-3.0 min 2% ACN at 1.8 mL/min.

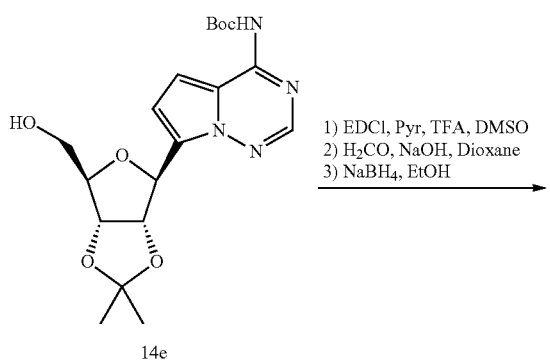

1) EDCl, Pyr, TFA, DMSO
2) H₂CO, NaOH, Dioxane
3) NaBH₄, EtOH

14e

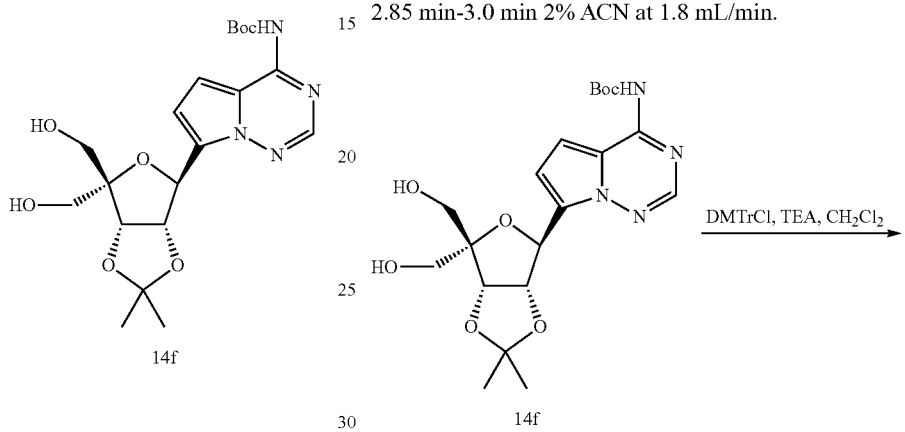

14f

Intermediate 14f—tert-butyl (7-((3aS,4S,6aS)-6,6-bis(hydroxymethyl)-2,2-dimethyltetrahydrofuro[3,4-d][1,3]dioxol-4-yl)pyrrolo[2,1-f][1,2,4]triazin-4-yl)carbamate Intermediate 14e (1.78 g, 4.38 mmol) was dissolved in DMSO (20 mL) and toluene (15 mL). Pyridine (0.35 mL, 4.38 mmol) and EDCl (1.26 g, 6.56 mmol) were added followed by TFA (0.178 mL, 2.39 mmol). After 90 min, additional pyridine (0.35 mL, 4.38 mmol) and EDCl (1.26 g, 6.56 mmol) were added and the reaction mixture was stirred for an additional 30 min. The reaction was quenched with water and the resulting mixture was extracted with CH₂Cl₂. The aqueous was back extracted with CH₂Cl₂. The organic layers were combined and were washed with brine, were dried over Na₂SO₄, were filtered, and were concentrated under reduced pressure. The crude was put under high vacuum for 15 min then was used as is for the next step.

The crude residue was dissolved in dioxane (15 mL) and formaldehyde (37% in water, 5.0 mL, 37.2 mmol) and 2N NaOH (5.34 mL, 10.7 mmol) were added sequentially. After 10 min, the reaction was quenched with AcOH and the resulting mixture was partitioned between sat. NaHCO₃(aq) and CH₂Cl₂. The aqueous layer was back extracted with CH₂Cl₂. The organic layers were combined and were wash with brine, were dried over Na₂SO₄, were filtered, and were concentrated under reduced pressure. The crude was placed under high vacuum for 15 min then were taken directly into the next reaction.

The crude residue was dissolved in EtOH (50 mL), and NaBH₄ (0.324 g, 8.76 mmol) was added in small portions. After 20 min, the reaction mixture was quenched with AcOH and was concentrated under reduced pressure. The crude residue was partitioned between with EtOAc and sat. NaHCO₃(aq). The organic layer was split, was dried over Na₂SO₄, was filtered, and was concentrated under reduced pressure. The crude residue was purified by silica gel chromatography (50-100% EtOAc/Hex) to afford intermediate 14f (1.91 g, 68%) as a white solid.

¹H NMR (400 MHz, DMSO-d₆) δ 10.45 (s, 1H), 8.20 (s, 1H), 7.19 (d, J=4.3 Hz, 1H), 6.95 (d, J=4.7 Hz, 1H), 5.35 (d, J=5.2 Hz, 1H), 5.06 (t, J=5.7 Hz, 1H), 4.79-4.74 (m, 2H), 4.45 (t, J=5.8 Hz, 1H), 3.73-3.46 (m, 3H), 3.40-3.30 (m, 1H), 1.50 (s, 12H), 1.27 (s, 3H).

LC/MS: t_R=1.45 min, MS m/z=437.09 [M+H]; LC system: Thermo Accela 1250 UHPLC; MS system: Thermo LCQ Fleet; Column: Kinetex 2.6μ XB-C18 100A, 50×3.00 mm; Solvents: Acetonitrile with 0.1% formic acid, Water with 0.1% formic acid; Gradient: 0 min-2.4 min 2-100% ACN, 2.4 min-2.80 min 100% ACN, 2.8 min-2.85 min 100%-2% ACN, 2.85 min-3.0 min 2% ACN at 1.8 mL/min.

14g

Intermediate 14g—tert-butyl (7-((3aS,4S,6S,6aS)-6-((bis(4-methoxyphenyl)(phenyl)methoxy)methyl)-6-(hydroxymethyl)-2,2-dimethyltetrahydrofuro[3,4-d][1,3]dioxol-4-yl)pyrrolo[2,1-f][1,2,4]triazin-4-yl)carbamate Intermediate 14f (1.15 g, 2.63 mmol) was dissolved in CH₂Cl₂ (50 mL) and TEA (0.73 mL, 5.27 mmol) was added. The resulting solution was cooled to 0° C. and DMTrCl (1.35 g, 3.95 mmol) was added. After 10 min, the reaction mixture was quenched with CH₃OH as was then diluted with CH₂Cl₂. The resulting mixture was washed with sat NaHCO₃(aq) and brine. The organic layer was dried over Na₂SO₄, was filtered, and was concentrated under reduced pressure. The crude residue was purified by silica gel chromatography (0-100% EtOAc/Hex) to afford 14g (1.95 g, 79%) as an off-white solid.

¹H NMR (400 MHz, DMSO-d₆) δ10.46 (s, 1H), 8.23 (s, 1H), 7.56-7.07 (m, 10H), 7.07-6.70 (m, 5H), 5.24 (d, J=5.2 Hz, 1H), 5.04 (t, J=5.9 Hz, 1H), 4.93-4.71 (m, 2H), 3.80-3.59 (m, 7H), 3.52 (dd, J=10.9, 4.8 Hz, 1H), 3.25 (d, J=9.9 Hz, 1H), 3.09 (d, J=9.9 Hz, 1H), 1.50 (s, 9H), 1.25 (s, 3H), 1.21 (s, 3H).

LC/MS: $t_R$=2.54 min, MS m/z=739.28 [M+H]; LC system: Thermo Accela 1250 UHPLC MS system: Thermo LCQ Fleet; Column: Kinetex 2.6µ XB-C18 100A, 50×3.00 mm; Solvents: Acetonitrile with 0.1% formic acid, Water with 0.1% formic acid; Gradient: 0 min-2.4 min 2-100% ACN, 2.4 min-2.80 min 100% ACN, 2.8 min-2.85 min 100%-2% ACN, 2.85 min-3.0 min 2% ACN at 1.8 mL/min.

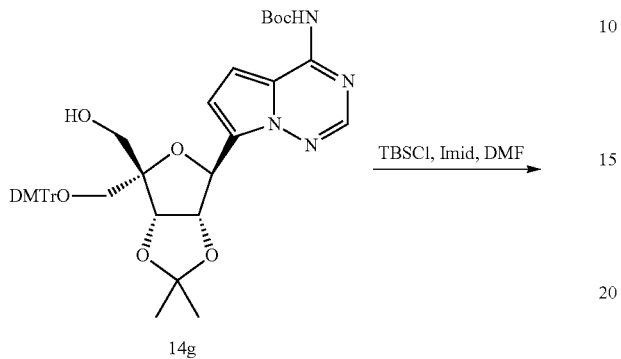

14g

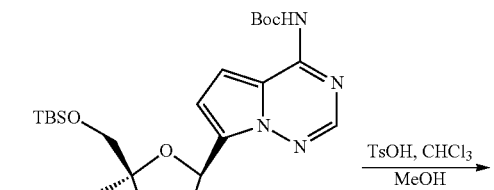

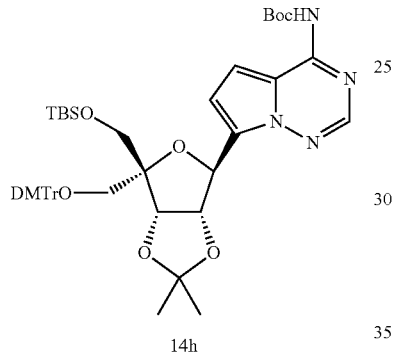

14h

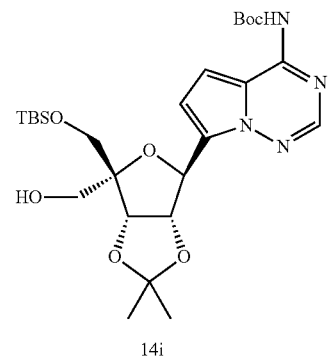

14i

Intermediate 14h—tert-butyl (7-((3aS,4S,6R,6aS)-6-((bis(4-methoxyphenyl)(phenyl)methoxy)methyl)-6-(((tert-butyldimethylsilyl)oxy)methyl)-2,2-dimethyltetrahydrofuro[3,4-d][1,3]dioxol-4-yl)pyrrolo[2,1-f][1,2,4]triazin-4-yl)carbamate Intermediate 14g (1.53 g, 2.08 mmol) was dissolved in DMF (10 mL) and imidazole (0.42 g, 6.23 mmol) was added followed by TBSCl (0.47 g, 3.11 mmol). After 1 h, the reaction was quenched with methanol and partitioned between EtOAc and 5% LiCl$_{(aq)}$. The phases were split and the organic layer was washed with brine, was dried over Na$_2$SO$_4$, was filtered, and was concentrated under reduced pressure. The crude residue was purified by silica gel chromatography (0-50% EtOAc/Hex) to afford 14h (1.77 g, 78%) as an off-white solid.

$^1$H NMR (400 MHz, DMSO-d$_6$) δ 10.47 (s, 1H), 8.23 (s, 1H), 7.56-6.66 (m, 15H), 5.31 (d, J=4.9 Hz, 1H), 5.14 (dd, J=6.5, 4.9 Hz, 1H), 4.73 (d, J=6.5 Hz, 1H), 3.87 (d, J=9.7 Hz, 1H), 3.72 (s, 6H), 3.53 (d, J=9.7 Hz, 1H), 3.31 (m, 1H), 3.08 (d, J=9.8 Hz, 1H), 1.50 (s, 9H), 1.25 (s, 3H), 1.22 (s, 3H), 0.75 (s, 9H), −0.04 (s, 3H), −0.08 (s, 3H).

LC/MS: $t_R$=2.34 min, MS m/z=853.50 [M+H]; LC system: Thermo Accela 1250 UHPLC; MS system: Thermo LCQ Fleet; Column: Kinetex 2.6µ XB-C18 100A, 50×3.00 mm; Solvents: Acetonitrile with 0.1% formic acid, Water with 0.1% formic acid; Gradient: 0 min-1.0 min 2-100% ACN, 1.0 min-2.80 min 100% ACN, 2.8 min-2.85 min 100%-2% ACN, 2.85 min-3.0 min 2% ACN at 1.8 mL/min.

Intermediate 14i—tert-butyl (7-((3aS,4S,6R,6aS)-6-(((tert-butyldimethylsilyl)oxy)methyl)-6-(hydroxymethyl)-2,2-dimethyltetrahydrofuro[3,4-d][1,3]dioxol-4-yl)pyrrolo[2,1-f][1,2,4]triazin-4-yl)carbamate Intermediate 14h (1.38 g, 1.62 mmol) was dissolved in chloroform (20 mL) and the resulting solution was cooled to 0° C. A solution of TsOH (0.34 g, 1.78 mmol) in CH$_3$OH (16 mL) was then add slowly. After 30 min, the reaction was quenched with sat. NaHCO$_{3(aq)}$, and the resulting mixture was partitioned between EtOAc and brine. The layers were split and the organic layer was dried over Na$_2$SO$_4$, was filtered, and was concentrated under reduced pressure. The crude residue was purified by silica gel chromatography (0-100% EtOAc/Hex) to afford intermediate 14i (0.84 g, 94%) as a white solid.

$^1$H NMR (400 MHz, DMSO-d$_6$) δ 10.42 (s, 1H), 8.20 (s, 1H), 7.19 (s, 1H), 6.89 (s, 1H), 5.37 (d, J=4.8 Hz, 1H), 5.05 (dd, J=6.2, 4.8 Hz, 1H), 4.71 (d, J=6.2 Hz, 1H), 4.51 (t, J=5.5 Hz, 1H), 3.70 (d, J=10.2 Hz, 1H), 3.59 (d, J=5.5 Hz, 2H), 3.49 (d, J=10.2 Hz, 1H), 1.49 (s, 12H), 1.28 (s, 3H), 0.82 (s, 9H), −0.01 (s, 3H), −0.02 (s, 3H).

LC/MS: $t_R$=1.88 min, MS m/z=551.25 [M+H]; LC system: Thermo Accela 1250 UHPLC MS system: Thermo LCQ Fleet; Column: Kinetex 2.6µ XB-C18 100A, 50×3.00 mm; Solvents: Acetonitrile with 0.1% formic acid, Water with 0.1% formic acid; Gradient: 0 min-1.0 min 2-100% ACN, 1.0 min-2.80 min 100% ACN, 2.8 min-2.85 min 100%-2% ACN, 2.85 min-3.0 min 2% ACN at 1.8mL/min.

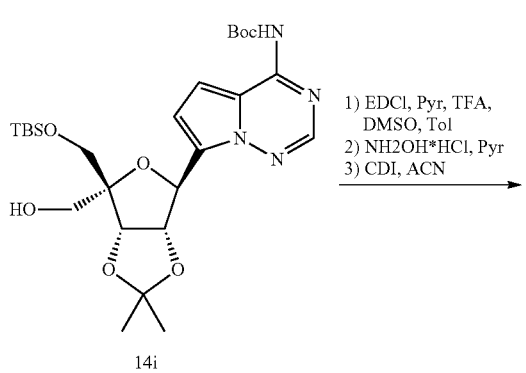

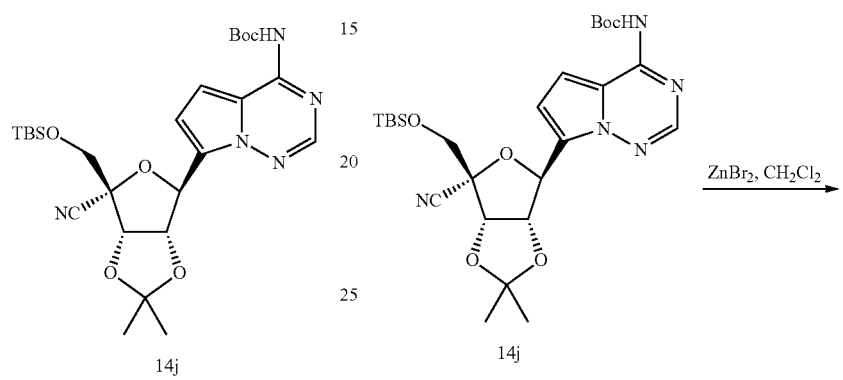

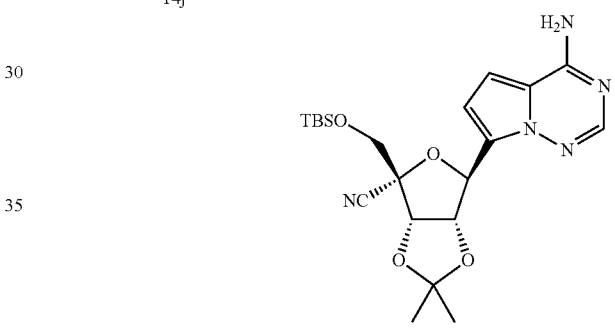

Intermediate 14j—tert-butyl (7-((3aS,4S,6R,6aS)-6-(((tert-butyldimethylsilyl)oxy)methyl)-6-cyano-2,2-dimethyltetrahydrofuro[3,4-d][1,3]dioxol-4-yl)pyrrolo[2,1-f][1,2,4]triazin-4-yl)carbamate Intermediate 14i (0.838 g, 1.52 mmol) was dissolved in DMSO (5 mL) and toluene (3 mL). Pyridine (0.14 mL, 1.67 mmol) and EDCl (0.438 g, 2.28 mmol) were added followed by TFA (0.057 mL, 0.761 mmol). After 30 min, additional pyridine (0.14 mL, 1.67 mmol) and EDCl (0.438 g, 2.28 mmol) were added. After 1 h, additional pyridine (0.14 mL, 1.67 mmol) and EDCl (0.438 g, 2.28 mmol) were added. After 2 h, the reaction mixture was quenched with ½ sat. $NaHCO_{3(aq)}$ and was partitioned between EtOAc and ½ sat. $NaHCO_{3(aq)}$. The layers were separated and the organic layer was dried over $Na_2SO_4$, was filtered, and was concentrated under reduced pressure. The residue was dissolved in $CH_2Cl_2$ was concentrated under high vacuum for 1 h to afford a residue that was used directly in the next step.

The residue was dissolved in pyridine (8 mL) and hydroxylamine hydrochloride (0.159 g, 2.28 mmol) was added in one portion. After 15 min, the reaction mixture was concentrated under reduced pressure and was partitioned between EtOAc and water. The organic layer was dried over $Na_2SO_4$, was filtered, and was concentrated under reduced pressure. The crude residue was placed under high vacuum for 30 min and used as is for the third step.

The crude residue was dissolved in ACN (8 mL). CDI (0.37 g, 2.28 mmol) was added in one portion. After 45 min, additional CDI (0.37 g, 2.28 mmol) was added. After 1 h, the reaction was quenched with ½ sat. $NaHCO_{3(aq)}$. The crude was partitioned between EtOAc and ½ sat. $NaHCO_{3(aq)}$. The layers were separated and the organic layer was dried over $Na_2SO_4$, was filtered, and was concentrated under reduced pressure. The crude residue was purified by silica gel chromatography (0-50% EtOAc/Hex) to afford intermediate 14j (0.72 g, 87%) as a white solid.

$^1$H NMR (400 MHz, DMSO-$d_6$) δ 10.53 (s, 1H), 8.25 (s, 1H), 7.21 (s, 1H), 7.00 (d, J=4.6 Hz, 1H), 5.62 (d, J=3.6 Hz, 1H), 5.28 (dd, J=6.6, 3.7 Hz, 1H), 4.93 (d, J=6.6 Hz, 1H), 3.83 (s, 2H), 1.62 (s, 3H), 1.50 (s, 9H), 1.33 (s, 3H), 0.83 (s, 9H), 0.00 (s, 6H).

LC/MS: $t_R$=2.50 min, MS m/z=546.15 [M+H]; LC system: Thermo Accela 1250 UHPLC; MS system: Thermo LCQ Fleet; Column: Kinetex 2.6μ XB-C18 100A, 50×3.00 mm; Solvents: Acetonitrile with 0.1% formic acid, Water with 0.1% formic acid; Gradient: 0 min-2.4 min 2-100% ACN, 2.4 min-2.80 min 100% ACN, 2.8 min-2.85 min 100%-2% ACN, 2.85 min-3.0 min 2% ACN at 1.8 mL/min.

Intermediate 14k—(3aS,4R,6S,6aS)-6-(4-aminopyrrolo[2,1-f][1,2,4]triazin-7-yl)-4-(((tert-butyldimethylsilyl)oxy)methyl)-2,2-dimethyltetrahydrofuro[3,4-d][1,3]dioxole-4-carbonitrile Intermediate 14j (0.688 g, 1.26 mmol) was dissolved in $CH_2Cl_2$ (15 mL). Zinc bromide (0.567 g, 2.52 mmol) was added in one portion and the reaction mixture was stirred at ambient temperature. After 3 h, the reaction mixture was added to a silica load cartridge and was purified by silica gel chromatography (40-100% EtOAc/Hex) to afford intermediate 14k (0.56 g, 99%) as a white solid.

$^1$H NMR (400 MHz, DMSO-$d_6$) δ 7.86 (s, 1H), 7.80 (s, 2H), 6.85 (d, J=4.5 Hz, 1H), 6.79 (d, J=4.5 Hz, 1H), 5.55 (d, J=3.7 Hz, 1H), 5.25 (dd, J=6.6, 3.8 Hz, 1H), 4.92 (d, J=6.6 Hz, 1H), 3.82 (s, 2H), 1.61 (s, 3H), 1.33 (s, 3H), 0.83 (s, 9H), −0.13 (s, 6H).

LC/MS: $t_R$=2.27 min, MS m/z=446.68 [M+H]; LC system: Thermo Accela 1250 UHPLC; MS system: Thermo LCQ Fleet; Column: Kinetex 2.6μ XB-C18 100A, 50×3.00 mm; Solvents: Acetonitrile with 0.1% formic acid, Water with 0.1% formic acid; Gradient: 0 min-2.4 min 2-100% ACN, 2.4 min-2.80 min 100% ACN, 2.8 min-2.85 min 100%-2% ACN, 2.85 min-3.0 min 2% ACN at 1.8 mL/min.

143

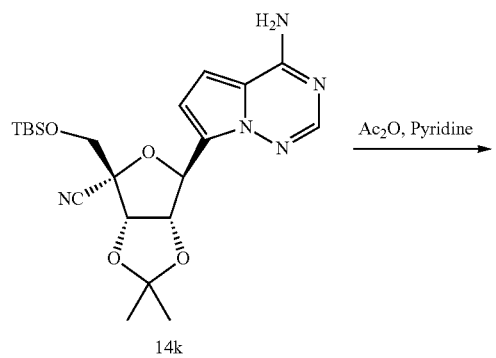

14k

Ac₂O, Pyridine →

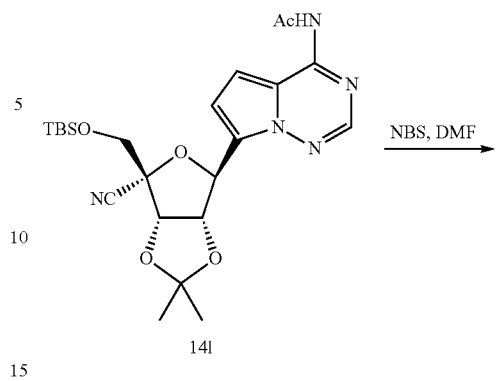

14l

NBS, DMF →

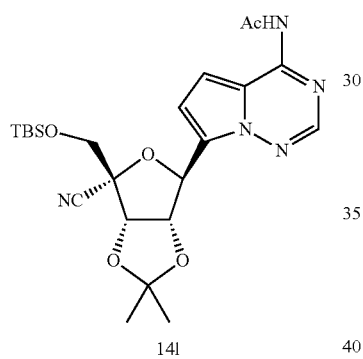

14l

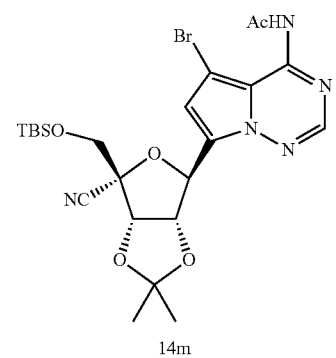

14m

Intermediate 14l—N-(7-((3aS,4S,6R,6aS)-6-(((tert-butyldimethylsilyl)oxy)methyl)-6-cyano-2,2-dimethyltetrahydrofuro[3,4-d][1,3]dioxol-4-yl)pyrrolo[2,1-f][1,2,4]triazin-4-yl)acetamide Intermediate 14k (0.20 g, 0.449 mmol) was dissolved in pyridine (2 mL) then acetic anhydride (0.21 mL, 2.24 mmol) was added and the reaction was stirred at ambient temperature. After 30 min, the reaction mixture was quenched with methanol and was concentrated under reduced pressure. The crude residue was purified directly by silica gel chromatography (0-100% EtOAc/Hex) to afford intermediate 14l (0.185 g, 85%) as a white solid.

$^1$H NMR (400 MHz, DMSO-d$_6$) δ 10.87 (s, 1H), 8.31 (s, 1H), 7.24 (d, J=4.7 Hz, 1H), 7.05 (d, J=4.7 Hz, 1H), 5.65 (d, J=3.6 Hz, 1H), 5.29 (dd, J=6.6, 3.6 Hz, 1H), 4.93 (d, J=6.6 Hz, 1H), 3.84 (s, 2H), 2.36 (s, 3H), 1.62 (s, 3H), 1.33 (s, 3H), 0.83 (s, 9H), 0.00 (s, 3H), −0.01 (s, 3H).

LC/MS: t$_R$=1.14 min, MS m/z=488.38 [M+1]; LC system: Thermo Accela 1250 UHPLC; MS system: Thermo LCQ Fleet; Column: Kinetex 2.6μ XB-C18 100A, 50×3.00 mm; Solvents: Acetonitrile with 0.1% formic acid, Water with 0.1% formic acid; Gradient: 0 min-1.4 min 2-100% ACN, 1.4 min-1.80 min 100% ACN, 1.8 min-1.85 min 100%-2% ACN, 1.85 min-2 min 2% ACN at 1.8 mL/min.

Intermediate 14m—N-(5-bromo-7-((3aS,4S,6R,6aS)-6-(((tert-butyldimethylsilyl)oxy)methyl)-6-cyano-2,2-dimethyltetrahydrofuro[3,4-d][1,3]dioxol-4-yl)pyrrolo[2,1-f][1,2,4]triazin-4-yl)acetamide Intermediate 14l (80 mg, 0.164 mmol) was dissolved in DMF (2 mL) and NBS (29 mg, 0.164 mmol) was added in one portion. After 45 min, the reaction was diluted with methanol. The solvent was removed under reduced pressure. The crude residue was purified by silica gel chromatography (0-50% EtOAc/Hex) to afford intermediate 14m (50 mg, 54%) as an off-white solid.

$^1$H NMR (400 MHz, DMSO-d$_6$) δ 10.13 (s, 1H), 8.42 (s, 1H), 7.29 (s, 1H), 5.65 (d, J=3.2 Hz, 1H), 5.29 (dd, J=6.6, 3.2 Hz, 1H), 4.91 (d, J=6.5 Hz, 1H), 3.84 (d, J=1.6 Hz, 2H), 2.27 (s, 3H), 1.62 (s, 3H), 1.33 (s, 3H), 0.83 (s, 9H), 0.02 (s, 3H), 0.00 (s, 3H).

LC/MS: t$_R$=1.79 min, MS m/z=566.40 [M+1]; LC system: Thermo Accela 1250 UHPLC; MS system: Thermo LCQ Fleet; Column: Kinetex 2.6μ XB-C18 100A, 50×3.00 mm; Solvents: Acetonitrile with 0.1% formic acid, Water with 0.1% formic acid; Gradient: 0 min-1.4 min 2-100% ACN, 1.4 min-1.80 min 100% ACN, 1.8 min-1.85 min 100%-2% ACN, 1.85 min-2 min 2% ACN at 1.8 mL/min.

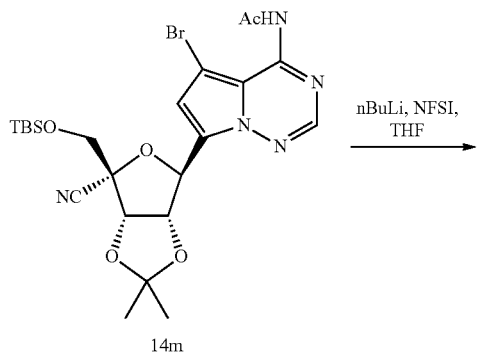

14m

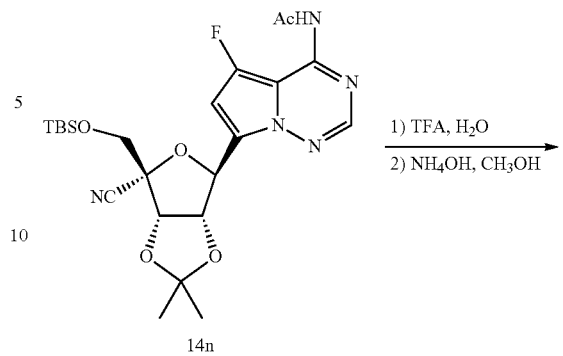

14n

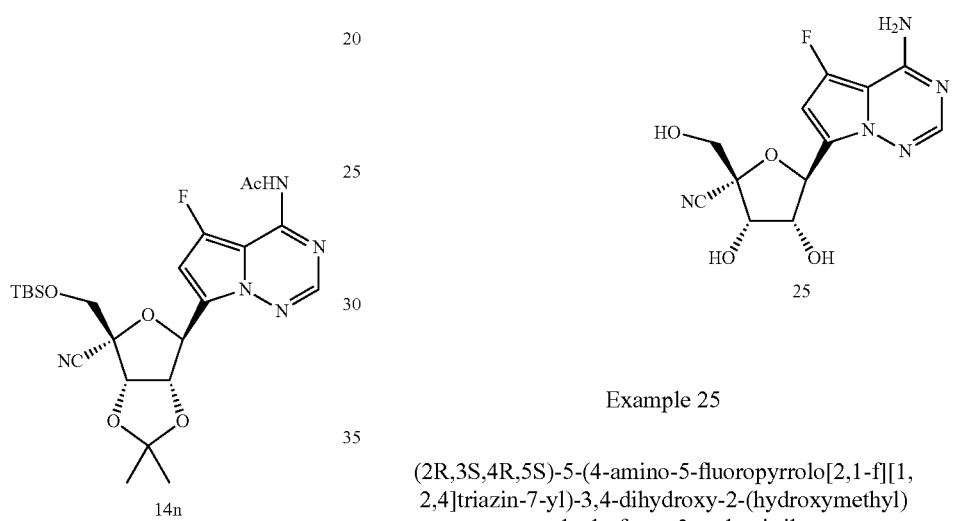

Example 25

(2R,3S,4R,5S)-5-(4-amino-5-fluoropyrrolo[2,1-f][1,2,4]triazin-7-yl)-3,4-dihydroxy-2-(hydroxymethyl)tetrahydrofuran-2-carbonitrile Intermediate 14n—N-(7-((3aS,4S,6R,6aS)-6-(((tert-butyldimethylsilyl)oxy)methyl)-6-cyano-2,2-dimethyltetrahydrofuro[3,4-d][1,3]dioxol-4-yl)-5-fluoropyrrolo[2,1-f][1,2,4]triazin-4-yl)acetamide Intermediate 14m (50 mg, 0.088 mmol) was dissolved in THF (2 mL) and the solution was cooled to −78° C. nBuLi (2.5M in hexanes, 0.071 mL, 0.18 mmol) was added. After 5 min, N-fluorobenzenesulfonimide (NSFI, 33.4 mg, 0.106 mmol) was added and the reaction mixture was stirred for 5 min. The reaction was then quenched with AcOH. The solvents were removed under reduced pressure. The crude residue was purified by reverse phase HPLC to afford intermediate 14n (10 mg, 22%) as a white solid.

$^1$H NMR (400 MHz, Methanol-$d_4$) δ 8.13 (s, 1H), 6.80 (s, 1H), 5.65 (d, J=3.5 Hz, 1H), 5.23 (dd, J=6.7, 3.6 Hz, 1H), 4.97 (d, J=6.7 Hz, 1H), 3.92 (d, J=1.7 Hz, 2H), 2.37 (s, 3H), 1.70 (s, 3H), 1.38 (s, 3H), 0.90 (s, 9H), 0.08 (s, 6H).

$^{19}$F NMR (376 MHz, Methanol-$d_4$) δ −156.43 (s).

LC/MS: $t_R$=1.65 min, MS m/z=506.18 [M+H]; LC system: Thermo Accela 1250 UHPLC; MS system: Thermo LCQ Fleet; Column: Kinetex 2.6μ XB-C18 100A, 50×3.00 mm; Solvents: Acetonitrile with 0.1% formic acid, Water with 0.1% formic acid; Gradient: 0 min-2.4 min 2-100% ACN, 2.4 min-2.80 min 100% ACN, 2.8 min-2.85 min 100%-2% ACN, 2.85 min-3.0 min 2% ACN at 1.8 mL/min.

Intermediate 14n (11 mg, 0.022 mmol) was taken up into a solution of 50% TFA in water at ambient temperature. After 2 h, the reaction mixture was quenched with solid $Na_2CO_3$ to achieve a pH=8. The solvent was removed under reduced pressure and the crude residue was purified by reverse phase HPLC. The fractions containing example 25 were combined and set aside and the fractions containing the N6-Acyl were combined and concentrated under reduced pressure. The N6-Acyl intermediate residue was taken up in conc. $NH_4OH_{(aq)}$ (1 mL) and the mixture was allowed to stir at ambient temperature. After 30 min, the resulting mixture was concentrated under reduced pressure and the crude residue was purified by HPLC. The fractions containing example 25 were combined with the previously set aside fractions containing example 25 to afford example 25 (4 mg, 58%) as a white solid.

$^1$H NMR (400 MHz, Methanol-$d_6$) δ 7.71 (s, 1H), 6.56 (s, 1H), 5.44 (d, J=5.6 Hz, 1H), 4.48 (t, J=5.6 Hz, 1H), 4.36 (d, J=5.5 Hz, 1H), 3.83 ((ABq, Δδ=0.05 ppm, J=12 Hz, 2H).

$^{19}$F NMR (376 MHz, Methanol-$d_4$) δ −161.81 (s)

LC/MS: $t_R$=0.47 min, MS m/z=310.13 [M+H]; LC system: Thermo Accela 1250 UHPLC; MS system: Thermo LCQ Fleet; Column: Kinetex 2.6μ XB-C18 100A, 50×3.00 mm; Solvents: Acetonitrile with 0.1% formic acid, Water with 0.1% formic acid; Gradient: 0 min-1.4 min 2-100% ACN, 1.4 min-1.80 min 100% ACN, 1.8 min-1.85 min 100%-2% ACN, 1.85 min-2 min 2% ACN at 1.8 mL/min.

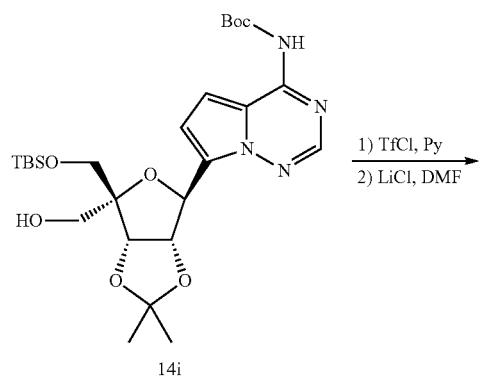

14i

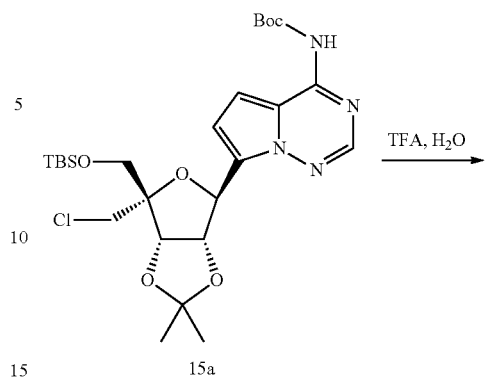

15a

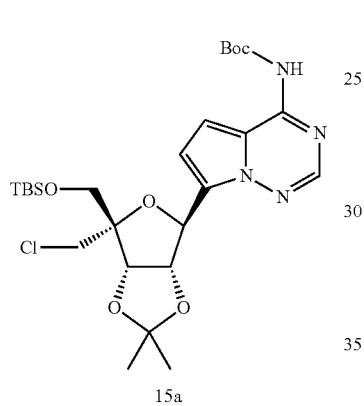

15a

Intermediate 15a—tert-butyl (7-((3aS,4S,6R,6aS)-6-(((tert-butyldimethylsilyl)oxy)methyl)-6-(chloromethyl)-2,2-dimethyltetrahydrofuro[3,4-d][1,3]dioxol-4-yl)pyrrolo[2,1-f][1,2,4]triazin-4-yl)carbamate Intermediate 14i (100 mg, 0.18 mmol) was dissolved in anhydrous pyridine (5 mL). Trifluoromethanesulfonyl chloride (23 μL, 0.22 mmol) was added in one portion and the reaction mixture was stirred for 45 min at RT. Additional trifluoromethanesulfonyl chloride (100 μL) was then added. After 30 min, additional trifluoromethanesulfonyl chloride (100 μL) was added. After an additional 30 min, more trifluoromethanesulfonyl chloride (100 μL) was added and the reaction was stirred for 30 min, at which point the reaction mixture was concentrated under reduced pressure. The crude residue was dissolved in anhydrous DMF (5 mL) and lithium chloride (153 mg, 3.6 mmol) was then added in one portion. The resulting mixture was stirred at RT for 16 h. The reaction mixture was diluted with ethyl acetate (50 mL) and was washed with saturated aqueous sodium chloride solution (3×20 mL). The organic layer was dried over anhydrous sodium sulfate and was concentrated under reduced pressure. The crude residue was purified with silica gel chromatography (0-20% ethyl acetate in hexanes) to afford intermediate 15a.

MS m/z=569.0 [M+H]. MS system: Thermo LCQ Advantage

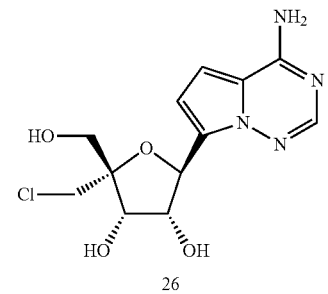

26

Example 26

(2R,3S,4R,5S)-5-(4-aminopyrrolo[2,1-f][1,2,4]triazin-7-yl)-2-(chloromethyl)-2-(hydroxymethyl)tetrahydrofuran-3,4-diol Intermediate 15a was dissolved in a solution of TFA and water (1:1, 5 mL) and the resulting mixture was stirred for 16 h. The reaction mixture was then concentrated under reduced pressure. The crude residue was dissolved in aqueous sodium bicarbonate solution and acetonitrile and was purified with prep HPLC to afford example 26 (19 mg, 34%) as white powder.

$^1$H NMR (400 MHz, D$_2$O) δ 7.61 (s, 1H), 6.72-6.64 (m, 2H), 5.19 (d, J=9.1 Hz, 1H), 4.73-4.66 (m, 1H), 4.28 (d, J=5.2 Hz, 1H), 3.78 (s, 2H), 3.72-3.57 (m, 2H). MS m/z=315.3 [M+H]. MS system: Thermo LCQ Advantage

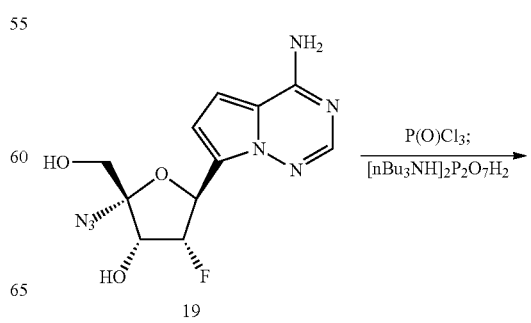

19

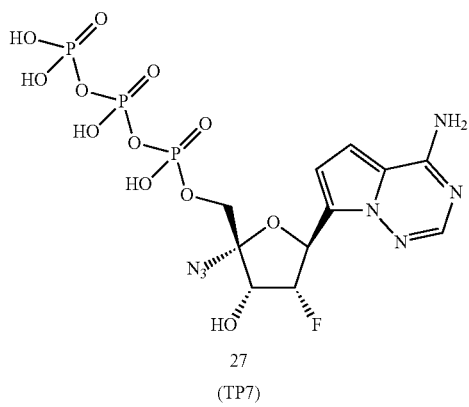

27

(TP7)

Example 27 (also TP7)

((2R,3R,4R,5S)-5-(4-aminopyrrolo[2,1-f][1,2,4]tri-azin-7-yl)-2-azido-4-fluoro-3-hydroxytetrahydrofuran-2-yl)methyl tetrahydrogen triphosphate Example 27 was prepared as the tetra-sodium salt in a manner similar to that described for example TP4 starting with example 19.

$^1$H NMR (400 MHz, D$_2$O) δ 7.76 (s, 1H), 6.83 (d, J=4.4 Hz, 1H), 6.80 (d, J=4.8 Hz, 1H), 5.94 (d, J=25.2 Hz, 1H), 5.24 (dd, J=55.2, 5.2 Hz, 1H), 4.78 (dd, J=26.8, 5.2 Hz, 1H), 4.08-4.18 (m, 2H).

$^{19}$F NMR (376 MHz, D$_2$O) δ -193.74--194.02 (m).

$^{31}$P NMR (162 MHz, D$_2$O) δ -4.60 (d, J=53.2 Hz, 1P), -10.25 (d, J=48.4 Hz, 1P), -20.28 (t, J=48.4 Hz, 1P).

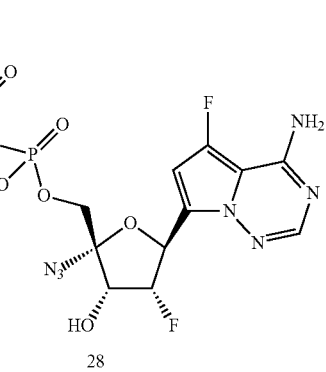

21

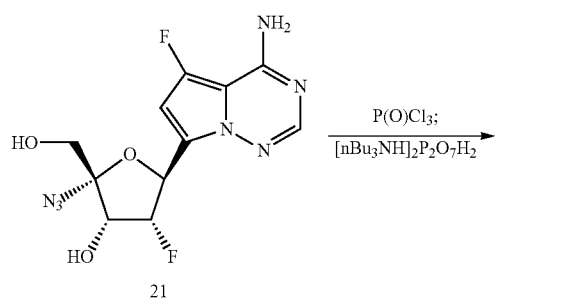

28

Example 28

((2R,3R,4R,5S)-5-(4-amino-5-fluoropyrrolo[2,1f-][1,2,4]triazin-7-yl)-2-azido-4-fluoro-3-hydroxytetrahydrofuran-2-yl)methyl tetrahydrogen triphosphate Example 28 was prepared as the tetra-sodium salt in a manner similar to that described for example TP4 starting with example 21.

$^1$H NMR (400 MHz, D$_2$O) δ 7.64 (s, 1H), 6.60 (s, 1H), 5.90 (d, J=24.4 Hz, 1H), 5.20 (dd, J=54.8, 4.8 Hz, 1H), 4.72 (dd, J=27.2, 4.8 Hz, 1H), 4.05-4.18 (m, 2H).

$^{19}$F NMR (376 MHz, D$_2$O) δ -161.00 (s), -196.39--196.69 (m).

$^{31}$P NMR (162 MHz, D$_2$O) δ -8.24 (d, J=50.4 Hz), -14.20 (d, J=46.0 Hz), -24.08 (t, J=48.4 Hz). MS m/z=567.87 [M+1]. MS system: Thermo LCQ Advantage

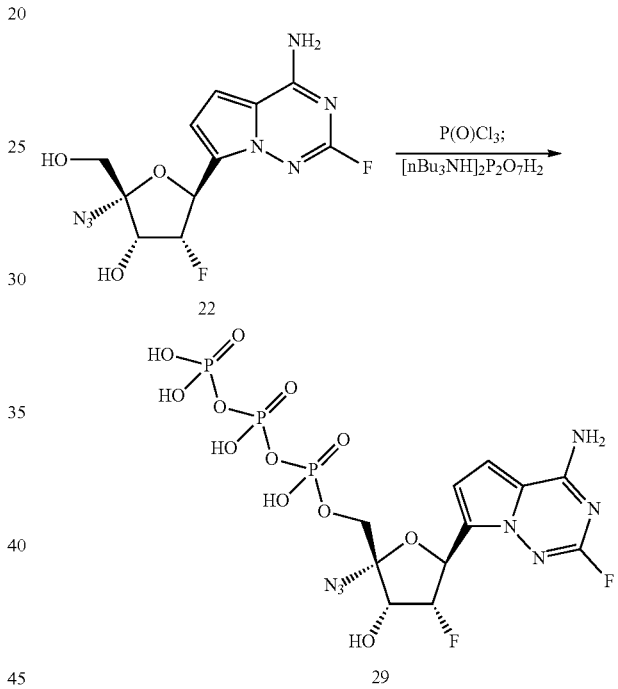

22

29

Example 29

((2R,3R,4R,5S)-5-(4-amino-2-fluoropyrrolo[2,1-f][1,2,4]triazin-7-yl)-2-azido-4-fluoro-3-hydroxytetrahydrofuran-2-yl)methyl tetrahydrogen triphosphate Example 29 was prepared as the tetra-sodium salt in a manner similar to that described for example TP4 starting with example 22.

$^1$H NMR (400 MHz, D$_2$O) δ 6.81 (d, J=4.4 Hz, 1H), 6.75 (d, J=4.8 Hz, 1H), 5.81 (d, J=24.4 Hz, 1H), 5.16 (dd, J=54.4, 4.8 Hz, 1H), 4.70 (dd, J=26.8, 4.4 Hz, 1H), 4.02-4.12 (m, 2H).

$^{19}$F NMR (376 MHz, D$_2$O) δ -75.95 (s), -196.51--196.80 (m).

$^{31}$P NMR (162 MHz, D$_2$O) δ -8.29 (d, J=53.2 Hz), -14.22 (d, J=48.4 Hz), -24.09 (t, J=48.4 Hz).

MS m/z=567.59 [M+1]. MS system: Thermo LCQ Advantage

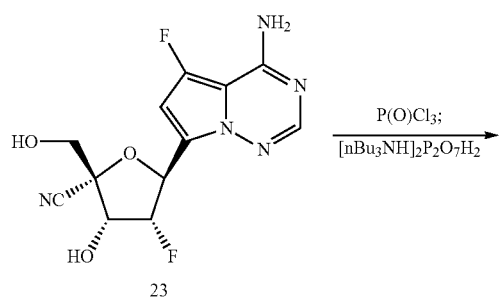

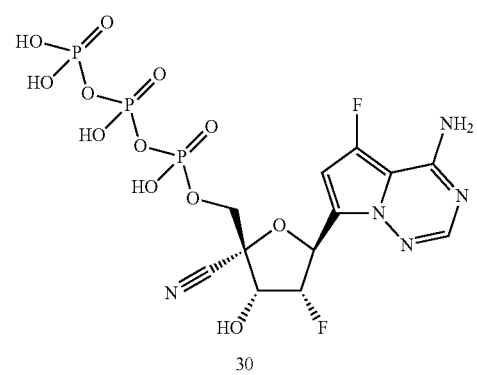

Example 30

((2R,3R,4R,5S)-5-(4-amino-5-fluoropyrrolo[2,1f-][1,2,4]triazin-7-yl)-2-cyano-4-fluoro-3-hydroxytetrahydrofuran-2-yl)methyl tetrahydrogen triphosphate Example 30 was prepared as the tetra-sodium salt in a manner similar to that described for example TP4 starting with example 23.

$^1$H NMR (400 MHz, D$_2$O) δ 7.64 (s, 1H), 6.57 (s, 1H), 5.87 (d, J=24.8 Hz, 1H), 5.26 (dd, J=53.6, 4.0 Hz, 1H), 4.82 (dd, J=25.2, 4, 4 Hz, 1H), 4.26-4.35 (m, 2H).

$^{19}$F NMR (376 MHz, D$_2$O) δ −161.05 (s), −194.92-−195.19 (m).

$^{31}$P NMR (162 MHz, D$_2$O) 5-8.22 (d, J=50.8 Hz), −14.48 (d, J=48.4 Hz), −24.01 (t, J=48.4 Hz).

MS m/z=551.91 [M+1]. MS system: Thermo LCQ Advantage

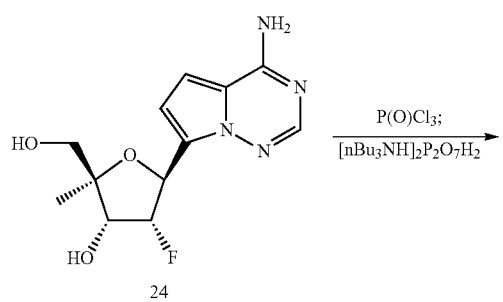

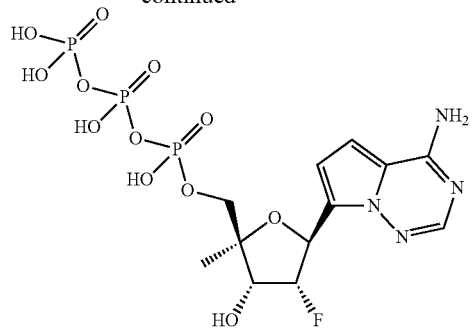

TP11
Example 31

Example 31 (also TP11)

((2R,3R,4R,5S)-5-(4-aminopyrrolo[2,1-f][1,2,4]triazin-7-yl)-4-fluoro-3-hydroxy-2-methyltetrahydrofuran-2-yl)methyl tetrahydrogen triphosphate Example 31 was prepared as the tetra-sodium salt in a manner similar to that described for example TP4 starting with example 24

$^1$H NMR (400 MHz, D$_2$O) δ 7.66 (s, 1H), 6.78 (d, J=4.8 Hz, 1H), 6.72 (d, J=4.4 Hz, 1H), 5.58 (dd, J=23.6, 2.4 Hz, 1H), 5.16 (ddd, J=55.2, 5.2, 2.8 Hz, 1H), 4.51 (dd, J=23.2, 5.2 Hz, 1H), 3.88 (dd, J=11.6, 6.0 Hz, 1H), 3.78 (dd, J=10.8, 4.0 Hz, 1H), 1.2 (s, 3H).

$^{19}$F NMR (376 MHz, D$_2$O) δ −195.74-−196.01 (m).

$^{31}$P NMR (162 MHz, D$_2$O) δ −8.24 (d, J=50.4 Hz), −13.54 (d, J=45.6 Hz), −24.11 (t, J=48.0 Hz).

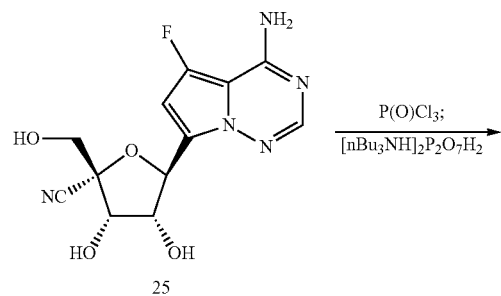

25

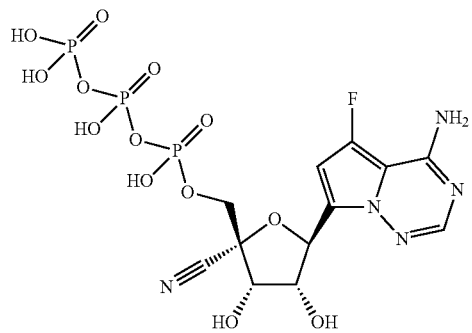

TP12
Example 32

Example 32 (also TP12)

((2R,3S,4R,5S)-5-(4-amino-5-fluoropyrrolo[2,1f-][1,2,4]triazin-7-yl)-2-cyano-3,4-dihydroxytetrahydrofuran-2-yl)methyl tetrahydrogen triphosphate Example 32 was prepared as the tetra-sodium salt in a manner similar to that described for example TP4 starting with example 25.

$^1$H NMR (400 MHz, D$_2$O) δ 7.59 (s, 1H), 0.57 (s, 1H), 5.44 (d, J=6.0 Hz, 1H), 4.56 (d, J=5.2 Hz, 1H), 4.48 (dd, J=5.6 Hz, 1H), 4.16 (dd, J=11.6, 6.0 Hz, 1H), 4.08 (dd, J=11.2, 5.2 Hz, 1H).
$^{19}$F NMR (376 MHz, D$_2$O) δ −161.25 (s).
$^{31}$P NMR (162 MHz, D$_2$O) δ −8.29 (d, J=48.4 Hz), −14.49 (d, J=53.2 Hz), −24.15 (t, J=48.4 Hz).
MS m/z=549.90 [M+1]. MS system: Thermo LCQ Advantage

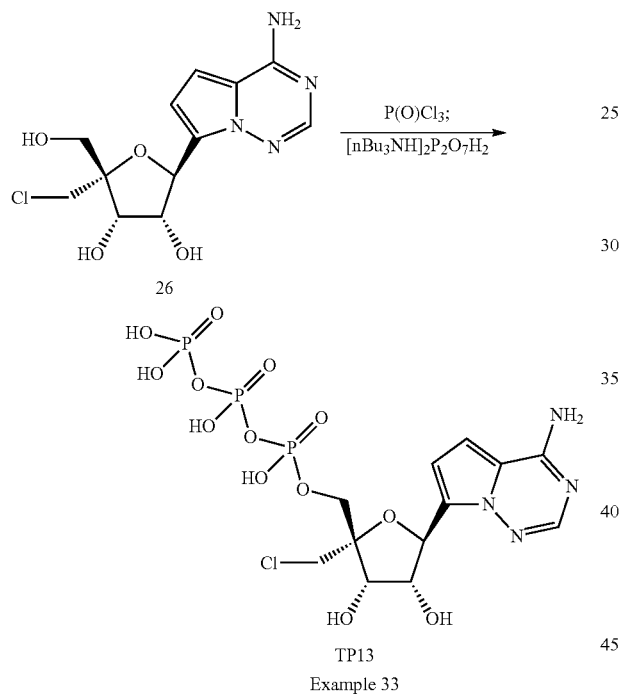

TP13
Example 33

Example 33 (also TP13)

((2R,3S,4R,5S)-5-(4-aminopyrrolo[2,1-f][1,2,4]triazin-7-yl)-2-(chloromethyl)-3,4-dihydroxytetrahydrofuran-2-yl)methyl tetrahydrogen triphosphate Example 33 was prepared as the tetra-triethylamine salt in a manner similar to that described for example TP3 starting with example 26.

$^1$H NMR (400 MHz, D$_2$O) δ 7.76 (s, 1H), 6.92 (br s, 1H), 6.85 (br s, 1H), 5.32 (d, J=9.6 Hz, 1H), 4.78 (dd, J=8, 6.4 Hz, 1H), 4.53 (d, J=5.6 Hz, 1H), 4.08 (dd, J=10.0, 4.0 Hz, 1H), 3.83-3.95 (m, 3H), 3.07 (q, J=7.6 Hz, 24H), 1.16 (t, J=7.6 Hz, 36H).
$^{31}$P NMR (162 MHz, D$_2$O) δ −9.44 (d, J=45.6 Hz), −11.51 (d, J=48.8 Hz), −22.95 (t, J=48.4 Hz).
MS m/z=555.06 [M+1]. MS system: Thermo LCQ Advantage

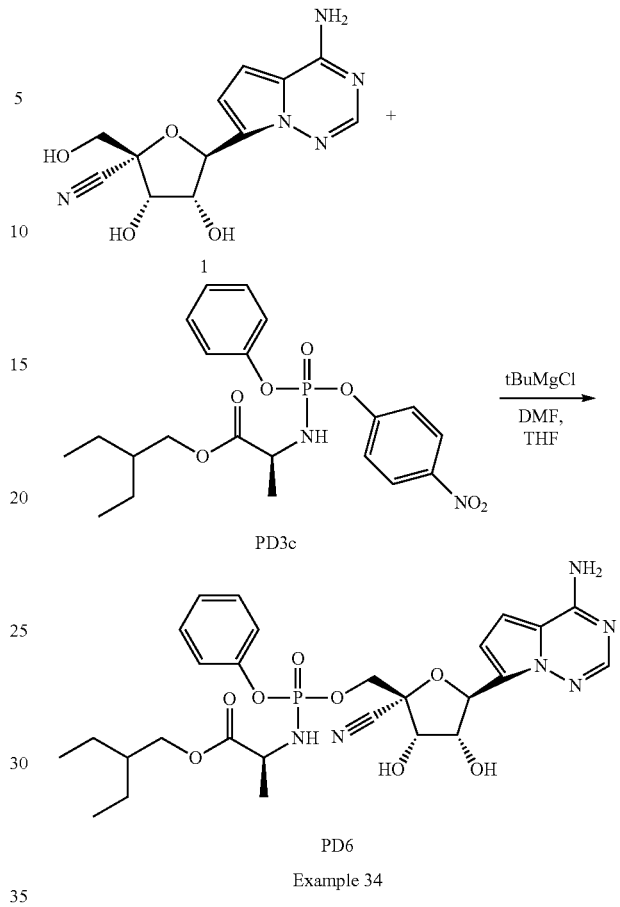

Example 34

Example 34 (also PD6)

(2S)-2-ethylbutyl 2-(((((2R,3R,4R,5S)-5-(4-aminopyrrolo[2,1-f][1,2,4]triazin-7-yl)-2-cyano-4-fluoro-3-hydroxytetrahydrofuran-2-yl)methoxy)(phenoxy)phosphoryl)amino)propanoate Example 1 (3.8 mg, 0.013 mmol) was dissolved in anhydrous N-methyl-2-pyrrolidone (0.2 mL) and THF (0.1 mL) was added under an argon atmosphere. tert-Butyl magnesium chloride (1 M in THF, 20 μL, 0.024 mmol) was then added at RT, and white solids precipitated. After 5 min, a solution of p-nitrophenylphosphoramidate PD3c (12 mg, 0.026 mmol) in THF (0.1 mL) was added to the reaction mixture in one portion, and the resulting mixture was heated to 50° C. After 20 h, the reaction mixture was allowed to cool to RT and was then purified directly by preparatory HPLC (Phenominex Synergi 4u Hydro-RR 80A 150×30 mm column, 40-100% acetonitrile/water gradient). The fractions containing the desired product were combined and were lyophilized to afford example 34 (2.9 mg, 37%, 3:2 diastereomeric mixture) as a white solid.

$^1$H NMR (400 MHz, CD$_3$OD) δ 7.80 (s, 0.3H), 7.78 (s, 0.6H), 7.38-7.10 (m, 5H), 6.85 (br dd, J=4.7, 2.2 Hz, 1H), 6.75-6.71 (m, 1H), 5.54-5.46 (m, 1H), 4.65-4.58 (m, 1H), 4.53-4.31 (m, 3H), 4.07-3.84 (m, 3H), 1.54-1.39 (m, 1H), 1.38-1.19 (m, 7H), 0.92-0.81 (m, 6H) 29H
$^{31}$P NMR (162 MHz, CD$_3$OD) δ 3.25 (br s).
LC/MS: t$_R$=1.55 min, MS m/z=603.19 [M+H]; LC system: Thermo Accela 1250 UHPLC; MS system: Thermo LCQ Fleet; Column: Kinetex 2.6μ XB-C18 100A, 50×4.6 mm; Solvents: Acetonitrile with 0.1% acetic acid, Water with 0.1% acetic acid; Gradient: 0 min-2.0 min 2-100% ACN, 2.0 min-3.05 min 100% ACN, 3.05 min-3.2 min 100%-2% ACN, 3.2 min-3.5 min 2% ACN at 2 μl/min.

HPLC: $t_R$=2.98 min; HPLC system: Agilent 1100 series.; Column: Gemini 5μ C18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min.

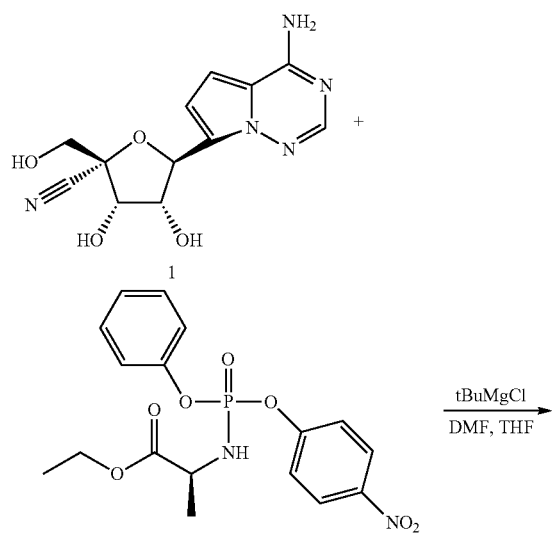

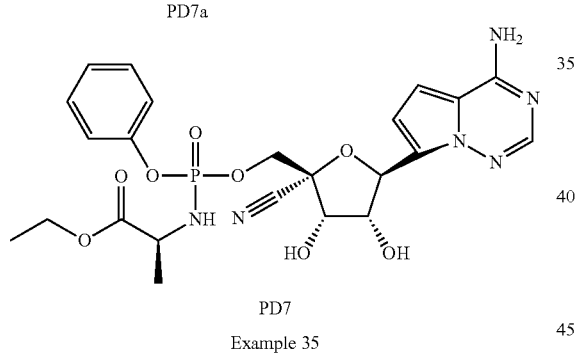

Example 35

Example 35 (also PD7)

(2S)-ethyl 2-(((((2R,3S,4R,5S)-5-(4-aminopyrrolo[2,1-f][1,2,4]triazin-7-yl)-2-cyano-3,4-dihydroxytetrahydrofuran-2-yl)methoxy)(phenoxy)phosphoryl)amino) propanoate Example 1 (19 mg, 65.3 μmol) was dissolved in NMP (0.2 mL). THF (0.1 mL) was added followed by tert-butyl magnesium chloride (1.0M solution in tetrahydrofuran, 0.098 mL) at RT under an argon atmosphere. After 5 min, a solution of intermediate PD7a (Prepared according to US20120009147A1, 51.4 mg, 130 μmol) in THF (0.1 mL) was added, and the resulting mixture was warmed to 50° C. After 1 h, the reaction mixture was allowed to cool to RT and was purified directly by preparatory HPLC (Phenominex Synergi 4u Hydro-RR 80A 150×30 mm column, 5-100% acetonitrile/water gradient). The fractions containing product were combined, and concentrated and the resulting residue was repurified by preparatory HPLC (Phenominex Luna 5u C18 100×30 mm column, 5-100% acetonitrile/water gradient) to afford example 35 (12 mg, 34%, 3:2 mixture of diastereomers) as a white solid.

$^1$H NMR (400 MHz, CD$_3$OD) δ 7.80 (d, J=2.3 Hz, 0.4H), 7.78 (d, J=2.3 Hz, 0.6H), 7.36-7.12 (m, 5H), 6.88-6.81 (m, 1H), 6.76-6.70 (m, 1H), 5.53-5.46 (m, 1H), 4.66-4.60 (m, 1H), 4.55-4.30 (m, 3H), 4.15-3.98 (m, 2H), 3.93-3.79 (m, 1H), 1.30-1.12 (m, 6H).

$^{31}$P NMR (162 MHz, CD$_3$OD) δ 3.27 (br s).

LC/MS: major diastereomer $t_R$=1.28 min, MS m/z=547.14 [M+H], minor diastereomer $t_R$=1.30 min, MS m/z=547.04 [M+H]; LC system: Thermo Accela 1250 UHPLC; MS system: Thermo LCQ Fleet; Column: Kinetex 2.6μ XB-C18 100A, 50×4.6 mm; Solvents: Acetonitrile with 0.1% acetic acid, Water with 0.1% acetic acid; Gradient: 0 min-2.0 min 2-100% ACN, 2.0 min-3.05 min 100% ACN, 3.05 min-3.2 min 100%-2% ACN, 3.2 min-3.5 min 2% ACN at 2 μl/min.

HPLC: major diastereomer $t_R$=2.44 min, minor diastereomer $t_R$=2.46 min; HPLC system: Agilent 1100 series.; Column: Gemini 5μ C18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min.

Also provided are separate embodiments comprising, respectively, compounds of Formula (A), Formula (B), Formula (C), Formula (D), and Formula (E):

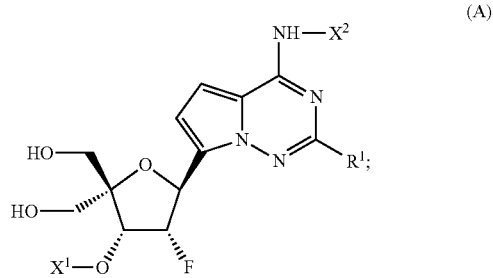

(A)

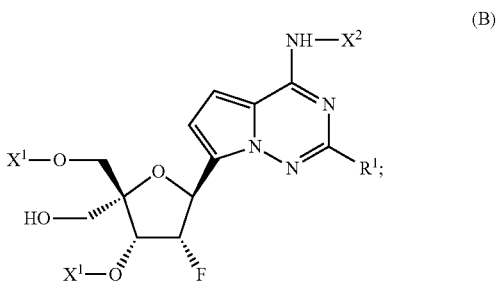

(B)

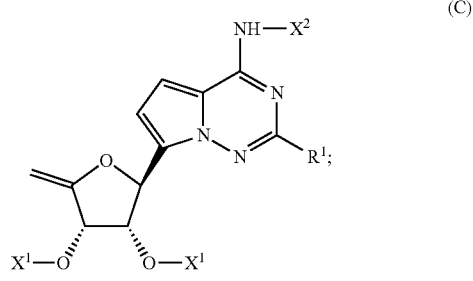

(C)

-continued

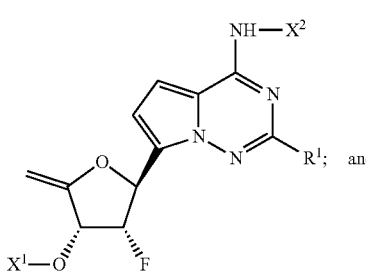
(D)

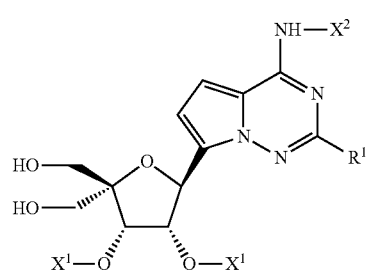
(F)

wherein, in each instance, $X^1$ represents an oxygen protecting group and $X^2$ represents an amine protecting group.

Useful oxygen protecting groups include a silyl ether protecting group or a benzyl-type protecting group, including methoxybenzyl groups.

Useful silyl ether protecting groups include Trimethylsilyl (TMS), Triethylsilyl (TES), Dimethylisopropylsilyl (IPDMS), Diethylisopropylsilyl (DEIPS), Dimethylthexylsilyl (TDS), t-Butyldimethylsilyl (TBS or TBDMS), t-Butyldiphenylsilyl (TBDPS), Tribenzylsilyl, Tri-p-xylylxilyl, Triisopropylsilyl (TIPS), Diphenylmethylsilyl (DPMS), Di-t-butylmethylsilyl (DTBMS), Triphenylsilyl (TPS), Methyldiphenyisilyl (MDPS), t-butylmethoxyphenylsilyl, Tris(trimethylsilyl)silyl (sisyl), (2-Hydroxystyryl)dimethylsilyl (HSDMS), (2-Hydroxystyryl)diisopropylsilyl(HSDIS). t-Butylmethoxyphenylsilyl (TBMPS), and t-Butoxydiphenylsilyl (DPTBOS) protecting groups.

Useful benzyl-type protecting groups include benzyl, halogenated benzyl, p-methoxybenzyl, benzyloxymethyl, 2,4-dimethoxybenzyl, 3,4-dimethoxybenzyl, 2,6-dimethoxybenzyl, p-CF$_3$-benzyl, p-methylbenzyl, p-methoxylbenzyl, 3,5-dimethylbenzyl, p-tert-butylbenzyl, o-nitrobenzyl, p-nitrobenzyl, p-halobenzyl, including p-Br-benzyl, 2,6-dichlorobenzyl, p-cyanobenzyl, p-phenylbenzyl, 2,6-difluorobenzyl, p-acylaminobenzyl (PAB), p-azidobenzyl (Azb), 4-azido-3-chlorobenzyl, 2-trifluoromethylbenzyl, p-(methylsulfinyl)benzyl, 2-picolyl, 4-picolyl, 3-methyl-2-picolyl N-oxido, 2-quinolinylmethyl, diphenylmethyl (DPM), p,p'-dinitrobenzhydryl, triphenylmethyl, alpha-naphthyldiphenylmethyl, p-methoxyphenyldiphenylmethyl, di(p-methoxyphenyl)phenylmethyl, tri(p-methoxyphenyl)methyl, 4,4',4"-tris(benzoyloxyphenyl)methyl, and 2-naphthylmethyl protecting groups.

Useful amine protecting groups include p-methoxybenzyl carbonyl (Moz or MeOZ), acetyl (Ac), benzoyl (Bz), p-methoxybenzyl (PMB), 3,4-dimethoxybenzyl (DMPM), p-methoxyphenyl (PMP), tosyl (Ts or Tos), trifluoroacetamide, and trityl protecting groups. Useful amine protecting groups also include carbamate and amide protecting groups. Examples of carbamate protecting groups include methyl and ethyl carbamates such as 9-fluorenylmethyloxycarbonyl (FMOC), 9-(2-sulfo)fluorenylmethyl, 9-(2,7-dibromo)fluorenylmethyl, 17-tetrabenzo[a,c,g,i]fluorenylmethyl (Tbfmoc), 2-chloro-3-indenylmethyl (Climoc), benz[f]inden-3-ylmethyl (Bimoc), 2,7-di-t-butyl[9-(10,10-dioxo-10,10,10,10-tetrahydrothioxanyl)]methyl (DBD-Tmoc), [2-(1,3-dithianyl)methyl (Dmoc), and 1,1-dioxobenzo[b]thiophene-2-ylmethyl (Bsmoc) carbamates.

Examples of useful substituted ethyl carbamates include 1,1-dimethyl-2-cyanoethyl, 2-phosphonioethyl (Peoc), 2-methylthioethyl, 2-(p-toluenesulfonyl)ethyl, 2,2,2,-trichloroethyl (Troc), 2-(trimethylsilyl)ethyl (Teoc), 2-phenylethyl (hZ), 1-(1-adamantyl)-1-methylethyl (Adpoc), 1,1-dimethyl-2-bromoethyl, 1,1-dimethyl-2-chloroethyl, 1,1-dimethyl-2,2-dibromoethyl (DB-t-BOC), 1,1-dimethyl-2,2,2-trichloroethyl (TCBOC), 1-methyl-1-(4-biphenylyl)ethyl (Bpoc), di-t-butylphenyl)-1-methylethyl (t-Bumeoc), 2-(2'pyridyl)ethyl, 2-(4'pyridyl)ethyl, 2,2-bis(4'-nitrophenyl)ethyl (Bnpeoc), N-(2-pivaloylamino)-1,1,dimethylethyl, 2-[(2-nitrophenyl)dithio]-1-phenylethyl (NpSSPeoc), 2-(N,N-dicyclohexylcarboxamido)ethyl, t-butyl (Boc or BOC), 1-adamantyl (1-Adoc), 2-adamantyl (2-Adoc), vinyl (Voc), allyl (Aloe or alloc), 1-isopropylallyl (Ipaoc), cinnamyl (Coc), 4-nitrocinnamyl (Noc), 3-(3'-pyridyl)prop-2-enyl (Paloc), 8-quinolyl, and N-hydroxypiperidinyl, carbamates, as well as alkyldithio carbamates, including methyldithio, ethyldithio, isopropyldithio, t-butyldithio, and phenyldithio carbamates.

Also useful are aryl-containing and substituted aryl-containing carbamates such as benzyl, p-methoxybenzyl, p-nitrobenzyl, p-bromobenzyl, p-chlorobenzyl, 2,4-dichlorobenzyl, 4-methylsulfinylbenzyl (Msz), 9-anthrylmethyl, 4-methylthiophenyl (Mtpc), 1-methyl-1-(triphenylphosphonio)ethyl (2-triphenylphosphonioisopropyl) (Ppoc), 2-dansylethyl (Dnseoc), 2-(4-nitrophenyl)ethyl (Npeoc), 4-phenylacetoxybenzyl (PhAcOZ), 4-azidobenzyl (ACBZ), 4-azidomethoxybenzyl, m-chloro-p-acyloxybenzyl, p-(dihydroxyboryl)benzyl, carbobenzyloxy (Cbz), 4-benzisoxazolylmethyl (Bic), 2-(trifluoromethyl)-6-chromonylmethyl (Tcroc), phenyl, and diphenylmethyl carbamates. Additional carbamates include butynyl, cyclopentyl, cyclohexyl, cyclopropylmethyl, 1-methylcyclobutyl, 1-methylcyclohexyl, 1,1-dimethylpropynyl, and 1-methyl-1-cyclopropylmethyl carbamates.

Useful amide protecting groups for amines include N-formyl, N-acetyl, N-chloroacetyl, N-trichloroacetyl, N-trifluoroacetyl (TFA), N-phenylacetyl, N-3-phenylpropionyl, N-4-pentenoyl, N-picolinoyl, N-3-pyridylcarboxamido, N-benzoylphenylalanyl, N-benzoyl, and N-p-phenylbenzoyl amides.

Antiviral Activity

Another embodiment relates to methods of inhibiting viral infections, comprising the step of treating a sample or subject suspected of needing such inhibition with a composition herein.

Considered herein are samples suspected of containing a virus include natural or man-made materials such as living organisms; tissue or cell cultures; biological samples such as biological material samples (blood, serum, urine, cerebrospinal fluid, tears, sputum, saliva, tissue samples, and the like); laboratory samples; food, water, or air samples; bioproduct samples such as extracts of cells, particularly recombinant cells synthesizing a desired glycoprotein; and the like. Typically the sample will be suspected of containing an organism which induces a viral infection, frequently a pathogenic organism such as a tumor virus. Samples can be contained in any medium including water and organic solvent\water mixtures. Samples include living organisms such as humans, and manmade materials such as cell cultures.

If desired, the anti-virus activity of a compound after application of the composition can be observed by any method including direct and indirect methods of detecting such activity. Quantitative, qualitative, and semiquantitative methods of determining such activity are all contemplated. Typically one of the screening methods described above are applied, however, any other method such as observation of the physiological properties of a living organism are also applicable.

The antiviral activity of a compound can be measured using standard screening protocols that are known. For example, the antiviral activity of a compound can be measured using the following general protocols.

Respiratory Syncytial Virus (RSV) Antiviral Activity and Cytotoxicity Assays
Anti-RSV Activity Antiviral activity against RSV is determined using an infectious cytopathic cell protection assay in HEp-2 cells. In this assay, compounds inhibiting viral infection and/or replication produce a cytoprotective effect against the virus-induced cell killing that can be quantified using a cell viability reagent. The techniques used here are novel adaptations of methods described in published literature (Chapman et al., *Antimicrob Agents Chemother.* 2007, 51(9):3346-53.)

HEp-2 cells are obtained from ATCC (Manassas, VI) and maintained in MEM media supplemented with 10% fetal bovine serum and penicillin/streptomycin. Cells are passaged twice a week and kept at subconfluent stage. Commercial stock of RSV strain A2 (Advanced Biotechnologies, Columbia, Md.) is titered before compound testing to determine the appropriate dilution of the virus stock that generates desirable cytopathic effect in HEp-2 cells.

For antiviral tests, HEp-2 cells are grown in large cell culture flasks to near confluency but not fully so. The compounds to be tested are prediluted in DMSO in 384-well compound dilution plates, either in an 8 or 40 sample per plate standardized dose response format. 3-fold serial dilution increments of each test compound are prepared in the plates and test samples are transferred via acoustic transfer apparatus (Echo, Labcyte) at 100 nl per well into cell culture assay 384-well plates. Each compound dilution is transferred in single or quadruplicate samples into dry assay plates, which are stored until assay is ready to go. The positive and negative controls are laid out in opposite on ends of the plate in vertical blocks (1 column).

Subsequently, an infectious mixture is prepared using an appropriate dilution of virus stock previously determined by titration with cells at a density of 50,000/ml and 20 uL/well is added to test plates w/compounds via automation (uFlow, Biotek). Each plate includes negative and positive controls (16 replicates each) to create 0% and 100% virus inhibition standards, respectively. Following the infection with RSV, testing plates are incubated for 4 days in a 37° C. cell culture incubator. After the incubation, a cell viability reagent, Cell TiterGlo (Promega, Madison, Wis.) is added to the assay plates, which are incubated briefly, and a luminescent readout is measured (Envision, Perkin Elmer) in all the assay plates. The RSV-induced cytopathic effect, percentage inhibition, is determined from the levels of remaining cell viability. These numbers are calculated for each tested concentration relative to the 0% and 100% inhibition controls, and the $EC_{50}$ value for each compound is determined by non-linear regression as a concentration inhibiting the RSV-induced cytopathic effect by 50%. Various potent anti-RSV tool compounds are used as positive controls for antiviral activity.

Cytotoxicity Assay in HEp-2 Cells

Cytotoxicity of tested compounds is determined in uninfected HEp-2 cells in parallel with the antiviral activity using the cell viability reagent in a similar fashion as described before for other cell types (Cihlar et al., *Antimicrob Agents Chemother.* 2008, 52(2):655-65.). The same protocol as for the determination of antiviral activity is used for the measurement of compound cytotoxicity except that the cells are not infected with RSV. Instead, an uninfected cell mixture at the same density is added at 20 ul/well to plates containing prediluted compounds, also at 100 nl/sample. Assay plates are then incubated for 4 days followed by a cell viability test using the same CellTiter Glo reagent addition and measurement of luminescent readouts. Untreated cell and cells treated at 2 uM puromycin (Sigma, St. Louis, Mo.) serve as 100% and 0% cell viability control, respectively. The percent of cell viability is calculated for each tested compound concentration relative to the 0% and 100% controls and the $CC_{50}$ value is determined by non-linear regression as a compound concentration reducing the cell viability by 50%.

Cytotoxicity Assay in MT-4 Cells

The MT-4 cell line was obtained from the NIH AIDS Research and Reference Reagent Program (Germantown, Md.) and cultured in RPMI-1640 medium (Irvine Scientific, Santa Ana, Calif., Cat #9160) supplemented with 10% FBS, 100 units/mL penicillin, 100 units/mL streptomycin, and 2 mM L-Glutamine. The MT-4 cells were passaged twice per week to maintain cell densities below $0.6 \times 10^6$ cells/mL. Complete RPMI-1640 media containing 100× concentrations of 3-fold serially diluted compound, ranging from 26 nM to 530 µM, were stamped in quadruplicate into black 384-well plates. After compound addition, $2 \times 10^3$ MT-4 cells were added to each well using a MicroFlo liquid dispenser (BioTek, Winooski, Vt.) and the cells were cultured for 5 days at 37° C. in a 5% $CO_2$ incubator. Following the incubation the cells were allowed to equilibrate to 25° C. and cell viability was determined by adding 25 µL of Cell-Titer Glo viability reagent. The mixture was incubated for 10 minutes at 25° C., and the luminescence signal was quantified on a Victor Luminescence plate reader. The $CC_{50}$ value is defined as the concentration of compound that reduces cell viability by 50% as determined by the Cell-Titer Glo signal. The data were analyzed using Pipeline Pilot Plate Data Analytics Collection software (Version 7.0, Accelrys, San Diego, Calif.). $CC_{50}$ values were calculated from a non-linear regression analysis using a 4-parameter sigmoidal dose-response equation: $Y = Bottom + (Top - Bottom)/(1 + 10^{\wedge}[(Log\ CC50 - X)*HillSlope])$ where the Top and Bottom were fixed at 100% and 0% cell viability, respectively. $CC_{50}$ values were calculated as the average±standard deviation of 3 independent experiments.

| Example | $EC_{50}/\mu M$ | HEp-2 $CC_{50}/\mu M$ | MT-4 $CC_{50}/\mu M$ |
|---|---|---|---|
| 1 | 7.3 | >50 | >53 |
| 2 | 9.6 | >100 | >106 |
| 3 | 2.0 | >100 | >106 |
| 4 | 30 | >50 | >53 |
| 5 | 2.1 | >50 | >53 |
| 10 (PD1) | 1.0 | 39 | 7.3 |
| 11 (PD2) | 1.2 | 42 | 19.7 |
| 12 (PD3) | 3.0 | >50 | 27 |
| 13 | 10.5 | >100 | >106 |
| 14 | 40 | >100 | >106 |
| 15 (PD4) | 1.6 | 35 | 7.9 |
| 16 (PD5) | 0.3 | 18 | 25 |
| 19 | 0.40 | >44 | 16 |
| 20 | >50 | >50 | |
| 21 | 50 | 36 | 15 |
| 22 | 0.57 | >100 | 32 |
| 23 | 23.5 | 72 | 21 |
| 24 | 1.0 | >100 | 11 |
| 25 | 9.2 | >100 | >93 |

-continued

| Example | EC$_{50}$/µM | HEp-2 CC$_{50}$/µM | MT-4 CC$_{50}$/µM |
|---|---|---|---|
| 26 | >50 | 42 | >57 |
| 34 (PD6) | 0.21 | >50 | >50 |
| 35 (PD7) | 0.34 | >50 | 47 |

Another benefit relates to advantage that compounds bearing R$^4$ substitution provides in comparison to compounds lacking R$^4$ substitution (i.e. those in which R$^4$=H) with regard to MT-4 cytotoxicity. For example, compound (2S,3R,4S,5R)-2-(4-aminopyrrolo[1,2-t][1,2,4]triazin-7-yl)-5-(hydroxymethyl)tetrahydrofuran-3,4-diol (Patil, S. A.; Otter, R. A.; Klein, R. S. Tetrahedron Lett. 1994, 35, 5339-5342), having the structure:

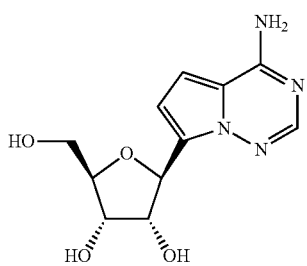 [SMILES: Nc1ncnn2c([C@@H]3O[C@H](CO)[C@@H](O)[C@H]3O)ccc12]

exhibits a MT-4 CC$_{50}$=0.007 µM; whereas Examples 1, 4, 5, 20, and 26 all exhibit a MT-4 CC$_{50}$>53 µM. Furthermore, compound (2R,3R,4R,5S)-5-(4-aminopyrrolo[1,2-f][1,2,4]triazin-7-yl)-4-fluoro-2-(hydroxymethyl)tetrahydrofuran-3-ol (WO2012037038A1), having the structure:

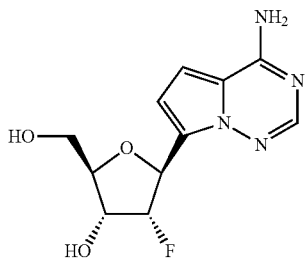 [SMILES: Nc1ncnn2c([C@@H]3O[C@H](CO)[C@@H](O)[C@H]3F)ccc12]

exhibits a MT-4 CC$_{50}$=30 µM; whereas Examples 2, 3, 13, and 14 all exhibit a MT-4 CCs>106 µM.

Another benefit relates to advantage that R$^3$=F compounds bearing R$^4$ substitution provides in comparison to compounds lacking R$^4$ substitution (i.e. those in which R$^4$=H) with regard to HEp-2 anti-RSV activity. For example the compound (2R,3R,4R,5S)-5-(4-aminopyrrolo[1,2-f][1,2,4]triazin-7-yl)-4-fluoro-2-(hydroxymethyl)tetrahydrofuran-3-ol (WO2012037038A1) having the structure above has a HEp-2 EC$_{50}$=>100 µM; whereas examples 2, 3, 13, 14, 19, 21, 22, 23, and 24 all exhibit EC$_{50}$=<100 uM.

RSV RNP Preparation

RSV ribonucleoprotein (RNP) complexes were prepared from a method modified from Mason at al (1). HEp-2 cells were plated at a density of 7.1×10$^4$ cells/cm$^2$ in MEM+10% fetal bovine serum (FBS) and allowed to attach overnight at 37° C. (5% CO$_2$). Following attachment, the cells were infected with RSV A2 (M01=5) in 35 mL MEM+2% FBS. At 20 hours post-infection, the media was replaced with MEM+2% FBS supplemented with 2 µg/mL actinomycin D and returned to 37° C. for one hour. The cells were then washed once with PBS and treated with 35 mL of PBS+250 µg/mL lyso-lecithin for one minute, after which all liquid was aspirated. The cells were harvested by scrapping them into 1.2 mL of buffer A [50 mM TRIS acetate (pH 8.0), 100 mM potassium acetate, 1 mM DTT and 2 µg/mL actinomycin D] and lysed by repeated passage through an 18 gauge needle (10 times). The cell lysate was placed in ice for 10 minutes and then centrifuged at 2400g for 10 minutes at 4° C. The supernatant (S1) was removed and the pellet (P1) was disrupted in 600 uL of Buffer B [10 mM TRIS acetate (pH 8.0), 10 mM potassium acetate and 1.5 mM MgCl$_2$] supplemented with 1% Triton X-100 by repeated passage through an 18 gauge needle (10 times). The resuspended pellet was placed in ice for 10 minutes and then centrifuged at 2400g for 10 minutes at 4° C. The supernatant (S2) was removed and the pellet (P2) was disrupted in 600 uL of Buffer B supplemented with 0.5% deoxycholate and 0.1% Tween 40. The resuspended pellet was placed in ice for 10 minutes and then centrifuged at 2400g for 10 minutes at 4° C. The supernatant (S3) fraction, containing the enriched RSV RNP complexes, was collected and the protein concentration determined by UV absorbance at 280 nm. Aliquoted RSV RNP S3 fractions were stored at −80° C.

RSV RNP Assay

Transcription reactions contained 25 µg of crude RSV RNP complexes in 30 µL of reaction buffer [50 mM TRIS-acetate (pH 8.0), 120 mM potassium acetate, 5% glycerol, 4.5 mM MgCl$_2$, 3 mM DTT, 2 mM ethyleneglycol-bis(2-aminoethylether)-tetraacetic acid (EGTA), 50 µg/mL BSA, 2.5 U RNasin (Promega), ATP, GTP, UTP, CTP and 1.5 uCi [α-$^{32}$P] NTP (3000 Ci/mmol)]. The radiolabeled nucleotide used in the transcription assay was selected to match the nucleotide analog being evaluated for inhibition of RSV RNP transcription. Cold, competitive NTP was added at a final concentration of one-half its K$_m$ (ATP=20 µM, GTP=12.5 µM, UTP=6 µM and CTP=2 µM). The three remaining nucleotides were added at a final concentration of 100 µM.

To determine whether nucleotide analogs inhibited RSV RNP transcription, compounds were added using a 6 step serial dilution in 5-fold increments. Following a 90 minute incubation at 30° C., the RNP reactions were stopped with 350 µL of Qiagen RLT lysis buffer and the RNA was purified using a Qiagen RNeasy 96 kit. Purified RNA was denatured in RNA sample loading buffer (Sigma) at 65° C. for 10 minutes and run on a 1.2% agarose/MOPS gel containing 2M formaldehyde. The agarose gel was dried and exposed to a Storm phosphorimager screen and developed using a Storm phosphorimager (GE Healthcare). The concentration of compound that reduced total radiolabeled transcripts by 50% (IC$_{50}$) was calculated by non-linear regression analysis of two replicates.

REFERENCE

Mason, S., Lawetz, C., Gaudette, Y., Do, F., Scouten, E., Lagace, L., Simoneau, B. and Liuzzi, M. (2004) Polyadenylation-dependent screening assay for respiratory syncytial virus RNA transcriptase activity and identification of an inhibitor. Nucleic Acids Research, 32, 4758-4767.

| Example | IC$_{50}$/µM |
|---|---|
| 6 (TP1) | 0.086 |
| 7 (TP2) | 1 |
| 8 (TP3) | 0.025 |

163
-continued

| Example | IC$_{50}$/µM |
|---|---|
| 9 (TP4) | 0.12 |
| 17 (TP5) | 0.56 |
| 18 (TP6) | 0.42 |
| 27 (TP7) | 0.097 |
| 28 (TP8) | 0.086 |
| 29 (TP9) | 0.080 |
| 30 (TP10) | |
| 31 (TP11) | |
| 32 (TP12) | 0.022 |
| 33 (TP13) | |

A further consideration relates to advantage that compounds exemplified exhibit potent inhibition of the RSV RNP transcription in comparison to compounds with 2'CMe substitution. For example, ((2R,3R,4R,5S)-5-(4-aminopyrrolo[2,1-f][1,2,4]triazin-7-yl)-3,4-dihydroxy-4-methyltetrahydrofuran-2-yl)methyl tetrahydrogen triphosphate (WO2008089105A2, and WO2010002877A2), having the structure:

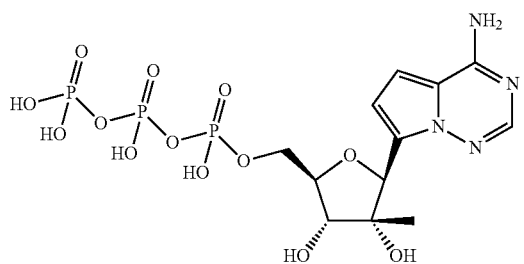 [SMILES: C[C@@]1(O)[C@H](O)[C@@H](COP(=O)(O)OP(=O)(O)OP(=O)(O)O)O[C@H]1c1ccc2c(N)ncnn12]

exhibits an IC$_{50}$=8.5 µM; whereas Example TP3 exhibits an IC$_{50}$=0.025 µM. Furthermore, compound ((2R,3R,4R,5S)-5-(4-aminopyrrolo[2,1-f][1,2,4]triazin-7-yl)-4-fluoro-3-hydroxy-4-methyltetrahydrofuran-2-yl)methyl tetrahydrogen triphosphate (WO 2011035231 A1), having the structure:

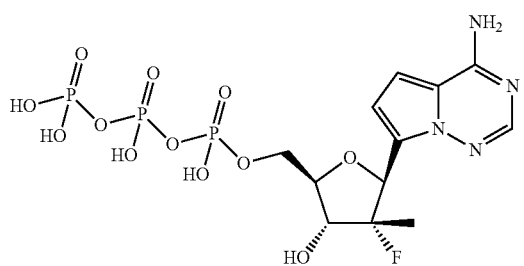 [SMILES: C[C@@]1(F)[C@H](O)[C@@H](COP(=O)(O)OP(=O)(O)OP(=O)(O)O)O[C@H]1c1ccc2c(N)ncnn12]

exhibits an IC$_{50}$=>100 µM; whereas Examples TP1 exhibits an IC$_{50}$=0.086 µM. and TP2 exhibits an IC$_{50}$=1 µM.

164

What is claimed:
1. A compound of Formula (I), or a pharmaceutically acceptable salt thereof:

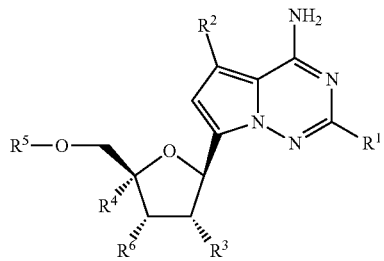

wherein:
R$^1$ is H or F;
R$^2$ is H or F;
R$^3$ is OH or F;
R$^4$ is CN, C$_1$-C$_4$ alkyl, C$_2$-C$_4$ alkenyl, C$_2$-C$_4$ alkynyl, C$_3$-C$_4$ cycloalkyl, azido, halogen, or C$_1$-C$_2$ haloalkyl, with the proviso that, when R$^3$ is F, R$^4$ is not methyl;
R$^6$ is OH;
R$^5$ is selected from the group of H and:

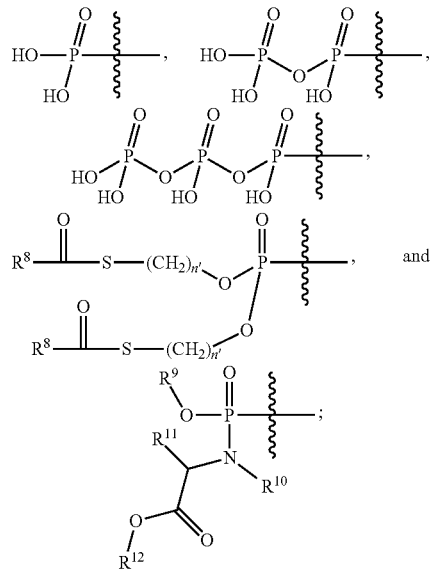

wherein:
n' is selected from 1, 2, 3, and 4;
R$^8$ is selected from C$_1$-C$_8$ alkyl, —O—C$_1$-C$_8$ alkyl, benzyl, —O-benzyl, —CH$_2$-C$_3$-C$_6$ cycloalkyl, —O—CH$_2$-C$_3$-C$_6$ cycloalkyl, and CF$_3$;
R$^9$ is selected from phenyl, 1-naphthyl, 2-naphthyl,

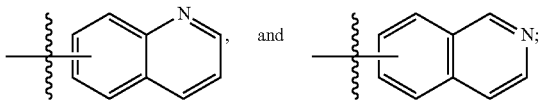

R$^{10}$ is selected from H and CH$_3$;
R$^{11}$ is selected from H or C$_1$-C$_6$ alkyl;
R$^{12}$ is selected from H, C$_1$-C$_8$ alkyl, benzyl, C$_3$-C$_6$ cycloalkyl, and —CH$_2$—C$_3$-C$_6$ cycloalkyl.

2. A compound according to claim 1, or a pharmaceutically acceptable salt thereof, wherein both $R^1$ and $R^2$ are H, and $R^3$ is OH.

3. A compound according to claim 1, or a pharmaceutically acceptable salt thereof, wherein both $R^1$ and $R^2$ are H, $R^3$ is F.

4. A compound according to claim 1, or a pharmaceutically acceptable salt thereof, of Formula (II):

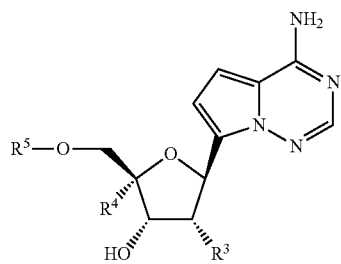

wherein:
$R^3$ is OH or F;
$R^4$ is CN, $C_1$-$C_4$ alkyl, $C_2$-$C_4$ alkenyl, $C_2$-$C_4$ alkynyl, $C_3$-$C_4$ cycloalkyl, azido, halogen, or $C_1$-$C_2$ haloalkyl, with the proviso that, when $R^3$ is F, $R^4$ is not methyl;
$R^5$ is selected from the group of H and:

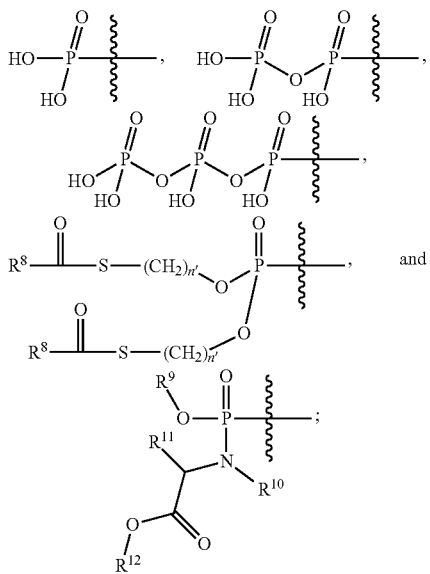

wherein:
n' is selected from 1, 2, 3, and 4;
$R^8$ is selected from $C_1$-$C_8$ alkyl, —O—$C_1$-$C_8$ alkyl, benzyl, —O-benzyl, —$CH_2$—$C_3$-$C_6$ cycloalkyl, —O—$CH_2$—$C_3$-$C_6$ cycloalkyl, and $CF_3$;
$R^9$ is phenyl;
$R^{10}$ is selected from H and $CH_3$;
$R^{11}$ is selected from H or $C_1$-$C_6$ alkyl;
$R^{12}$ is selected from H, $C_1$-$C_8$ alkyl, benzyl, $C_3$-$C_6$ cycloalkyl, and —$CH_2$—$C_3$-$C_6$ cycloalkyl.

5. A compound according to claim 4, or a pharmaceutically acceptable salt thereof, wherein $R^4$ is CN, methyl, ethyl, ethenyl, ethynyl, azido, F, Cl, —$CH_2$Cl, —$CH_2$F, —$CHF_2$, or —$CF_3$.

6. A compound according to claim 5, or a pharmaceutically acceptable salt thereof, wherein $R^3$ is F.

7. A compound according to claim 5, or a pharmaceutically acceptable salt thereof, wherein $R^3$ is OH.

8. A compound according to claim 5, or a pharmaceutically acceptable salt thereof, wherein $R^3$ is F and $R^4$ is CN.

9. A compound according to claim 5, or a pharmaceutically acceptable salt thereof, wherein $R^3$ is OH and $R^4$ is CN.

10. A compound according to claim 5, or a pharmaceutically acceptable salt thereof, wherein $R^3$ is F, and $R^4$ is methyl, ethyl, vinyl, or ethynyl.

11. A compound according to claim 5, or a pharmaceutically acceptable salt thereof, wherein $R^3$ is OH, and $R^4$ is methyl, ethyl, vinyl, or ethynyl.

12. A compound according to claim 5, or a pharmaceutically acceptable salt thereof, wherein $R^3$ is F and $R^4$ is halomethyl.

13. A compound according to claim 5, or a pharmaceutically acceptable salt thereof, wherein $R^3$ is OH and $R^4$ is halomethyl.

14. A compound according to claim 5, or a pharmaceutically acceptable salt thereof, wherein $R^5$ is H.

15. A compound according to claim 5, or a pharmaceutically acceptable salt thereof,
wherein $R^5$ is selected from the group of:

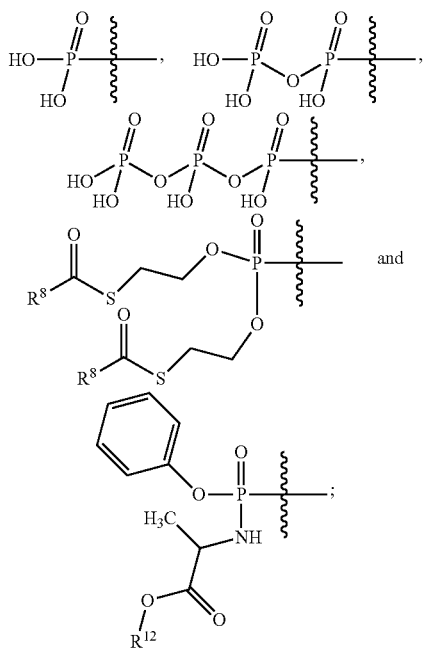

$R^8$ is selected from $C_1$-$C_8$ alkyl, —O—$C_1$-$C_8$ alkyl, benzyl, and —$CH_2$—$C_3$-$C_6$ cycloalkyl; and
$R^{12}$ is selected from $C_1$-$C_8$ alkyl, benzyl, $C_3$-$C_6$ cycloalkyl, and —$CH_2$—$C_3$-$C_6$ cycloalkyl.

16. A compound according to claim 15, or a pharmaceutically acceptable salt thereof, wherein $R^8$ and $R^9$ are each $C_1$-$C_8$ alkyl.

17. A compound according to claim 15, or a pharmaceutically acceptable salt thereof, wherein $R^8$ and $R^9$ are each selected from $C_1$-$C_6$ alkyl.

18. A compound according to claim 15, or a pharmaceutically acceptable salt thereof, wherein $R^8$ and $R^9$ are each selected from $C_1$-$C_4$ alkyl.

19. A compound according to claim 15, or a pharmaceutically acceptable salt thereof, wherein $R^5$ is selected from the group of H and:

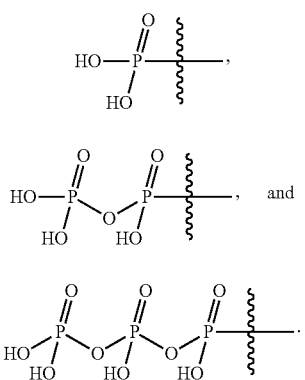
(a)
(b)
(c)
20. A compound according to claim 1, or a pharmaceutically acceptable salt thereof, selected from the group of:
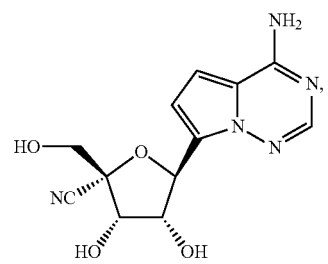
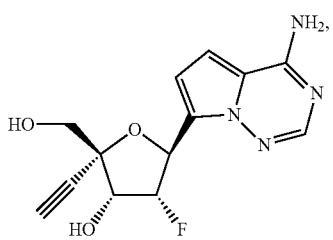
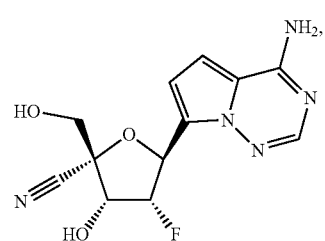
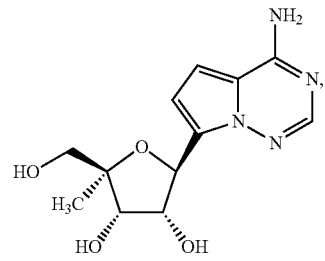
-continued
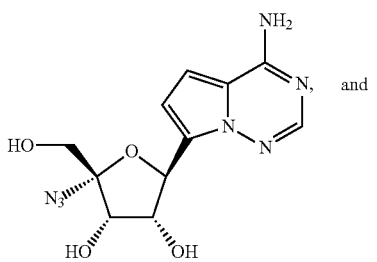
21. A compound according to claim 1, or a pharmaceutically acceptable salt thereof, selected from the group of:
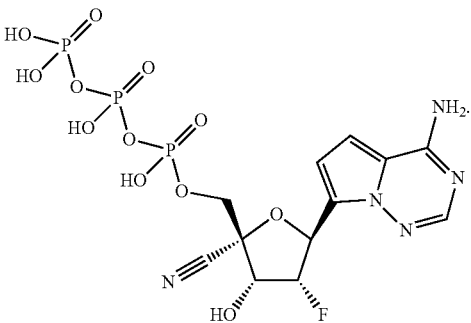
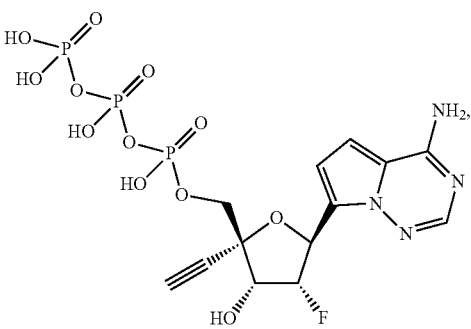
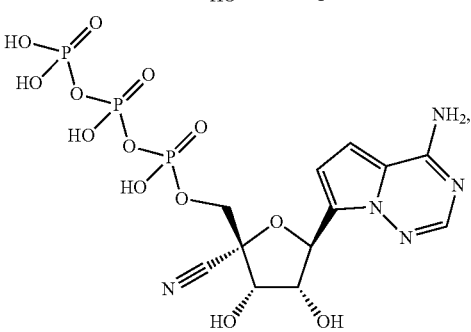
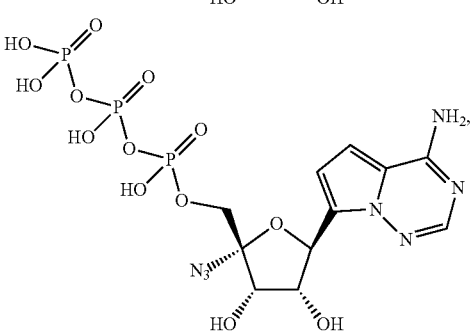

169
-continued
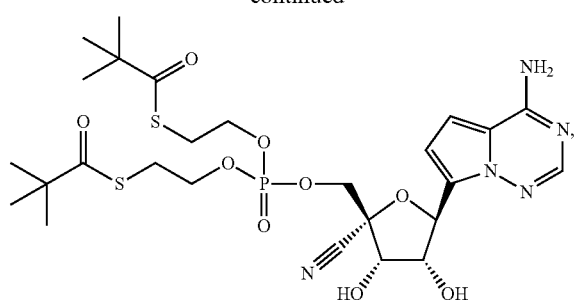
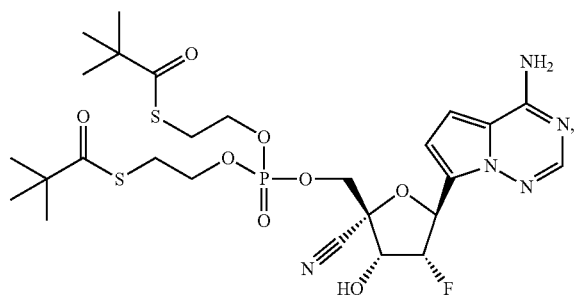
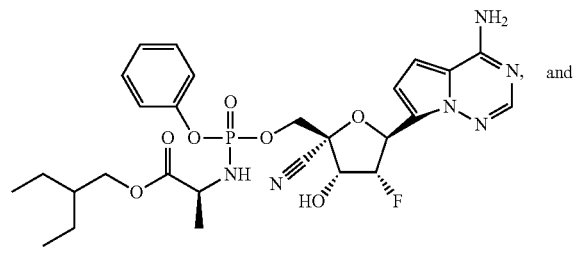
22. A compound according to claim 1, or a pharmaceutically acceptable salt thereof, selected from the group of:
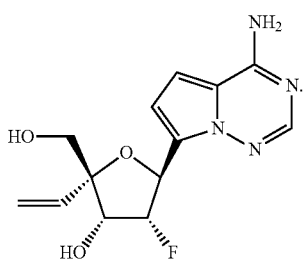
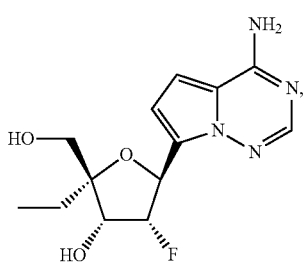
170
-continued
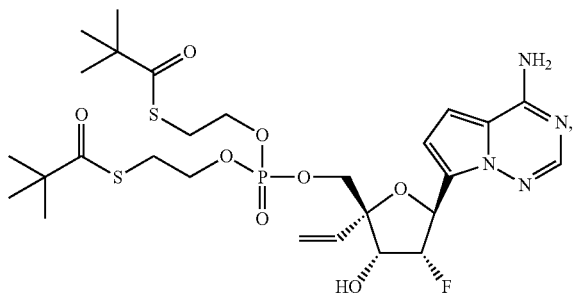
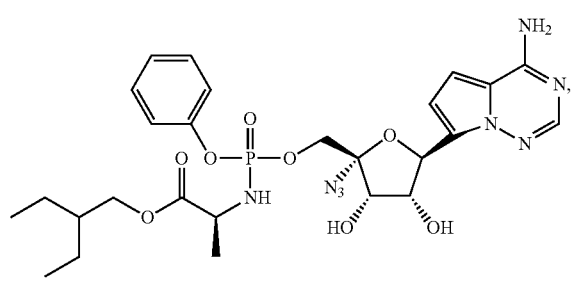
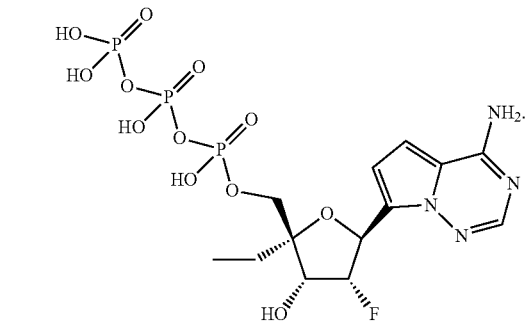
23. A compound according to claim 1, or a pharmaceutically acceptable salt thereof, selected from the group of:
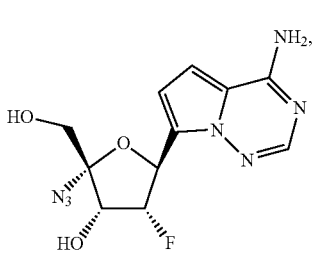

-continued
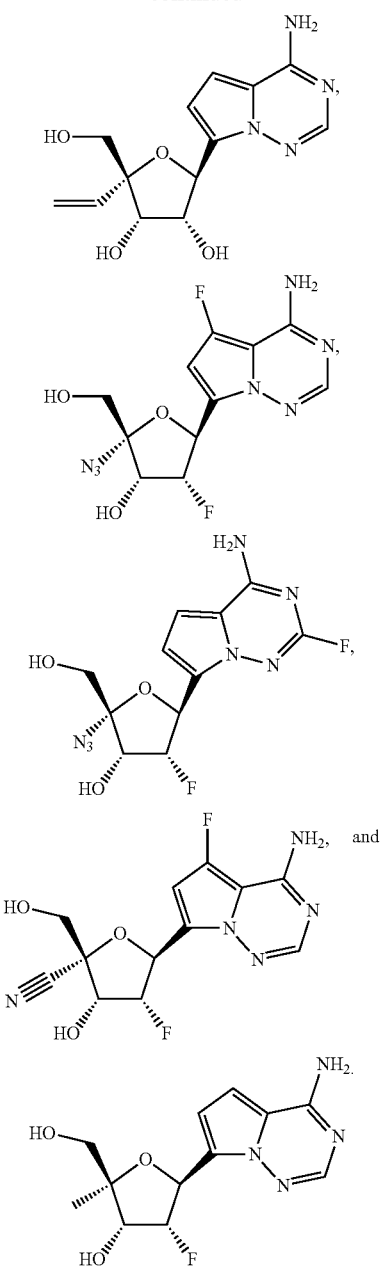
24. A compound according to claim 1, or a pharmaceutically acceptable salt thereof, selected from the group of:
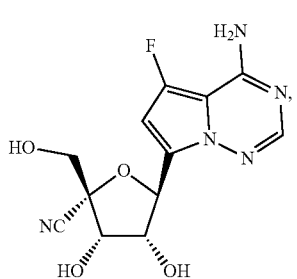
-continued
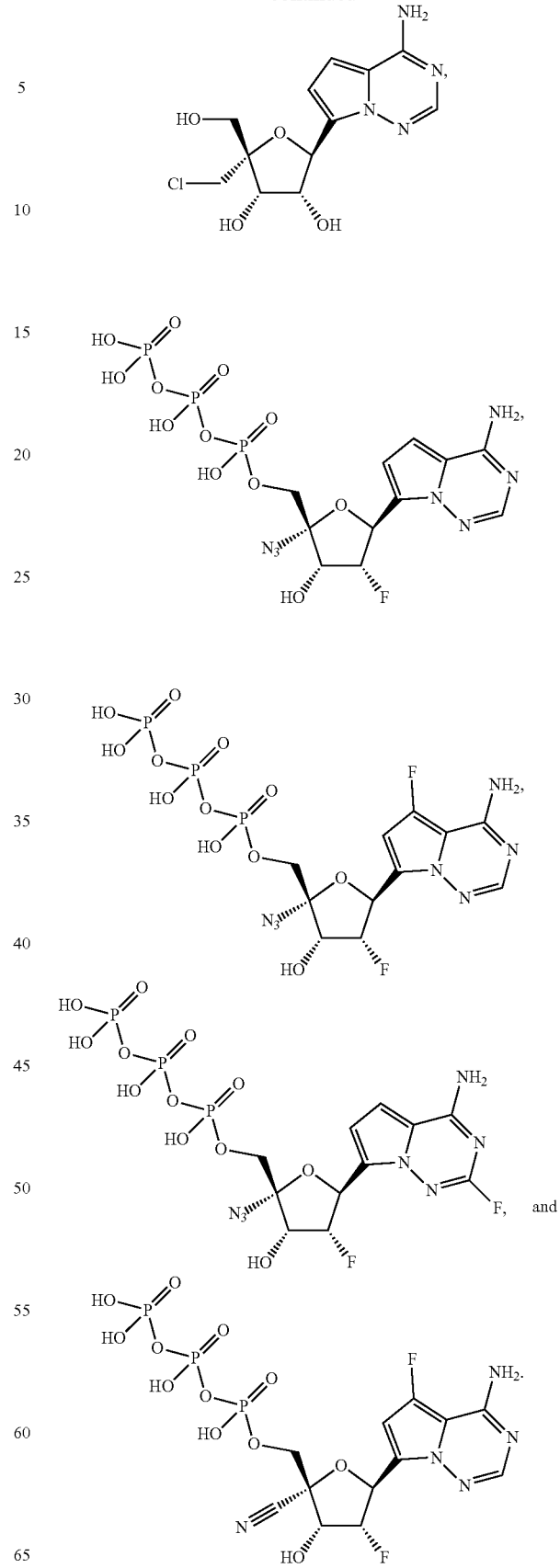

25. A compound according to claim 1, or a pharmaceutically acceptable salt thereof, selected from the group of:

[Chemical structures of four nucleotide analogs]

26. A method of treating Pneumovirinae virus infection in a human, the method comprising administering to the human a therapeutically effective amount of a compound of claim 1, or a pharmaceutically acceptable salt thereof.

27. The method of claim 26 wherein the Pneumovirinae virus infection in a human is a human respiratory syncytial virus infection.

28. A pharmaceutical formulation comprising a pharmaceutically effective amount of a compound of claim 1, or a pharmaceutically acceptable salt thereof, and a pharmaceutically acceptable carrier or excipient.

29. A compound selected from Formula (A), Formula (B), Formula (C), Formula (D), and Formula (E):

[Chemical structures labeled (A), (B), (C), (D), (E), (F)]

wherein $X^1$ is an oxygen protecting group and $X^2$ is an amine protecting group.

30. A compound of claim 29 selected from:
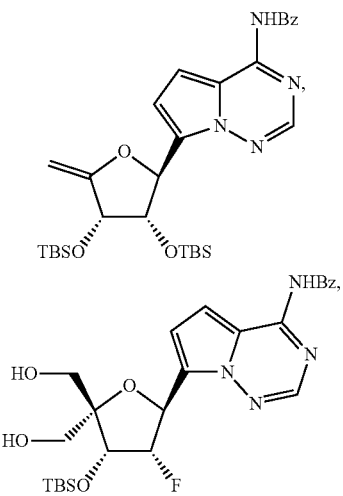
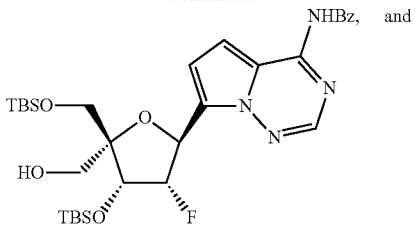
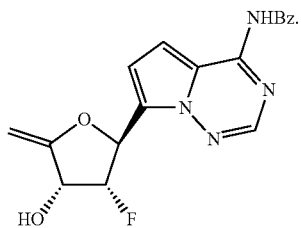
* * * * *